US009051344B2

(12) United States Patent
Lin et al.

(10) Patent No.: US 9,051,344 B2
(45) Date of Patent: *Jun. 9, 2015

(54) STABILITY OLED MATERIALS AND DEVICES

(75) Inventors: Chun Lin, Irwin, PA (US); Peter B. Mackenzie, Murrysville, PA (US); Robert W. Walters, Export, PA (US); Jui-Yi Tsai, Monroeville, PA (US); Cory S. Brown, Pittsburgh, PA (US); Jun Deng, Murrysville, PA (US)

(73) Assignee: Universal Display Corporation, Ewing, NJ (US)

( * ) Notice: Subject to any disclaimer, the term of this patent is extended or adjusted under 35 U.S.C. 154(b) by 2295 days.

This patent is subject to a terminal disclaimer.

(21) Appl. No.: 11/241,981

(22) Filed: Oct. 4, 2005

(65) Prior Publication Data
US 2006/0251923 A1 Nov. 9, 2006

Related U.S. Application Data

(60) Provisional application No. 60/678,170, filed on May 6, 2005, provisional application No. 60/701,929, filed on Jul. 25, 2005, provisional application No. 60/718,336, filed on Sep. 20, 2005.

(51) Int. Cl.
| H01L 51/54 | (2006.01) |
| C09K 11/06 | (2006.01) |
| C07F 15/00 | (2006.01) |
| H01L 51/00 | (2006.01) |
| H01L 51/50 | (2006.01) |

(52) U.S. Cl.
CPC ............ *C07F 15/0046* (2013.01); *C09K 11/06* (2013.01); *C07F 15/0033* (2013.01); *C09K 2211/1044* (2013.01); *H01L 51/5016* (2013.01); *C09K 2211/185* (2013.01); *H01L 51/0085* (2013.01)

(58) Field of Classification Search
None
See application file for complete search history.

(56) References Cited

U.S. PATENT DOCUMENTS

| 4,769,292 A | 9/1988 | Tang et al. |
| 5,247,190 A | 9/1993 | Friend et al. |
| 5,503,910 A * | 4/1996 | Matsuura et al. ............. 428/212 |
| 5,703,436 A | 12/1997 | Forrest et al. |
| 5,707,745 A | 1/1998 | Forrest et al. |
| 5,834,893 A | 11/1998 | Bulovic et al. |
| 5,844,238 A | 12/1998 | Sauer et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,310,360 B1 | 10/2001 | Forrest et al. |
| 6,337,102 B1 | 1/2002 | Forrest et al. |
| 6,468,819 B1 | 10/2002 | Kim et al. |
| 6,548,956 B2 | 4/2003 | Forrest et al. |
| 6,576,134 B1 | 6/2003 | Agner |
| 6,602,540 B2 | 8/2003 | Gu et al. |
| 6,687,266 B1 | 2/2004 | Ma et al. |
| 6,830,828 B2 | 12/2004 | Thompson et al. |
| 6,835,469 B2 | 12/2004 | Kwong et al. |
| 6,936,716 B1 * | 8/2005 | Lin .................... 546/2 |
| 7,902,374 B2 * | 3/2011 | Lin et al. ........ 548/103 |
| 8,367,223 B2 * | 2/2013 | Xia et al. ......... 428/690 |
| 2001/0019782 A1 * | 9/2001 | Igarashi et al. .............. 428/690 |
| 2002/0182441 A1 | 12/2002 | Lamansky et al. |
| 2003/0230980 A1 | 12/2003 | Forrest et al. |
| 2004/0174116 A1 | 9/2004 | Lu et al. |
| 2004/0253478 A1 | 12/2004 | Thompson et al. |
| 2005/0031903 A1 | 2/2005 | Park et al. |
| 2005/0116626 A1 | 6/2005 | Cheng et al. |
| 2005/0260444 A1 | 11/2005 | Forrest et al. |
| 2005/0260445 A1 | 11/2005 | Walters et al. |
| 2006/0008670 A1 * | 1/2006 | Lin et al. ........ 428/690 |
| 2006/0008673 A1 | 1/2006 | Kwong et al. |
| 2006/0078758 A1 * | 4/2006 | Lin ............... 428/690 |
| 2006/0094875 A1 * | 5/2006 | Itoh et al. .......... 546/2 |
| 2006/0127696 A1 * | 6/2006 | Stossel et al. ........ 428/690 |
| 2006/0240279 A1 | 10/2006 | Adamovich et al. |
| 2007/0075631 A1 | 4/2007 | Tung et al. |

(Continued)

FOREIGN PATENT DOCUMENTS

| CN | 1583772 A | 2/2005 |
| DE | 102 38 903 A1 * | 3/2004 |
| JP | 2003-253129 A | 9/2003 |

(Continued)

OTHER PUBLICATIONS

Adachi et al., "Nearly 100% internal phosphorescent efficiency in an organic light emitting device," J. Appl. Phys. 90(10): 5048-5051, 2001.
Adamovich, "Novel materials and techniques of fabrication for organic light emitting diodes", A Dissertation Presented to Faculty of the Graduate School, University of Southern California, Chapter 4, pp. 107-142, Dec. 2002.
Baldo et al., "Very high-efficiency green organic light-emitting devices based on electrophosphorescence," Appl. Phys. Lett. 75(1): 4-6, 1999.
Baldo et al., "Highly efficient phosphorescent emission from organic electroluminescent devices," Nature 395: 151-154, 1998.
Hansch et al., Chem. Rev. 91: 165, 1991.
Kulkarni et al., "Electron transport materials for organic light-emitting diodes" Chem. Mater., 16: 4556-4573, 2004.
Lin et al., U.S. Appl. No. 60/678,170, filed May 6, 2005, entitled "Improved stability OLED materials and devices."

(Continued)

*Primary Examiner* — Marie R. Yamnitzky
(74) *Attorney, Agent, or Firm* — Duane Morris LLP

(57) ABSTRACT

Organic light emitting materials and devices comprising phosphorescent metal complexes comprising ligands comprising aryl or heteroaryl groups substituted at both ortho positions are described. An organic light emitting device, comprising: an anode; a hole transport layer; an organic emissive layer comprising an emissive layer host and an emissive dopant; an electron impeding layer; an electron transport layer; and a cathode disposed, in that order, over a substrate.

93 Claims, 63 Drawing Sheets

(56) References Cited

U.S. PATENT DOCUMENTS

2007/0184301 A1* 8/2007 Oshiyama et al. ............ 428/690
2008/0233287 A1 9/2008 Shtein et al.

FOREIGN PATENT DOCUMENTS

| TW | 200420540 | | 10/2004 |
|----|-----------|---|---------|
| WO | WO 02/074015 | | 9/2002 |
| WO | WO 2004/026886 A2 | | 4/2004 |
| WO | WO 2004/039781 A1 | * | 5/2004 |
| WO | WO 2004/101707 | | 11/2004 |
| WO | WO 2005/007767 | | 1/2005 |
| WO | WO 2005/083033 A1 | * | 9/2005 |
| WO | WO 2006/093466 A1 | * | 9/2006 |

OTHER PUBLICATIONS

Lin et al., U.S. Appl. No. 60/701,929, filed Jul. 25, 2005, entitled "Improved stability OLED materials and devices."

Lin et al., U.S. Appl. No. 60/718,336, filed Sep. 20, 2005, entitled "Improved stability OLED materials and devices."

Miessler et al., "Inorganic Chemistry," 2$^{nd}$ Edition, Prentice Hall, 1999., pp. 1-3, 422-424, 442.

Naka et al., "High electron mobility in bathophenanthroline," Appl. Phys. Lett. 76(2): 197-199, 2000.

Strohriegl et al., "Charge-transporting molecular glasses," Advanced Materials 14(20): 1439-1452, 2002.

Yasuda et al., "Carrier mobilities in organic electron transport materials determined from space charge limited current," Jpn. J. Appl. Phys. 41(9): 5626-5629, 2002.

Alcarazo, M., et al., "Imidazo[1,5-a]pyridine: A Versatile Architecture for Stable N-Heterocyclic Carbenes," *Journal of the American Chemical Society* 127:3290-3291, American Chemical Society Publications, United States (2005).

Chianese, A.R., et al., "Pincer and Chelate N-Heterocyclic Carbene Complexes of Rh, Ir and Pd: Synthetic Routes, Dynamics, Catalysis, Abnormal Binding and Counterion Effects," *ACS Symposium Series* 885:169-183, American Chemical Society Publications, United States (2004).

Gründemann, S., et al., "Abnormal Ligand Binding and Reversible Ring Hydrogenation in the Reaction of Imidazolium Salts with $IrH_5(PPh_3)_2$," *Journal of the American Chemical Society* 124:10473-10481, American Chemical Society Publications, United States (2002).

Hino, S., et al., "Low-Coordinate Species: Synthesis and Characterization of a Quasi-One-Coordinate Lead Cation," *Angewandte Chemie International Edition* 43:2655-2658, Wiley-VCH Verlag GmbH & Co. KGaA, Weinheim, Germany (2004).

Lainé, P., et al., "A New Class of Functionalized Terpyridyl Ligands as Building Blocks for Photosensitized Supramolecular Architectures. Synthesis, Structural, and Electronic Characterizations," *Journal of the American Chemical Society* 124:1364-1377, American Chemical Society Publications, United States (2002).

Lainé, P., et al., "Photoinduced Processes within Compact Dyads Based on Triphenylpyridinium-Functionalized Bipyridyl Complexes of Ruthenium (II)," *Chemistry—A European Journal* 11:3711-3727, Wiley-VCH Verlag GmbH & Co. KGaA, Weinheim, Germany (2005).

Lebel, H., et al., "Structure and Reactivity of "Unusual" N-Heterocyclic Carbene (NHC) Palladium Complexes Synthesized from Imidazolium Salts," *Journal of the American Chemical Society* 126:5046-5047, American Chemical Society Publications, United States (2004).

Luo, Q., et al., "Mono-Bisthienylethene Ring-Fused versus Multi-Bisthienylethene Ring-Fused Photochromic Hybrids," *Advanced Functional Materials* 13(3):233-239, Wiley-VCH Verlag GmbH & Co. KGaA, Weinheim, Germany (2003).

Taiwan Intellectual Property Office, Taiwan Office Action and English Translation regarding corresponding Taiwan Application No. TW103105012 issued Dec. 17, 2014, pp. 1-6.

Taiwan Intellectual Property Office, Taiwan Search Report and English Translation regarding corresponding Taiwan Application No. TW103105012 issued Dec. 17, 2014, pp. 1-2.

* cited by examiner

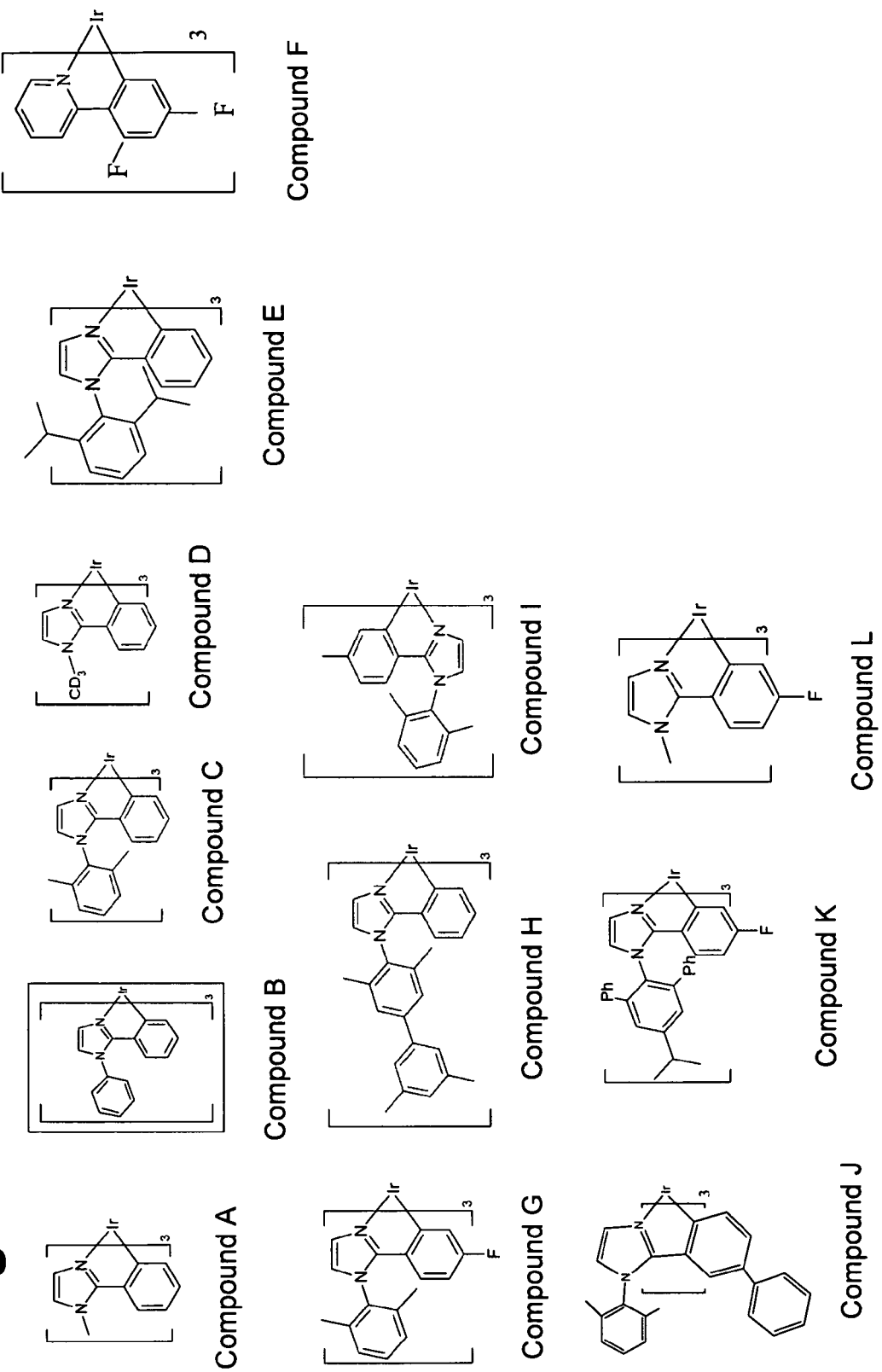

Figure 4    Devices (4" tool)

A. CuPc(100)/NPD(300)/CBP:cmpd A(6%,300)/BAlq₂(400)
B. CuPc(100)/NPD(300)/CBP:cmpd A(6%,300)/HPT(100)/BAlq₂(300)
C. CuPc(100)/NPD(300)/CBP:cmpd B(6%,300)/BAlq₂(400)
D. CuPc(100)/NPD(300)/CBP:cmpd B(6%,300)/HPT(100)/BAlq₂(300)
E. CuPc(100)/NPD(300)/CBP:cmpd C(6%,300)/BAlq₂(400)
F. CuPc(100)/NPD(300)/CBP:cmpd C(6%,300)/HPT(100)/BAlq₂(300)
G. CuPc(100)/NPD(300)/CBP:cmpd D(6%,300)/BAlq₂(400)
H. CuPc(100)/NPD(300)/CBP:cmpd D(6%,300)/HPT(100)/BAlq₂(300)
I. CuPc(100)/NPD(300)/CBP:cmpd D(4.5%,300)/BAlq₂(400)
J. CuPc(100)/NPD(300)/CBP:cmpd D(4.5%,300)/BAlq₂(400)
K. CuPc(100)/NPD(300)/mCBP:cmpd C(6%,300)/HPT(100)/BAlq₂(300)
L. CuPc(100)/NPD(300)/mCBP:cmpd C(6%,300)/BAlq₂(400)
M. CuPc(100)/NPD(300)/mCBP:cmpd C(9%,300)/BAlq₂(400)
N. CuPc(100)/NPD(300)/mCBP:cmpd E(6%,300)/HPT(100)/BAlq₂(300)
O. CuPc(100)/NPD(300)/mCBP:cmpd E(9%,300)/HPT(100)/BAlq₂(300)
P. CuPc(100)/NPD(300)/mCBP:cmpd E(6%,300)/BAlq₂(400)
Q. CuPc(100)/NPD(300)/mCBP:cmpd E(9%,300)/BAlq₂(400)
R. CuPc(100)/NPD(300)/mCBP:cmpd A(6%,300)/HPT(100)/BAlq₂(300)
S. CuPc(100)/NPD(300)/mCBP:cmpd A(6%,300)/BAlq₂(400)
T. CuPc(100)/NPD(300)/mCP:cmpd A(6%,300)/BAlq₂(400)
U. CuPc(100)/NPD(300)/mCP:cmpd A(6%,300)/HPT(100)/BAlq₂(300)
V. CuPc(100)/NPD(300)/mCP:cmpd C(6%,300)/BAlq₂(400)
W. CuPc(100)/NPD(300)/mCP:cmpd C(6%,300)/HPT(100)/BAlq₂(300)
X. CuPc(100)/NPD(300)/mCP:cmpd F(6%,300)/HPT(100)/BAlq₂(300)

Figure 5

Devices (4" tool)

XI. CuPc(100)/NPD(300)/mCP:cmpd E (9%, 300)/BAlq$_2$(400)
XII. CuPc(100)/NPD(300)/mCP:cmpd G (6%, 300)/BAlq$_2$(400)

Lifetime Devices V and XI

Figure 9 Lifetime Devices LLL and XII

Figure 10 Devices A and B
IV, QE vs. J and spectral data

Figure 11 Devices C and D
IV, QE vs. J and spectral data

Figure 12  Devices E and F
IV, QE vs. J and spectral data

Figure 13  Devices G, H, I and J
IV, QE vs. J and spectral data

Devices K, L, M, N, O, P and Q
IV, QE vs. J and spectral data

Devices R and S
IV, QE vs. J and spectral data

Devices T and U
IV, QE vs. J and spectral data

Devices V and W
IV, QE vs. J and spectral data

Devices X
IV, QE vs. J and spectral data

Lifetime (1 of 5)

Lifetime (2 of 5)

Lifetime (3 of 5)

Lifetime (4 of 5)

Lifetime (5 of 5)

Figure 24 Devices

4" tool

Z. CuPc(100)/NPD(300)/mCBP:cmpd C(9%,300)/BAlq₂(400)
BB. CuPc(100)/NPD(300)/mCP:cmpd C(9%,300)/BAlq₂(400)
EE. CuPc(100)/NPD(300)/mCBP:cmpd C(18%,300)/BAlq₂(400)

6" tool

FF. CuPc(100)/NPD(300)/mCBP:cmpd G(9%,300)/HPT(100)/Alq₃(400)
GG. CuPc(100)/NPD(300)/mCBP:cmpd G(9%,300)/BAlq₂(100)/Alq₃(400)
HH. CuPc(100)/NPD(300)/mCBP:cmpd G(12%,300)/HPT(100)/Alq₃(400)
II. CuPc(100)/NPD(300)/mCBP:cmpd G(12%,300)/BAlq₂(100)/Alq₃(400)
JJ. CuPc(100)/NPD(300)/mCP:cmpd G(9%,300)/HPT(100)/Alq₃(400)
KK. CuPc(100)/NPD(300)/mCP:cmpd G(9%,300)/BAlq₂(100)/Alq₃(400)

Devices Z, BB, EE
IV, QE vs. J and spectral data

Lifetime (Device BB)

Lifetime (Device EE)

Lifetime (Device Z)

Devices FF to II
IV, QE vs. J and spectral data

Lifetime (Devices FF and GG)

Lifetime (Devices HH, II)

Devices JJ and KK
IV, QE vs. J and spectral data

Figure 33  Devices (4" tool)

MM. CuPc(100)/NPD(300)/mCP:cmpd H(6%,300)/HPT(100)/BAlq$_2$(300)
NN. CuPc(100)/NPD(300)/mCBP:cmpd H(6%,300)/HPT(100)/BAlq$_2$(300)
OO. CuPc(100)/NPD(300)/mCBP:cmpd H(6%,300)/BAlq$_2$(400)
PP. CuPc(100)/NPD(300)/mCP:cmpd H(6%,300)/BAlq$_2$(400)
QQ. CuPc(100)/NPD(300)/mCBP:cmpd H(9%,300)/HPT(100)/BAlq$_2$(300)
RR. CuPc(100)/NPD(300)/mCP:cmpd H(9%,300)/BAlq$_2$(400)

UU. CuPc(100)/NPD(300)/mCBP:cmpd I(6%,300)/HPT(100)/BAlq$_2$(300)
VV. CuPc(100)/NPD(300)/mCBP:cmpd I(6%,300)/BAlq$_2$(400)
WW. CuPc(100)/NPD(300)/mCBP:cmpd I(9%,300)/BAlq$_2$(400)
XX. CuPc(100)/NPD(300)/mCBP:cmpd I(12%,300)/BAlq$_2$(400)
YY. CuPc(100)/NPD(300)/mCP:cmpd I(6%,300)/HPT(100)/BAlq$_2$(300)
ZZ. CuPc(100)/NPD(300)/mCP:cmpd I(9%,300)/BAlq$_2$(400)
AAA. CuPc(100)/NPD(300)/mCP:cmpd I(6%,300)/BAlq$_2$(400)
BBB. CuPc(100)/NPD(300)/mCP:cmpd I(12%,300)/BAlq$_2$(400)

CCC. CuPc(100)/NPD(300)/mCBP:cmpd J(6%,300)/HPT(100)/BAlq$_2$(300)
DDD. CuPc(100)/NPD(300)/mCBP:cmpd J(6%,300)/BAlq$_2$(400)
EEE. CuPc(100)/NPD(300)/mCBP:cmpd J(9%,300)/BAlq$_2$(400)
FFF. CuPc(100)/NPD(300)/mCBP:cmpd J(3%,300)/BAlq$_2$(400)
GGG. CuPc(100)/NPD(300)/CBP:cmpd J(9%,300)/BAlq$_2$(400)
HHH. CuPc(100)/NPD(300)/CBP:cmpd J(9%,300)/BAlq$_2$(100)/Alq$_3$(400)

Devices MM to RR
IV, QE vs. J and spectral data

Devices UU to XX
IV, QE vs. J and spectral data

Lifetime (Devices MM to PP)

Lifetime (Devices UU, VV, WW)

Figure 38
Devices YY to BBB
IV, QE vs. J and spectral data
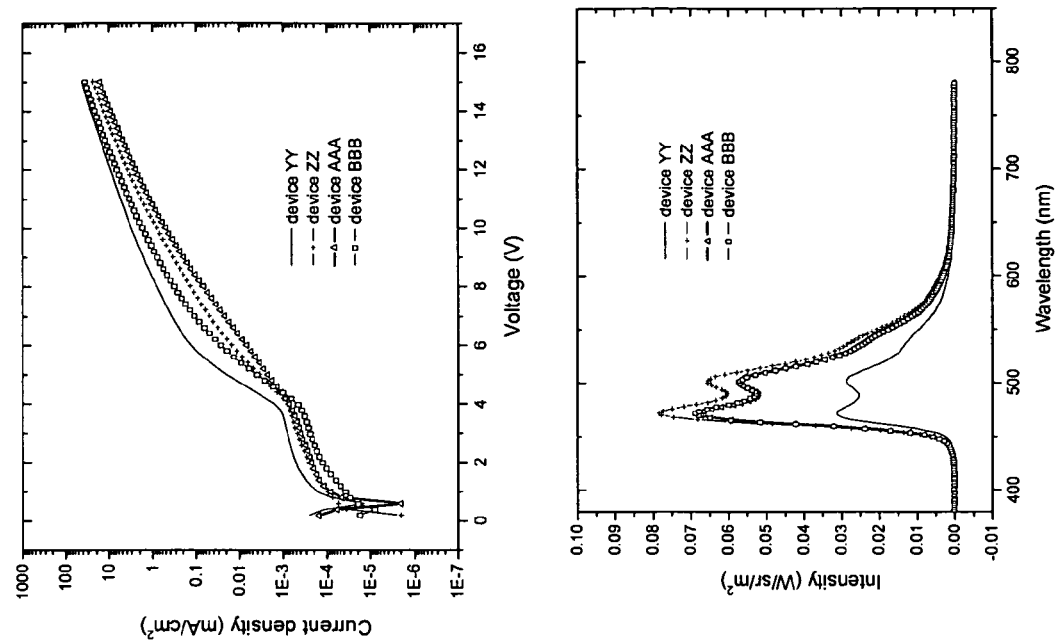
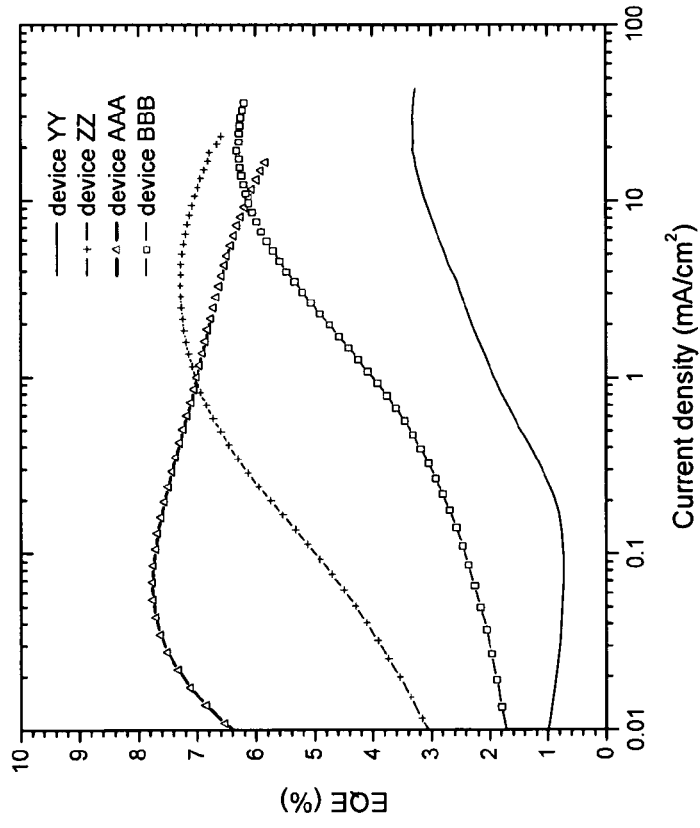

Lifetime (Devices YY to AAA)

Devices CCC to HHH
IV, QE vs. J and spectral data

Lifetime (Devices EEE, GGG, HHH)

Lifetime (Devices EEE, CCC, FFF)

Figure 43   Devices

III. CuPc(100)/NPD(300)/mCP:cmpd K(6%,300)/BAlq$_2$(400)
JJJ. CuPc(100)/NPD(300)/mCP:cmpd K(6%,300)/BAlq$_2$(400)
KKK. CuPc(100)/NPD(300)/mCBP:cmpd K(6%,300)/BAlq$_2$(400)

Devices III, JJJ, and KKK
IV, QE vs. J and spectral data

Figure 45  Devices

LLL. CuPc(100)/NPD(300)/mCP:cmpd L(6%,300)/BAlq$_2$(400)
MMM. CuPc(100)/NPD(300)/mCP:cmpd L(9%,300)/BAlq$_2$(400)
NNN. CuPc(100)/NPD(300)/mCP:cmpd K(9%,300)/BAlq$_2$(400)

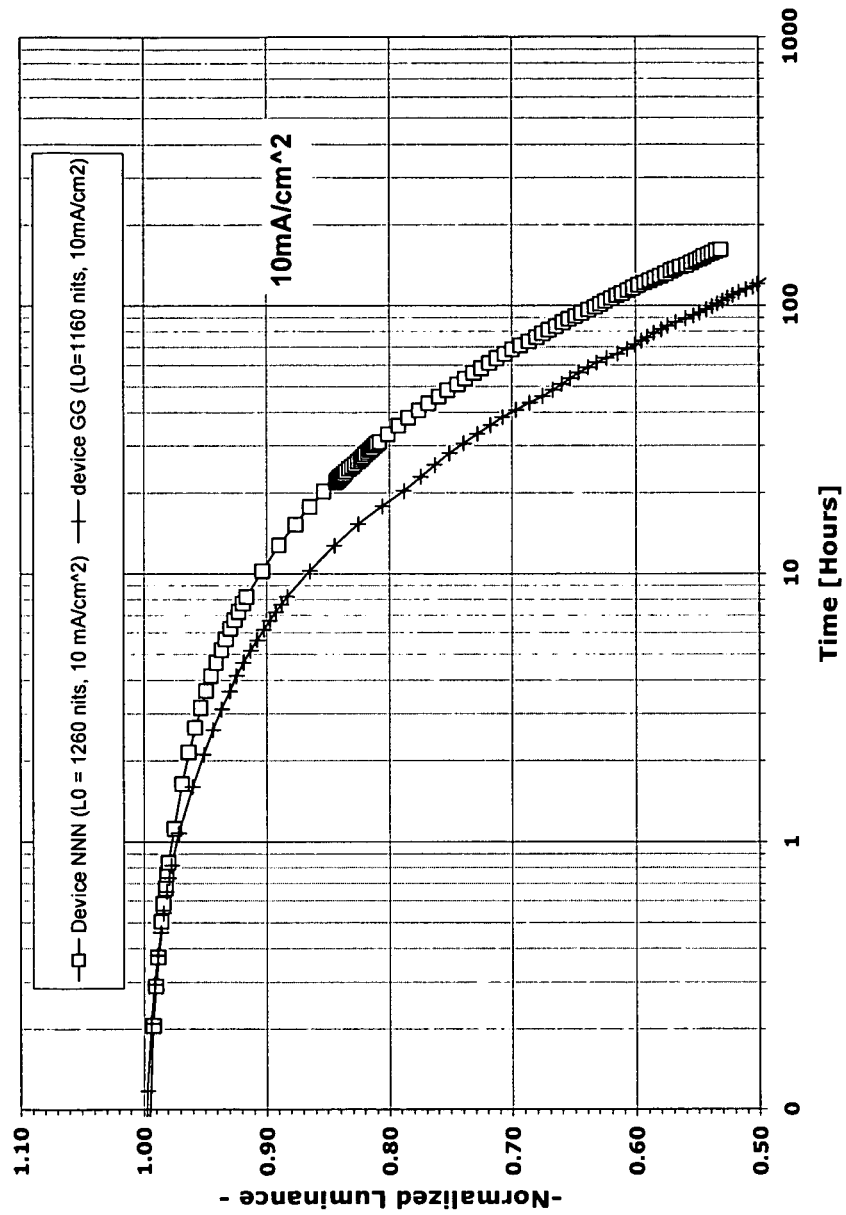
Figure 46  Lifetime – Devices GG and NNN

Devices LLL and MMM
IV, QE vs. J and spectral data

Lifetime – devices MMM and NNN

Device XII
IV, QE vs. J and spectral data

Device NNN
IV, QE vs. J and spectral data

Compound 4 devices (EQE)
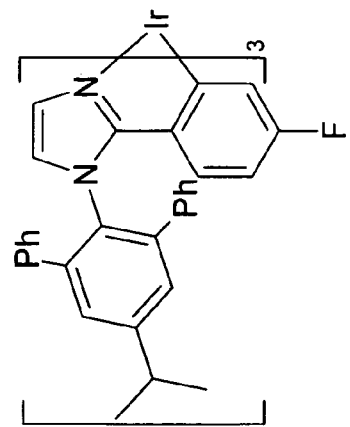
Compound 4
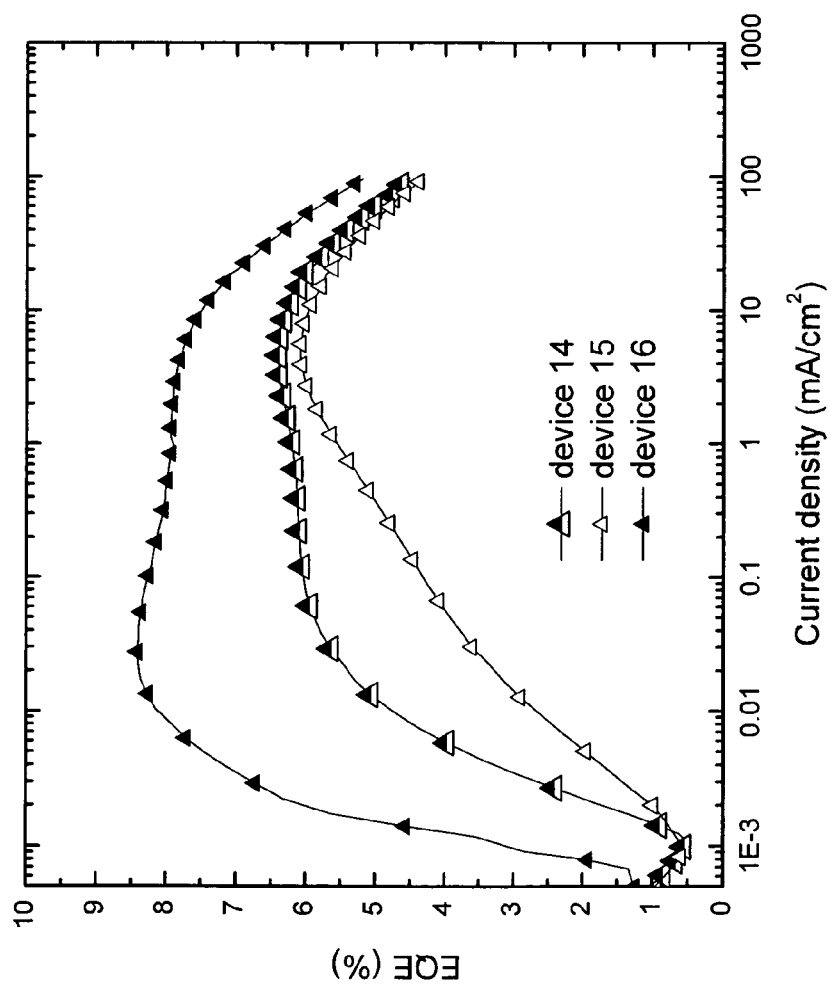
Figure 57

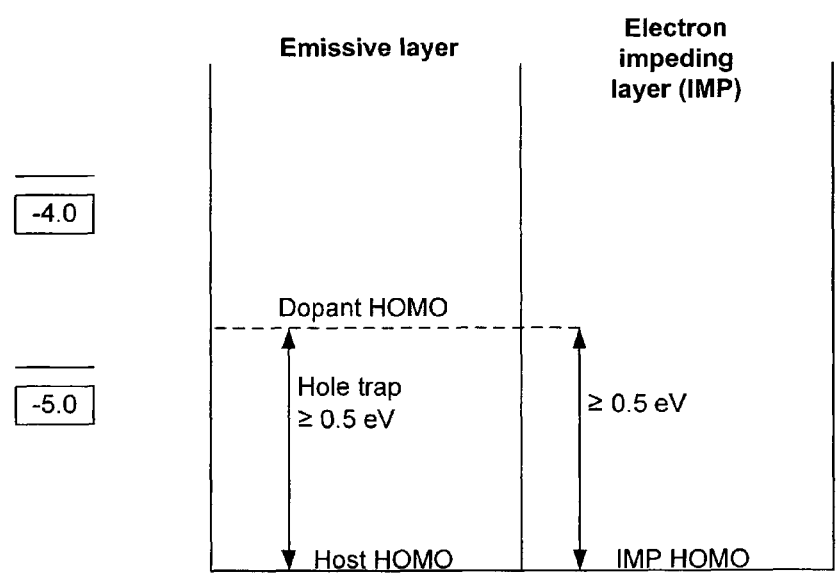
Figure 62: Exemplary HOMO Energy Levels for a Device Having an Electron Impeding Layer

Figure 63a: Device Having an Electron Impeding Layer
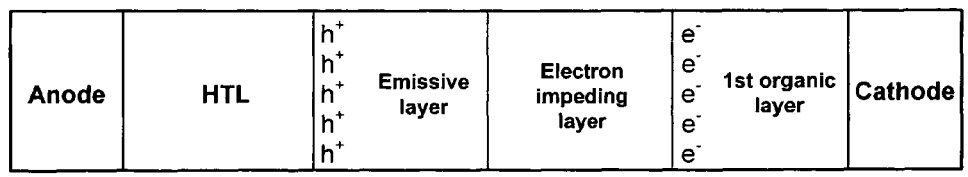
Figure 63b: Energy Level Diagram for a Device Having an Electron Impeding Layer
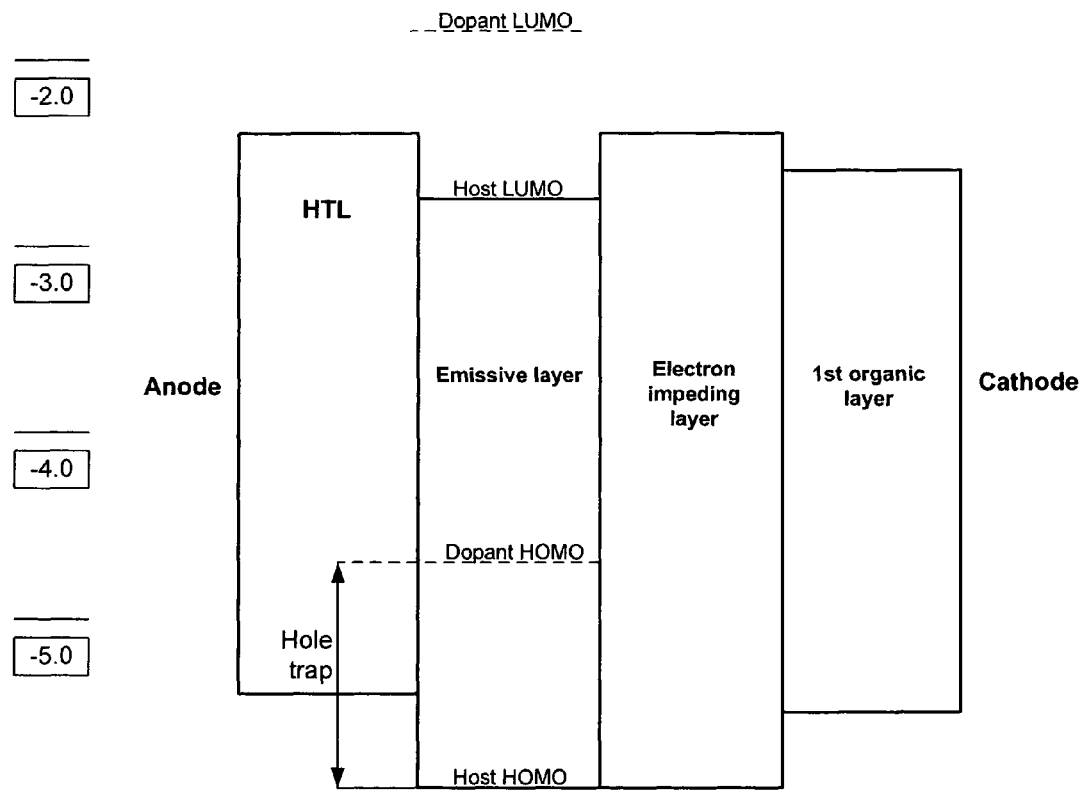

STABILITY OLED MATERIALS AND DEVICES

CROSS-REFERENCE TO RELATED APPLICATIONS

This application claims the benefit of priority of Provisional Application No. 60/678,170, filed May 6, 2005; Provisional Application No. 60/701,929, filed Jul. 25, 2005; and Provisional Application No. 60/718,336, filed Sep. 20, 2005. The contents of Provisional Application No. 60/678,170 and Provisional Application No. 60/701,929 are herein incorporated by reference in their entirety.

RESEARCH AGREEMENTS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention generally relates to organic light emitting devices (OLEDs), and organic compounds used in these devices, as well as phoshorescent OLEDs having an electron impeding layer.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

The development of long-lived blue emissive phosphorescent dopants is recognized as a key unfulfilled objective of current OLED research and development. While phosphorescent OLED devices with emission peaks in the deep blue or near-UV have been demonstrated, the lifetimes of blue-emissive devices exhibiting 100 nits initial luminance have been on the order of several hundred hours (where "lifetime" refers to the time for the luminance to decline to 50% of the initial level, at constant current). For example, iridium(III) complexes of bidentate ligands derived from N-methyl-2-phenylimidazoles can be used to prepare blue OLED devices, but very short lifetimes are observed with these dopants (about 250 hours at 100 nits initial luminescence).

Since most commercial applications are expected to require lifetimes in excess of 10,000 hours at 200 nits initial luminescence, major improvements in blue phosphorescent OLED device lifetimes are sought.

SUMMARY OF THE INVENTION

We have discovered that OLED devices that incorporate N-(2,6-disubstituted phenyl)-2-phenyl imidazole derived metal complexes can have lifetimes upwards of 5 times longer than devices incorporating the corresponding N-methyl imidazole complexes with the same $R^2$ substituents.

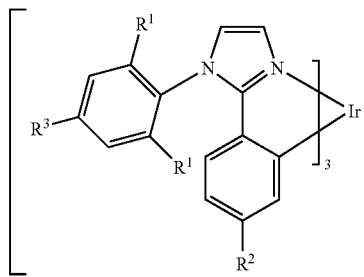

Compound C : $R^1$ = Me; $R^2$ = H; $R^3$ = H
Compound E: $R^1$ = $^i$Pr; $R^2$ = H; $R^3$ = H
Compound H: $R^1$ = Me; $R^2$ = H; $R^3$ = 3,5-Me$_2$C$_6$H$_3$
Compound G: $R^1$ = Me; $R^2$ = F; $R^3$ = H
Compound K: $R^1$ = Ph; $R^2$ = F; $R^3$ = $^i$Pr
Compound B: $R^1$ = H; $R^2$ = H; $R^3$ = H

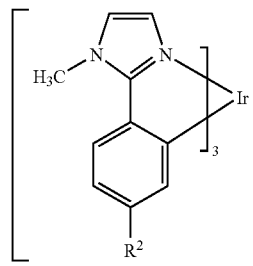

Compound A : $R^2$ = H
Compound L: $R^2$ = F

For example, as shown in FIG. 6, the lifetime of the Device V, which incorporated compound C and exhibited an initial luminescence of 830 nits, was about 270 h, while the lifetime of Device T, which incorporated compound A and exhibited an initial luminescence of 810 nits, was only about 44 hours. Even longer lifetimes were observed when the 4-position of 2,6-disubstituted N-phenyl ring was substituted by a 3,5-dimethylphenyl ring, as in compound H (Device PP, FIG. 8). In a similar vein, Device XII, which incorporated the deeper blue compound G, was longer lived than Device LLL, which incorporated compound L (FIG. 9); Device NNN, which incorporated compound K, was even longer-lived (FIGS. 46, 48). Since the emission maxima of the 2,6-di-substituted phenyl derivatives were in all cases comparable to those of the corresponding N-methyl derivatives, it was a surprising and unexpected discovery that changing a peripheral group would have such a large impact on device lifetime.

It is expected that the compounds described herein will be broadly applicable to phosphorescent OLED devices, including those based on small molecule metal complexes, including but not limited to dendridic metal complexes, and polymer-attached or polymer-blended metal complexes, processed by any of a variety of methods, including vapor phase deposition and solution processing methods, wherein the metal complexes in all of these devices may be homoleptic or heteroleptic complexes, wherein the donor atoms may comprise combinations of atoms selected from the group consisting of nitrogen, carbon, oxygen, sulfur, phosphorous, arsenic, silicon, selenium, or another metal.

In a first aspect, the invention provides a phosphorescent compound. The phosphorescent compound is a neutral metal complex of a monodentate, bidentate, tridentate, tetradentate, pentadentate, or hexadentate ligand. The ligand comprises at least one first aryl or heteroaryl ring directly bonded to the metal. The first ring is substituted by a second aryl or heteroaryl ring which is not directly bonded to the metal and which is independently substituted at both ortho positions by a substituent selected from the group consisting of aryl and heteroaryl groups. The second ring may be further substituted, and each of the substituents may independently be substituted or unsubstituted. The metal is selected from the group consisting of the non-radioactive metals with atomic numbers greater than 40.

In a second aspect, the invention provides a phosphorescent compound. The phosphorescent compound is a neutral metal complex of a monodentate, bidentate, tridentate, tetradentate, pentadentate, or hexadentate ligand. The ligand comprises at least one first aryl or heteroaryl ring directly bonded to the metal. The first ring is substituted by a second aryl or heteroaryl ring which is not directly bonded to the metal and which is substituted at both ortho positions by groups other than H or halide. The first ring is an imidazole, benzene, naphthalene, quinoline, isoquinoline, pyridine, pyrimidine, pyridazine, pyrrole, oxazole, thiazole, oxadiazole, thiadiazole, furan, or thiophene ring. The metal is selected from the group consisting of the non-radioactive metals with atomic numbers greater than 40.

In a third aspect, the invention provides a phosphorescent compound. The phosphorescent compound is a neutral metal complex of a monodentate, bidentate, tridentate, tetradentate, pentadentate, or hexadentate ligand. The ligand comprises at least one first aryl or heteroaryl ring directly bonded to the metal. This first ring is an imidazole, coordinated via a first nitrogen atom to the metal. The first ring is substituted by a second aryl or heteroaryl ring which is not directly bonded to the metal and which is substituted at both ortho positions by groups other than H or halide. The metal is selected from the group consisting of the non-radioactive metals with atomic numbers greater than 40.

Devices incorporating the phosphorescent organometallic compounds are also provided.

This application is also related to U.S. Utility application Ser. No. 11/242,025 entitled "Electron Impeding Layer for High Efficiency Phosphorescent OLEDs," being filed on Oct.

4, 2005. The contents of these applications is herein incorporated by reference in their entirety. In one embodiment, the present invention provides an organic light emitting device, comprising: an anode; a hole transport layer; an organic emissive layer comprising an emissive layer host and an emissive dopant; an electron impeding layer; an electron transport layer; and a cathode disposed, in that order, over a substrate.

Preferably, the HOMO of the emissive layer host is at least about 0.5 eV lower, more preferably about 0.5 eV to about 0.8 eV lower, than the HOMO of the emissive dopant. Preferably, the electron impeding layer consists essentially of a hole transporting material or an ambipolar material such as mCBP.

Preferably, the device emits blue light. In a specific preferred embodiment, the emissive dopant is compound 1.

In another embodiment, the present invention provides an OLED comprising an anode; a cathode; an organic emissive layer disposed between the anode and the cathode, the organic emissive layer comprising an emissive layer host and an emissive dopant, wherein the HOMO of the emissive layer host is at least about 0.5 eV lower, preferably about 0.5 eV to about 0.8 eV lower, than the HOMO of the emissive dopant; a first organic layer disposed between the organic emissive layer and the cathode; a second organic layer disposed between, and in direct contact with, the organic emissive layer and the first organic layer; wherein the second organic layer consists essentially of a hole transporting material or an ambipolar material.

In another embodiment, the present invention provides an OLED comprising an anode; a cathode; an organic emissive layer disposed between the anode and the cathode, the organic emissive layer comprising an emissive layer host and an emissive dopant, wherein the HOMO of the emissive layer host is at least about 0.5 eV lower, preferably about 0.5 eV to about 0.8 eV lower, than the HOMO of the emissive dopant; a first organic layer disposed between the organic emissive layer and the cathode; a second organic layer disposed between, and in direct contact with, the organic emissive layer and the first organic layer; wherein the second organic layer has a relative electron mobility not more than 0.001 of the electron mobility of Bphen. Preferably, the second organic layer consists essentially of a material, such that when said material is used in a similar device wherein the first organic layer is $Alq_3$, increasing the thickness of the second organic layer will cause emission from the first organic layer.

In another embodiment, the present invention provides an OLED comprising an anode; a cathode; an organic emissive layer disposed between the anode and the cathode, the organic emissive layer comprising an emissive layer host and an emissive dopant, wherein the HOMO of the emissive layer host is at least about 0.5 eV lower, preferably about 0.5 eV to about 0.8 eV lower, than the HOMO of the emissive dopant; and a means for accumulating electrons between the cathode and the emissive layer.

BRIEF DESCRIPTION OF THE DRAWINGS

FIG. 3 shows the materials definitions used in subsequent figures.

FIG. 4 shows the devices prepared.

FIG. 5 shows the devices prepared.

FIG. 24 shows the devices prepared.

FIG. 33 shows the devices prepared.

FIG. 38 shows IV, quantum efficiency (QE) vs current (J) and spectral data for devices YY, ZZ, AAA and BBB.

FIG. 43 shows the devices prepared.

FIG. 45 shows the devices prepared.

FIG. 46 shows the normalized luminescence as a function of time at 10 mA/cm² current density for devices GG and NNN.

FIG. 57 shows the external quantum efficiency versus current density for compound 4 devices.

FIG. 62 shows exemplary HOMO energy levels for a device having an electron impeding layer.

FIG. 63a and FIG. 63b show a device having an electron impeding layer and an energy level diagram for the device.

DETAILED DESCRIPTION

Figure 1:
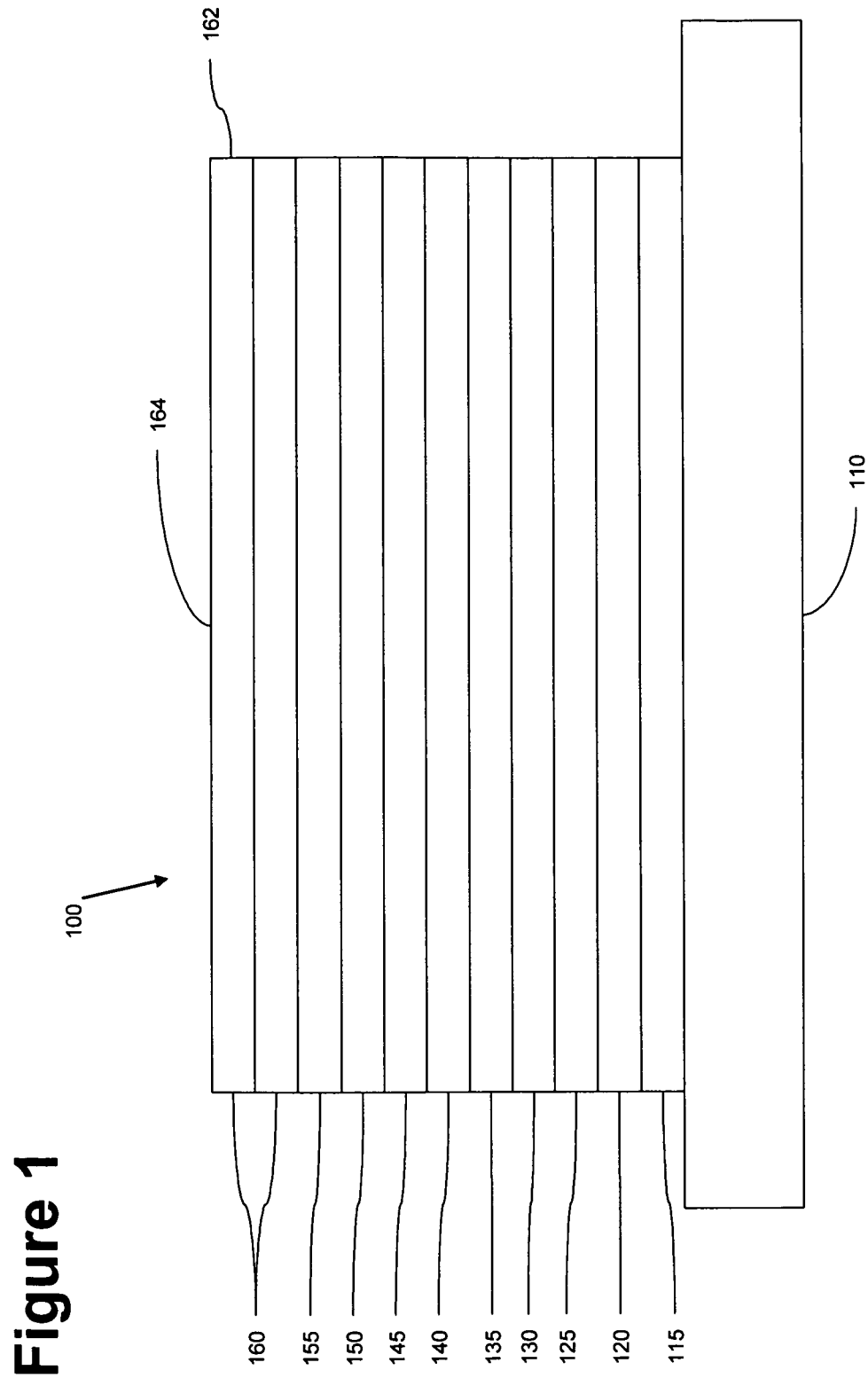
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238; 6,310,360; 6,830,828; and 6,835,469; U.S. Patent Application Publication No. 2002-0182441; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III). While not wishing to be bound by theory, it is believed that the organic metal to carbon bond in an organometallic complex is an especially preferred method of achieving the desired proximity of the organic molecule to an atom of high atomic number. Specifically, in the context of this application, the presence of the organic carbon-metal bond in the organometallic complex may promote greater MLCT character, which can be useful for the production of highly efficient devices.

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice organometallic compounds may comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(Ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., now U.S. Pat. No. 7,071,615, which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., now U.S. Pat. No. 7,071,615, which is incorporated by reference in its entirety.

Figure 2:
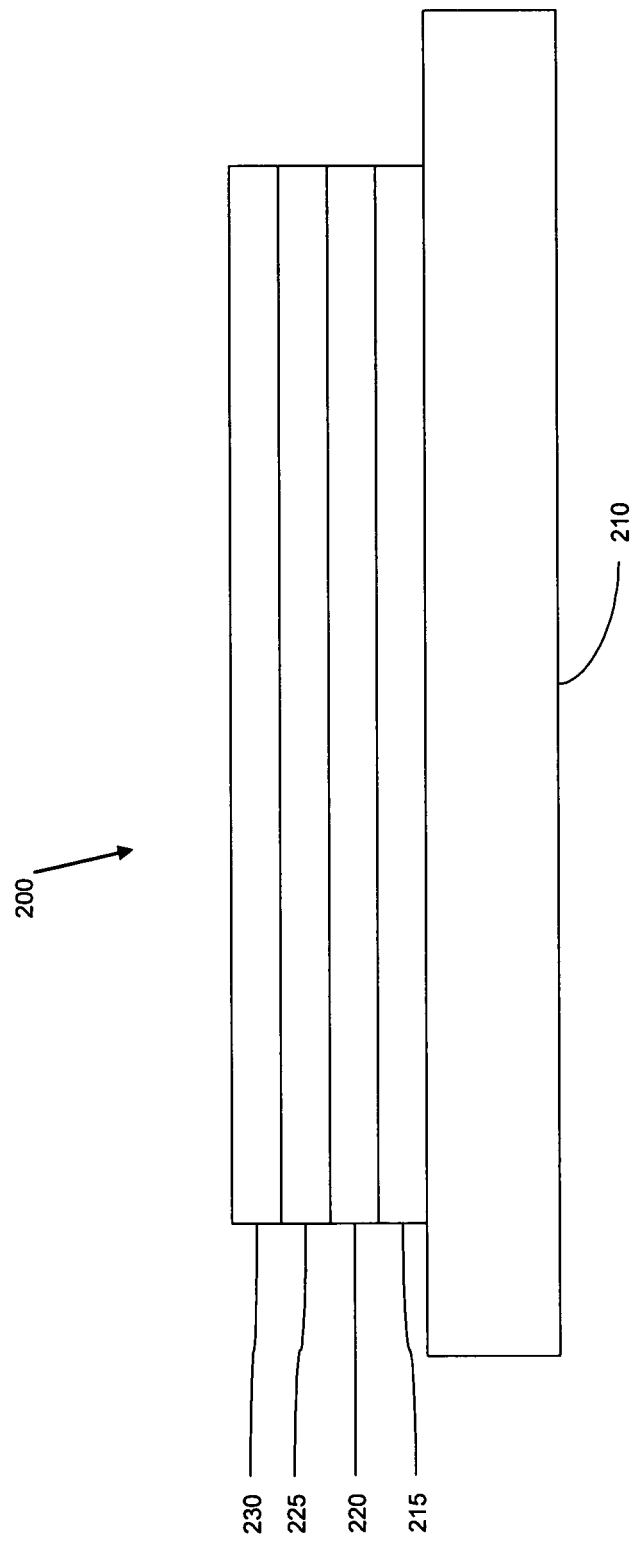
FIG. 2 shows an inverted organic light emitting device that does not have a separate electron transport layer.
Figure 6:
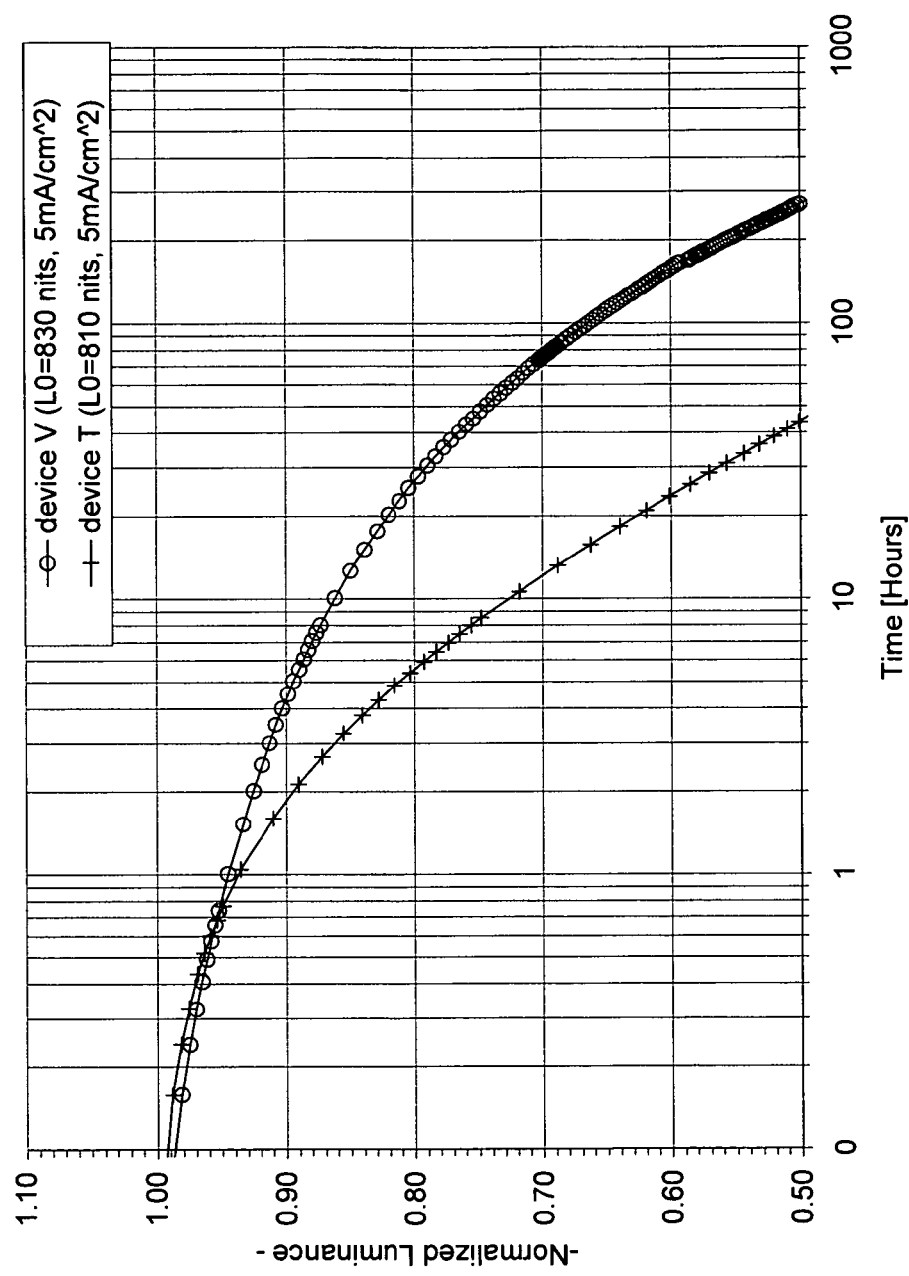
FIG. 6 shows the normalized luminescence as a function of time at 5 mA/cm$^2$ current density for devices V and T.
Figure 7:
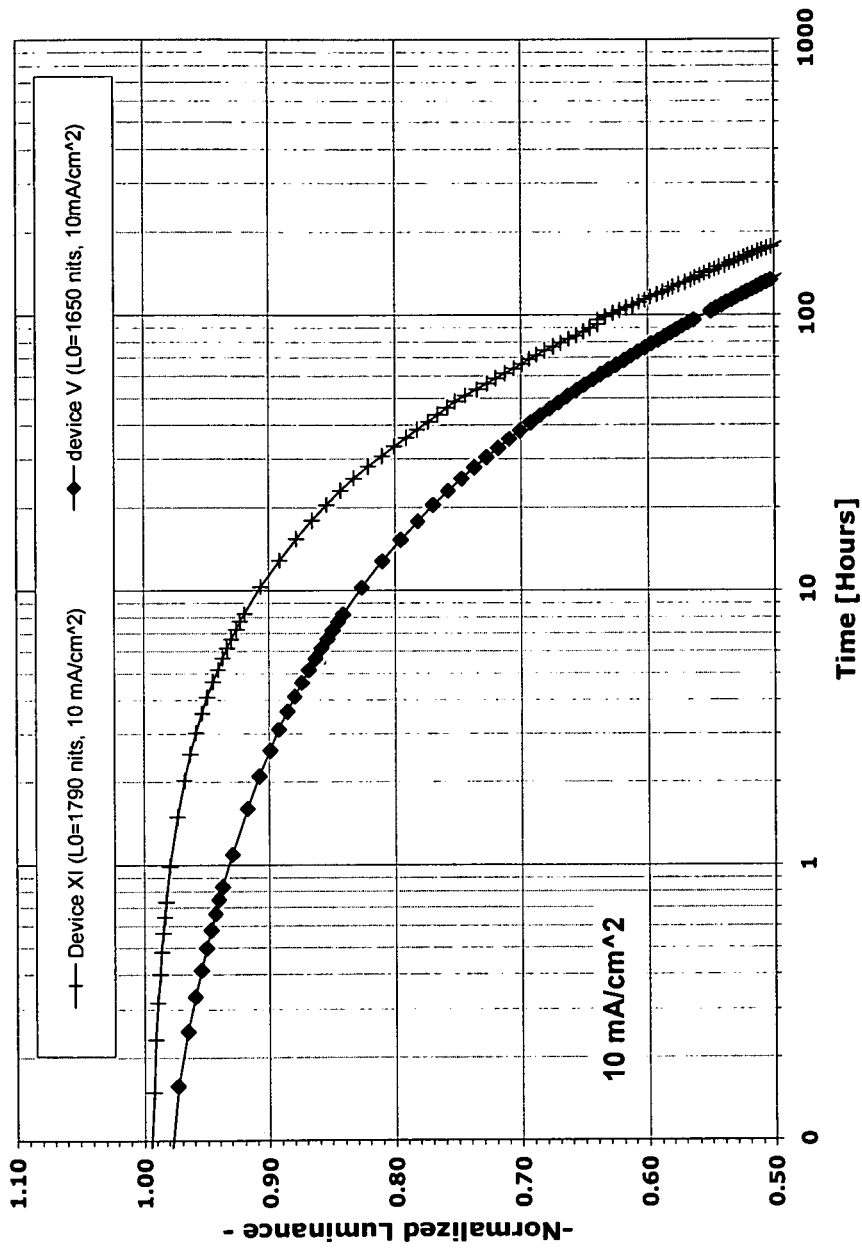
FIG. 7 shows the normalized luminescence as a function of time at 10 mA/cm$^2$ current density for devices V and XI.
Figure 8:
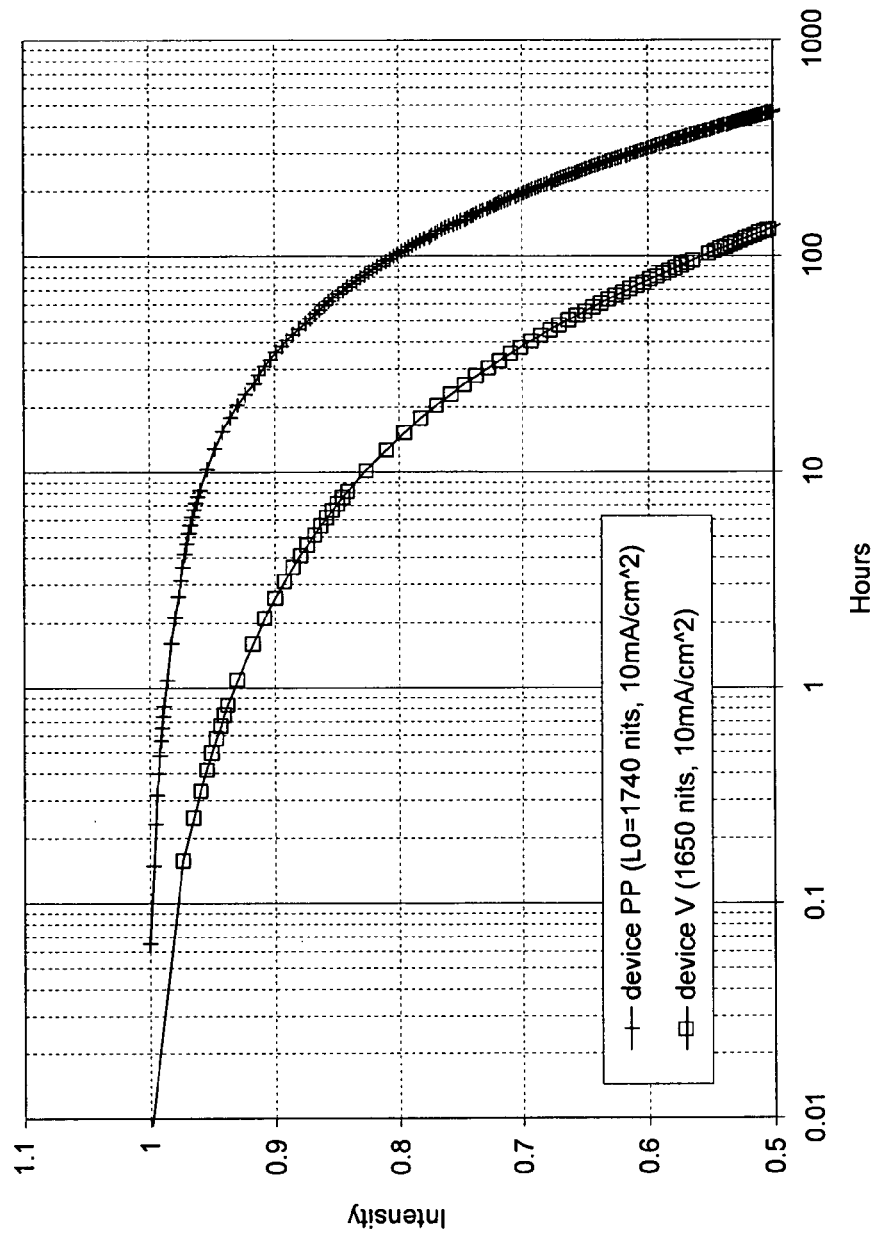
FIG. 8 shows the normalized luminescence as a function of time at 10 mA/cm$^2$ current density for devices V and PP.
Figure 9:
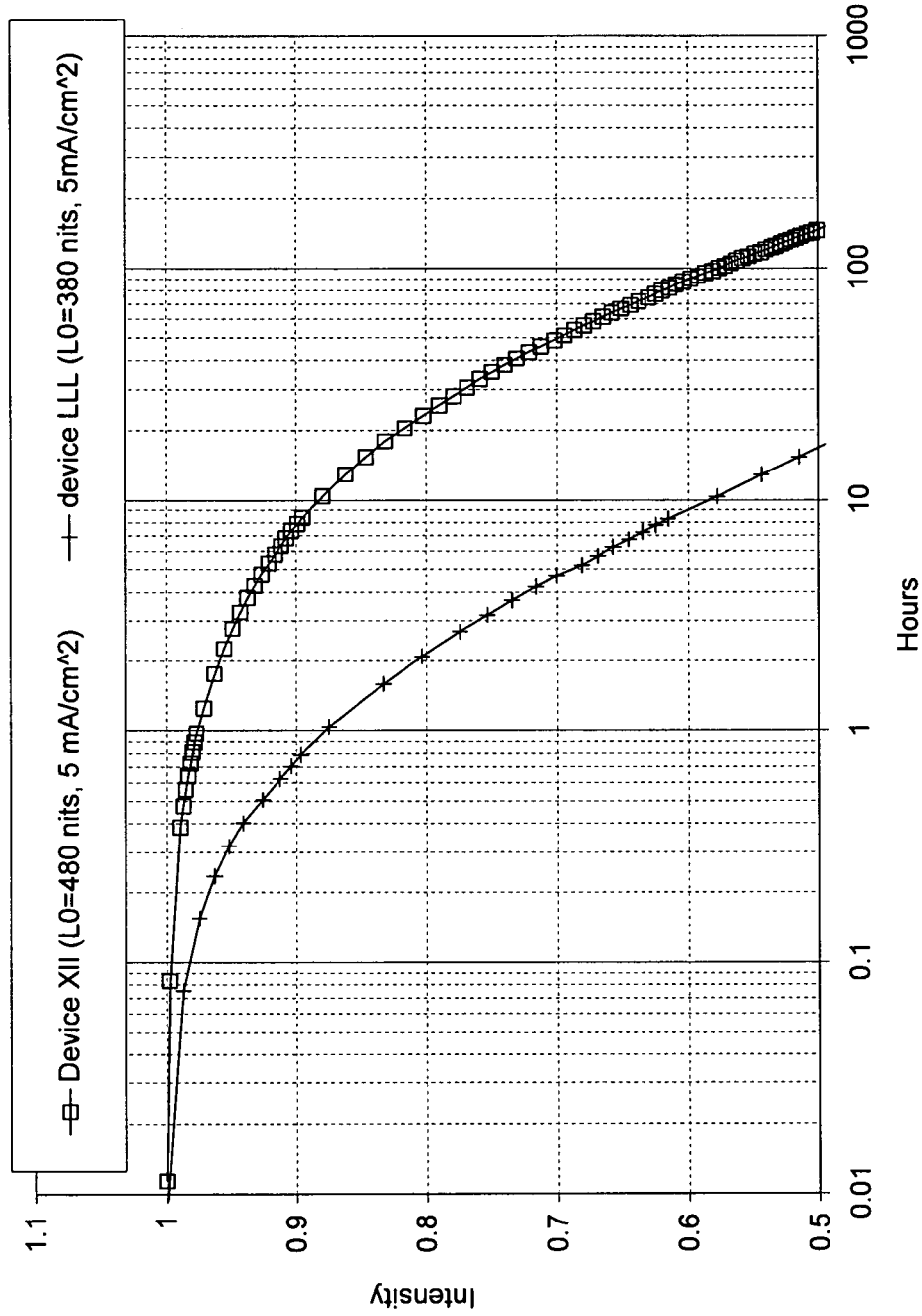
FIG. 9 shows the normalized luminescence as a function of time at 5 mA/cm$^2$ current density for devices LLL and XI.
Figure 10:
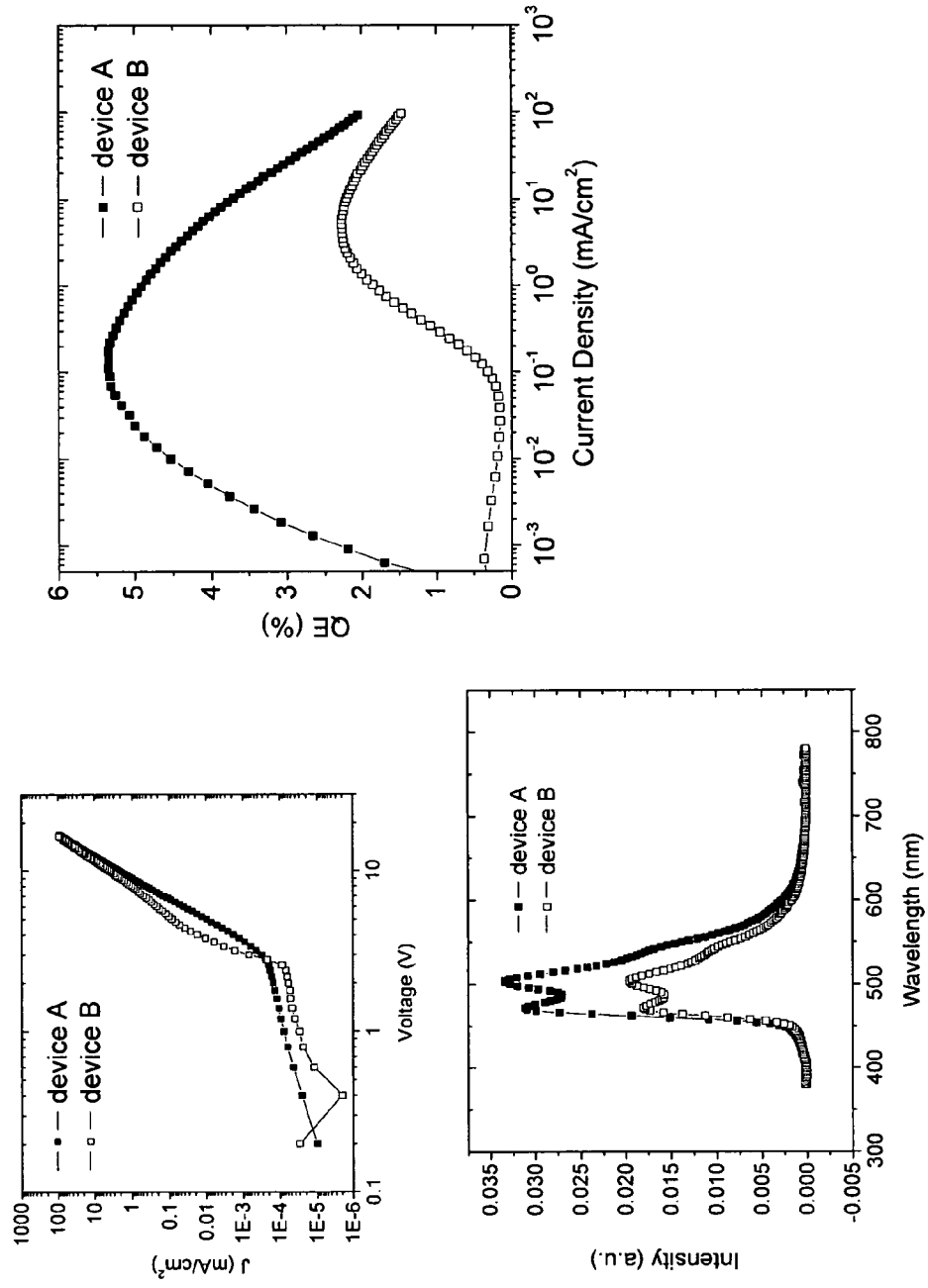
FIG. 10 shows IV, quantum efficiency (QE) vs current (J) and spectral data for devices A and B.
Figure 11:
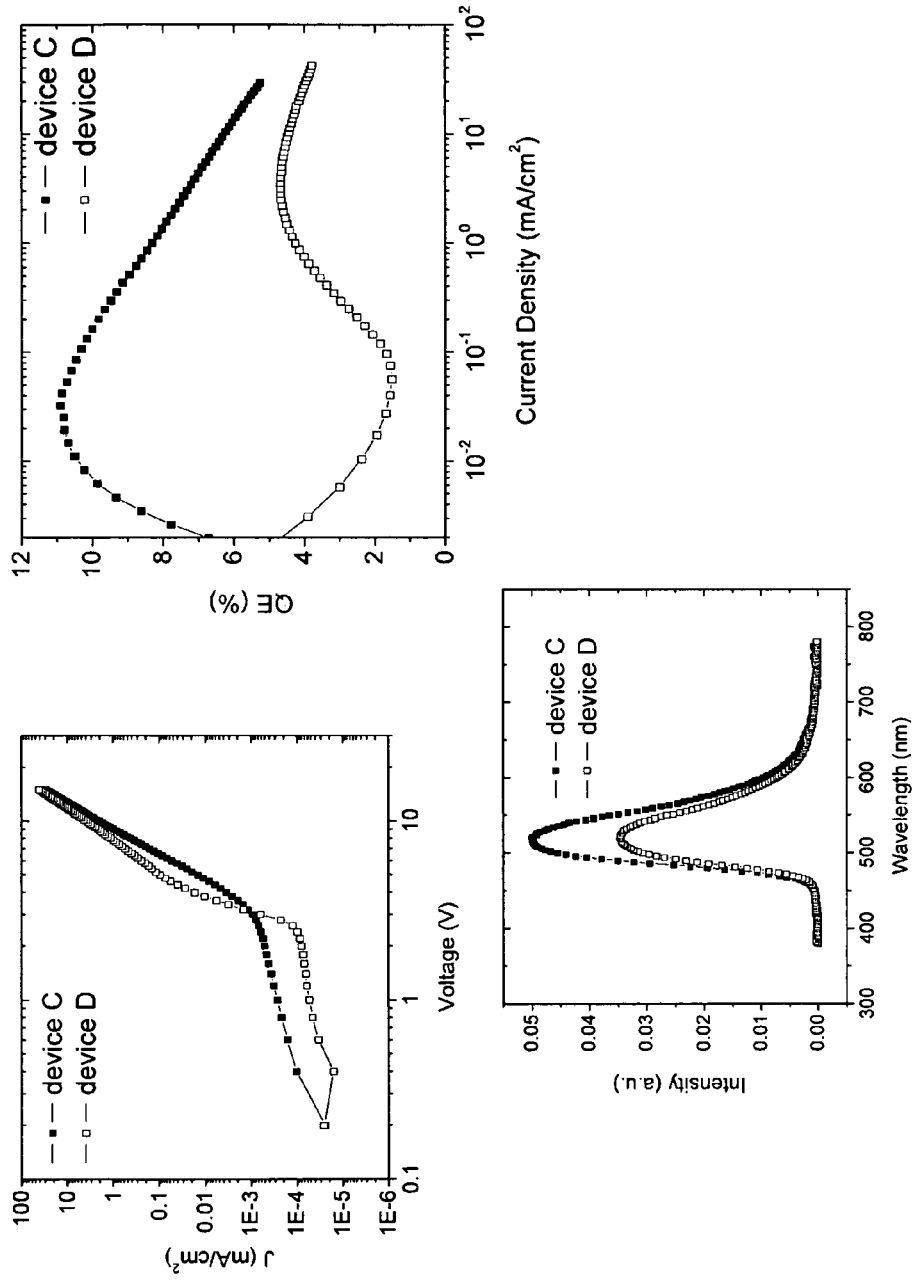
FIG. 11 shows IV, quantum efficiency (QE) vs current (J) and spectral data for devices C and D.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "aryl" refers to an aromatic carbocyclic monoradical. Unless otherwise specified, the aromatic carbocyclic monoradical may be substituted or unsubstituted. The substituents can be F, hydrocarbyl, heteroatom-substituted hydrocarbyl, cyano, and the like.

A "hydrocarbyl" group means a monovalent or divalent, linear, branched or cyclic group which contains only carbon and hydrogen atoms. Examples of monovalent hydrocarbyls include the following: $C_1$-$C_{20}$ alkyl; $C_1$-$C_{20}$ alkyl substituted with one or more groups selected from $C_1$-$C_{20}$ alkyl, $C_3$-$C_8$ cycloalkyl, and aryl; $C_3$-$C_8$ cycloalkyl; $C_3$-$C_8$ cycloalkyl substituted with one or more groups selected from $C_1$-$C_{20}$ alkyl, $C_3$-$C_8$ cycloalkyl, and aryl; $C_6$-$C_{18}$ aryl; and $C_6$-$C_{18}$ aryl substituted with one or more groups selected from $C_1$-$C_{20}$ alkyl, $C_3$-$C_8$ cycloalkyl, and aryl. Examples of divalent (bridging) hydrocarbyls include: —$CH_2$—; —$CH_2CH_2$—; —$CH_2CH_2CH_2$—; and 1,2-phenylene.

A "heteroatom" refers to an atom other than carbon or hydrogen. Examples of heteroatoms include oxygen, nitrogen, phosphorus, sulfur, selenium, arsenic, chlorine, bromine, silicon, and fluorine.

A "heteroaryl" refers to a heterocyclic monoradical that is aromatic. Unless otherwise specified, the aromatic heterocyclic monoradical may be substituted or unsubstituted. The substituents can be F, hydrocarbyl, heteroatom-substituted hydrocarbyl, cyano, and the like. Examples of heteroaryls include 1-pyrrolyl, 2-pyrrolyl, 3-pyrrolyl, furyl, thienyl, indenyl, imidazolyl, oxazolyl, isoxazolyl, carbazolyl, thiazolyl, pyrimidinyl, pyridyl, pyridazinyl, pyrazinyl, benzothienyl, and the like, and substituted derivatives thereof.

By "ortho positions," we mean the positions on the aryl or heteroaryl group which are adjacent to the point of attachment of the second ring to the first ring. In the case of a six-membered ring aryl group attached via the 1-position, such as 2,6-dimethylphenyl, the 2- and 6-positions are the ortho positions. In the case of a 5-membered ring heteroaryl group attached via the 1-position, such as 2,5-diphenylpyrrol-1-yl, the 2- and 5-positions are the ortho positions. In the context of this invention, ring fusion at a carbon adjacent to the point of attachment, as in 2,3,4,5,7,8,9,10-ocathydroanthracen-1-yl, is considered to be a type of ortho substitution.

Without wishing to be bound by theory, the inventors believe that dopant decomposition and excited state quenching are important factors in phosphorescent device failure, and that the enhanced stability of the devices of the current invention may be attributed to a combination of steric and electronics effects associated with the ortho-disubstituted aryl or heteroaryl group that comprises the second ring. It is believed that these factors may be of particular importance for blue emitting phosphorescent materials.

The inventors believe that dopants that are more difficult to rearrange may have longer lifetimes. In particular, the steric bulk associated with the ortho-disubstituted second ring is believed to rigidify the dopant, either through direct intramolecular interactions, or indirectly, by interactions with the surrounding solid state matrix, in such a way as to make it more difficult for the dopant to rearrange, and therefore more difficult for it to decompose. This is because some decomposition routes include as a step a rearrangement of the molecule, and making the rearrangement more difficult may potentially slow decomposition. Ways to make rearrangement more difficult include increasing the steric bulk specifically associated with large substituents on the second ring. It is believed that the presence of an aryl or heteroaryl group at the ortho positions of the second ring results in intramolecular interactions that rigidify the molecule relative to a molecule not having such ortho substitution, preventing certain types of molecular rearrangement, and thus preventing or making more difficult certain decomposition routes.

It is thought that any large substituent, regardless of position, may interact with the surrounding solid matrix making it more difficult for the molecule to rearrange. It is believed that this mechanism is different from rigidification because it relies on interaction with the host.

The inventors believe that restricting the approach of impurities to the metal center may also extend lifetime. This is because some decomposition may be caused by the chemical reaction of impurities with the metal center. The steric bulk associated with the ortho-disubstituted second ring will also restrict the close approach of reactive impurities to the metal center. Such reactive impurities include, for example, water or diffusible ions that would potentially react with the metal complex and alter the chemical structure of the metal complex. The substituents at the ortho positions of the second ring impede the approach of such impurities. Although any large group may work to impede the approach of impurities, certain positions on the ring may provide greater protection to the metal center. In this regard, the ortho positions may be especially effective in improving the lifetime of the metal center because these substituents are pointing inwards, creating a highly congested environment that impedes approach to the metal center.

In addition, the substituents at the ortho positions of the compounds according to the invention will also minimize quenching of the dopant excited state by impurities formed upon decomposition by increasing the dopant-to-quencher distance. Moreover, the use of metal complexes having ortho-disubstitution on the second ring will minimize dopant-to-dopant energy transfer by increasing the dopant-to-dopant distance, thereby minimizing exciton diffusion to decomposition-related quenching impurities.

It is also believed that the compounds having the ortho-disubstituted second ring will also increase the dihedral angle between the first and second rings, thereby substantially de-conjugating the second ring from the first ring. Electronic effects associated with such de-conjugation are believed to include: (i) a blue-shift of the phosphorescent emission, relative to an otherwise equivalent compound without ortho substitution, and (ii) a de-coupling of the singlet and triplet energies, such that it is possible to lower the energy of the singlet excited state and reduce the electrochemical gap of the dopant without red-shifting the phosphorescent emission. Lowering the singlet energy is expected to reduce the likelihood of singlet excited state decomposition, thereby resulting in improved device lifetimes. Reduction of the dopant electrochemical gap is expected to allow for the fabrication of lower operating voltage OLED devices. Density Functional Theory (DFT) calculations using Gaussian 98 with the G98/B31yp/cep-31 g basis set indicate that certain compounds of the current invention wherein the second ring is substituted with an aryl or heteroaryl ring or with an electron-withdrawing group are characterized by a LUMO which is substantially localized on the second ring and a HOMO which is substantially localized on the metal. These calculations further indicate that the lowest energy singlet transition has substantial metal-centered HOMO to second ring-centered LUMO character, while the lowest energy triplet transition is primarily from a metal-centered-HOMO to a higher-lying unoccupied orbital localized on the those rings directly bonded to the metal. As such, these calculations indicate that it is possible to reduce the LUMO energy of the dopant, and thence the both the singlet excited state energy and electrochemical gap, without reducing the triplet energy and redshifting the emission. It is a novel feature of this invention to provide a means of minimizing the energy of the singlet excited state of the dopant without reducing the triplet energy. Depending on the substitution pattern, it is expected to be possible to either localize the LUMO of the molecule on the second ring, or to localize the HOMO on the second ring, and in both cases associate the singlet transition with the second ring while localizing the triplet transition on the metal and those groups directly bonded to it. It is understood that whether the LUMO or HOMO is localized on the second ring will depend on the substitution pattern of the entire molecule. In general, however, substitution of the second ring with aryl, heteroaryl or electron-withdrawing groups will tend to lower the energies of the orbitals associated with the second ring and can be used to localize the LUMO on that ring, while substitution of the second ring with electron donating groups can be used to localize the HOMO on that ring.

In the context of this invention, by "Set 1", we mean structures d1-d19:

Set 1 d1
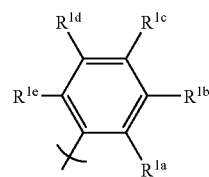

d2
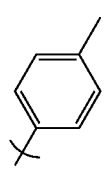

d3
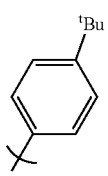

d4
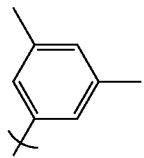

d5
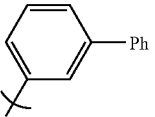

d6
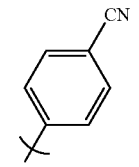

d7
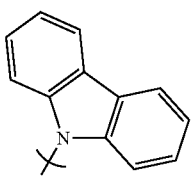

d8
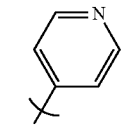

d9
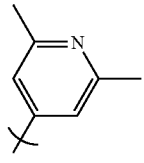

d10
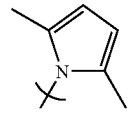

d11
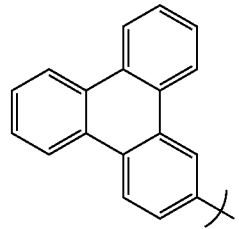

d12
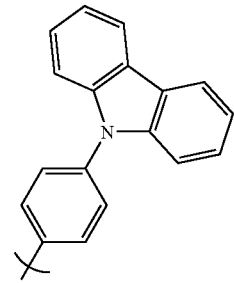

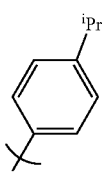 d13

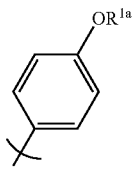 d14

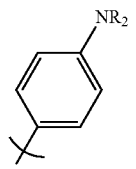 d15

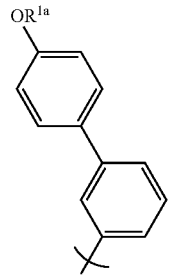 d16

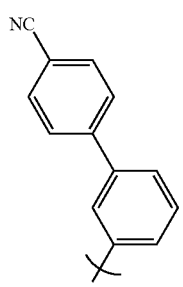 d17

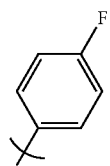 d18

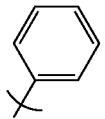 d19 wherein:

$R^{1a-e}$ are each independently selected from the group consisting of hydrogen, hydrocarbyl, heteroatom substituted hydrocarbyl, cyano, and F; in addition, any two of $R^{1a-e}$ may be linked to form a ring.

By "Set 2a" we mean the group consisting of 2,6-dimethylphenyl, 2,4,6-trimethylphenyl, 2,3,4,5,6-pentamethylphenyl, 2,6-dimethyl-4-phenylphenyl, 2,6-dimethyl-4-(3,5-dimethylphenyl)phenyl, 2,6-dimethyl-4-(2,6-dimethylphenyl)phenyl, 2,6-dimethyl-4-(4-pyridyl)phenyl, 2,6-dimethyl-4-(2,6-dimethyl-4-pyridyl)phenyl, 2,4-dimethyl-3-naphthyl, 2,6-dimethyl-4-cyanophenyl, 2,6-dimethyl-4-(9-carbazolyl)phenyl, 2,6-dimethyl-4-(9-phenyl-3-carbazolyl)phenyl, 2,6-dimethyl-4-(2,6-dimethyl-4-cyanophenyl)phenyl, and 1,8-dimethyl-9-carbazolyl.

By "Set 2b" we mean the group consisting of 2,6-di-isopropylphenyl, 2,4,6-tri-isopropylphenyl, 2,6-di-isopropyl-4-phenylphenyl, 2,6-di-isopropyl-4-(3,5-dimethylphenyl)phenyl, 2,6-di-isopropyl-4-(2,6-dimethylphenyl)phenyl, 2,6-di-isopropyl-4-(4-pyridyl)phenyl, 2,6-di-isopropyl-4-(2,6-dimethyl-4-pyridyl)phenyl, 2,4-di-isopropyl-3-naphthyl, 2,6-di-isopropyl-4-cyanophenyl, 2,6-di-isopropyl-4-(9-carbazolyl)phenyl, 2,6-di-isopropyl-4-(9-phenyl-3-carbazolyl)phenyl, 2,6-di-isopropyl-4-(2,6-dimethyl-4-cyanophenyl)phenyl, 2,6-di-tert-butylphenyl, 2,6-di-tert-butyl-4-(3,5-dimethylphenyl)phenyl, 2,6-bis(trimethylsilyl)phenyl, 2,6-bis(dimethylphenylsilyl)phenyl, and 2,6-bis(trimethylsilyl)-4-(3,5-dimethylphenyl)-phenyl.

By "Set 2c" we mean the group consisting of 2,6-di-phenylphenyl, 2,6-di(4-isopropylphenyl)-4-isopropylphenyl, 2,6-di(4-isopropylphenyl)-4-methylphenyl, 2,6-di(4-isopropylphenyl)-4-tert-butylphenyl, 2,4,6-triphenylphenyl, 2,6-di-(4-isopropylphenyl)phenyl, 2,6-di-(3,5-dimethylphenyl)phenyl, 2,4,6-tri(4-isopropylphenyl)phenyl, 2,6-di-(4-tert-butylphenyl)phenyl, 2,6-di-(4-fluorophenyl)phenyl, 2,6-di-(9-carbazolyl)-4-isopropylphenyl, 2,6-di-(9-phenyl-3-carbazolyl)-4-isopropylphenyl, 2,6-di-(4-methoxyphenyl)phenyl, 2,6-diphenyl-4-fluorophenyl, 2,6-di-(2-triphenylenyl)phenyl, 2,6-di-(2-triphenylenyl)-4-isopropylphenyl, 2,6-di-(2,6-dimethyl-4-pyridyl)phenyl, 2,6-di-(4-cyanophenyl)-4-isopropylphenyl, 2,6-di-2-naphthylphenyl, 2,6-di-(4-phenylphenyl)-4-isopropylphenyl, 2,6-di-(3-phenylphenyl)-4-isopropylphenyl, 2,6-di-(4-diphenylaminophenyl)phenyl, 2,6-di-(4-dimethylaminophenyl)phenyl, 2,6-di-(4-trimethylsilylphenyl)phenyl, 2,6-di-(4-triphenylsilylphenyl)phenyl, and 2,6-di-(4-diphenylmethylsilylphenyl)phenyl.

By "Set 2d" we mean structures c1-c9:

Set 2d

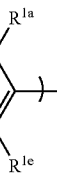 c1

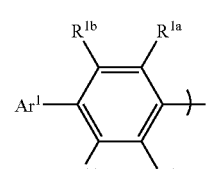 c2

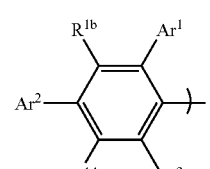 c3

-continued c4: [structure with NC, Ar¹, Ar²]

c5: [carbazole-phenyl structure with Ar¹, Ar²]

c6: [biphenyl structure with R¹ᵃ, R¹ᵇ, R¹ᶜ, R¹ᵈ, R¹ᵉ]

c7: [N-phenyl carbazole structure with Ar¹, Ar²]

c9: [triphenylene structure with Ar¹, Ar²];

wherein:

$R^{1a,e}$ are each independently selected from the group consisting of hydrocarbyl comprising two or more carbons, heteroatom substituted hydrocarbyl, aryl, and heteroaryl;

$R^{b-d}$ are each independently selected from the group consisting of H, F, cyano, alkoxy, aryloxy, hydrocarbyl, heteroatom substituted hydrocarbyl, aryl, and heteroaryl; in addition, any two of $R^{1b-d}$ may be linked to form a ring; and $Ar^{1,2}$ are each independently aryl or heteroaryl.

By "Set 3a," we mean the structures f1-f4:

Set 3a f1: [triazole/imidazole structure with R¹ᵃ, R²ᵃ, Arˢʳ, R²ᵇ]

f2: [imidazole structure with Arˢʳ, R²ᵇ]

f3: [imidazole structure with Arˢʳ, R¹ᵃ, R¹ᵇ, R²ᵇ]

f4: [imidazole structure with Arˢʳ, R²ᵃ]

wherein:

$Ar^{sr}$ is the second ring;

$R^{1a,b}$ are each independently selected from the group consisting of hydrogen, hydrocarbyl, and heteroatom substituted hydrocarbyl, cyano, and F; in addition, $R^{1a,b}$ may be linked to form a ring; and $R^{2a,b}$ are each independently selected from the group consisting of hydrogen, hydrocarbyl, heteroatom substituted hydrocarbyl, cyano, and F; in addition, $R^{2a,b}$ may comprise a group bonded to said metal.

By "Set 3b," we mean structures f5-f9:

Set 3b f5: [triazole structure with Arˢʳ, R²ᵃ]

f6: [triazole structure with Arˢʳ, R²ᵃ]

f7: [pyridine structure with Arˢʳ, R¹ᵃ, R²ᵃ, R¹ᵇ, R²ᵇ]

-continued

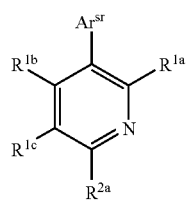
f8

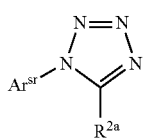
f9 wherein:

Ar$^{sr}$ is the second ring;

R$^{1a-c}$ are each independently selected from the group consisting of hydrogen, hydrocarbyl, heteroatom substituted hydrocarbyl, cyano, and F; in addition, any two of R$^{1a-c}$ may be linked to form a ring; and R$^{2a,b}$ are each independently selected from the group consisting of hydrogen, hydrocarbyl, and heteroatom substituted hydrocarbyl, cyano, and F; in addition, R$^{2a,b}$ may comprise a group bonded to said metal.

By "Set 4," we mean structures t1-t10:

Set 4

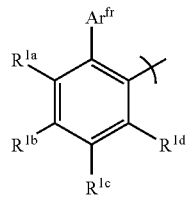
t1

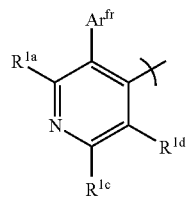
t2

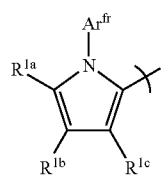
t3

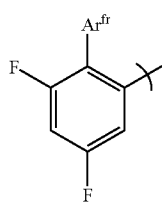
t4

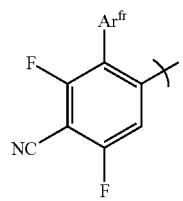
t5

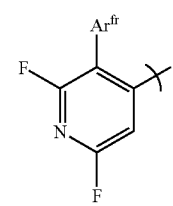
t6

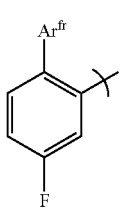
t7

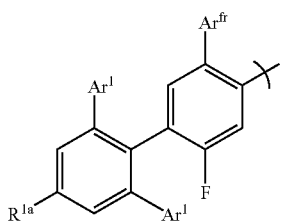
t8

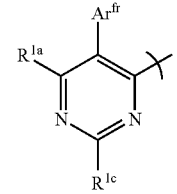
t9

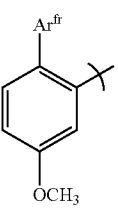
t10 wherein:

Ar$^{fr}$ is the first ring;

Ar$^{1}$ is aryl or heteroaryl; and

R$^{1a-d}$ are each independently selected from the group consisting of hydrogen, hydrocarbyl, heteroatom substituted hydrocarbyl, cyano, and F; in addition, any two of R$^{1a-d}$ may be linked to form a ring.

By "Set 5a," we mean structures I1-I7:

Set 5a

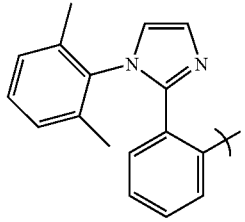
I1

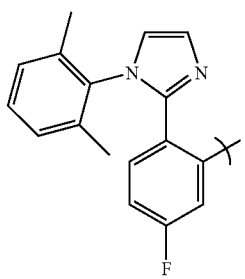
I2

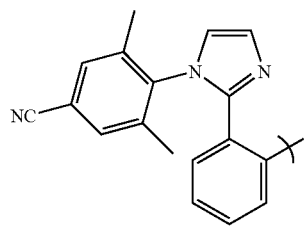
I3

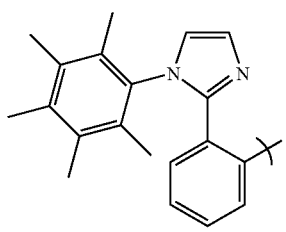
I4

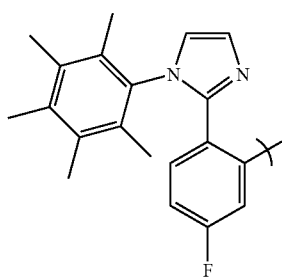
I5

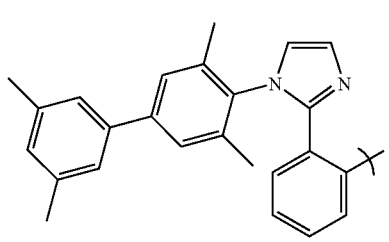
I6

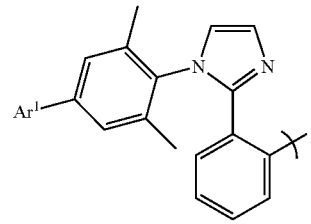
I7 wherein:
Ar$^1$ is aryl or heteroaryl.

By "Set 5b", we mean structures I20-I22:

Set 5b

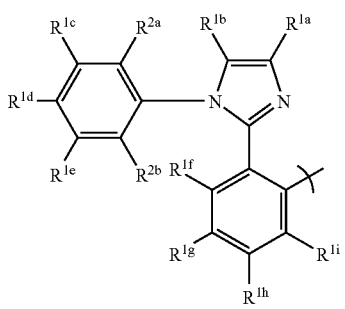
I20

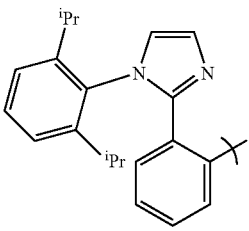
I21

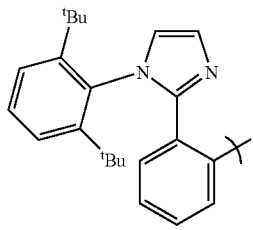
I22 wherein:
R$^{1a-i}$ are each independently selected from the group consisting of hydrogen, hydrocarbyl, heteroatom substituted hydrocarbyl, cyano, and F; in addition, any two of R$^{1c-i}$ may be linked to form a ring; and R$^{2a,b}$ are each independently selected from the group consisting of hydrocarbyl comprising two or more carbons, heteroatom substituted hydrocarbyl, aryl, and heteroaryl.

By "Set 5c", we mean structures I40-I46:

Set 5c

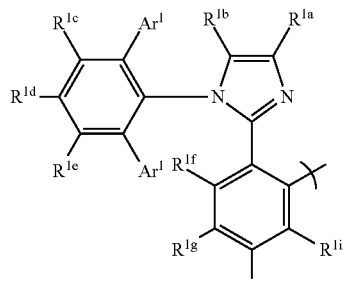
I41

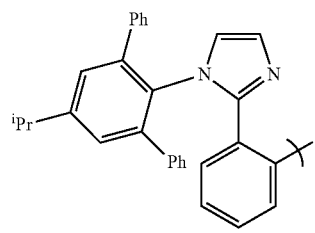
I42

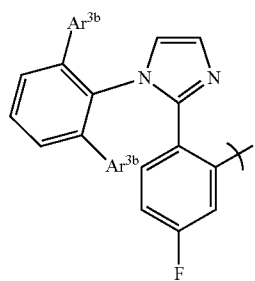
I43

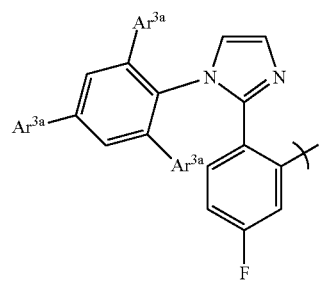
I44

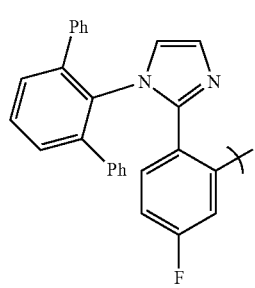
I45

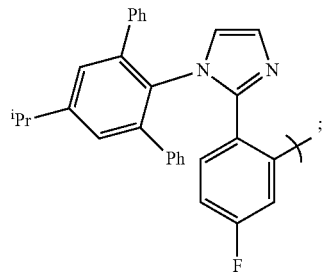
I46 wherein:
$R^{1a-i}$ are each independently selected from the group consisting of hydrogen, hydrocarbyl, heteroatom substituted hydrocarbyl, cyano, and F; in addition, any two of $R^{1c-i}$ may be linked to form a ring;

$Ar^1$ is aryl or heteroaryl;

$Ar^{3a}$ is 4-isopropylphenyl; and $Ar^{3b}$ is 3,5-dimethylphenyl.

By "Set 6a," we structures mc3, mc50, mc48, mc25, mc46, mc5, mc4, mc54, mc51, mc26a, mc26, mc39, mc49, mc6, mc9, mc8, mc4b, mc38b, mc15, mc26b, mc28b, mc32b, mc33b, mc34b, mc35b, mc29b, mc30b, mc31b, mc42b, mc43b, mc44b, and mc45b:

Set 6a

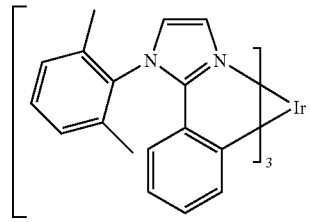
mc3

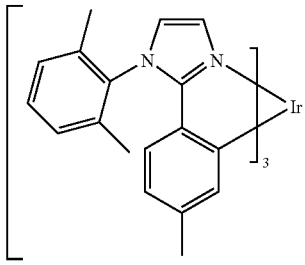
mc50

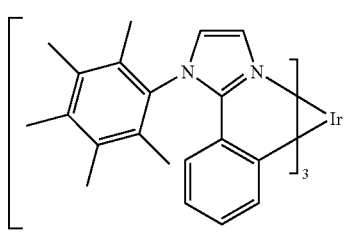
mc48 mc25 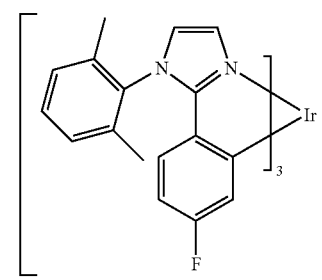
mc46 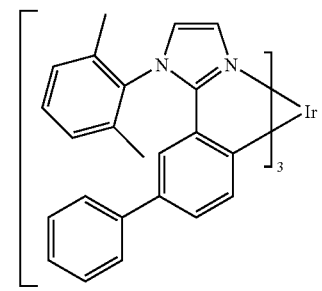
mc5 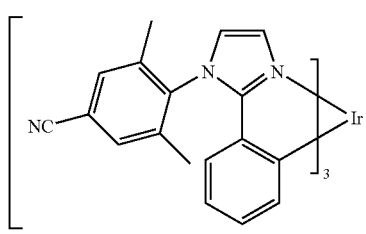
mc4 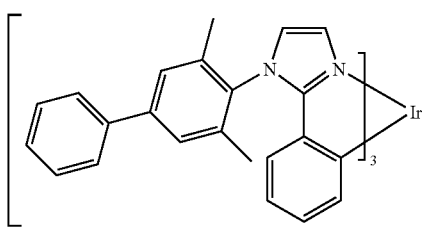
mc54 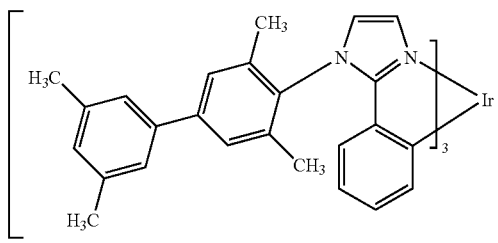
mc51 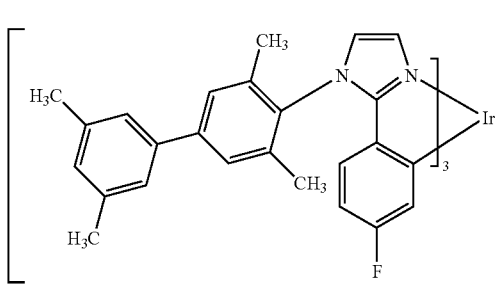
mc26a 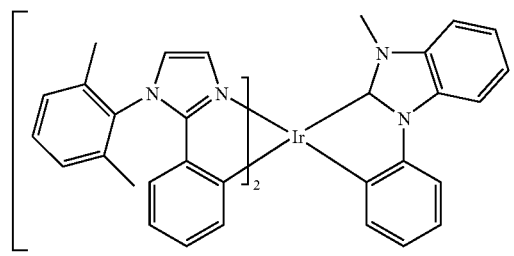
mc26 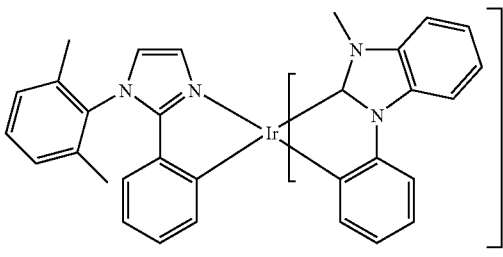
mc39 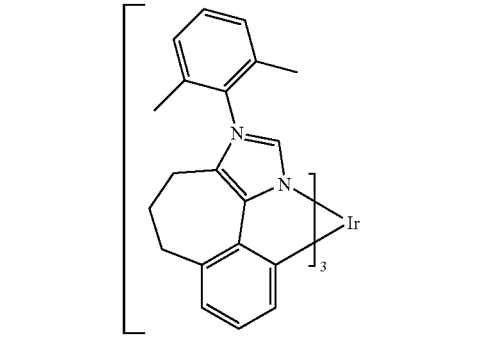
mc49 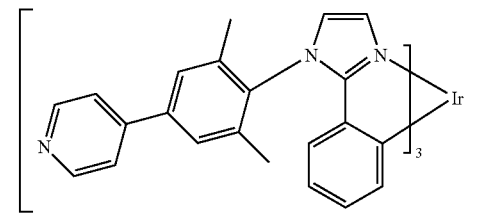
mc6 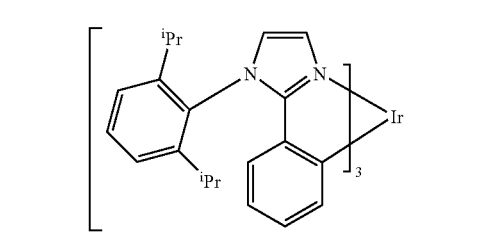
mc9 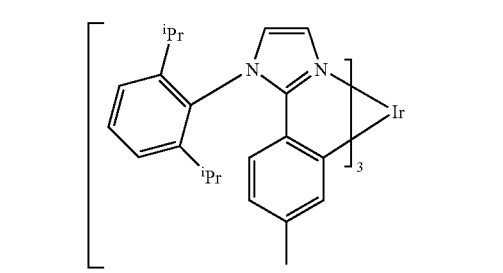

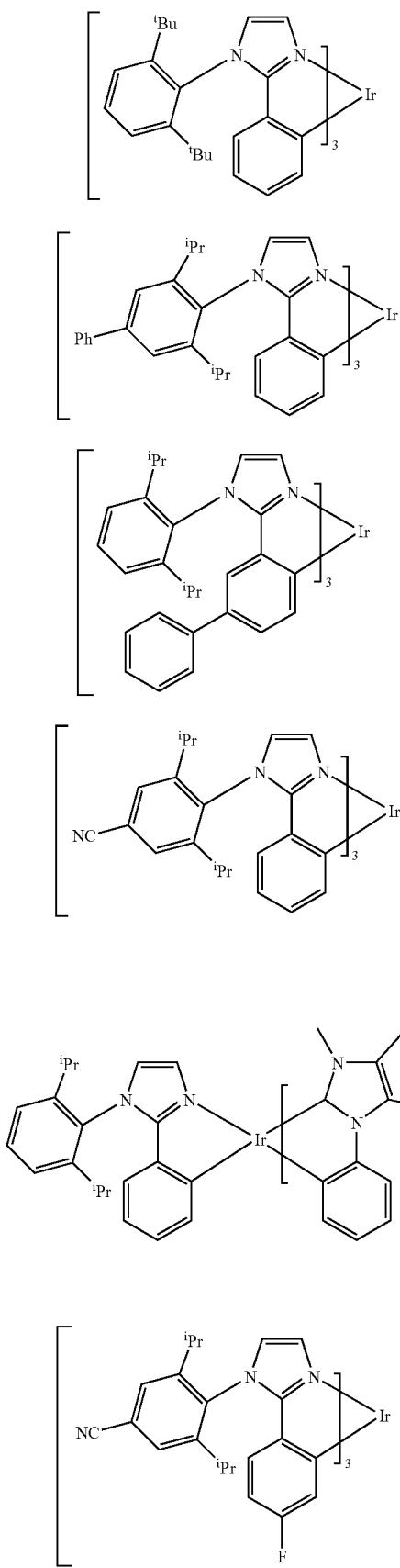
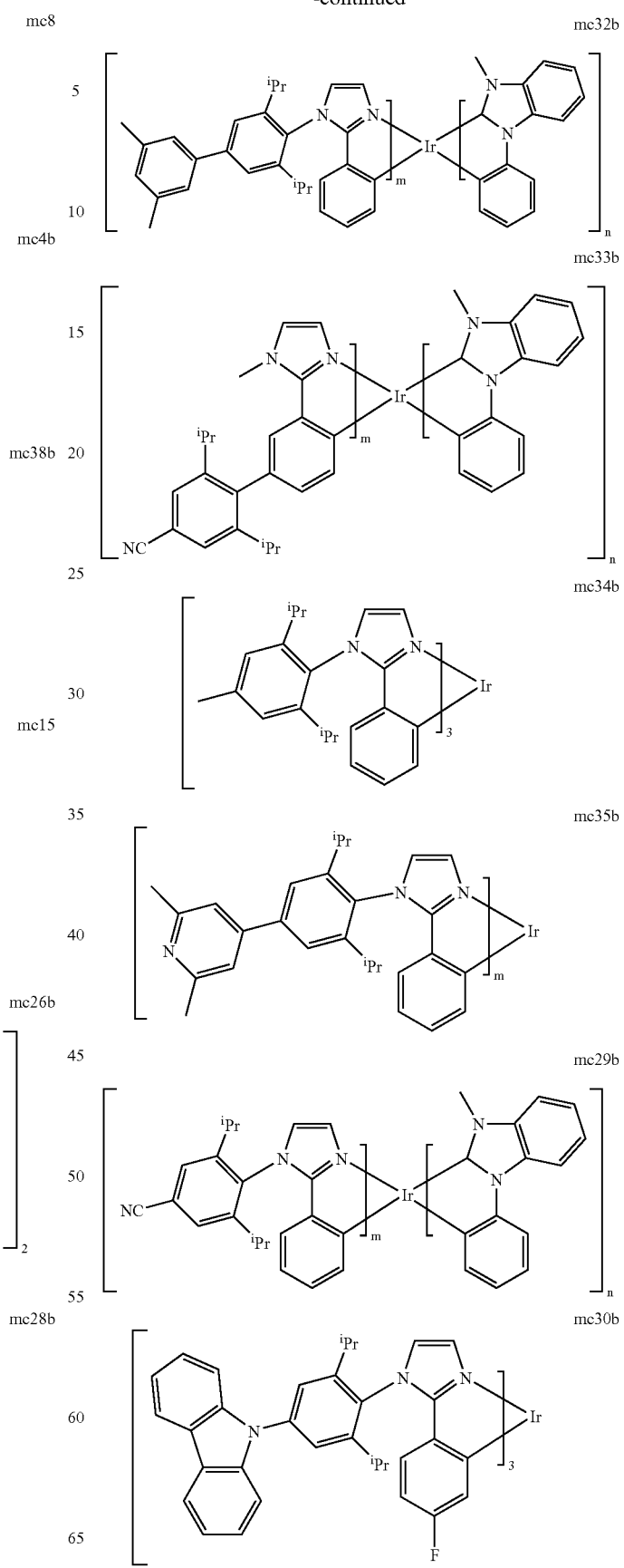

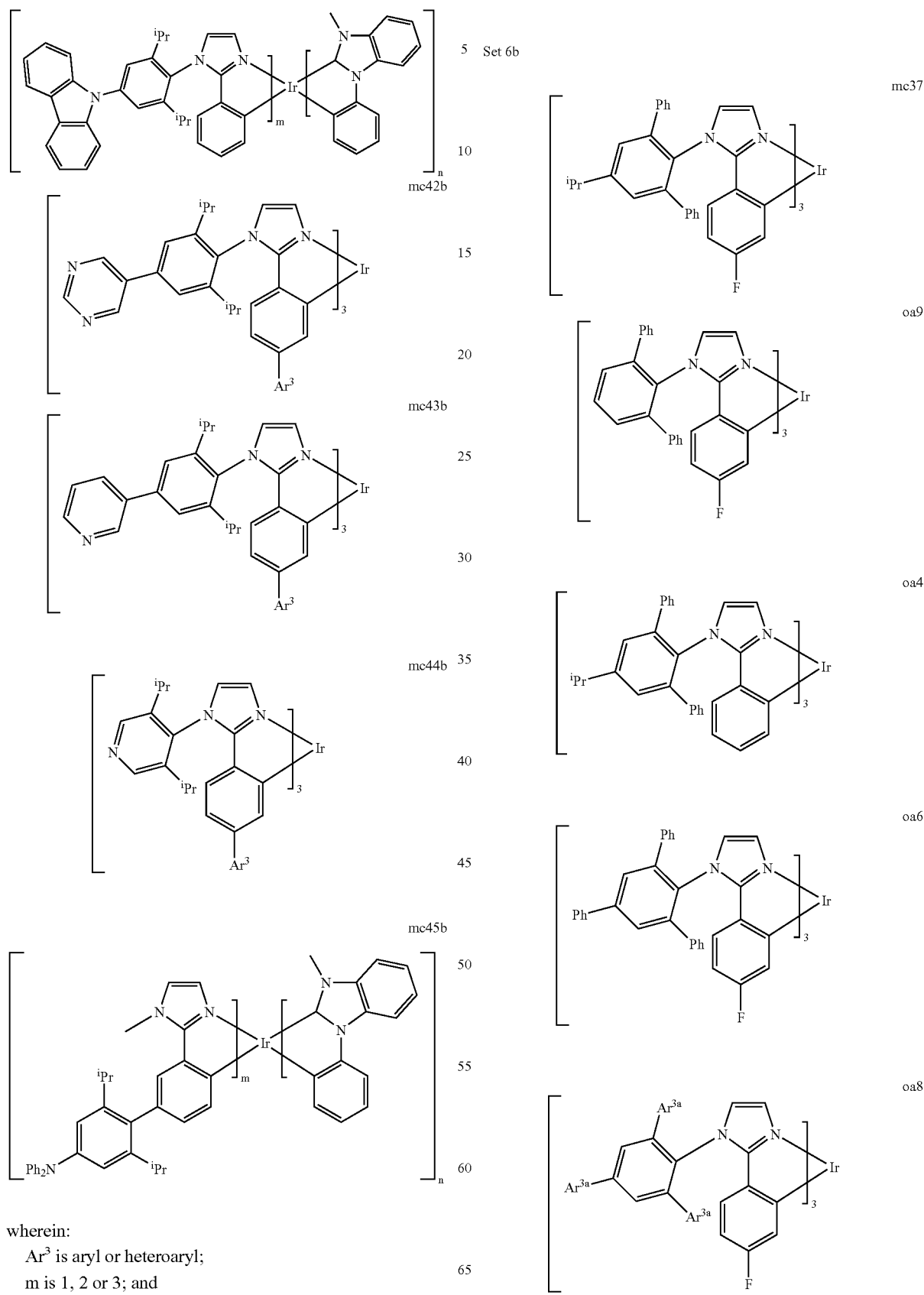
By "Set 6b," we mean structures mc37, oa9, oa4, oa6, oa8, u6, and oa5:
Set 6b
wherein:
Ar³ is aryl or heteroaryl;
m is 1, 2 or 3; and
n is an integer selected to satisfy the valency of the metal.

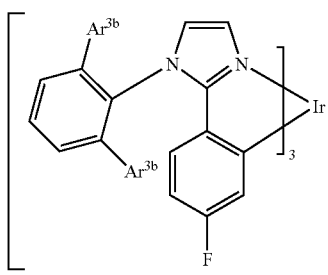
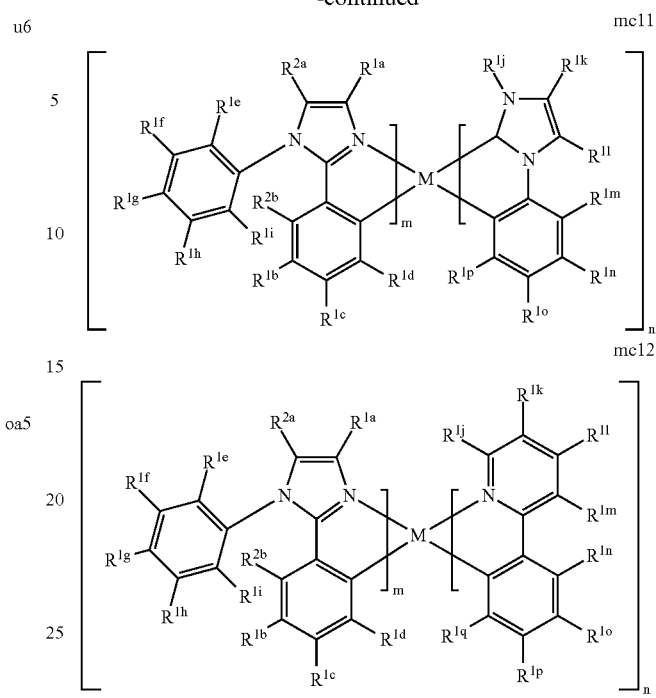
wherein:
Ar$^{3a}$ is 4-isopropylphenyl; and
Ar$^{3b}$ is 3,5-dimethylphenyl.
By "Set 6c," we mean structures mc1, mc2, mc11, mc12, mc13, mc17, mc18, mc19, mc20, mc21, mc22, mc23, mc24, mc27, mc36, oa11, mc51b, mc52b, oa12, oa1, oa2, oa3, oa8b, mc14, mc16, mc46b, mc49b, mc52b, mc53b, and mc51b:
Set 6c
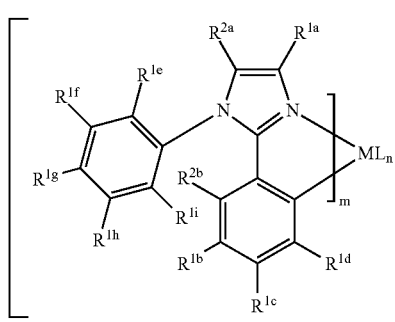
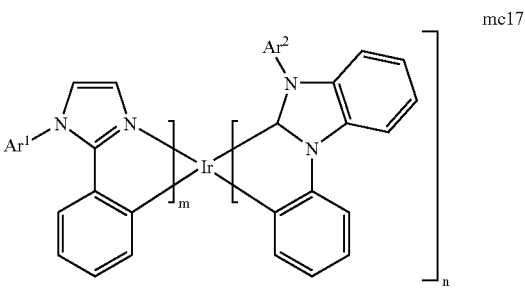
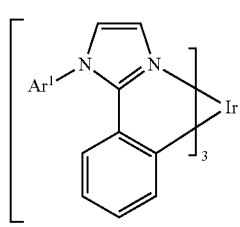
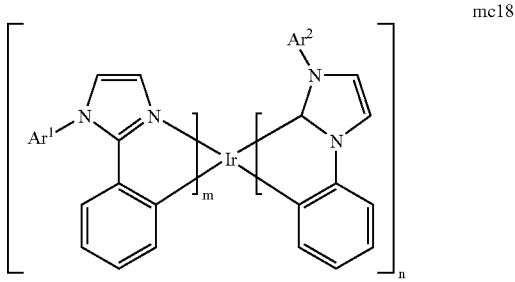

-continued
mc19
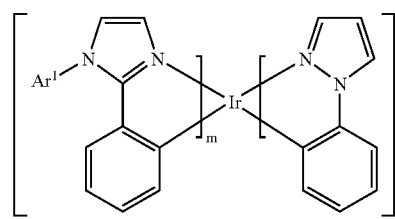
mc20
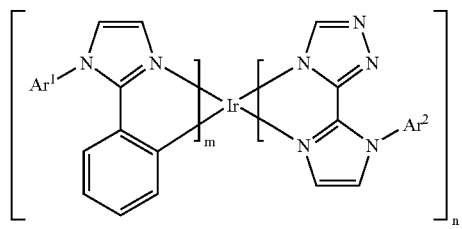
mc21
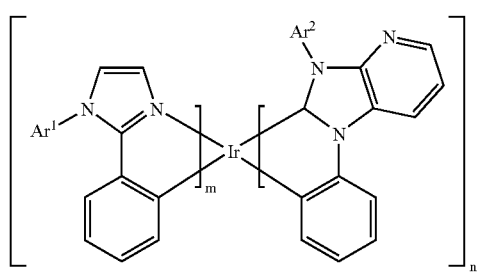
mc22
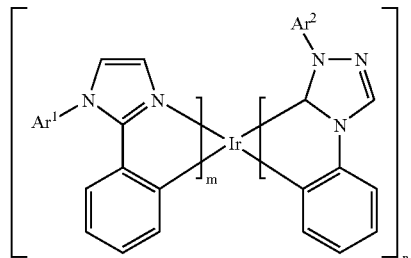
mc23
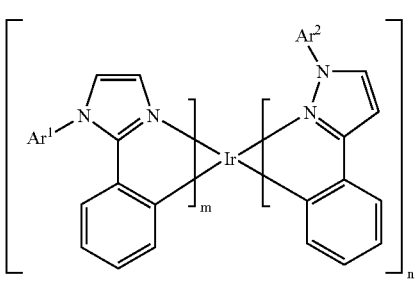
mc24
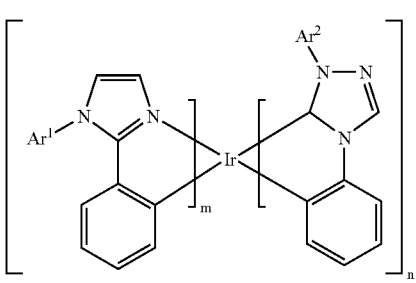
-continued
mc27
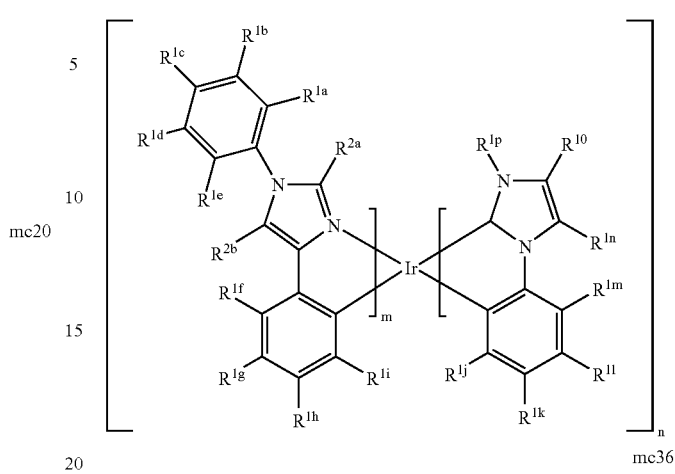
mc36
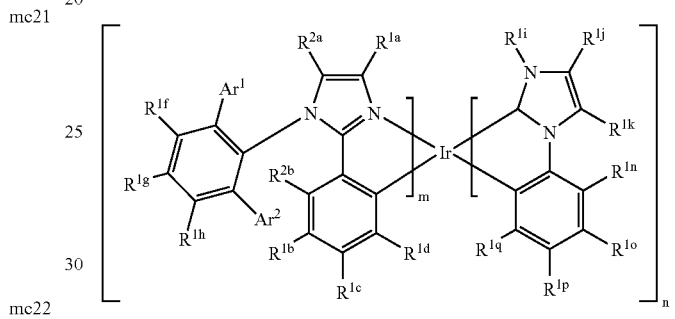
oa11
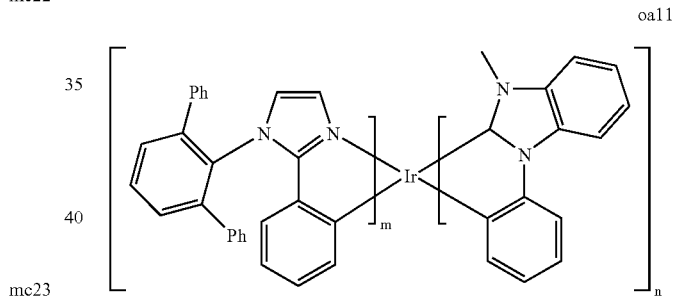
mc51b
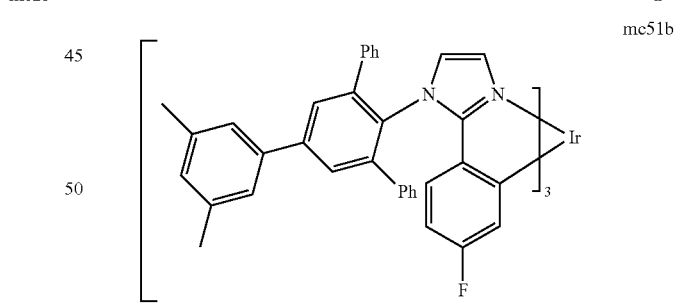
mc52b
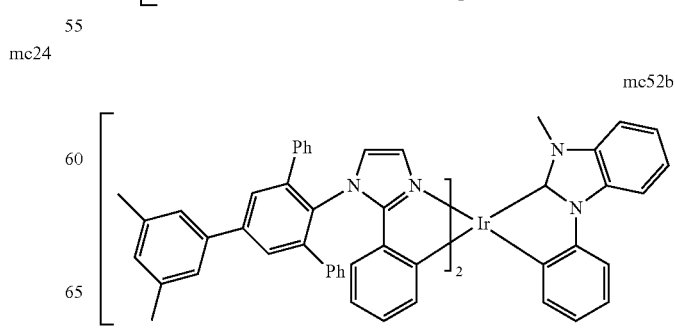

oa12 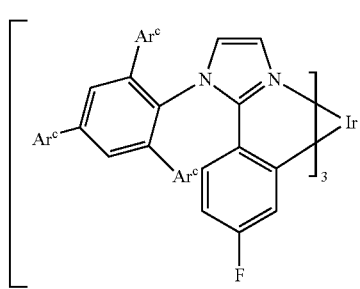
oa1 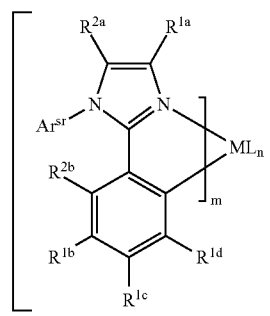
oa2 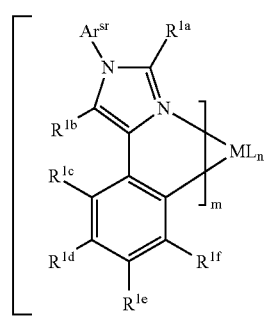
oa3 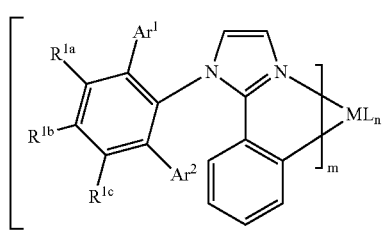
oa8b 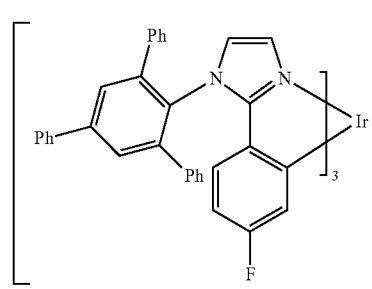
mc14 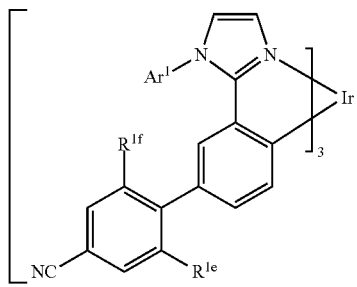
mc16 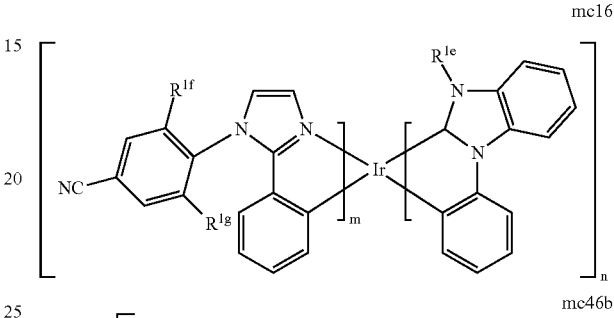
mc46b 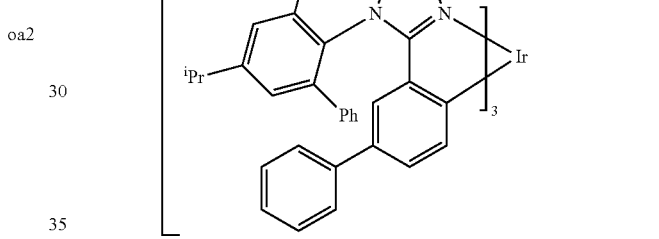
mc49b 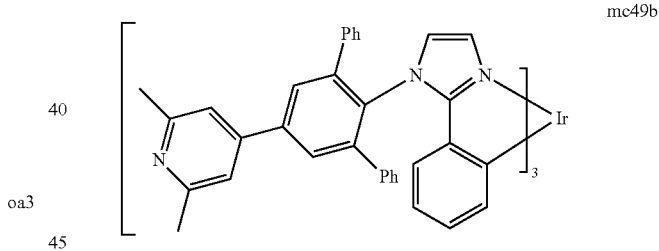
mc52b 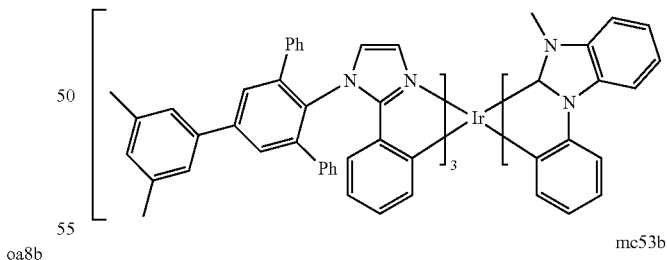
mc53b 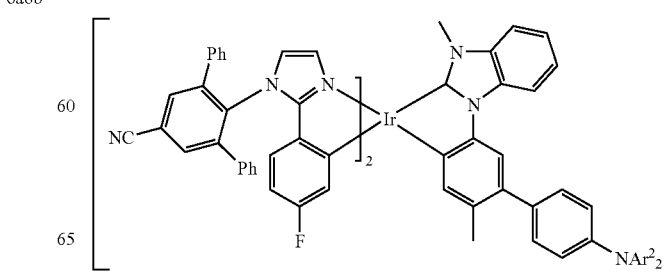

-continued

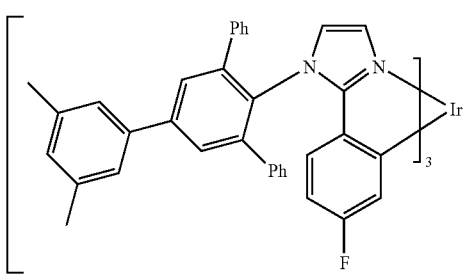

mc51b wherein:
$R^{2a-c}$ and $R^{1a-q}$ are each independently selected from the group consisting of hydrogen, hydrocarbyl, and heteroatom substituted hydrocarbyl, cyano, and F; in addition, any two of $R^{2a-c}$ and $R^{1a-q}$ may be linked to form a ring, provided that if $R^{1a}$ and $R^{2a}$ are linked the ring is a saturated ring;
$Ar^{1-3}$ are aryl or heteroaryl;
$Ar^{sr}$ is the second ring;
$Ar^c$ is 9-carbazolyl or substituted 9-carbazolyl;
$L_n$ are ancillary ligands, which may be the same or different;
m is 1, 2 or 3;
n is an integer selected to satisfy the valency of M; and
M is a metal selected from the group consisting of Re, Ru, Os, Rh, Ir, Pd, Pt, and Au. It will be understood that the aryl groups may be substituted. In certain preferred embodiments, the both ortho positions of the aryl or heteroaryl group of the second ring are substituted with substituents selected from the group consisting of aryl and heteroaryl.

By "Set 6d," we mean structures mc40b and mc41b:

Set 6d

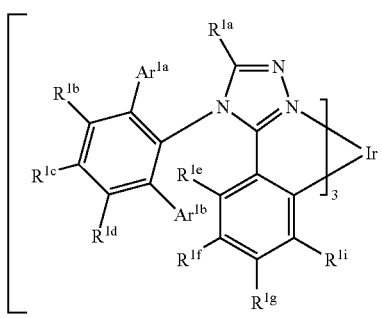

mc40b

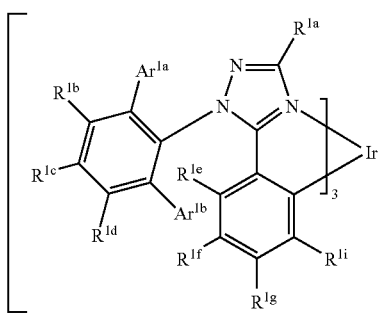

mc41b wherein:
$R^{1a-i}$ are each independently selected from the group consisting of hydrogen, hydrocarbyl, heteroatom substituted hydrocarbyl, cyano, and F; in addition, any two of $R^{1a-i}$ may be linked to form a ring; and
$Ar^{1a,b}$ are aryl or heteroaryl.

By "Set 6e," we mean structures m1-m72 in Table 2 below, wherein gs1, gs2, and gs3 are the general structures set forth in Set 7 and 3,5-Me$_2$Ph means 3,5-dimethylphenyl.

TABLE 2

| Specific Structure | General Structure | $R^{1a}$ | $R^{1b}$ | $R^{1c}$ | $R^{1d}$ | $R^{1e}$ | $R^{1f}$ |
|---|---|---|---|---|---|---|---|
| m1 | gs1 | CH$_3$ | H | CH$_3$ | H | H | H |
| m2 | gs1 | CH$_3$ | H | CH$_3$ | H | H | F |
| m3 | gs1 | CH$_3$ | H | CH$_3$ | F | H | F |
| m4 | gs1 | CH$_3$ | H | CH$_3$ | F | Ph | F |
| m5 | gs1 | $^i$Pr | H | $^i$Pr | H | H | H |
| m6 | gs1 | $^i$Pr | H | $^i$Pr | H | H | F |
| m7 | gs1 | $^i$Pr | H | $^i$Pr | F | H | F |
| m8 | gs1 | $^i$Pr | H | $^i$Pr | F | Ph | F |
| m9 | gs1 | Ph | $^i$Pr | Ph | H | H | H |
| m10 | gs1 | Ph | $^i$Pr | Ph | H | H | F |
| m11 | gs1 | Ph | $^i$Pr | Ph | F | H | F |
| m12 | gs1 | Ph | $^i$Pr | Ph | F | Ph | F |
| m13 | gs1 | Ph | $^i$Pr | Ph | H | H | H |
| m14 | gs1 | Ph | $^i$Pr | Ph | H | H | F |
| m15 | gs1 | Ph | $^i$Pr | Ph | F | H | F |
| m16 | gs1 | Ph | $^i$Pr | Ph | F | Ph | F |
| m17 | gs1 | 3,5-Me$_2$Ph | H | 3,5-Me$_2$Ph | H | H | H |
| m18 | gs1 | 3,5-Me$_2$Ph | H | 3,5-Me$_2$Ph | H | H | F |
| m19 | gs1 | 3,5-Me$_2$Ph | H | 3,5-Me$_2$Ph | F | H | F |
| m20 | gs1 | 3,5-Me$_2$Ph | H | 3,5-Me$_2$Ph | F | Ph | F |
| m21 | gs1 | 3,5-Me$_2$Ph | H | 3,5-Me$_2$Ph | H | H | H |
| m22 | gs1 | 3,5-Me$_2$Ph | H | 3,5-Me$_2$Ph | H | H | F |
| m23 | gs1 | 3,5-Me$_2$Ph | H | 3,5-Me$_2$Ph | F | H | F |
| m24 | gs1 | 3,5-Me$_2$Ph | H | 3,5-Me$_2$Ph | F | Ph | F |
| m25 | gs2 | CH$_3$ | H | CH$_3$ | H | H | H |
| m26 | gs2 | CH$_3$ | H | CH$_3$ | H | H | F |
| m27 | gs2 | CH$_3$ | H | CH$_3$ | F | H | F |
| m28 | gs2 | CH$_3$ | H | CH$_3$ | F | Ph | F |
| m29 | gs2 | $^i$Pr | H | $^i$Pr | H | H | H |
| m30 | gs2 | $^i$Pr | H | $^i$Pr | H | H | F |
| m31 | gs2 | $^i$Pr | H | $^i$Pr | F | H | F |
| m32 | gs2 | $^i$Pr | H | $^i$Pr | F | Ph | F |
| m33 | gs2 | Ph | $^i$Pr | Ph | H | H | H |
| m34 | gs2 | Ph | $^i$Pr | Ph | H | H | F |
| m35 | gs2 | Ph | $^i$Pr | Ph | F | H | F |
| m36 | gs2 | Ph | $^i$Pr | Ph | F | Ph | F |
| m37 | gs2 | Ph | $^i$Pr | Ph | H | H | H |
| m38 | gs2 | Ph | $^i$Pr | Ph | H | H | F |
| m39 | gs2 | Ph | $^i$Pr | Ph | F | H | F |
| m40 | gs2 | Ph | $^i$Pr | Ph | F | Ph | F |
| m41 | gs2 | 3,5-Me$_2$Ph | H | 3,5-Me$_2$Ph | H | H | H |
| m42 | gs2 | 3,5-Me$_2$Ph | H | 3,5-Me$_2$Ph | H | H | F |
| m43 | gs2 | 3,5-Me$_2$Ph | H | 3,5-Me$_2$Ph | F | H | F |
| m44 | gs2 | 3,5-Me$_2$Ph | H | 3,5-Me$_2$Ph | F | Ph | F |
| m45 | gs2 | 3,5-Me$_2$Ph | H | 3,5-Me$_2$Ph | H | H | H |
| m46 | gs2 | 3,5-Me$_2$Ph | H | 3,5-Me$_2$Ph | H | H | F |
| m47 | gs2 | 3,5-Me$_2$Ph | H | 3,5-Me$_2$Ph | F | H | F |
| m48 | gs2 | 3,5-Me$_2$Ph | H | 3,5-Me$_2$Ph | F | Ph | F |
| m49 | gs3 | CH$_3$ | H | CH$_3$ | H | H | H |
| m50 | gs3 | CH$_3$ | H | CH$_3$ | H | H | F |
| m51 | gs3 | CH$_3$ | H | CH$_3$ | F | H | F |
| m52 | gs3 | CH$_3$ | H | CH$_3$ | F | Ph | F |
| m53 | gs3 | $^i$Pr | H | $^i$Pr | H | H | H |
| m54 | gs3 | $^i$Pr | H | $^i$Pr | H | H | F |
| m55 | gs3 | $^i$Pr | H | $^i$Pr | F | H | F |
| m56 | gs3 | $^i$Pr | H | $^i$Pr | F | Ph | F |
| m57 | gs3 | Ph | $^i$Pr | Ph | H | H | H |
| m58 | gs3 | Ph | $^i$Pr | Ph | H | H | F |
| m59 | gs3 | Ph | $^i$Pr | Ph | F | H | F |
| m60 | gs3 | Ph | $^i$Pr | Ph | F | Ph | F |
| m61 | gs3 | Ph | $^i$Pr | Ph | H | H | H |
| m62 | gs3 | Ph | $^i$Pr | Ph | H | H | F |
| m63 | gs3 | Ph | $^i$Pr | Ph | F | H | F |
| m64 | gs3 | Ph | $^i$Pr | Ph | F | Ph | F |
| m65 | gs3 | 3,5-Me$_2$Ph | H | 3,5-Me$_2$Ph | H | H | H |
| m66 | gs3 | 3,5-Me$_2$Ph | H | 3,5-Me$_2$Ph | H | H | F |
| m67 | gs3 | 3,5-Me$_2$Ph | H | 3,5-Me$_2$Ph | F | H | F |
| m68 | gs3 | 3,5-Me$_2$Ph | H | 3,5-Me$_2$Ph | F | Ph | F |

TABLE 2-continued

| Specific Structure | General Structure | $R^{1a}$ | $R^{1b}$ | $R^{1c}$ | $R^{1d}$ | $R^{1e}$ | $R^{1f}$ |
|---|---|---|---|---|---|---|---|
| m69 | gs3 | 3,5-Me$_2$Ph | H | 3,5-Me$_2$Ph | H | H | H |
| m70 | gs3 | 3,5-Me$_2$Ph | H | 3,5-Me$_2$Ph | H | H | F |
| m71 | gs3 | 3,5-Me$_2$Ph | H | 3,5-Me$_2$Ph | F | H | F |
| m72 | gs3 | 3,5-Me$_2$Ph | H | 3,5-Me$_2$Ph | F | Ph | F |

By "Set 7," we mean structures gs1-gs3:

Set 7

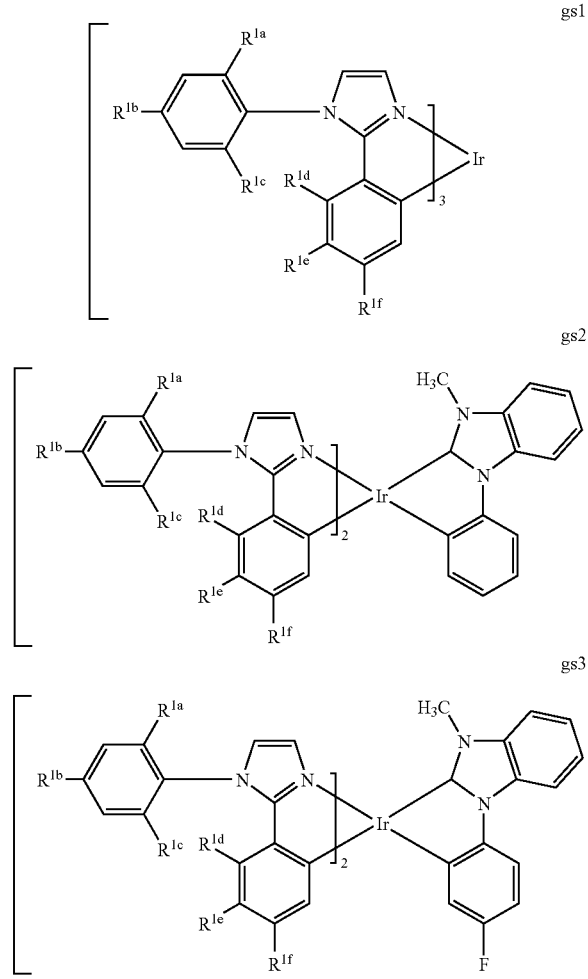

wherein $R^{1a-f}$ are as defined in Table 2 above.

In a first aspect, the invention provides a phosphorescent compound. The phosphorescent compound is a neutral metal complex of a monodentate, bidentate, tridentate, tetradentate, pentadentate, or hexadentate ligand. The ligand comprises at least one first aryl or heteroaryl ring directly bonded to the metal. The first ring is substituted by a second aryl or heteroaryl ring which is not directly bonded to the metal and which is independently substituted at both ortho positions by a substituent selected from the group consisting of aryl and heteroaryl groups. The second ring may be further substituted, and each of the substituents may independently be substituted or unsubstituted. The metal is selected from the group consisting of the non-radioactive metals with atomic numbers greater than 40.

In a first preferred embodiment of the first aspect, the metal is selected from the group consisting of Re, Ru, Os, Rh, Ir, Pd, Pt, Cu, and Au. In a second preferred embodiment, the metal is selected from the group consisting of Os, Ir, and Pt. In a third preferred embodiment, the metal is Ir.

In a fourth preferred embodiment, the second ring is substituted by an aryl, heteroaryl, or electron withdrawing group. By "electron withdrawing group," we mean a group with a positive value for the Hammett Substituent Constant corresponding to that group. Hammett Substituent Constants are known to those skilled in the art (see, for example, Hansch, C; Leo, A.; Taft, R. W.; Chem. Rev. 1991, Vol. 91, p. 165). A number of electron withdrawing groups have been reported in the literature as being compatible with OLED devices. Such groups are preferred. Examples of such groups include cyano, 9-carbazolyl, and 1-triazolyl.

In a fifth preferred embodiment, the second ring is substituted by a triphenylene group.

In an sixth preferred embodiment, the second ring is substituted by a group that comprises a carbazole.

In a seventh preferred embodiment, the substituents at the ortho position of the second ring comprise one or more diarylaminoaryl groups.

In a eighth preferred embodiment, the compound has a highest energy peak in a phosphorescence emission spectrum at a wavelength less than about 480 nm.

In a ninth preferred embodiment, the compound is homoleptic.

In a tenth preferred embodiment, the compound is heteroleptic.

In a eleventh preferred embodiment, the compound is sublimable. By "sublimable," we mean that the compound has sufficient volatility and thermal stability at elevated temperatures that it can be incorporated into a vapor phase processed OLED device. Typically, this means that more than about a 25% yield of greater than about 98% pure sublimed material can be recovered upon sublimation over a period of at least about several hours at temperatures between about 200 and about 400° C. In some cases, the compound may melt or soften in the process, in which case the process may resemble a distillation.

In a twelfth preferred embodiment, the second ring is attached to a nitrogen atom of the first ring.

In an thirteenth preferred embodiment, the first ring is an imidazole ring. In a fourteenth preferred embodiment, the first ring is a pyrazole ring. In a fifteenth preferred embodiment, the first ring is a triazole ring. In a sixteenth preferred embodiment, the first ring is a pyridine ring. In a seventeenth preferred embodiment, the first ring is a benzene ring.

In an eighteenth preferred embodiment, the first ring is substituted by a third aryl or heteroaryl ring, which is also directly bonded to the metal.

In a nineteenth preferred embodiment, the first and third rings collectively comprise a monoanionic bidentate ligand.

In a twentieth preferred embodiment, the third ring is selected from the group consisting of phenyl, pyridyl, thiophenyl, furanyl, pyrrolyl, triazolyl, and pyrimidyl.

In a twenty-first preferred embodiment, the third ring is a phenyl ring substituted by one or more fluoro groups.

In a twenty-second preferred embodiment, the first and third rings collectively comprise a monoanionic tridentate ligand.

In a twenty-third preferred embodiment, the first and third rings collectively comprise a neutral bidentate ligand.

In an twenty-fourth preferred embodiment, the groups attached to the ortho positions of the second ring are selected from Set 1, as defined above.

In a twenty-fifth preferred embodiment, the second ring is selected from Sets 2c and 2d as defined above.

In a twenty-sixth preferred embodiment, the first ring is selected from Sets 3a and 3b, as defined above.

In a twenty-seventh preferred embodiment, the third ring is selected from Set 4 as defined above.

In a twenty-eighth preferred embodiment, the ligand is selected from Set 5c as defined above.

In an twenty-ninth preferred embodiment, the metal complex is selected from the group consisting of compound mc2 from Set 6c, compound mc13 from Set 6c, compound mc17 from Set 6c, compound mc18 from Set 6c, compound mc19 from Set 6c, compound mc20 from Set 6c, compound mc21 from Set 6c, compound mc22 from Set 6c, compound mc23 from Set 6c, compound mc24 from Set 6c, compound mc36 from Set 6c, compound oa11 from Set 6c, compound mc51b from Set 6c, compound mc52b from Set 6c, compound oa12 from Set 6c, compound oa1 from Set 6c, compound oa2 from Set 6c, compound oa3 from Set 6c, compound oa8b from Set 6c, compound mc46b from Set 6c, compound mc49b from Set 6c, compound mc52b from Set 6c, compound mc53b from Set 6c, compound mc51b from Set 6c, compound mc40b from Set 6d and compound mc41b from Set 6d.

In a thirtieth preferred embodiment, the metal complex comprises a bidentate, monoanionic, N,N-donor ligand.

In a thirty-first preferred embodiment, the metal complex comprises a carbene donor.

In a thirty-second preferred embodiment, the carbene donor is part of a bidentate, monoanionic ligand.

In a thirty-third embodiment, the second ring is substituted by groups other than fluoride.

In a thirty-fourth embodiment, the triplet energy of the arene or heteroarene corresponding to the second ring is greater than about 2.5 eV. By "arene or heteroarene corresponding to the second ring", we mean the molecule obtained by attaching a hydrogen atom to the second ring in place of the first ring. For example, when the second ring is 2,6-dimethylphenyl, the corresponding arene would be 1,3-dimethylbenzene. Similarly, when the second ring is 2,6-dimethyl-4-phenylphenyl, the corresponding arene would be 1,5-dimethyl-3-phenylbenzene. Triplet energies for common arenes and heteroarenes may be found in a variety of reference texts, including "Handbook of Photochemistry" $2^{nd}$ edition (S. L. Murov, I. Carmichael, G. L. Hug, eds; Dekker, 1993, New York), or may be calculated by methods known to those skilled in the art, for example, by Density Functional Theory (DFT) calculations using Gaussian 98 with the G98/B31yp/cep-31 g basis set. Triplet energies greater than about 2.5 eV correspond to triplet transition wavelengths shorter than about 500 nm. Without wishing to be bound by theory, the inventors suppose that in some cases, an excessively low triplet energy on the second ring will either red-shift the phosphorescent emission, or reduce the radiative quantum yield, or both.

In a thirty-fifth preferred embodiment, the molecular weight of the arene or heteroarene corresponding to the second ring is greater than about 230 g/mol.

In a thirty-sixth preferred embodiment, the molecular weight of the arene or heteroarene corresponding to the second ring is greater than about 430 g/mol.

In a thirty-seventh second preferred embodiment, the molecular weight of the arene or heteroarene corresponding to the second ring is greater than about 530 g/mol.

In a thirty-eighth preferred embodiment, the molecular weight of the arene or heteroarene corresponding to the second ring is greater than about 750 g/mol.

In a thirty-ninth preferred embodiment, the calculated singlet-triplet gap is less than about 0.4 eV. By "calculated singlet-triplet gap" we mean the difference in energy between the lowest lying singlet excited state and the lowest lying triplet excited state of the metal complex as calculated by Density Functional Theory (DFT) methods using Gaussian 98 with the G98/B31yp/cep-31 g basis set. In a fortieth preferred embodiment, the calculated singlet-triplet gap is less than about 0.3 eV. In a forty-first preferred embodiment, the calculated singlet-triplet gap is less than about 0.2 eV. In a forty-second preferred embodiment, the calculated singlet-triplet gap is less than about 0.1 eV.

In a forty-third preferred embodiment, the reduction potential of the ligand is less negative than that of the corresponding ligand with a methyl group in place of the second ring by at least about 0.1 V. By "reduction potential of the ligand" we mean the electrochemical reduction potential in solution for the neutral compound corresponding to the ligand. If the ligand is a monoanionic bidentate donor derived from an N-aryl-2-phenylimidazole, the "neutral compound corresponding to the ligand" is the N-aryl-2-phenylimidazole. More generally, if the ligand is a neutral donor, then the "neutral compound corresponding to the ligand" and the ligand are the same compound, or are tautomers; if the ligand is a monoanionic donor, then the "neutral compound corresponding to the ligand" is the compound wherein the atom of the ligand that is bonded to the metal and bears a formal negative charge in the metal complex has a proton in place of the metal in the neutral compound corresponding to the ligand.

In a forty-fourth preferred embodiment, the reduction potential of the ligand is less negative than that of the corresponding ligand with a methyl group in place of the second ring by at least about 0.2 V. In a forty-fifth preferred embodiment, the reduction potential of the ligand is less negative than that of the corresponding ligand with a methyl group in place of the second ring by at least about 0.3 V. In a forty-sixth preferred embodiment, the reduction potential of the ligand is less negative than that of the corresponding ligand with a methyl group in place of the second ring by at least about 0.4 V. In a forty-seventh preferred embodiment, the reduction potential of the ligand is less negative than that of the corresponding ligand with a methyl group in place of the second ring by at least about 0.5 V.

In a forty-eighth preferred embodiment, delta E is less than about 0.6 eV; wherein delta E=(triplet energy in eV)−(modified electrochemical gap in eV); wherein the modified electrochemical gap in eV is equal to is the energy difference associated with one electron crossing the difference in voltage between the oxidation potential of the metal complex and the reduction potential of the neutral compound corresponding to the ligand. In a forty-ninth preferred embodiment, delta E is less than about 0.5 eV. In a fiftieth preferred embodiment, delta E is less than about 0.4 eV. In a fifty-first preferred embodiment, delta E is less than about 0.3 eV. In a fifty-second preferred embodiment, delta E is less than about 0.2 eV.

In a second aspect, the invention provides a phosphorescent compound. The phosphorescent compound is a neutral metal complex of a monodentate, bidentate, tridentate, tetradentate, pentadentate, or hexadentate ligand. The ligand comprises at least one first aryl or heteroaryl ring directly bonded to the metal. The first ring is substituted by a second aryl or heteroaryl ring which is not directly bonded to the metal and which is substituted at both ortho positions by groups other than H or halide. The first ring is an imidazole, benzene, naphthalene, quinoline, isoquinoline, pyridine, pyrimidine, pyridazine, pyrrole, oxazole, thiazole, oxadiazole, thiadiazole, furan, or thiophene ring. The metal is selected from the group consisting of the non-radioactive metals with atomic numbers greater than 40.

In a first preferred embodiment of the second aspect, the first ring is an imidazole coordinated via a first nitrogen to the metal. In a second preferred embodiment, the second ring is attached to a second nitrogen of the first ring.

In a third preferred embodiment, the metal is selected from the group consisting of Re, Ru, Os, Rh, Ir, Pd, Pt, Cu, and Au. In a fourth preferred embodiment, the metal is selected from the group consisting of Os, Ir, and Pt. In a fifth preferred embodiment, the metal is Ir.

In a sixth preferred embodiment, the second ring is substituted by one or more aryl, heteroaryl, or electron withdrawing groups.

In a seventh preferred embodiment, the second ring is substituted by a triphenylene group.

In an eighth preferred embodiment, the second ring is substituted by a group that comprises a carbazole.

In a ninth preferred embodiment, the groups other than H or halide are alkyl groups.

In a tenth preferred embodiment, the groups other than H or halide are alkyl groups comprising two or more carbons.

In a eleventh preferred embodiment, the groups other than H or halide are aryl groups. In a twelfth preferred embodiment, the groups other than H or halide are heteroaryl groups.

In a thirteenth preferred embodiment, the groups other than H or halide comprise one or more diarylaminoaryl groups.

In a fourteenth preferred embodiment, the compound has a highest energy peak in a phosphorescence emission spectrum at a wavelength less than about 480 nm.

In a fifteenth preferred embodiment, the compound is homoleptic.

In an sixteenth preferred embodiment, the compound is heteroleptic.

In a seventeenth preferred embodiment, the compound is sublimable.

In a eighteenth preferred embodiment, the first ring is substituted by a third aryl or heteroaryl ring also directly bonded to the metal.

In a nineteenth preferred embodiment, the first and third rings collectively comprise a monoanionic bidentate ligand.

In a twentieth preferred embodiment, the third ring is a benzene, naphthalene, quinoline, isoquinoline, pyridine, pyrimidine, pyridazine, pyrrole, oxazole, thiazole, oxadiazole, thiadiazole, furan, or thiophene ing.

In a twenty-first preferred embodiment, the first and third rings collectively comprise a monoanionic tridentate ligand.

In a twenty-second preferred embodiment, the first and third rings collectively comprise a neutral bidentate ligand.

In an twenty-third preferred embodiment, the groups other than H or halide are selected from (i) the group consisting of methyl, ethyl, n-propyl, isopropyl, and tert-butyl, or (ii) Set 1 as defined above.

In a twenty-fourth preferred embodiment, the second ring is selected from Sets 2a-2d as defined above.

In a twenty-fifth preferred embodiment, the first ring is selected from Set 3a, as defined above.

In a twenty-sixth preferred embodiment, the third ring is selected from Set 4 as defined above.

In a twenty-seventh preferred embodiment, the ligand is selected from Sets 5a-5c as defined above.

In a twenty-eighth preferred embodiment, the metal complex is selected from Sets 6a-6c and 6e as defined above.

In a twenty-ninth preferred embodiment, the first ring is a benzene ring.

In a thirtieth preferred embodiment, the first ring is a naphthalene ring.

In a thirty-first preferred embodiment, the first ring is a quinoline ring.

In a thirty-second preferred embodiment, the first ring is a isoquinoline ring.

In a thirty-third preferred embodiment, the first ring is a pyridine ring.

In a thirty-fourth preferred embodiment, the first ring is a pyrimidine ring.

In a thirty-fifth preferred embodiment, the first ring is a pyridazine ring.

In a thirty-sixth preferred embodiment, the first ring is a pyrrole ring.

In a thirty-seventh preferred embodiment, the first ring is a oxaole ring.

In a thirty-eighth preferred embodiment, the first ring is a thiazole ring.

In a thirty-ninth preferred embodiment, the first ring is a oxadiazole ring.

In a fortieth preferred embodiment, the first ring is a thiadiazole ring.

In a forty-first preferred embodiment, the first ring is a furan ring.

In a forty-second preferred embodiment, the first ring is a thiophene ring.

In a forty-third preferred embodiment, the metal complex comprises a bidentate, monoanionic, N,N-donor ligand.

In a forty-fourth preferred embodiment, the metal complex comprises a carbene donor.

In a forty-fifth preferred embodiment, the carbene donor is part of a bidentate, monoanionic ligand.

In a forty-sixth preferred embodiment, the second ring is substituted by groups other than fluoride.

In a forty-seventh preferred embodiment, the triplet energy of the arene or heteroarene corresponding to the second ring is greater than about 2.5 eV.

In a forty-eighth preferred embodiment, the molecular weight of the arene or heteroarene corresponding to the second ring is greater than about 230 g/mol. In a forty-ninth preferred embodiment, the molecular weight of the arene or heteroarene corresponding to the second ring is greater than about 430 g/mol. In a fiftieth preferred embodiment, the molecular weight of the arene or heteroarene corresponding to the second ring is greater than about 530 g/mol. In a fifty-first preferred embodiment, the molecular weight of the arene or heteroarene corresponding to the second ring is greater than about 750 g/mol.

In a fifty-second preferred embodiment, the calculated singlet-triplet gap is less than about 0.4 eV. In a fifty-third preferred embodiment, the calculated singlet-triplet gap is less than about 0.3 eV. In a fifty-fourth preferred embodiment, the calculated singlet-triplet gap is less than about 0.2 eV. In a fifty-fifth preferred embodiment, the calculated singlet-triplet gap is less than about 0.1 eV.

In a fifty-sixth preferred embodiment, the reduction potential of the ligand is less negative than that of the corresponding ligand with a methyl group in place of the second ring by at least about 0.1 V. In a fifty-seventh preferred embodiment, the reduction potential of the ligand is less negative than that of the corresponding ligand with a methyl group in place of the second ring by at least about 0.2 V. In a fifty-eighth preferred embodiment, the reduction potential of the ligand is less negative than that of the corresponding ligand with a methyl group in place of the second ring by at least about 0.3 V. In a fifty-ninth preferred embodiment, the reduction potential of the ligand is less negative than that of the corresponding ligand with a methyl group in place of the second ring by at least about 0.4 V. In a sixtieth preferred embodiment, the reduction potential of the ligand is less negative than that of the corresponding ligand with a methyl group in place of the second ring by at least about 0.5 V.

In a sixtty-first preferred embodiment, delta E is less than about 0.6 eV; wherein delta E=(triplet energy in eV)−(modified electrochemical gap in eV); wherein the modified electrochemical gap in eV is equal to is the energy difference associated with one electron crossing the difference in voltage between the oxidation potential of the metal complex and the reduction potential of the neutral compound corresponding to the ligand. In a sixty-second preferred embodiment, delta E is less than about 0.5 eV. In a sixty-third preferred embodiment, delta E is less than about 0.4 eV. In a sixty-fourth preferred embodiment, delta E is less than about 0.3 eV. In a sixty-fourth preferred embodiment, delta E is less than about 0.2 eV.

In a third aspect, the invention provides a phosphorescent compound. The phosphorescent compound is a neutral metal complex of a monodentate, bidentate, tridentate, tetradentate, pentadentate, or hexadentate ligand. The ligand comprises at least one first aryl or heteroaryl ring directly bonded to the metal. This first ring is an imidazole, coordinated via a first nitrogen atom to the metal. In yet another preferred embodiment, the second ring is attached to a second nitrogen atom of the first ring. The first ring is substituted by a second aryl or heteroaryl ring which is not directly bonded to the metal and which is substituted at both ortho positions by groups other than H or halide. The metal is selected from the group consisting of the non-radioactive metals with atomic numbers greater than 40.

In a first preferred embodiment, the second ring is attached to a second nitrogen of the first ring.

In a second preferred embodiment, the metal is selected from the group consisting of Re, Ru, Os, Rh, Ir, Pd, Pt, Cu, and Au. In a third preferred embodiment, the metal is selected from the group consisting of Os, Ir, and Pt. In a fourth preferred embodiment, the metal is Ir.

In an fifth preferred embodiment, the second ring is substituted by one or more aryl, heteroaryl, or electron withdrawing groups.

In an sixth preferred embodiment, the groups other than H or halide are alkyl groups. Examples of suitable alkyl groups include methyl, ethyl, n-propyl, iso-propyl, sec-butyl, tert-butyl, 2-ethylhexyl and cyclohexyl. In a seventh preferred embodiment, the alkyl groups comprise two or more carbon atoms.

In an eighth preferred embodiment, the groups other than H or halide are aryl groups. In an ninth preferred embodiment, the groups other than H or halide are heteroaryl groups.

In a tenth preferred embodiment, the compound has a highest energy peak in a phosphorescence emission spectrum at a wavelength less than about 480 nm.

In a eleventh preferred embodiment, the compound is homoleptic.

In a twelfth preferred embodiment, the compound is heteroleptic.

In a thirteenth preferred embodiment, the compound is sublimable.

In a fourteenth preferred embodiment, the first ring is substituted by a third aryl or heteroaryl ring, which is also directly bonded to the metal.

In a fifteenth preferred embodiment, the first and third rings collectively comprise a monoanionic bidentate ligand.

In an sixteenth preferred embodiment, the third ring is selected from the group consisting of phenyl, pyridyl, thiophenyl, furanyl, pyrrolyl, triazolyl, and pyrimidyl.

In a seventeenth preferred embodiment, the first and third rings collectively comprise a monoanionic tridentate ligand.

In a eighteenth preferred embodiment, the first and third rings collectively comprise a neutral bidentate ligand.

In a nineteenth preferred embodiment, the groups attached to the ortho positions of the second ring are selected from (i) the group consisting of methyl, ethyl, n-propyl, isopropyl, and tert-butyl, or (ii) Set 1.

In a twentieth preferred embodiment, the second ring is selected from Sets 2a-2d.

In a twenty-first preferred embodiment, the third ring is selected from Set 3a.

In a twenty-second preferred embodiment, the third ring is selected from Set 4.

In a twenty-third preferred embodiment, the ligand is selected from Sets 5a-5c.

In a twenty-fourth preferred embodiment, the metal complex is selected from Sets 6a-6c and 6e.

In a twenty-fifth preferred embodiment, the metal complex comprises a bidentate, monoanionic, N,N-donor ligand.

In a twenty-sixth preferred embodiment, the metal complex comprises a carbene donor. In a twenty-seventh preferred embodiment, the carbene donor is part of a bidentate, monoanionic ligand.

In a twenty-eighth preferred embodiment, the second ring is substituted by groups other than fluoride.

In a twenty-ninth preferred embodiment, the triplet energy of the arene or heteroarene corresponding to the second ring is greater than about 2.5 eV.

In a thirtieth preferred embodiment, the molecular weight of the arene or heteroarene corresponding to the second ring is greater than about 230 g/mol. In a thirty-first preferred embodiment, the molecular weight of the arene or heteroarene corresponding to the second ring is greater than about 430 g/mol. In a thirty-second preferred embodiment, the molecular weight of the arene or heteroarene corresponding to the second ring is greater than about 530 g/mol. In a thirty-third preferred embodiment, the molecular weight of the arene or heteroarene corresponding to the second ring is greater than about 750 g/mol.

In a thirty-fourth preferred embodiment, the calculated singlet-triplet gap is less than about 0.4 eV. In a thirty-fifth preferred embodiment, the calculated singlet-triplet gap is less than about 0.3 eV. In a thirty-sixth preferred embodiment, the calculated singlet-triplet gap is less than about 0.2 eV. In a thirty-seventh preferred embodiment, the calculated singlet-triplet gap is less than about 0.1 eV.

In a thirty-eighth preferred embodiment, the reduction potential of the ligand is less negative than that of the corresponding ligand with a methyl group in place of the second ring by at least about 0.1 V. In a thirty-ninth preferred embodiment, the reduction potential of the ligand is less negative than that of the corresponding ligand with a methyl group in place of the second ring by at least about 0.2 V. In a fortieth preferred embodiment, the reduction potential of the ligand is less negative than that of the corresponding ligand with a methyl group in place of the second ring by at least about 0.3 V. In a forty-first preferred embodiment, the reduction potential of the ligand is less negative than that of the corresponding ligand with a methyl group in place of the second ring by at least about 0.4 V. In a forty-second preferred embodiment, the reduction potential of the ligand is less negative than that of the corresponding ligand with a methyl group in place of the second ring by at least about 0.5 V.

In a forty-third preferred embodiment, delta E is less than about 0.6 eV; wherein delta E=(triplet energy in eV)−(modified electrochemical gap in eV); wherein the modified electrochemical gap in eV is equal to is the energy difference associated with one electron crossing the difference in voltage between the oxidation potential of the metal complex and the reduction potential of the neutral compound corresponding to the ligand. In a forty-fourth preferred embodiment, delta E is less than about 0.5 eV. In a forty-fifth preferred embodiment, delta E is less than about 0.4 eV. In a forty-sixth preferred embodiment, delta E is less than about 0.3 eV. In a forty-seventh preferred embodiment, delta E is less than about 0.2 eV.

The compounds described herein are particularly useful as light-emitting phosphorescent materials in the emissive layer of OLED devices. These devices typically contain an anode, a cathode, and an emissive layer. The emissive layer is located between the anode and the cathode. The emissive layer would comprise the phosphorescent compounds of the invention, and optionally a host.

In one embodiment, the present invention provides a device that addresses issues that arise when an OLED has an electron majority emissive layer. An electron majority emissive layer occurs when electrons migrate faster toward the anode side of the emissive layer than holes migrate toward the cathode side of the emissive layer. One type of electron majority emissive layer that is of particular concern is a hole trap, which occurs in some blue phosphorescent devices. A hole trap in the emissive layer can be achieved when the HOMO of the emissive layer host is at least about 0.5 eV lower, preferably about 0.5 eV to about 0.8 eV lower, than the HOMO of the emissive dopant. When holes enter such an emissive layer, the holes accumulate on dopant molecules near the hole transport layer/emissive layer interface. This, in turn, localizes recombination near the hole transport layer/emissive layer interface where excitons may be quenched by the hole transport layer. Localization of recombination can be measured by techniques known in the art, such as by using a probe doped layer as described in U.S. patent application Ser. No. 11/110,776, now U.S. Pat. No. 7,807,275, which is incorporated herein by reference in its entirety. To avoid localization near the hole transport layer, it is desirable to shift the holes, and thus recombination, further into the emissive layer. Hole shifting can be accomplished by a variety of architectural features including, but not limited to, inserting an electron impeding layer, creating a LUMO barrier, using an electron transport layer that is actually a poor electron transporter, inserting a thick organic layer between the emissive layer and the cathode, selecting an emissive layer host material that is a poor electron transporter, selecting a dopant to alter electron mobility of the emissive or transport layers, or otherwise reducing the electron density of the emissive layer.

One way to lure the holes further into the emissive layer is to include a means for accumulating electrons between the emissive layer and the cathode. The accumulation of electrons redistributes the electric field across the emissive layer and forces recombination away from the hole transport layer/emissive layer interface. The means for accumulating electrons can be, for example, an electron impeding layer.

Accordingly, in one embodiment, the present invention provides an OLED comprising an anode; a cathode; an organic emissive layer disposed between the anode and the cathode, the organic emissive layer comprising an emissive layer host and an emissive dopant, wherein the HOMO of the emissive layer host is at least about 0.5 eV lower, preferably about 0.5 eV to about 0.8 eV lower, than the HOMO of the emissive dopant; and a means for accumulating electrons between the cathode and the emissive layer. Preferably, the electrons are accumulated at the interface between the first and second organic layer.

In a preferred embodiment, the present invention provides an organic light emitting device, comprising: an anode; a hole transport layer; an organic emissive layer comprising an emissive layer host and an emissive dopant; an electron impeding layer; an electron transport layer; and a cathode disposed, in that order, over a substrate.

Figure 12:
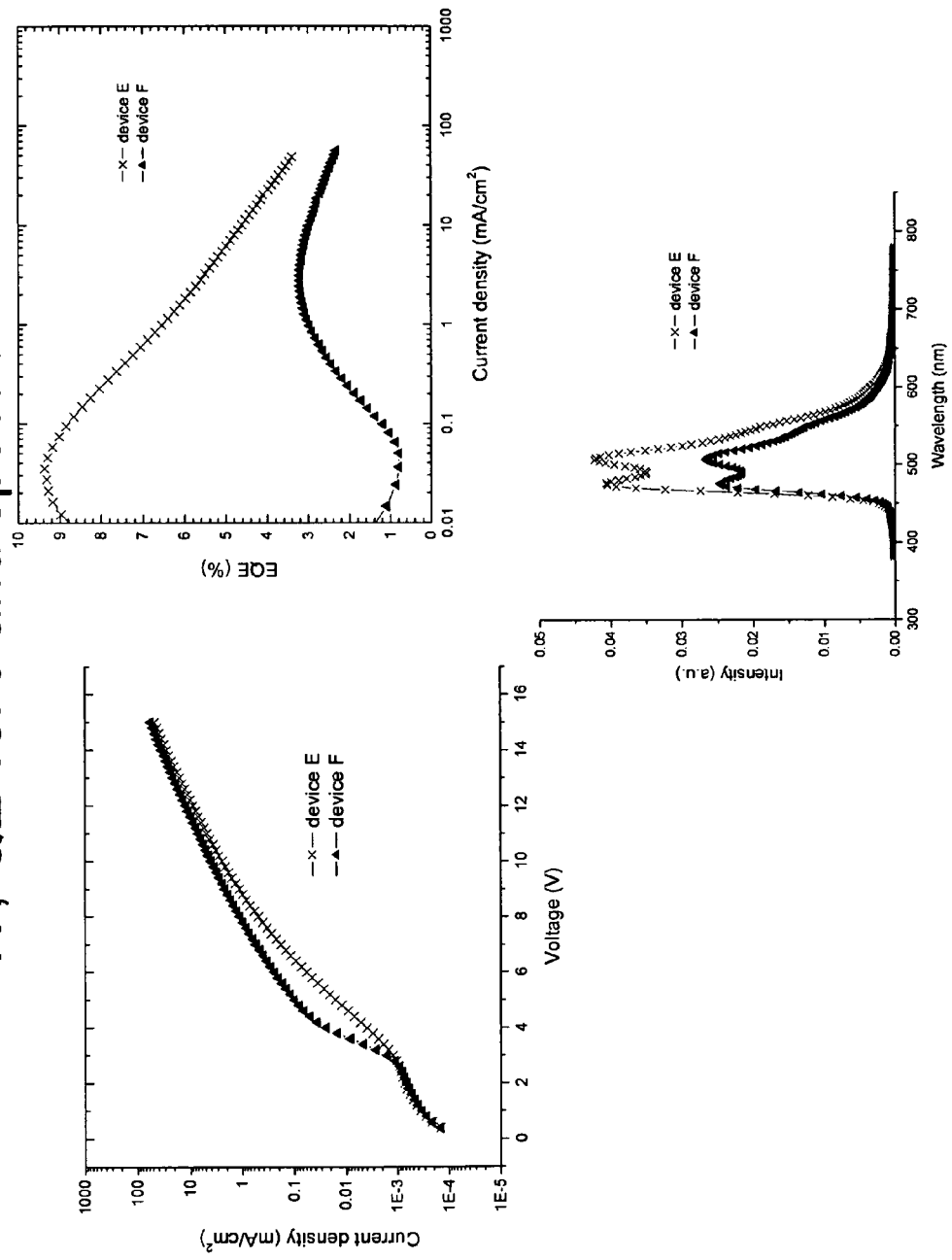
FIG. 12 shows IV, quantum efficiency (QE) vs current (J) and spectral data for devices E and F.
Figure 13:
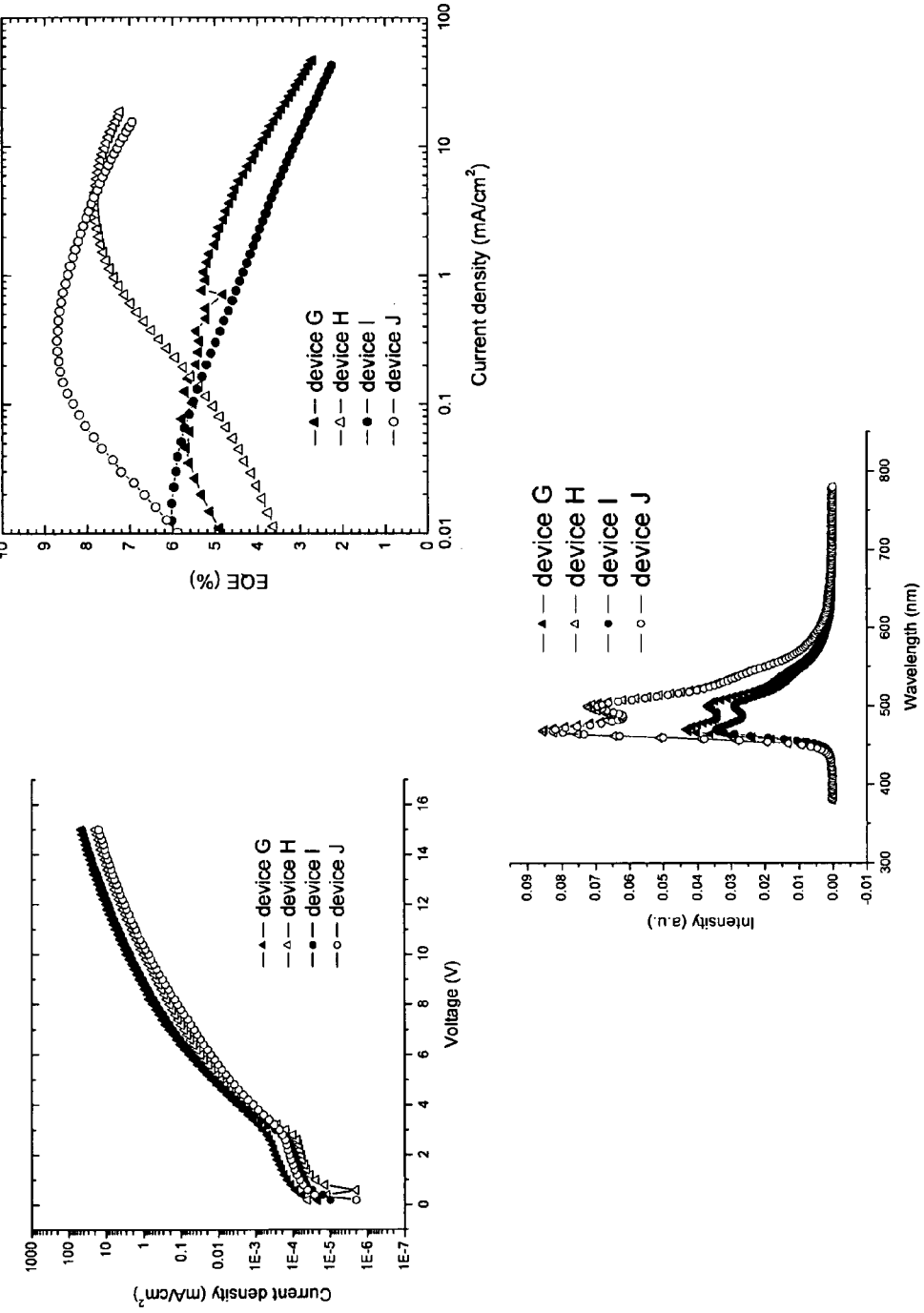
FIG. 13 shows IV, quantum efficiency (QE) vs current (J) and spectral data for devices G, H, I and J.
Figure 14:
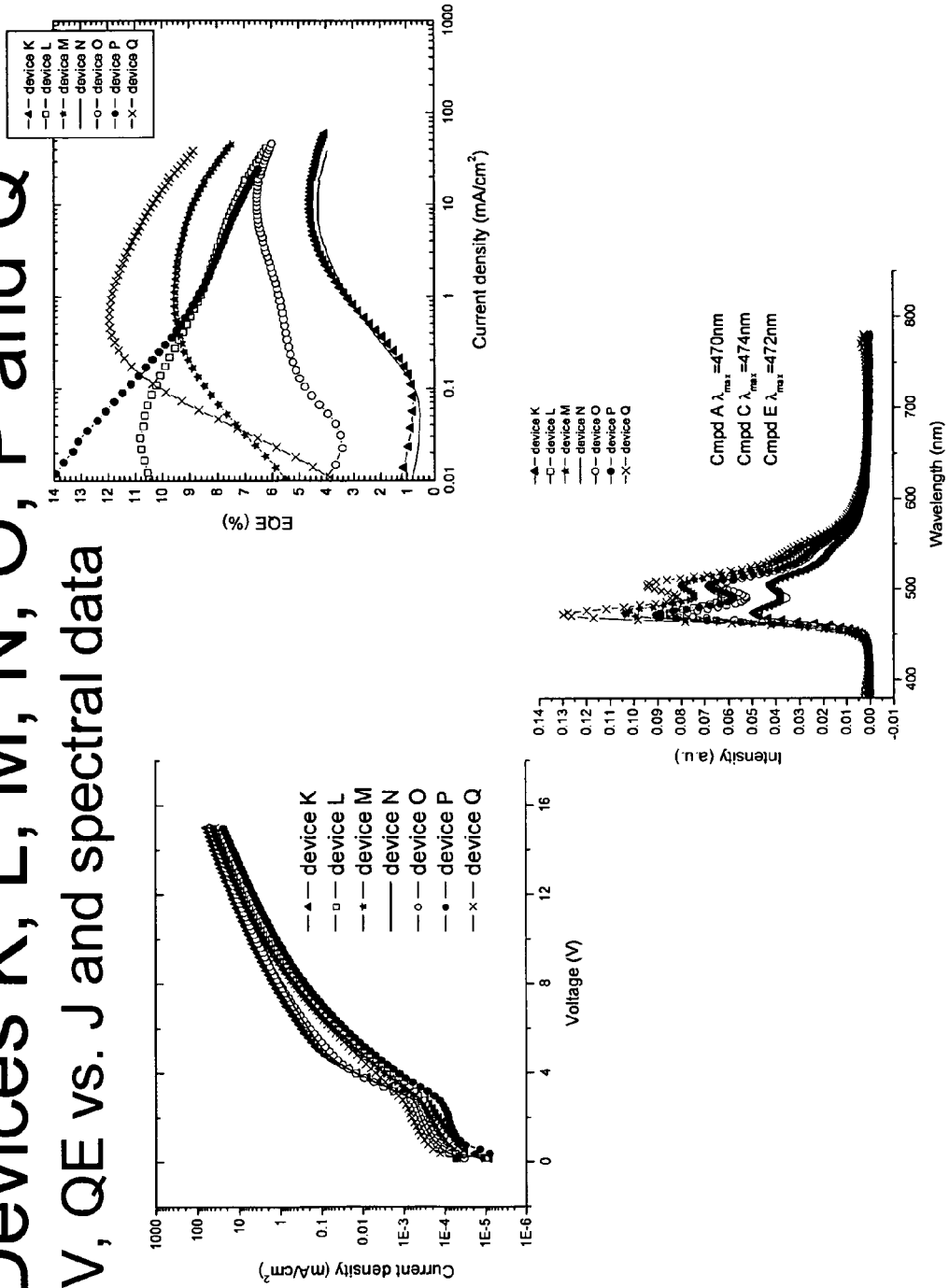
FIG. 14 shows IV, quantum efficiency (QE) vs current (J) and spectral data for devices K to Q.
Figure 15:
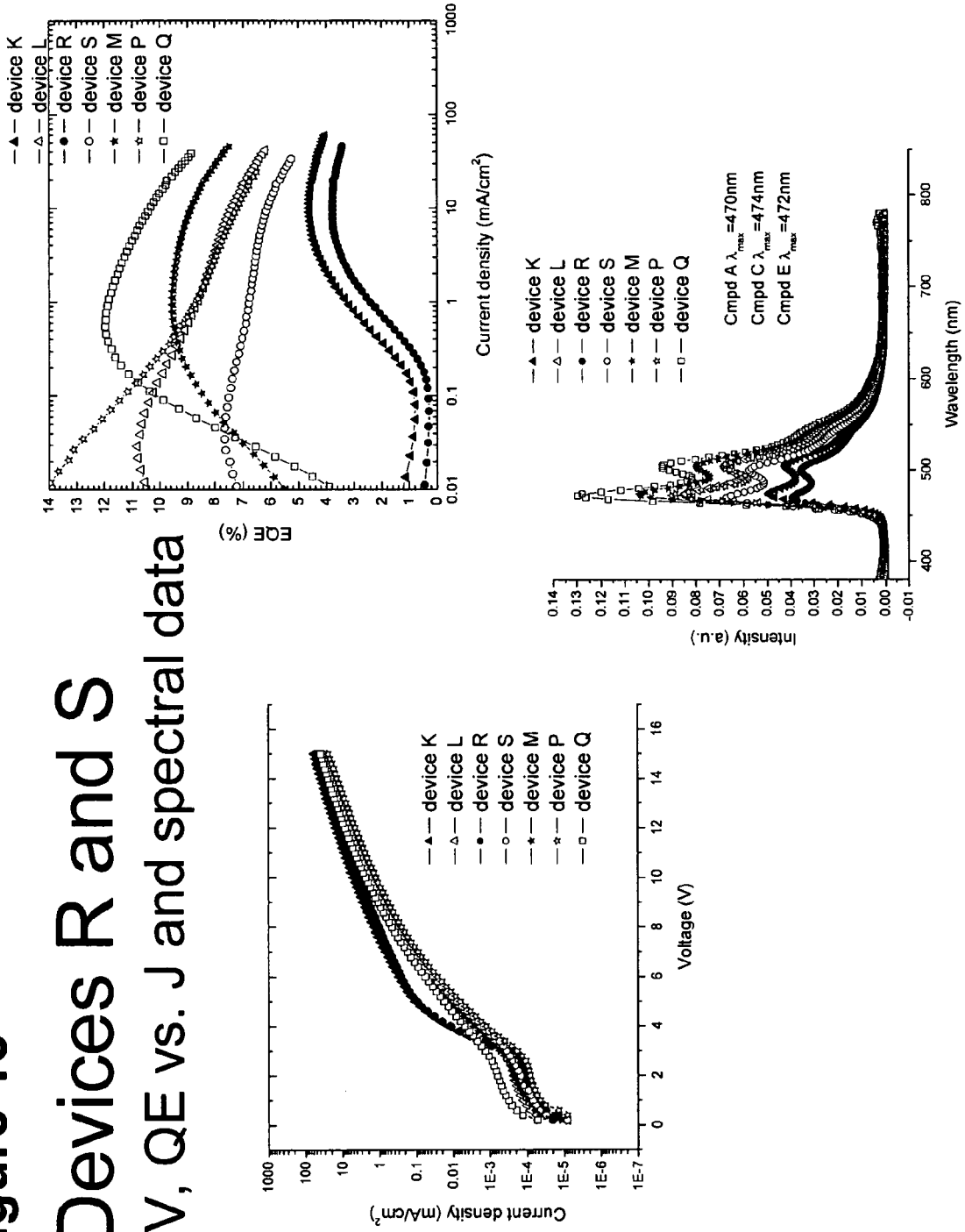
FIG. 15 shows IV, quantum efficiency (QE) vs current (J) and spectral data for devices R and S.
Figure 16:
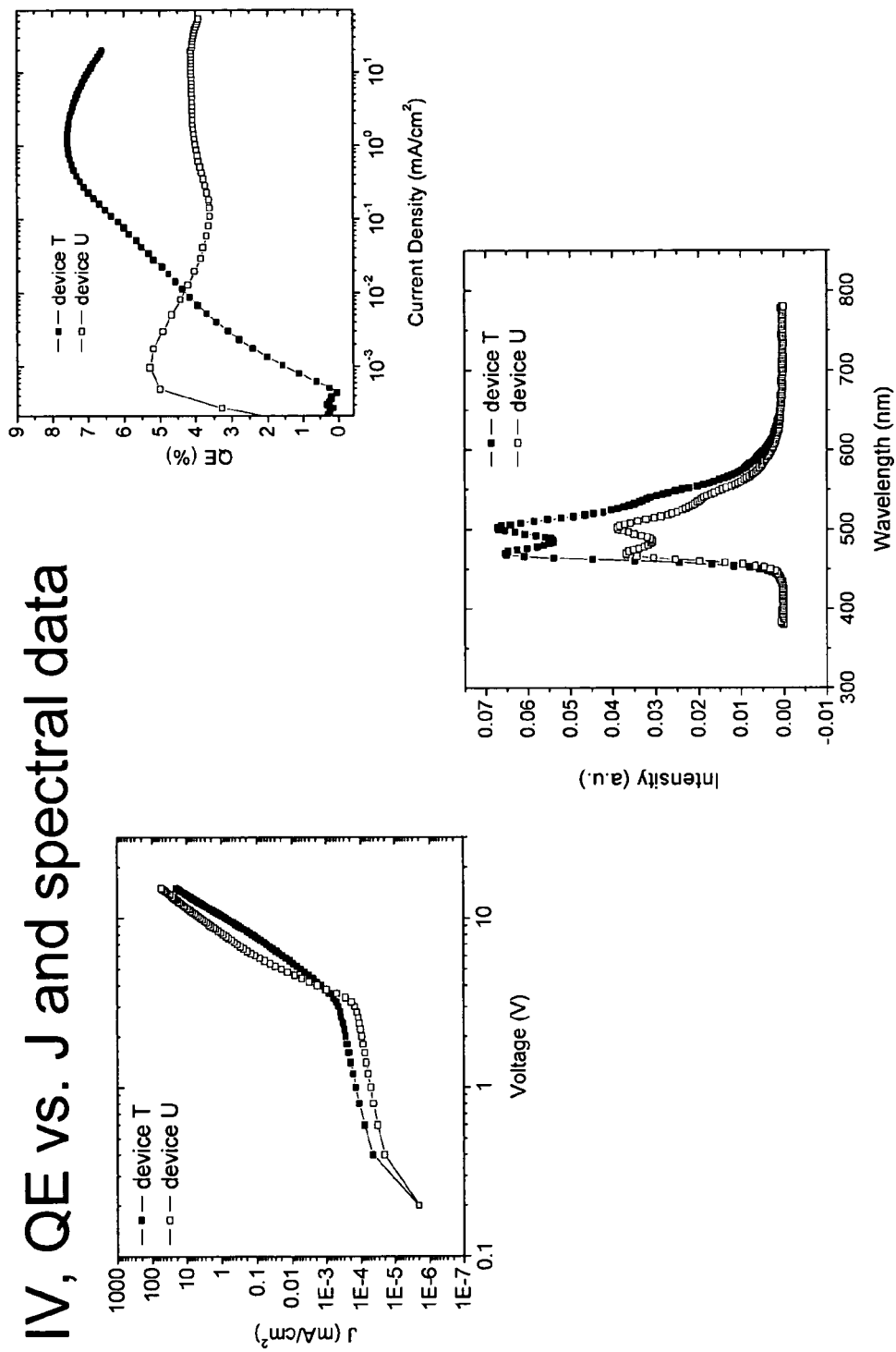
FIG. 16 shows IV, quantum efficiency (QE) vs current (J) and spectral data for devices T and U.
Figure 17:
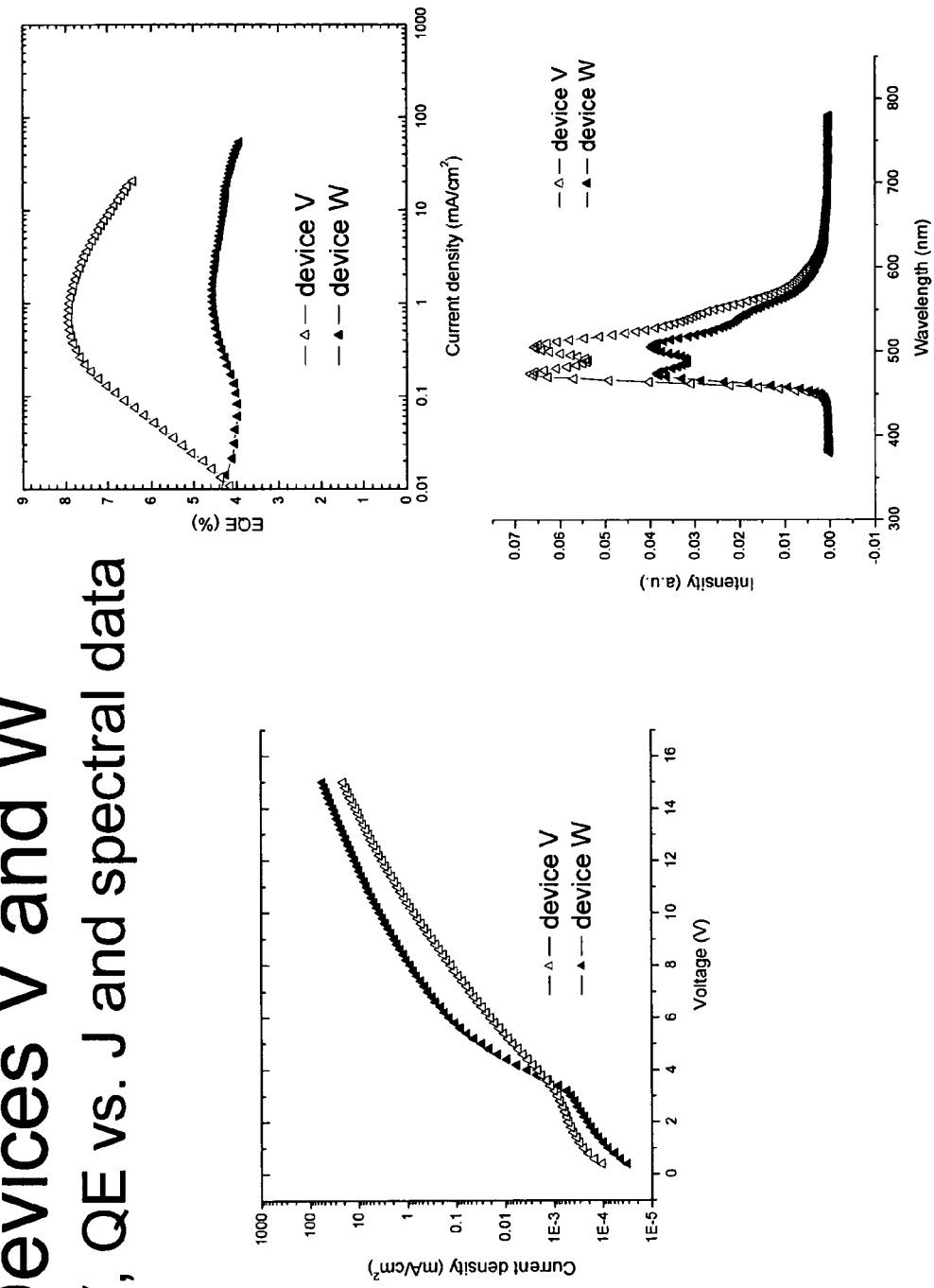
FIG. 17 shows IV, quantum efficiency (QE) vs current (J) and spectral data for devices V and W.
Figure 18:
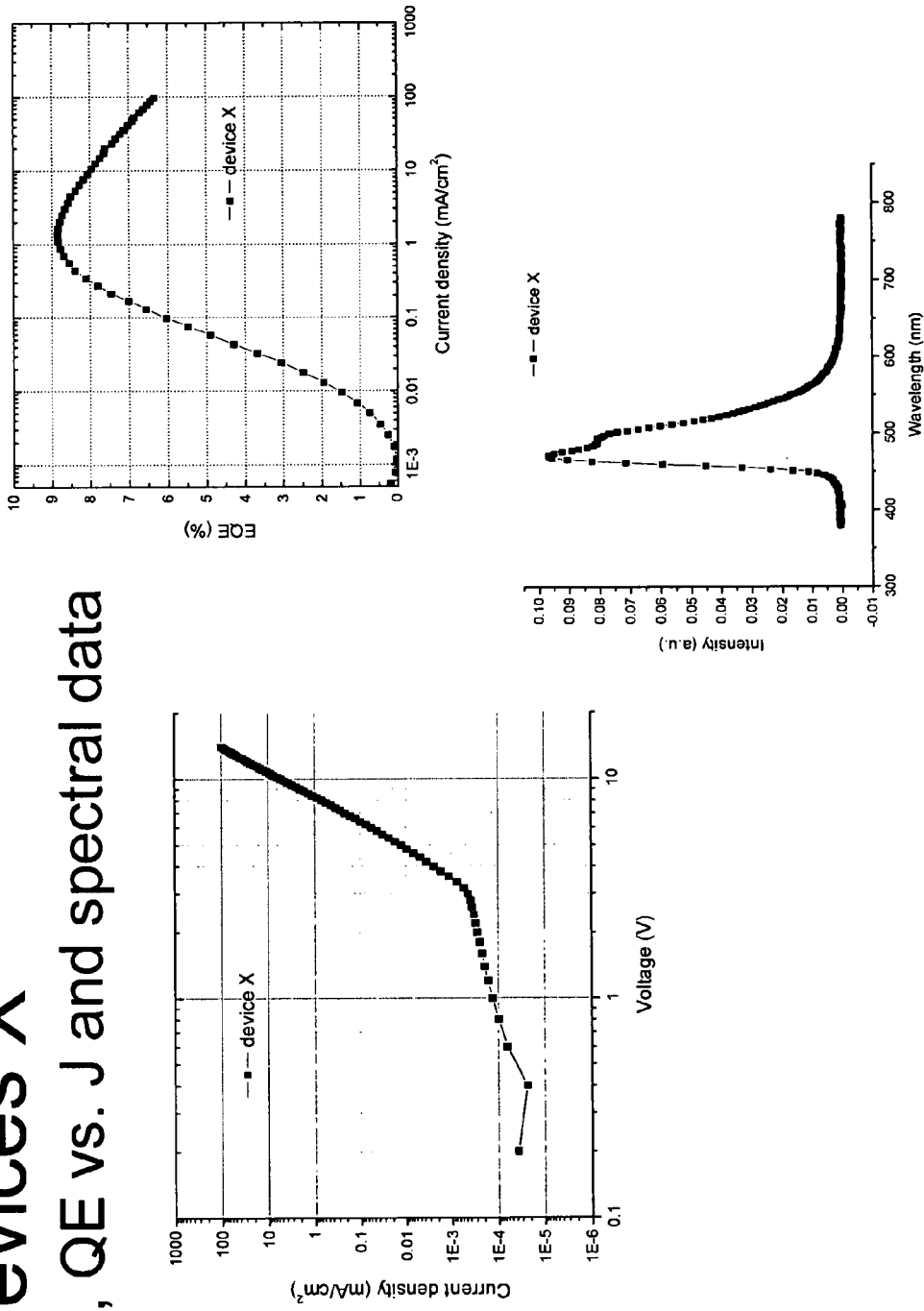
FIG. 18 shows IV, quantum efficiency (QE) vs current (J) and spectral data for device X.
Figure 19:
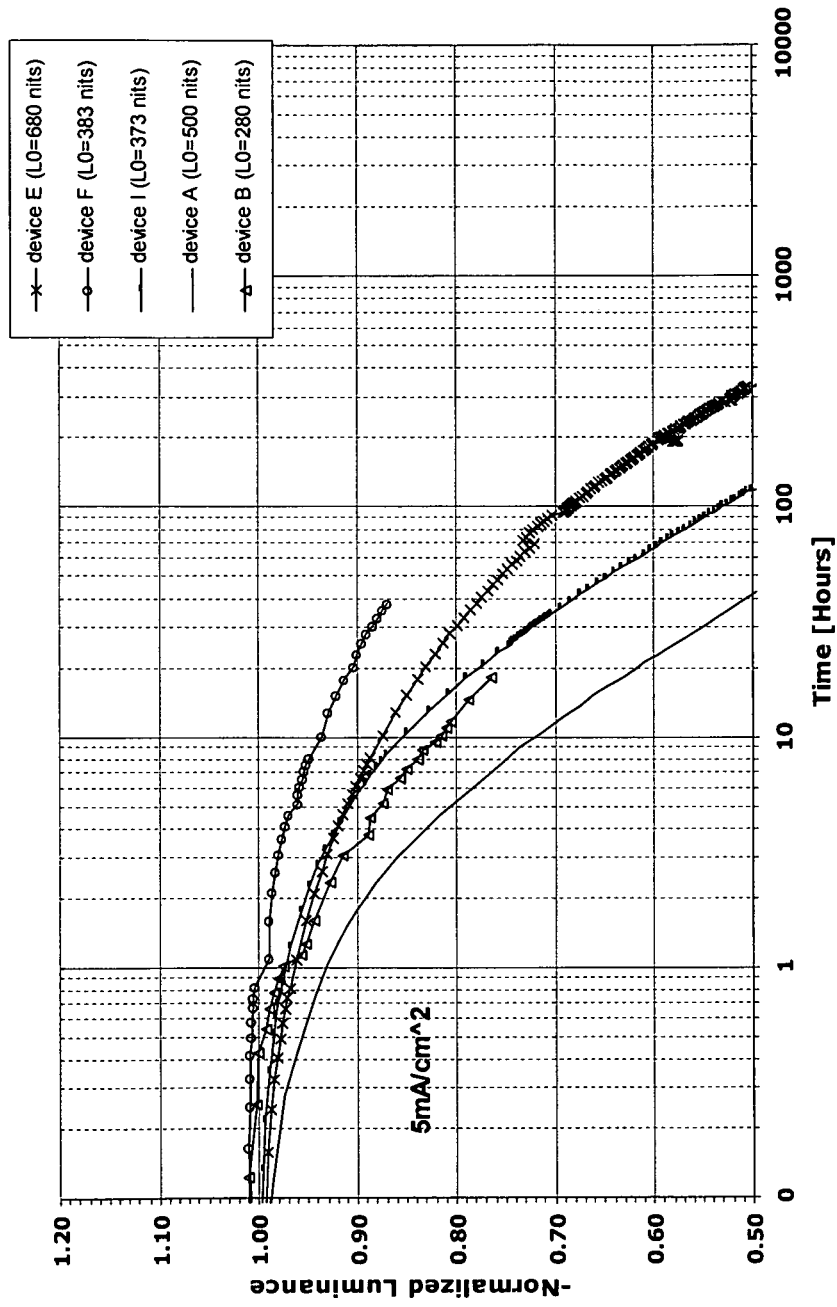
FIG. 19 shows the normalized luminescence as a function of time at 5 mA/cm$^2$ current density for devices A, B, E, F and I.
Figure 20:
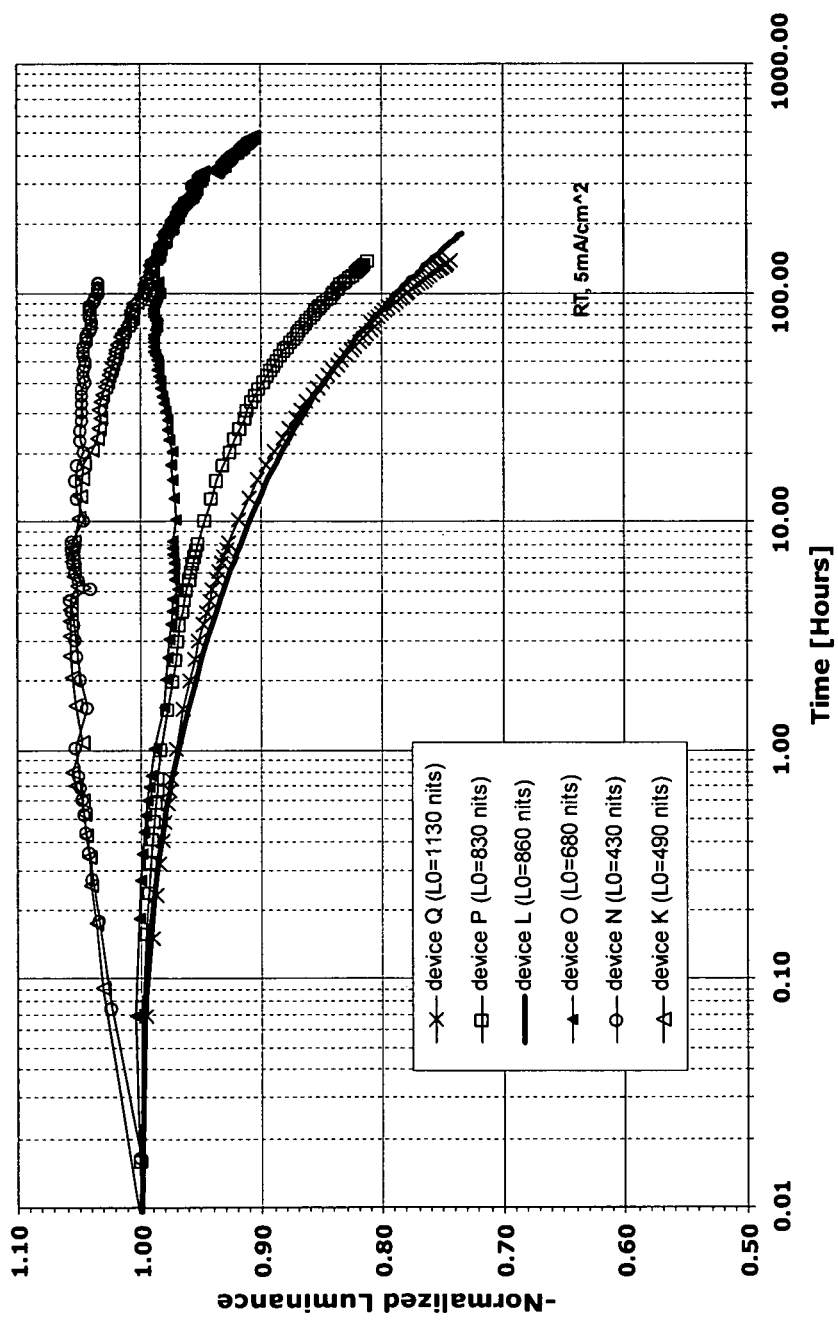
FIG. 20 shows the normalized luminescence as a function of time at 5 mA/cm$^2$ current density for devices K, L, N, O, P, and Q.
Figure 21:
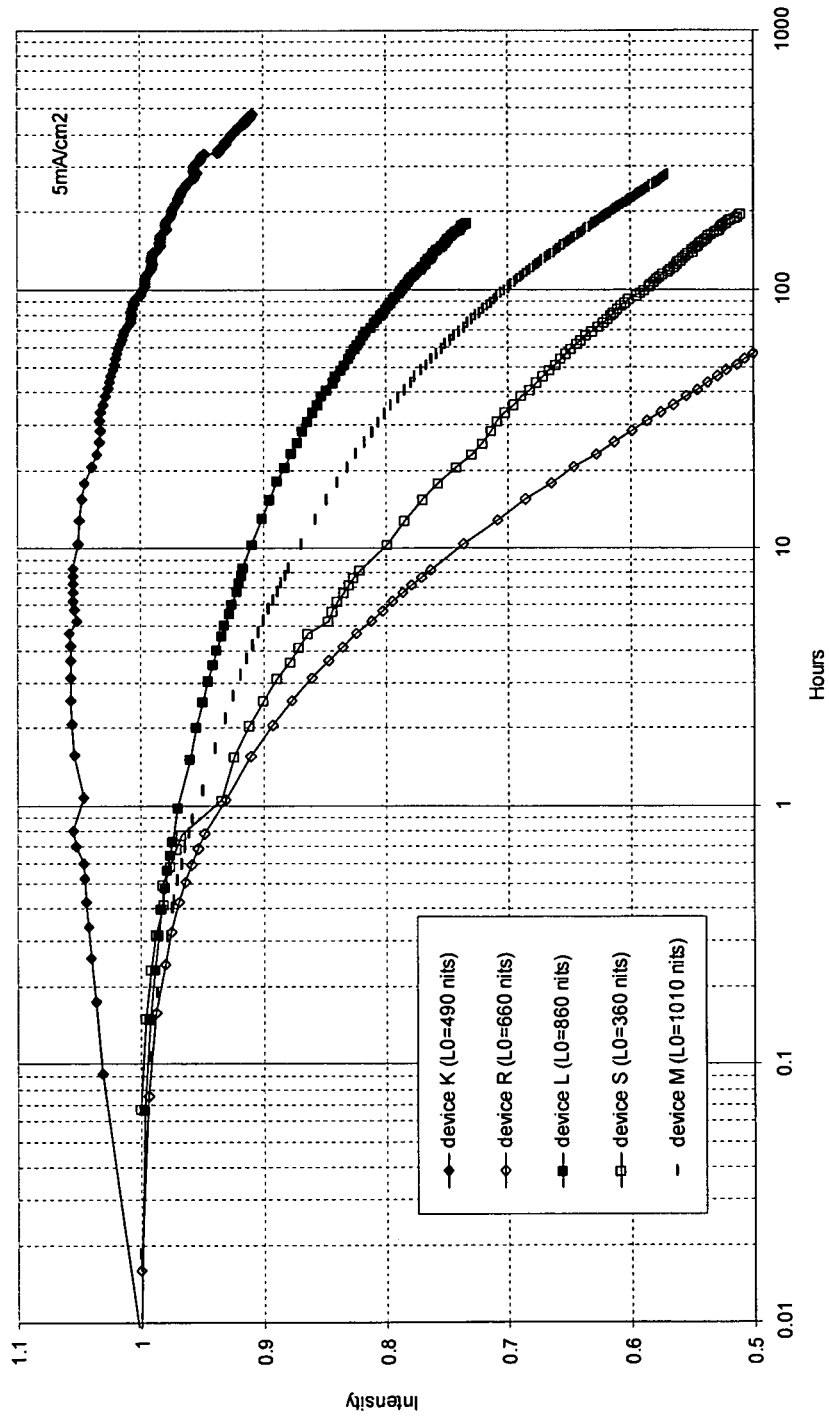
FIG. 21 shows the normalized luminescence as a function of time at 5 mA/cm$^2$ current density for devices K, R, L, S, and M.
Figure 22:
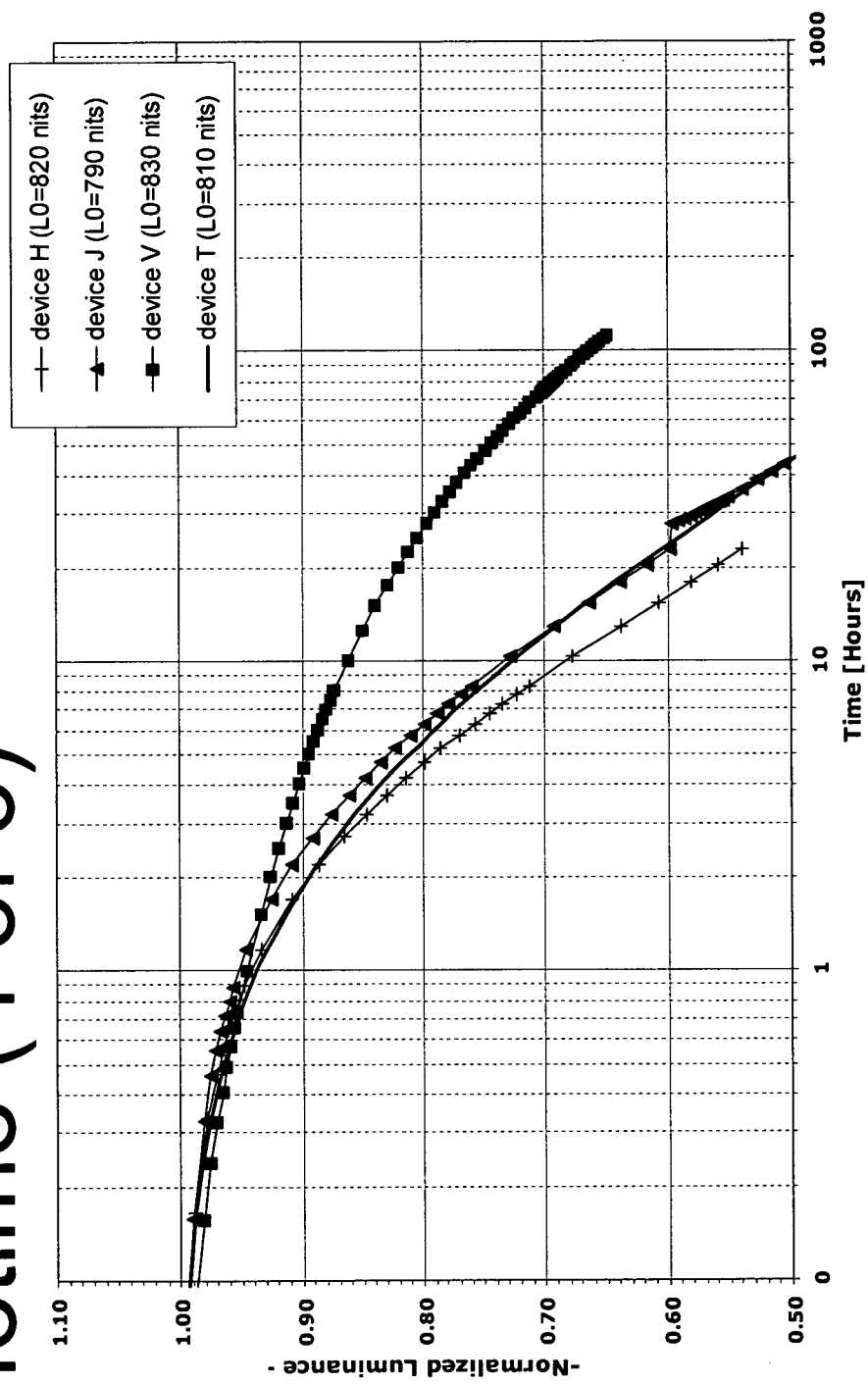
FIG. 22 shows the normalized luminescence as a function of time at 5 mA/cm$^2$ current density for devices H, J, V and T.
Figure 23:
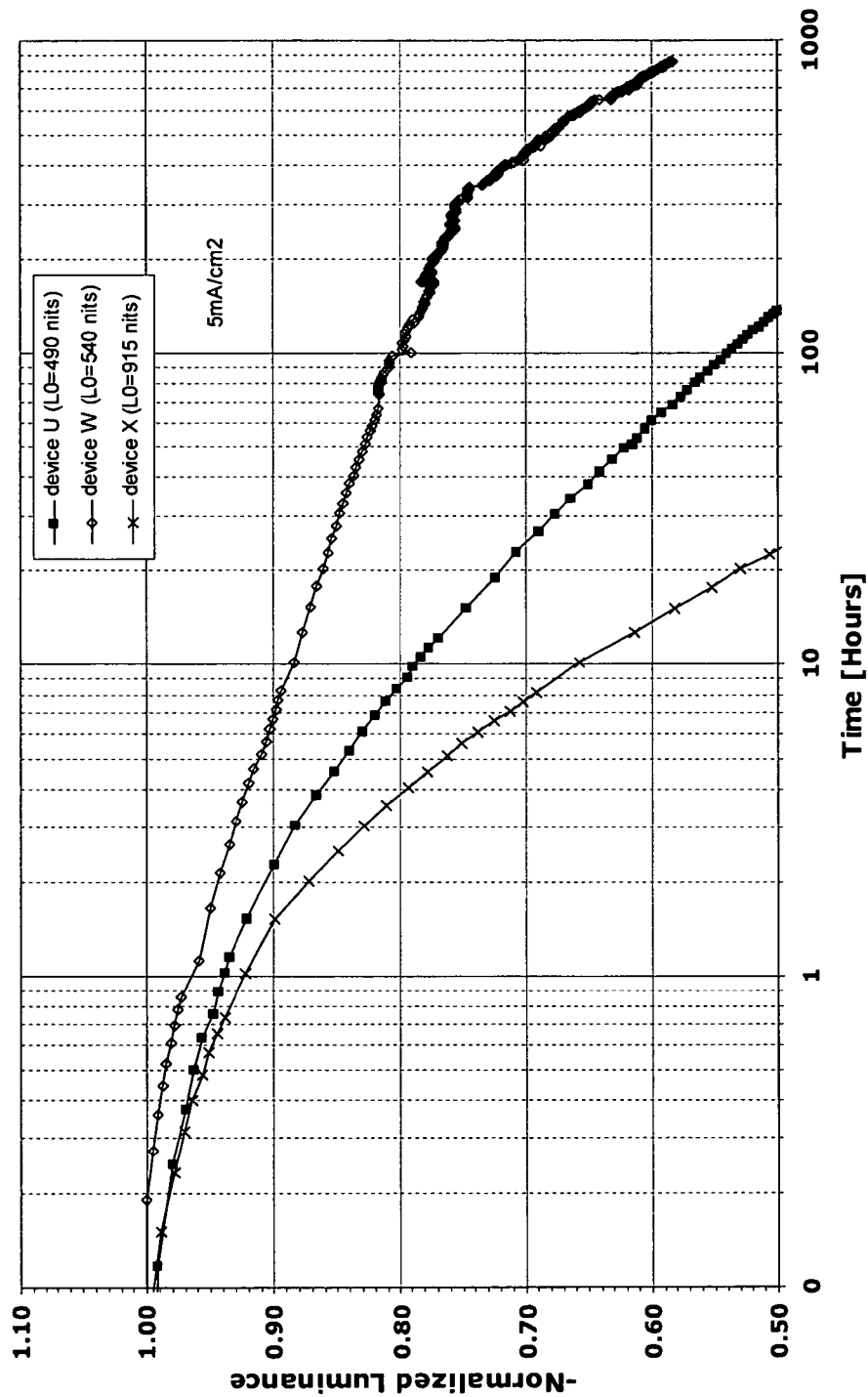
FIG. 23 shows the normalized luminescence as a function of time at 5 mA/cm$^2$ current density for devices U, W and X.
Figure 25:
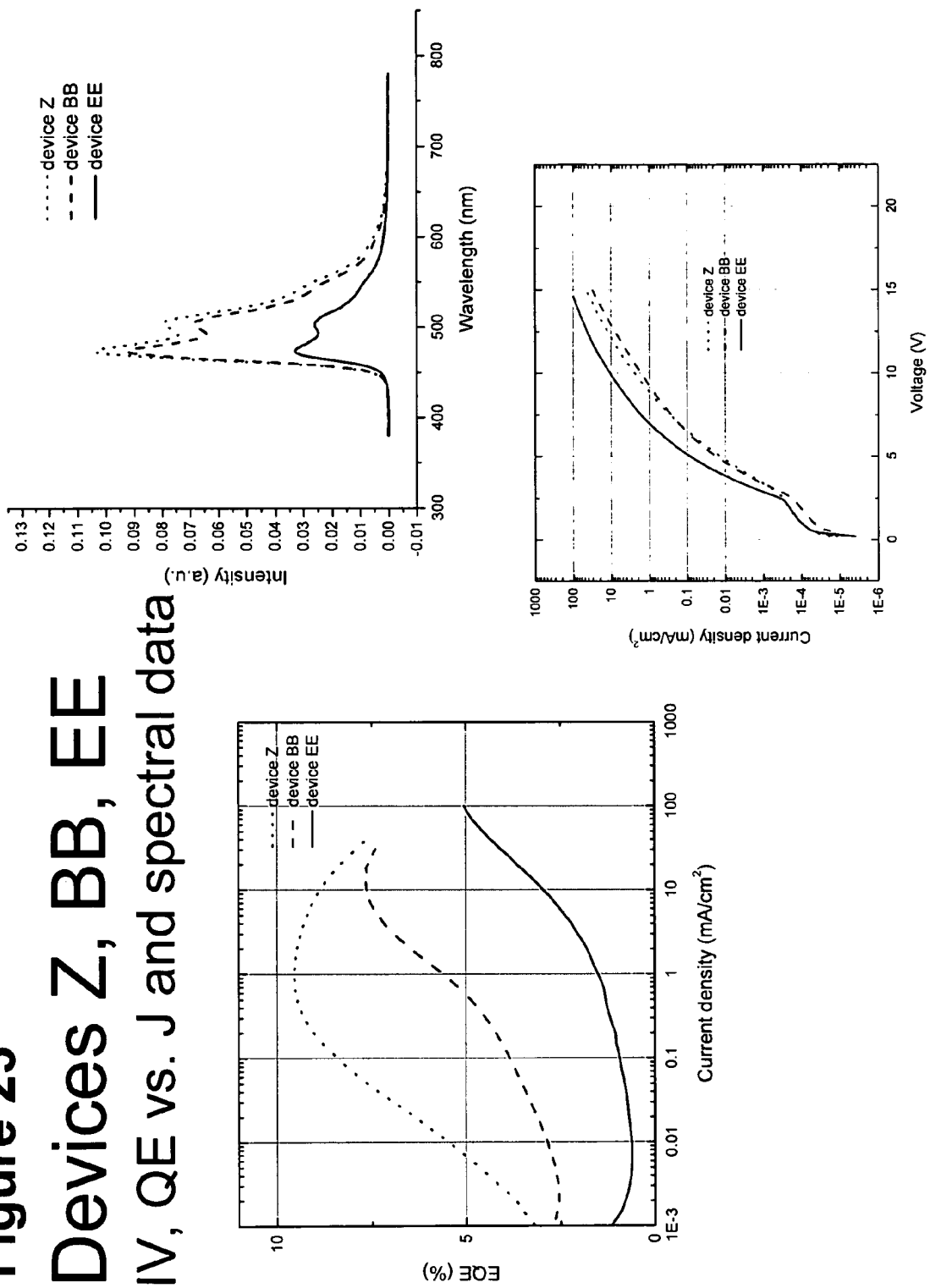
FIG. 25 shows IV, quantum efficiency (QE) vs current (J) and spectral data for devices Z, BB and EE.
Figure 26:
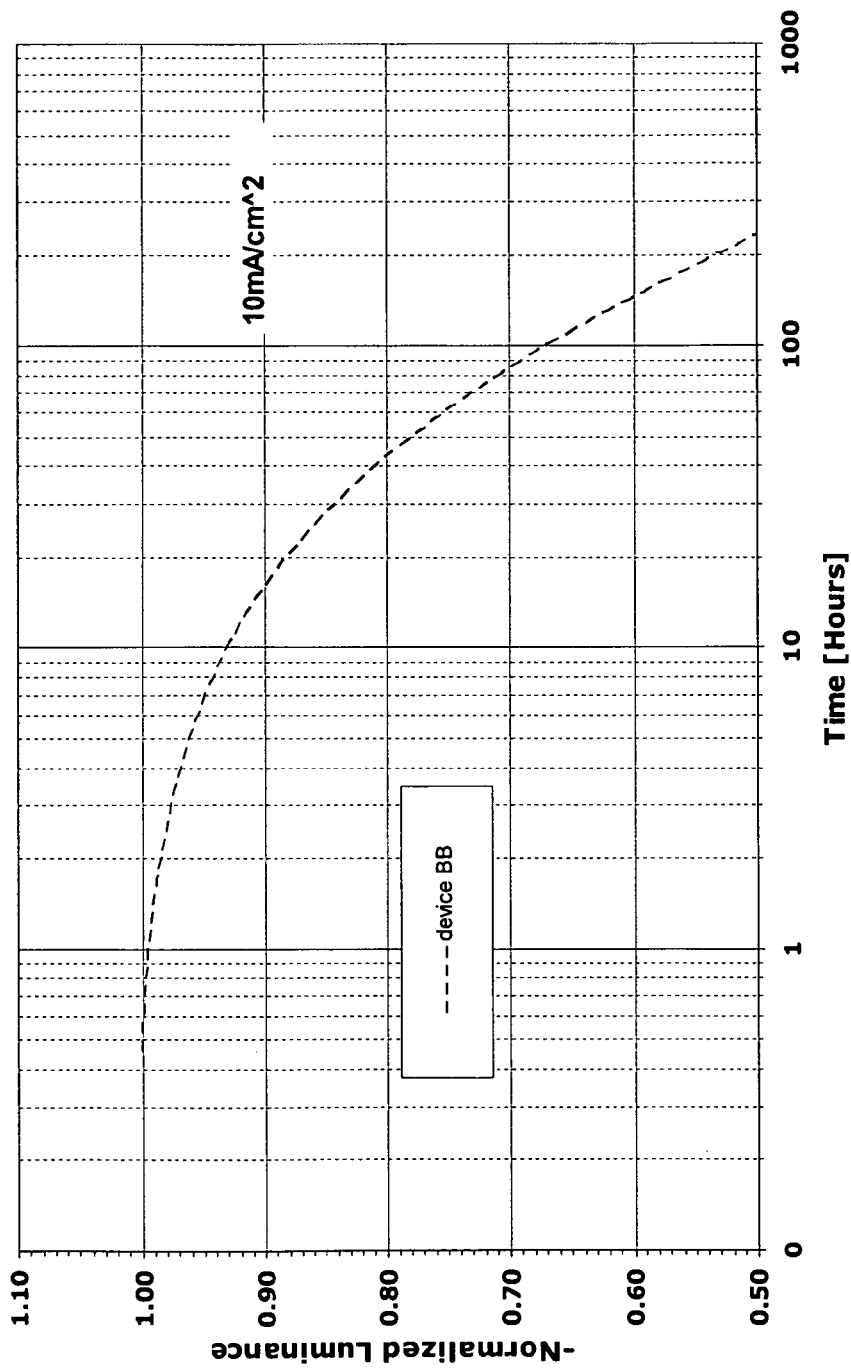
FIG. 26 shows the normalized luminescence as a function of time at 10 mA/cm$^2$ current density for device BB.
Figure 27:
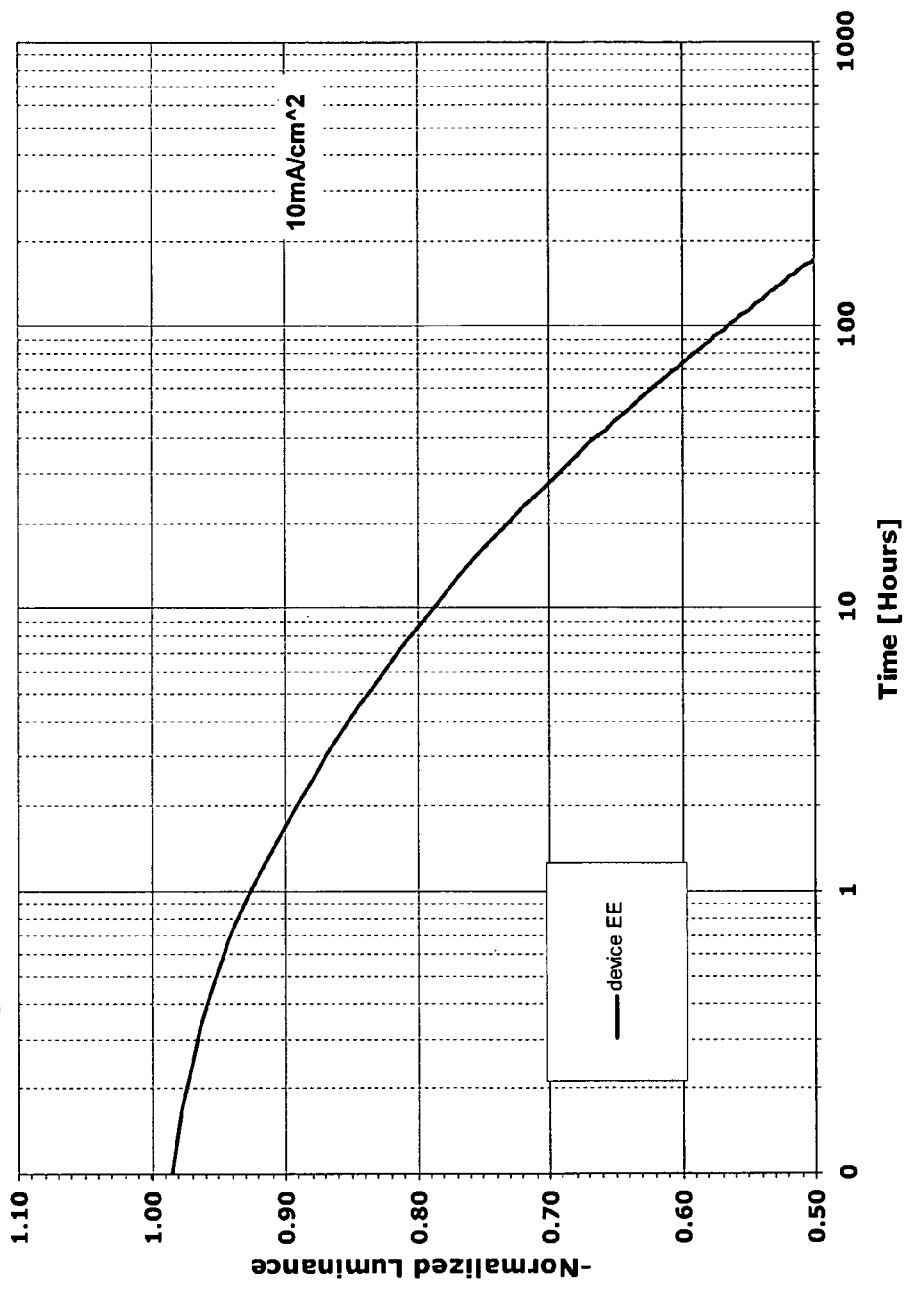
FIG. 27 shows the normalized luminescence as a function of time at 10 mA/cm$^2$ current density for device EE.
Figure 28:
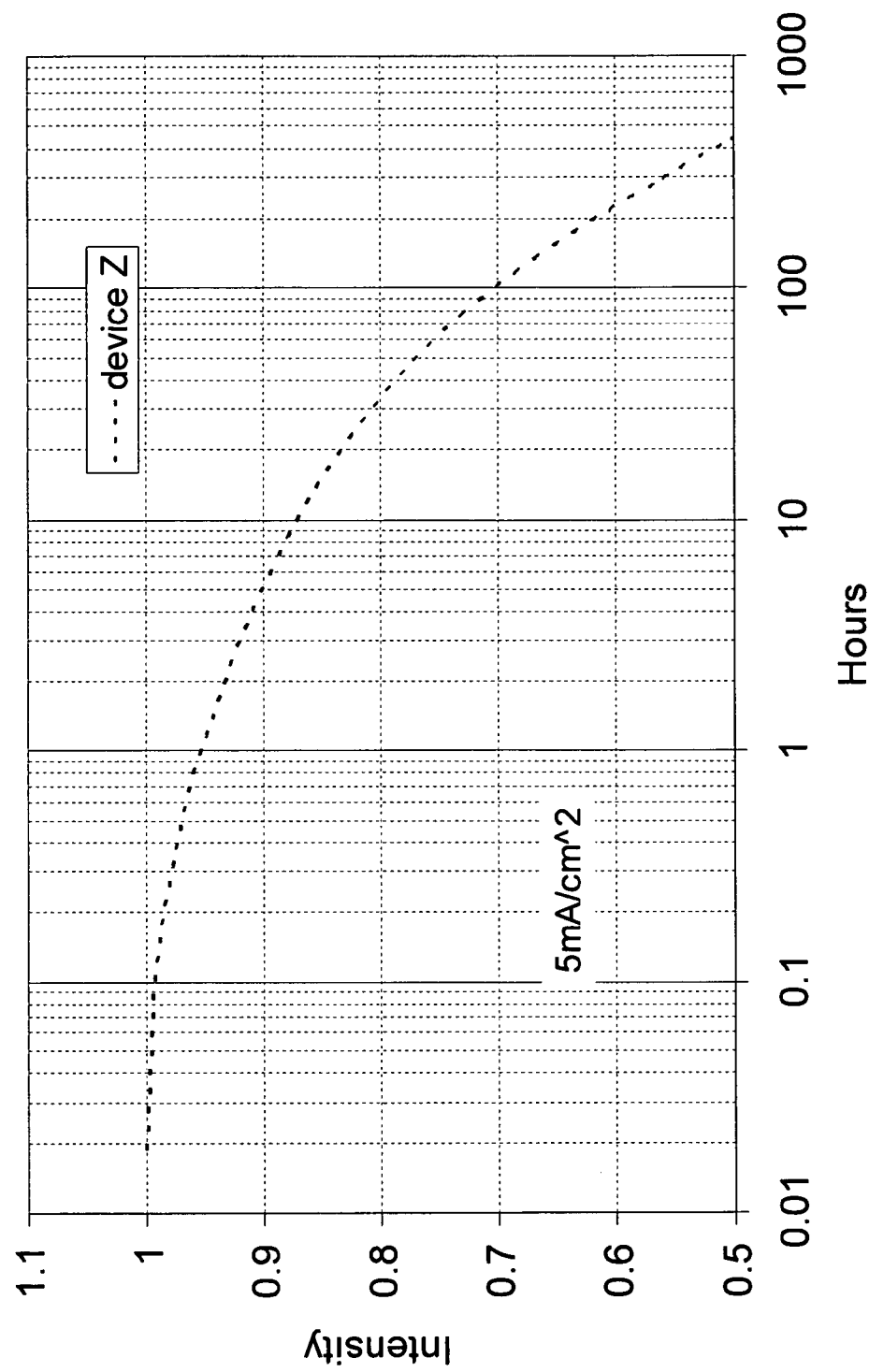
FIG. 28 shows the normalized luminescence as a function of time at 5 mA/cm$^2$ current density for device Z.
Figure 29:
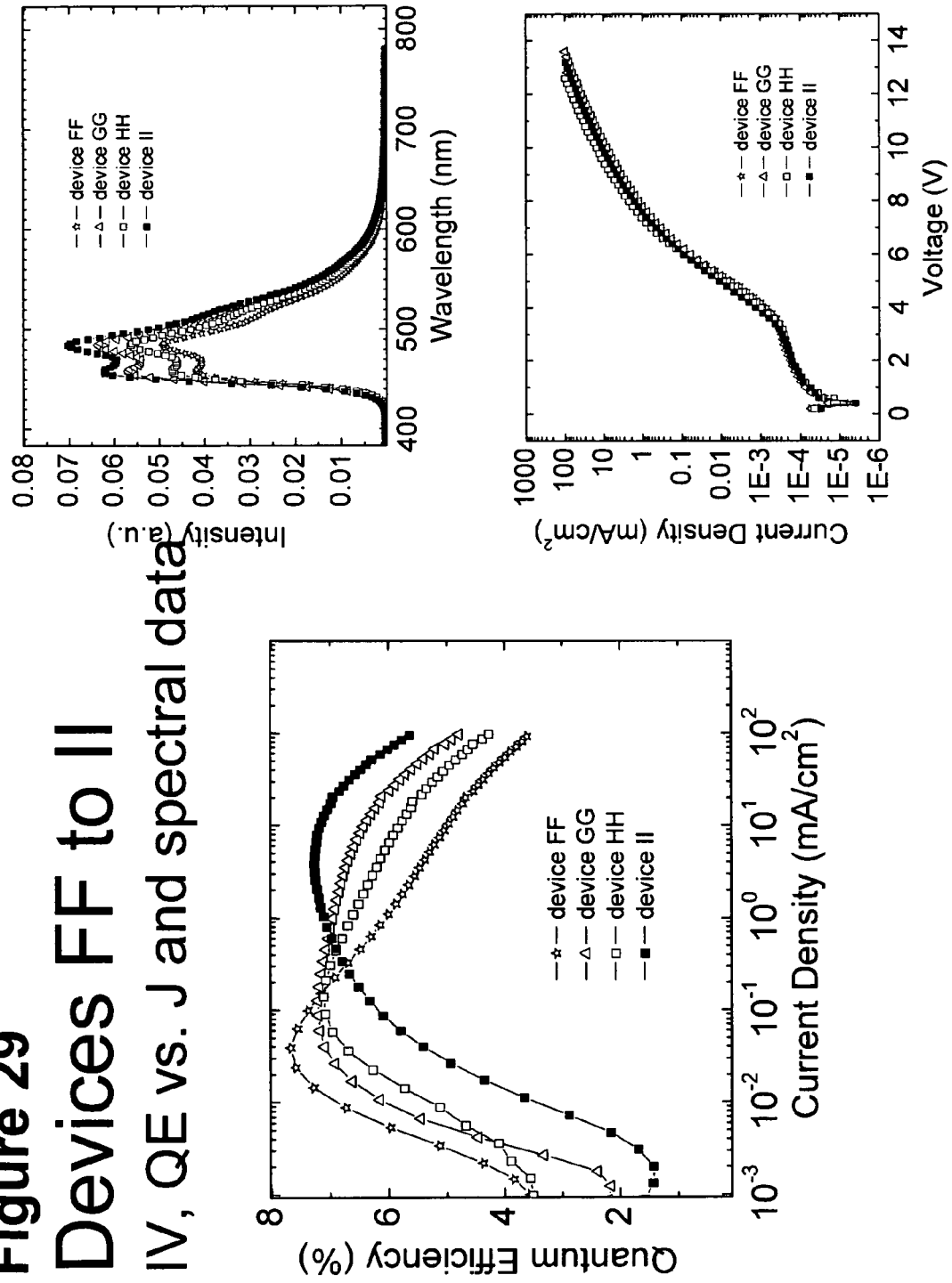
FIG. 29 shows IV, quantum efficiency (QE) vs current (J) and spectral data for devices FF, GG, HH and II.
Figure 30:
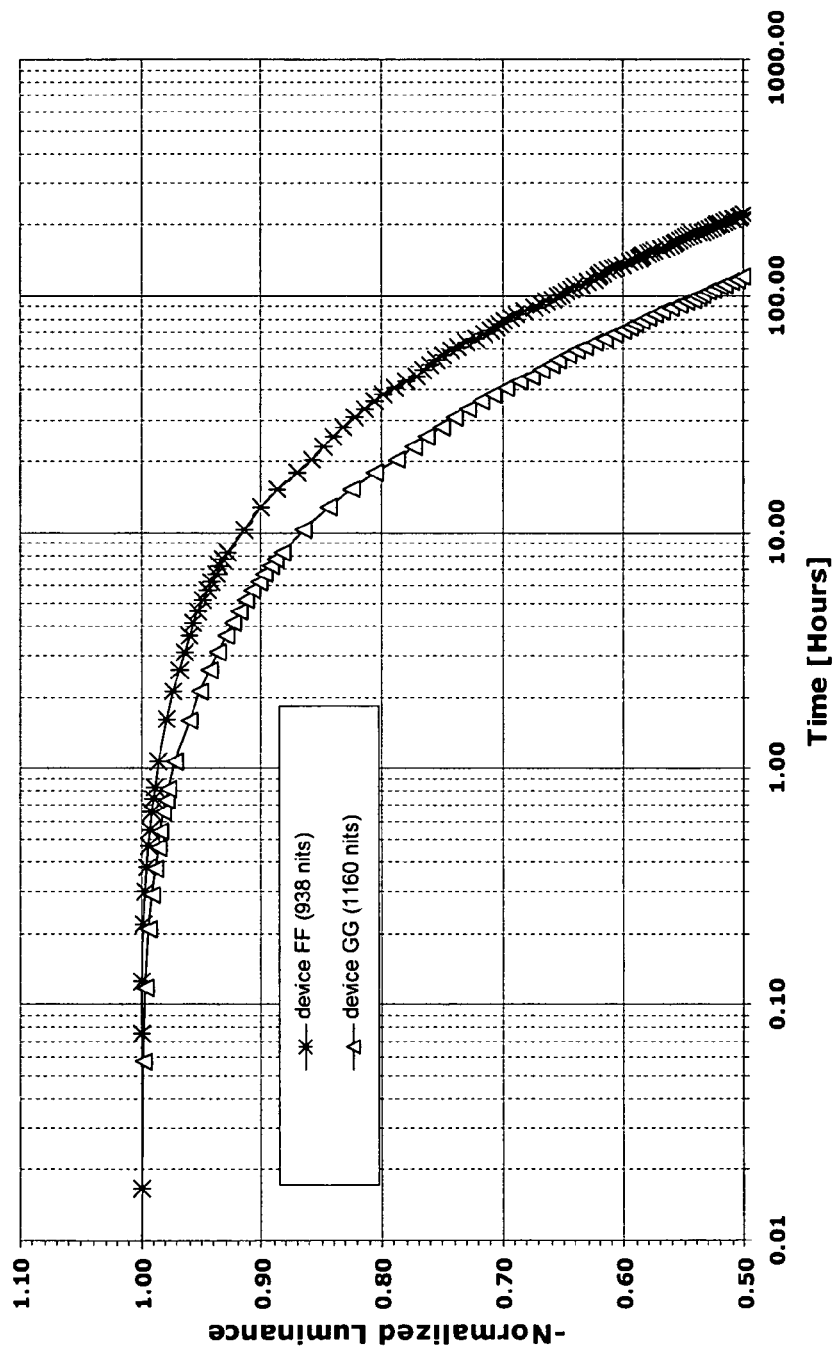
FIG. 30 shows the normalized luminescence as a function of time at 10 mA/cm$^2$ current density for devices FF and GG.
Figure 31:
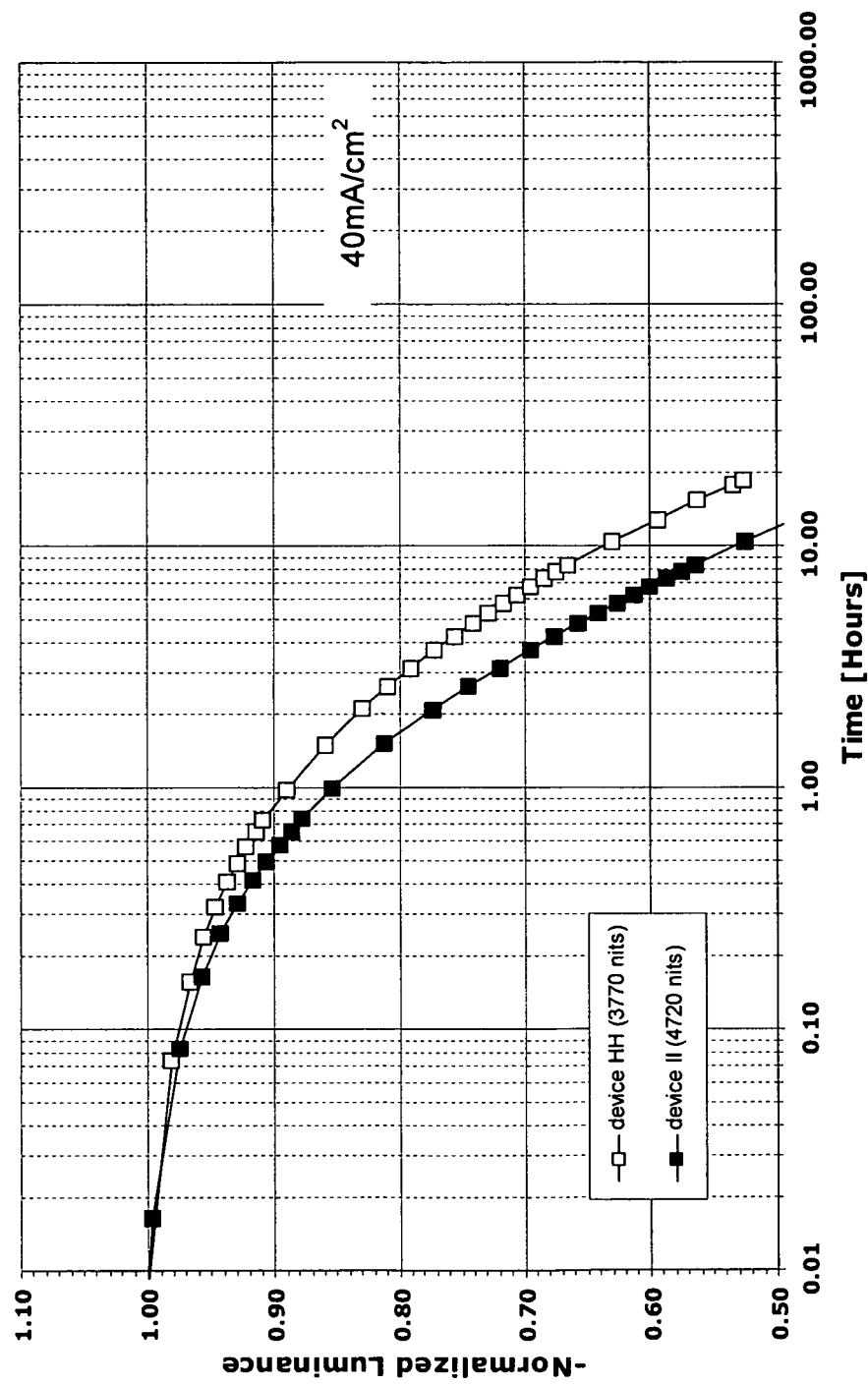
FIG. 31 shows the normalized luminescence as a function of time at 40 mA/cm$^2$ current density for devices HH and II.
Figure 32:
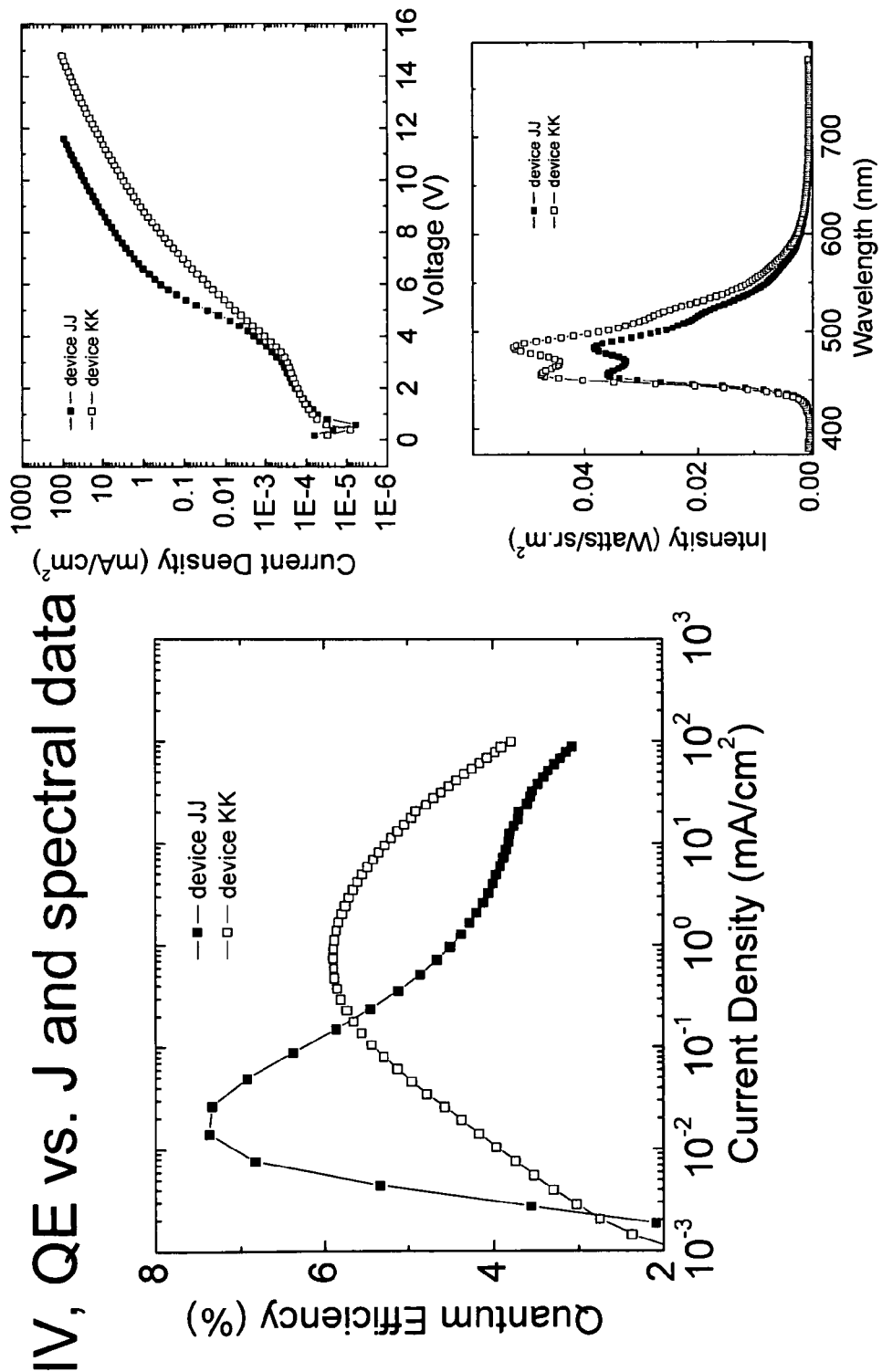
FIG. 32 shows IV, quantum efficiency (QE) vs current (J) and spectral data for devices JJ and KK.
Figure 34:
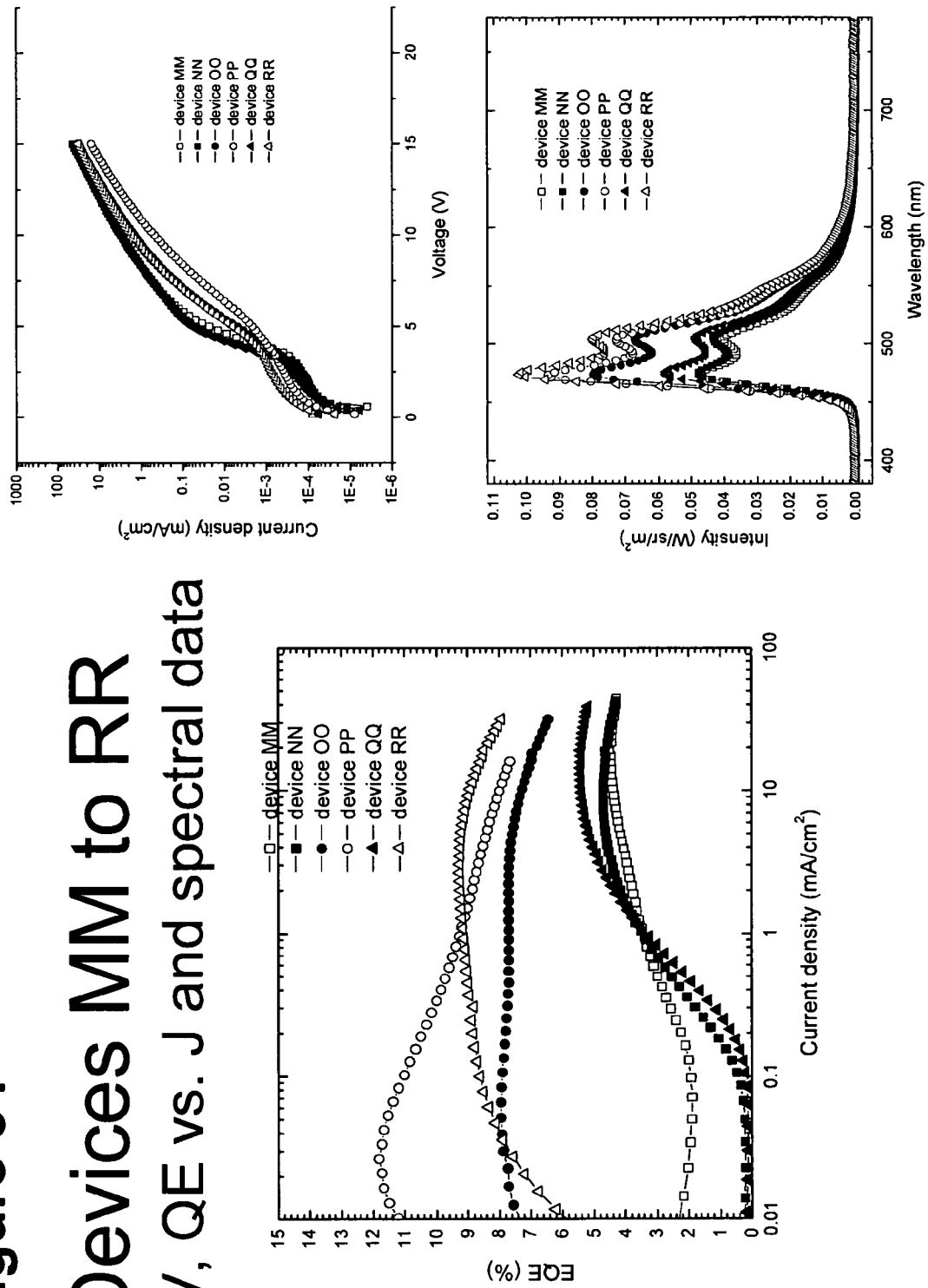
FIG. 34 shows IV, quantum efficiency (QE) vs current (J) and spectral data for devices MM, NN, OO, PP and RR.
Figure 35:
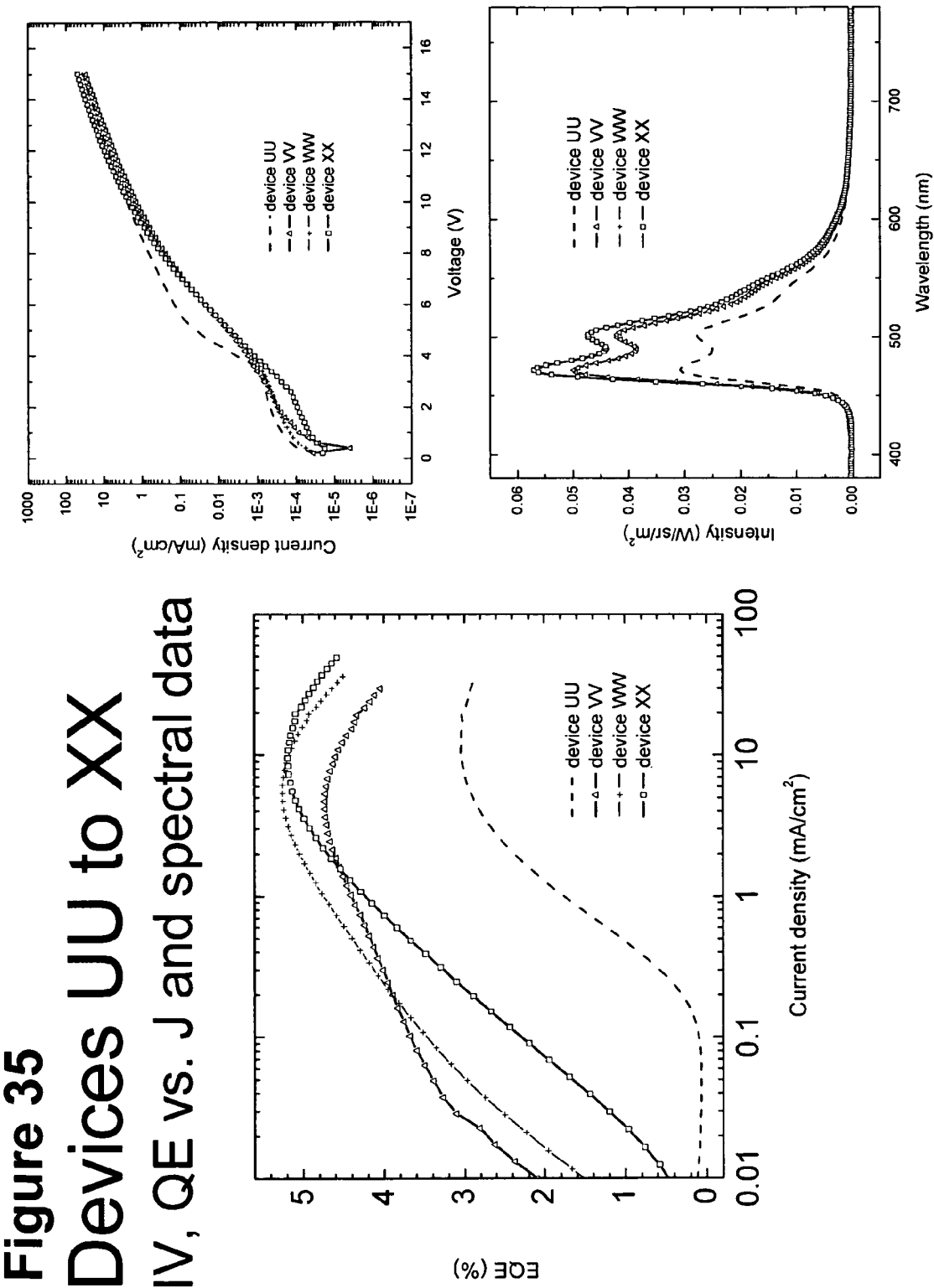
FIG. 35 shows IV, quantum efficiency (QE) vs current (J) and spectral data for devices UU, VV, WW, XX.
Figure 36:
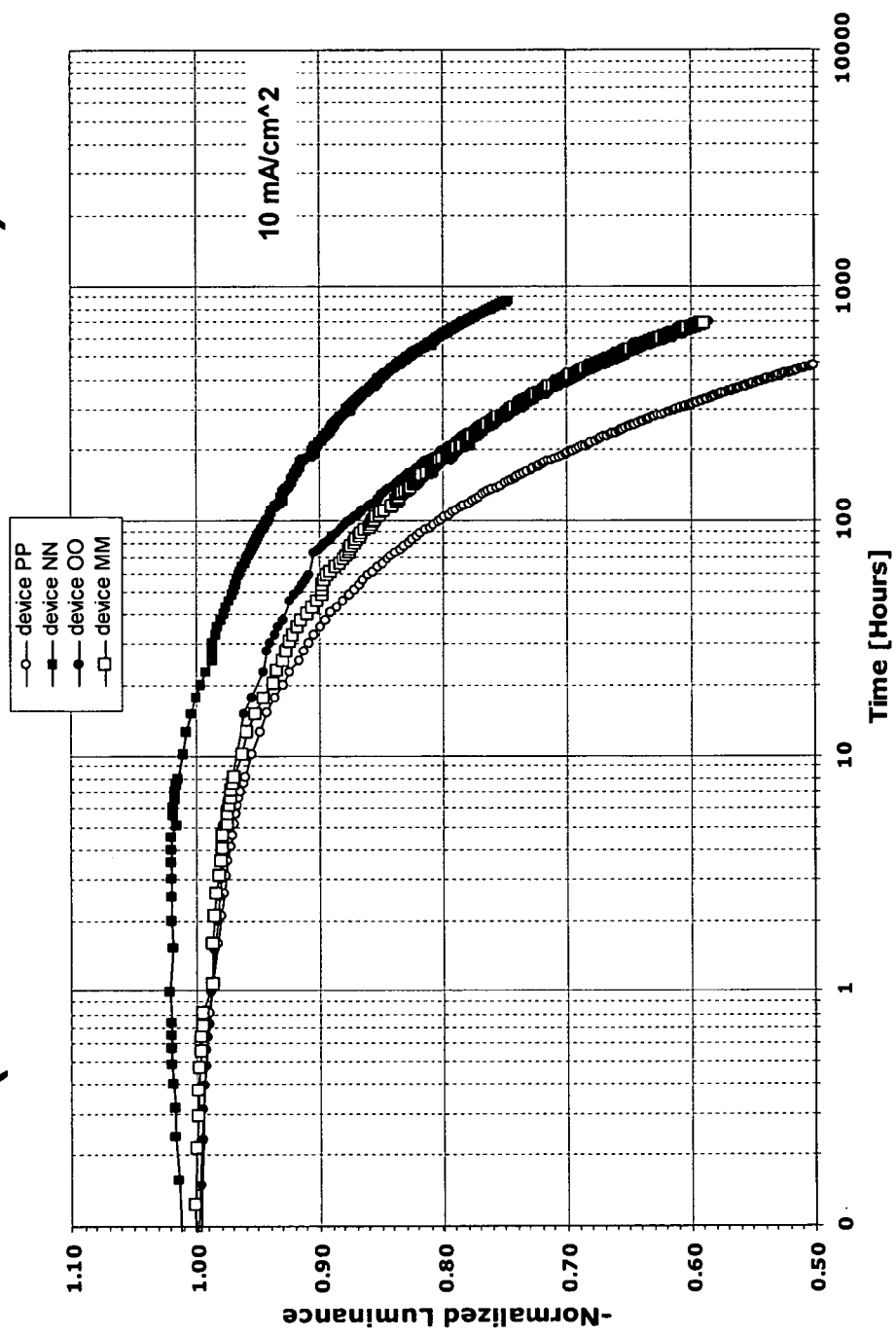
FIG. 36 shows the normalized luminescence as a function of time at 10 mA/cm$^2$ current density for devices MM, NN, OO and PP.
Figure 37:
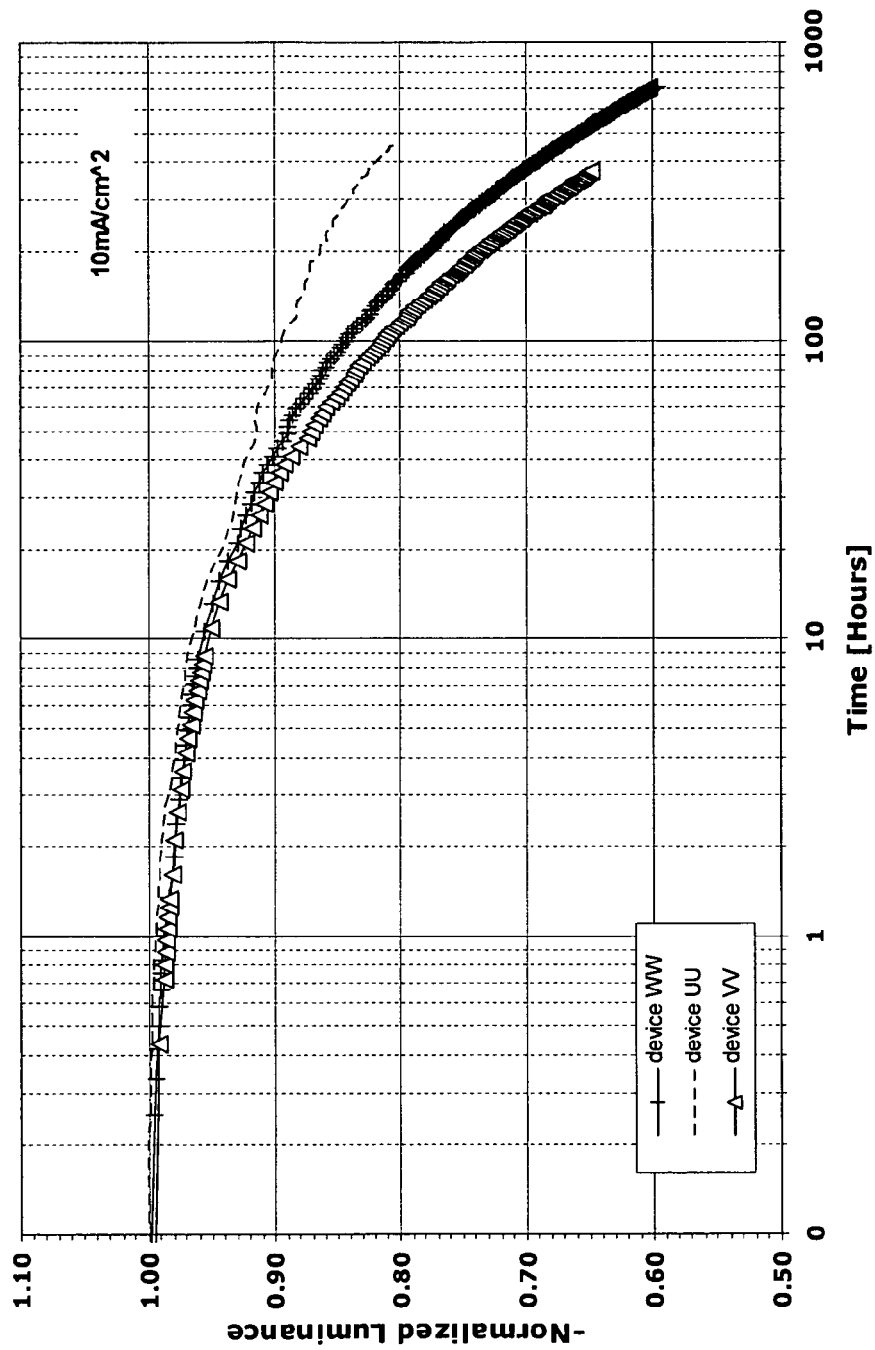
FIG. 37 shows the normalized luminescence as a function of time at 10 mA/cm$^2$ current density for devices UU, VV and WW.
Figure 39:
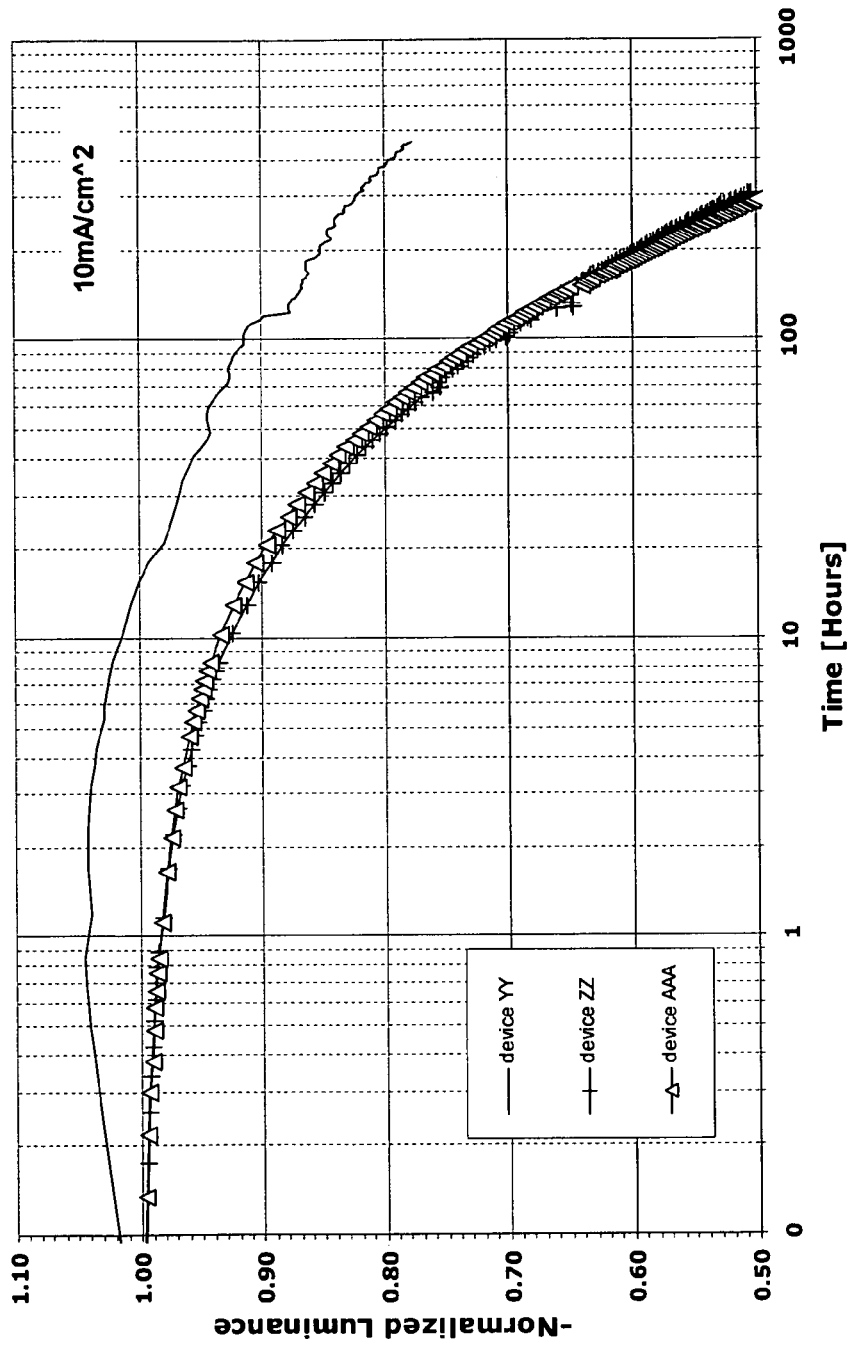
FIG. 39 shows the normalized luminescence as a function of time at 10 mA/cm² current density for devices YY, ZZ and AAA.
Figure 40:
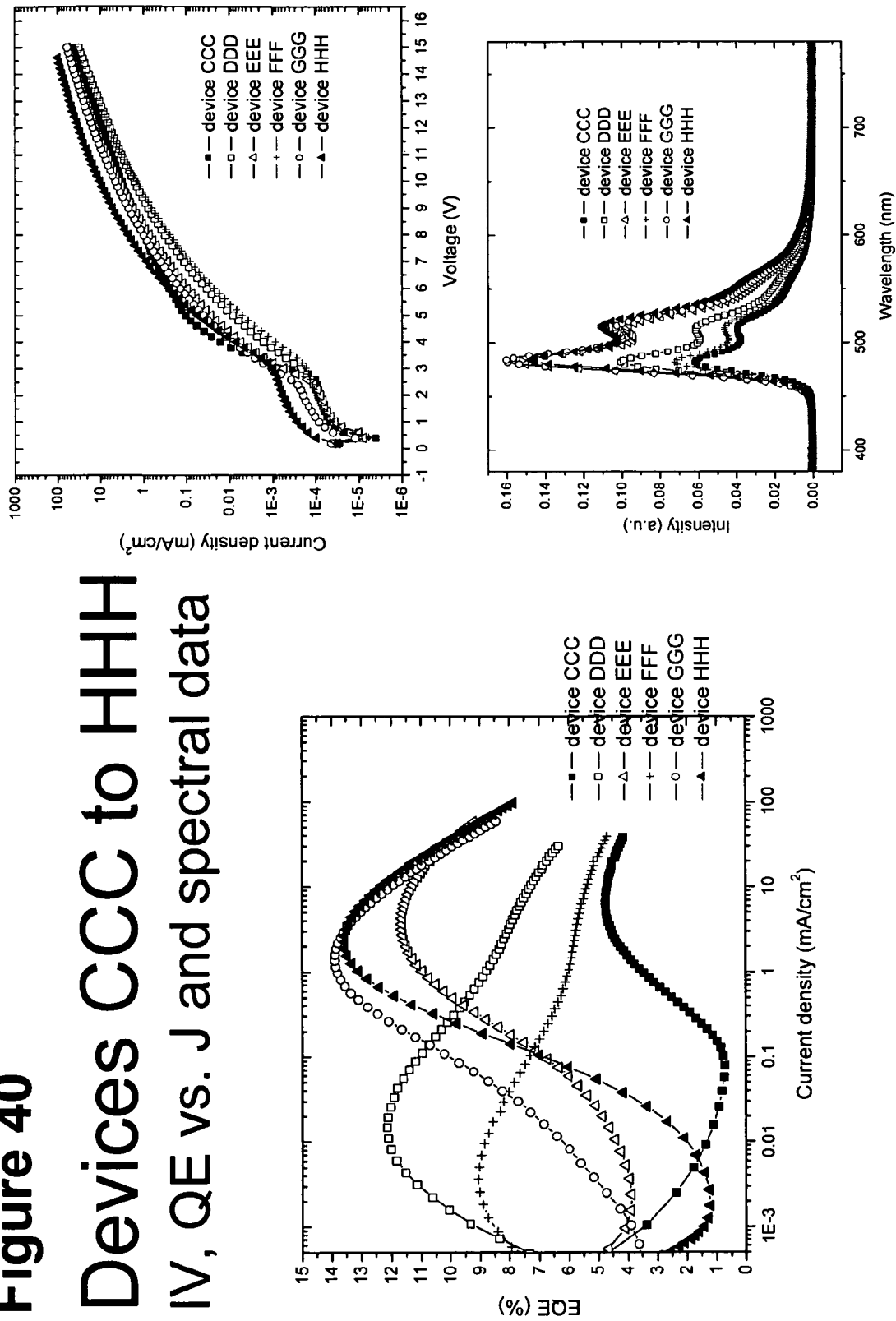
FIG. 40 shows IV, quantum efficiency (QE) vs current (J) and spectral data for devices CCC, DDD, EEE, FFF, GGG and HHH.
Figure 41:
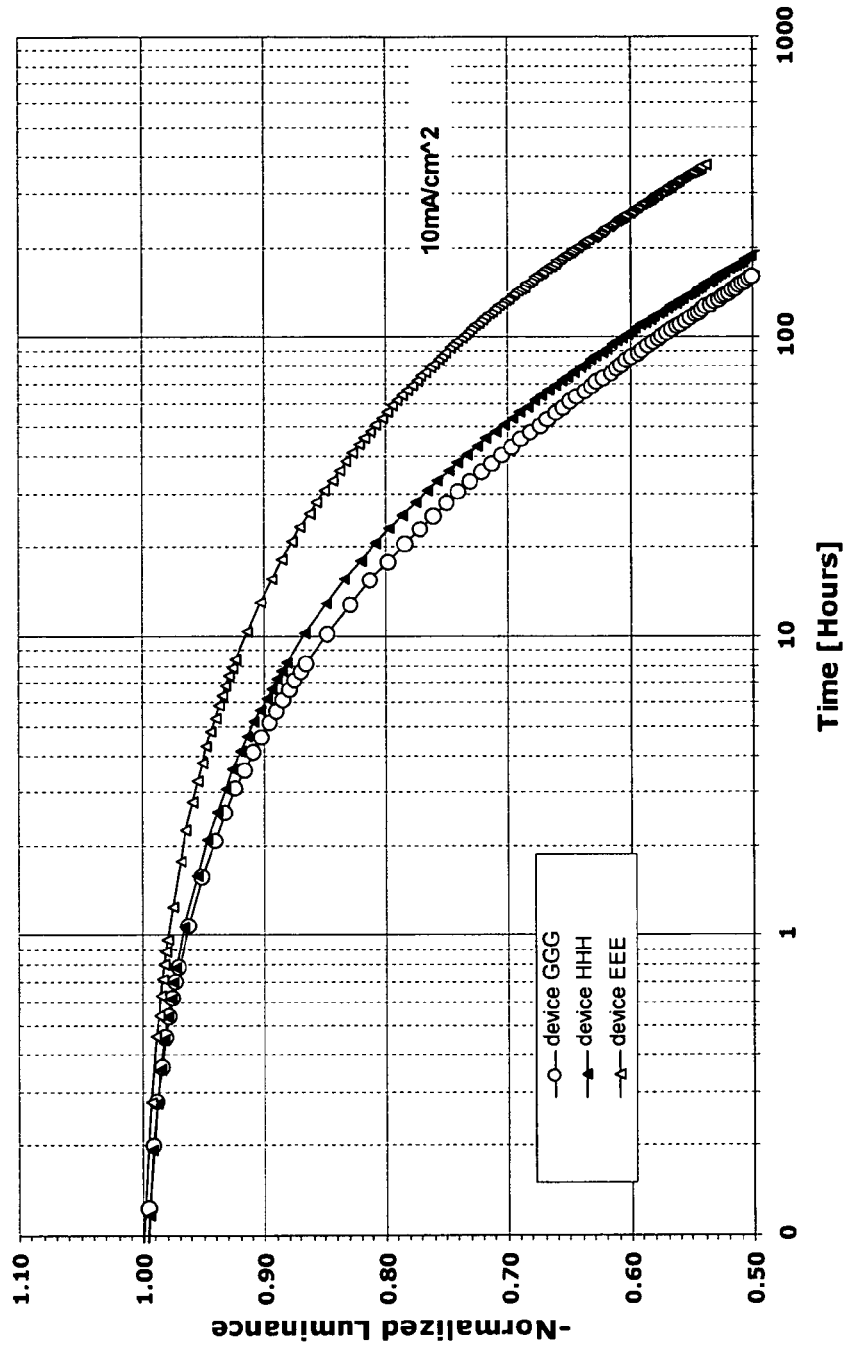
FIG. 41 shows the normalized luminescence as a function of time at 10 mA/cm² current density for devices EEE, GGG and HHH.
Figure 42:
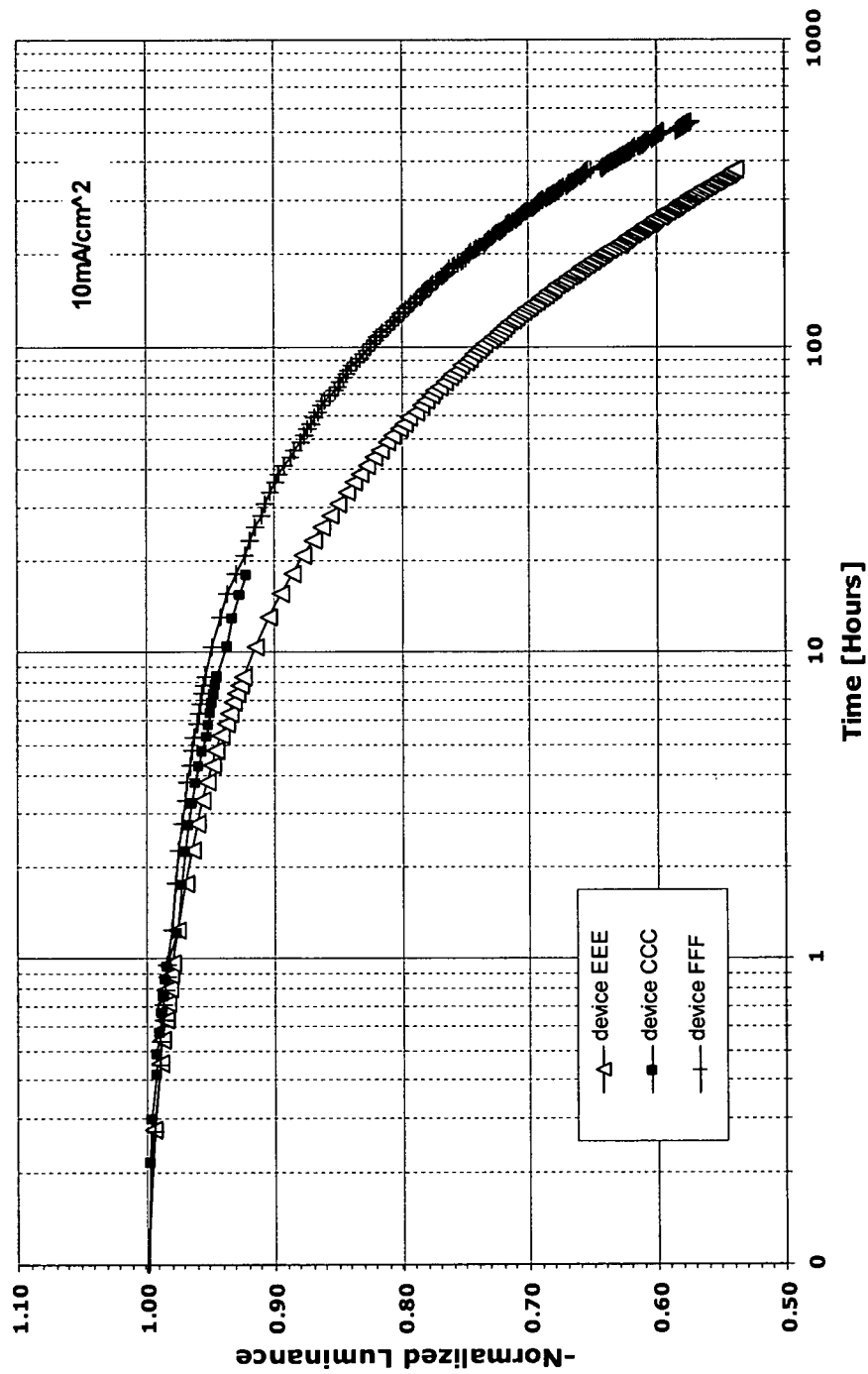
FIG. 42 shows the normalized luminescence as a function of time at 10 mA/cm² current density for devices EEE, CCC and FFF.
Figure 44:
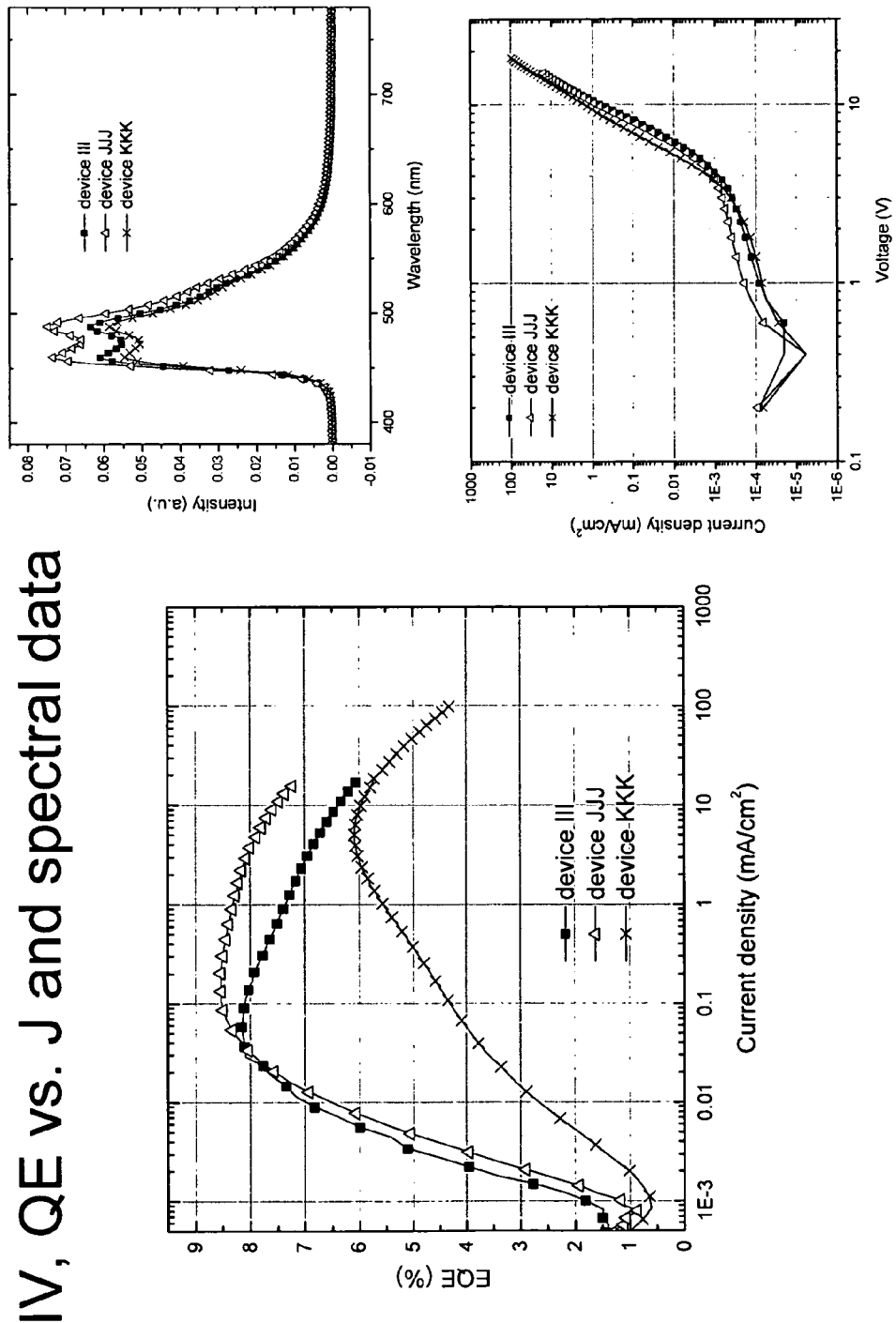
FIG. 44 shows IV, quantum efficiency (QE) vs current (J) and spectral data for devices III, JJJ and KKK.
Figure 47:
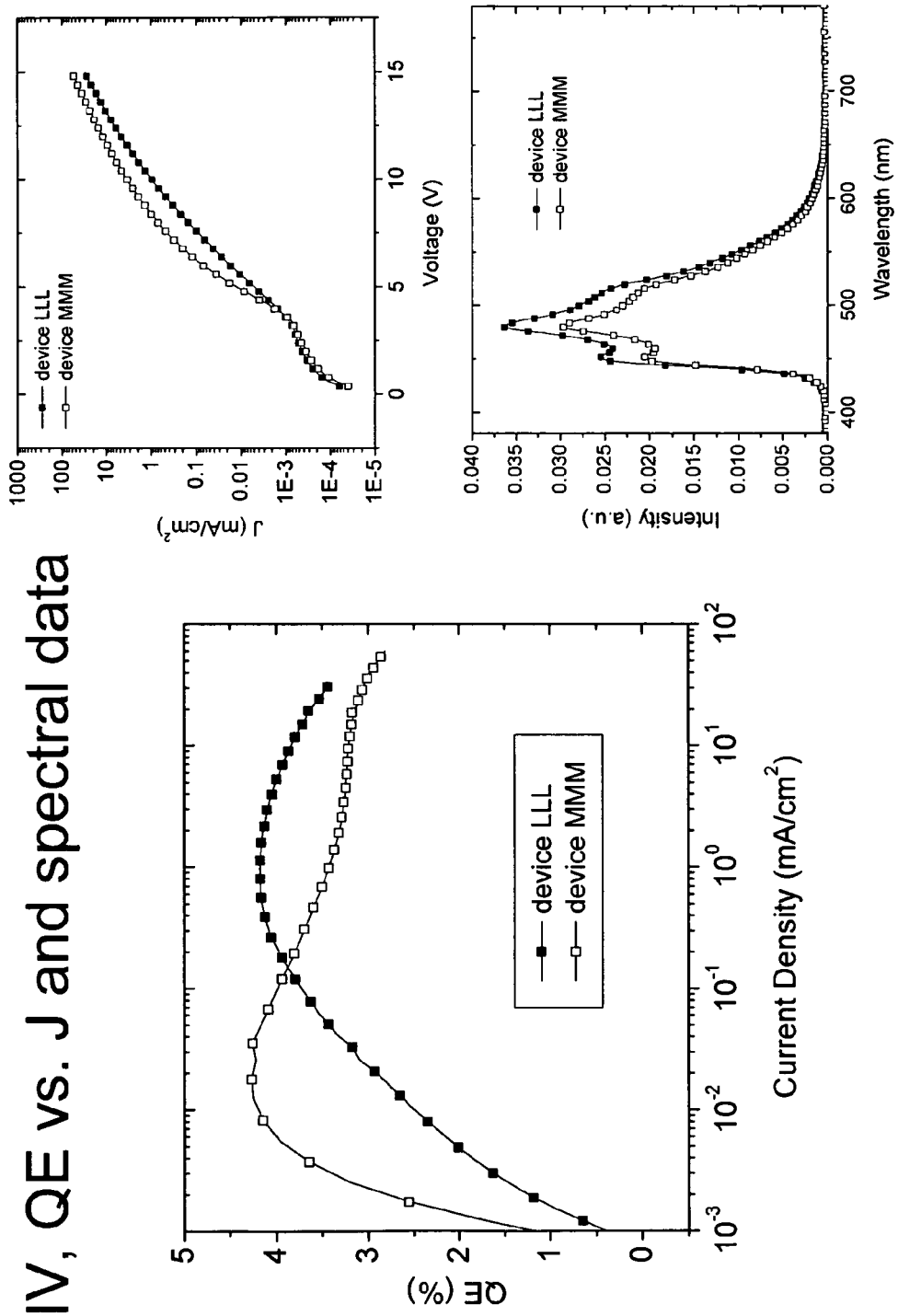
FIG. 47 shows IV, quantum efficiency (QE) vs current (J) and spectral data for devices LLL and MMM.
Figure 48:
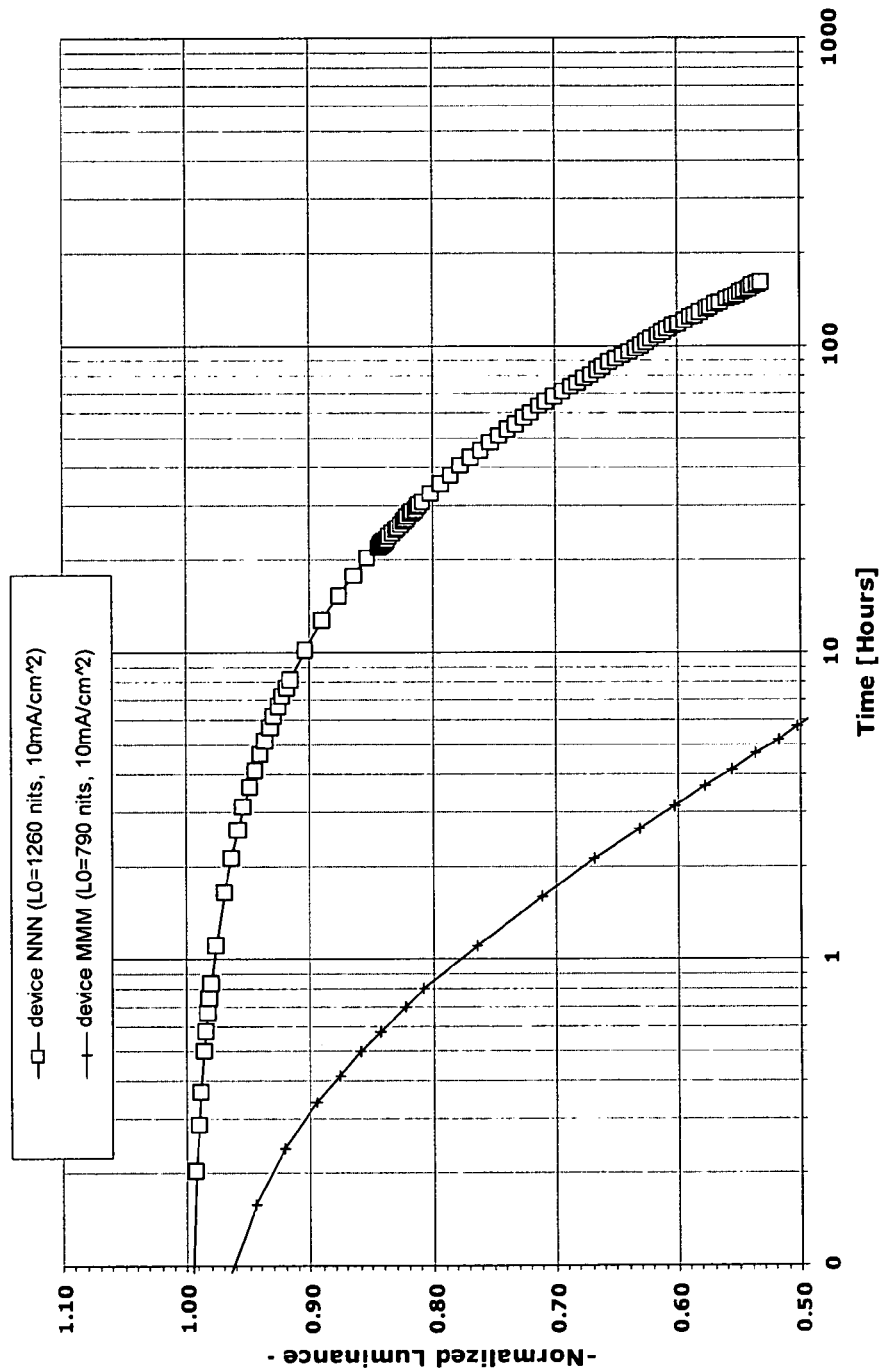
FIG. 48 shows the normalized luminescence as a function of time at 10 mA/cm² current density for devices MMM and NNN.
Figure 49:
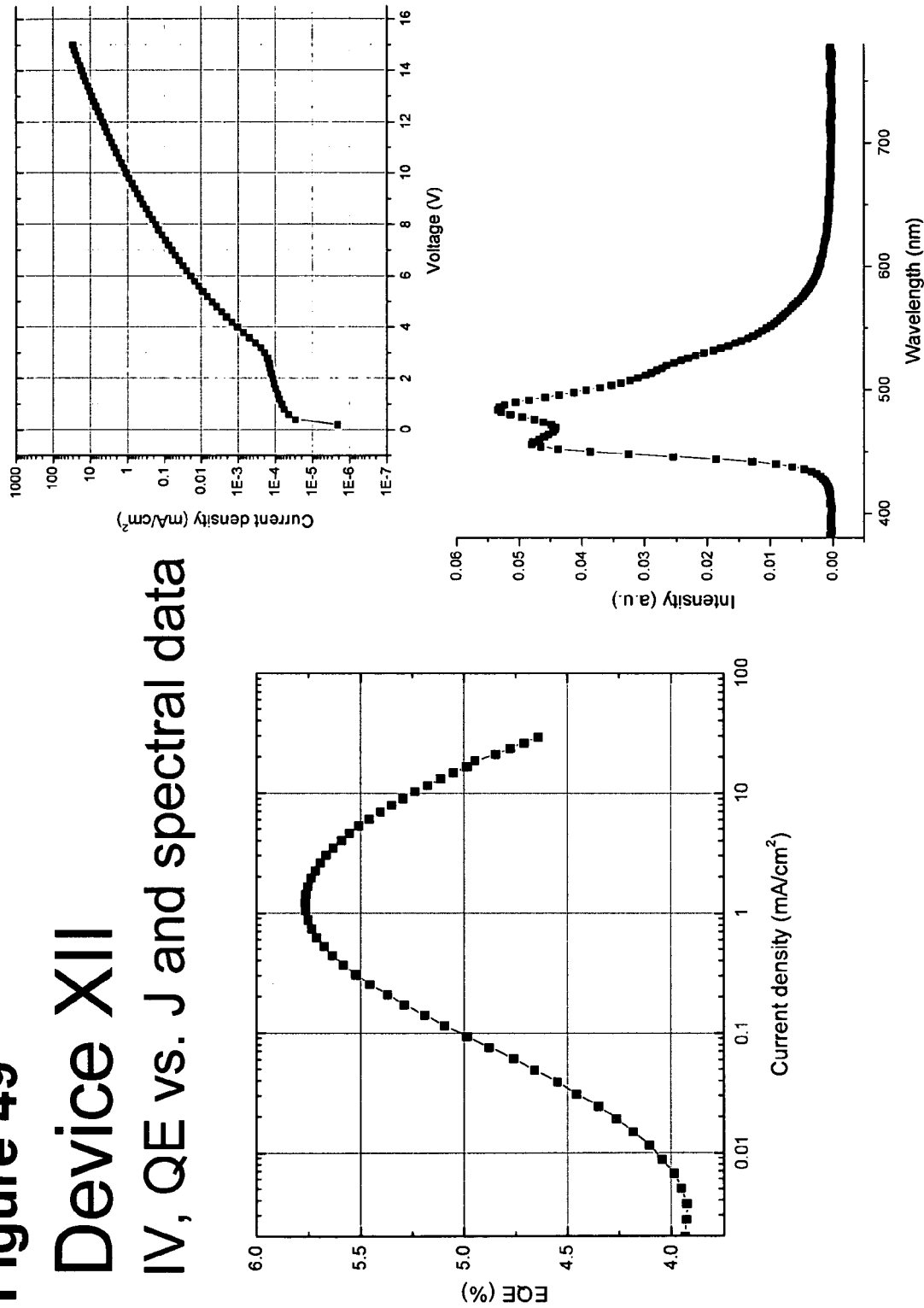
FIG. 49 shows IV, quantum efficiency (QE) vs current (J) and spectral data for device XII.
Figure 50:
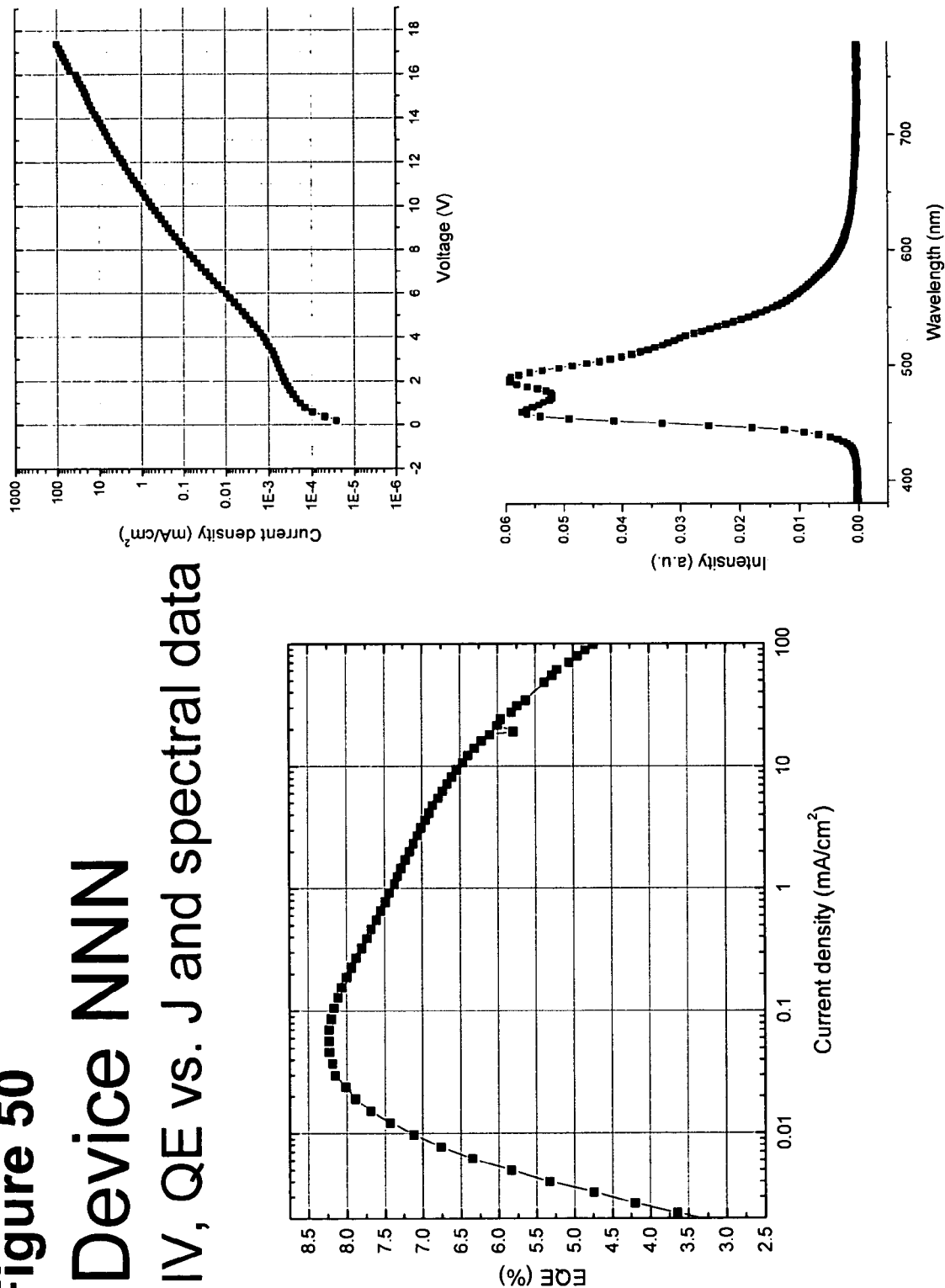
FIG. 50 shows IV, quantum efficiency (QE) vs current (J) and spectral data for device NNN.
Figure 51:
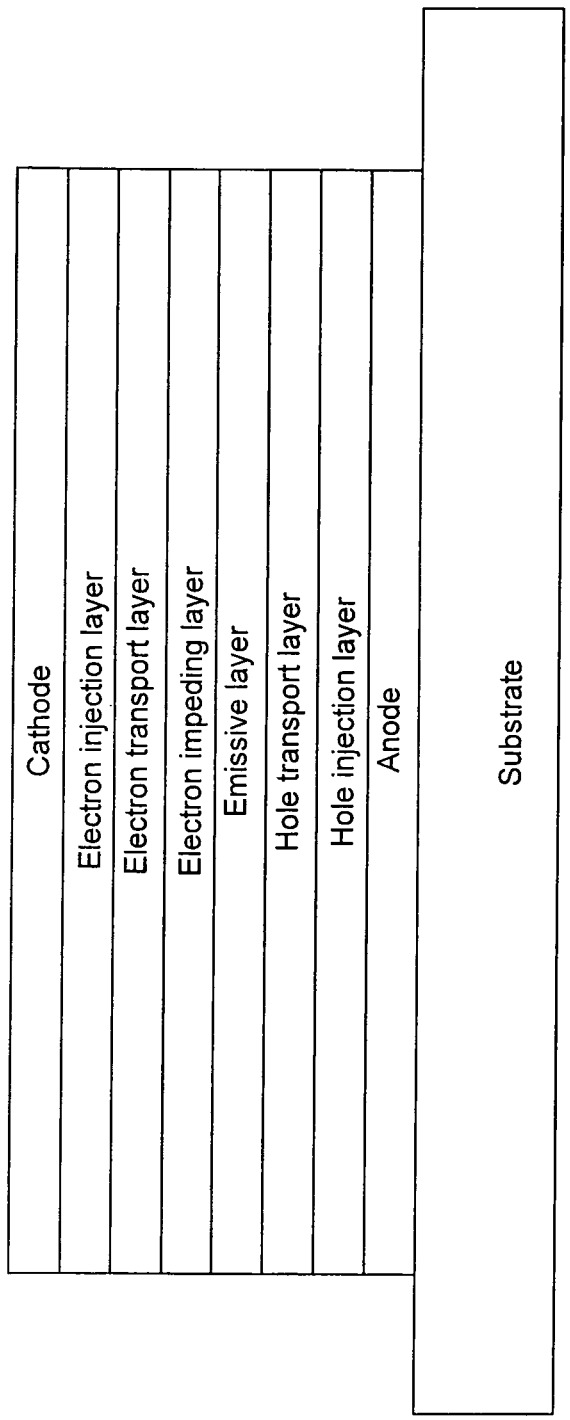
FIG. 51 shows an organic light emitting device including an electron impeding layer.

An electron impeding layer (IMP) is defined as a layer within the device, between the emissive layer and the cathode, that slows the transport of electrons to the emissive layer (EML), that has a current that is comprised of a majority of electrons, and that has a negligible hole current. Above a critical thickness (~50 Å) of the IMP, electron current is reduced, and hole-electron recombination can occur in the ETL. If the ETL is emissive, this recombination leads to undesired emission from the ETL. Hole blocking layers (HBLs) can be differentiated from IMPs because thicker HBLs generally do not restrict electron flow to the extent that recombination occurs in the ETL. The contrast between the emission spectra obtained by increasing the thickness of an electron impeding layer versus increasing the thickness of a hole blocking layer is demonstrated by FIGS. 12 and 13. See Example 2.

IMP layers generally have relative electron conductivities less than typical hole blocking layers (HBLs), e.g., $BAlq_2$, HPT, or BAlq. Preferably, the IMP layer has a relative electron conductivity that is not more than 0.001 of the electron mobility of Bphen, preferably not more than 0.0005 of the electron mobility of Bphen, and more preferably not more than 0.0001 of the electron mobility of Bphen. Suitable materials for the IMP include hole transporting materials and ambipolar materials. Materials can be characterized as hole transporting or ambipolar by fabricating a test OLED with the material in question sandwiched by an emissive HTL on its anode side and by an emissive ETL on its cathode side. Under applied voltage, such a device that contains a hole transporting material will have an EL spectrum dominated by the characteristic ETL EL. Under applied voltage, such a device that contains an ambipolar material will have an EL spectrum that contains substantial emission from both the HTL and ETL layers. Suitable test devices for characterizing a material as hole transporting or ambipolar could be fabricated, for example, as follows: CuPc(100 Å)/NPD(300 Å)/material-in-question (300 Å)/$BAlq_2$(400 Å)/LiF(10 Å)/Al(1000 Å) or CuPc(100 Å)/NPD(300 Å)/material-in-question (300 Å)/$Alq_3$(400 Å)/LiF(10 Å)/Al(1000 Å).

Suitable materials for the electron impeding layer include mCBP, which can be used in combination with many emissive layer materials, such as an emissive layer host that is mCP or mCBP and an emissive dopant that is one of compounds 1-5. See Table 3 and FIG. 52. This application is related to U.S. Provisional Application No. 60/678,170, filed on May 6, 2005, U.S. Provisional Application No. 60/701,929, filed on Jul. 25, 2005, and U.S. Provisional Application No. 60/718,336, entitled "IMPROVED STABILITY OLED MATERIALS AND DEVICES,", which was filed on Sep. 20, 2005. The contents of these applications is are herein incorporated by reference in their entirety.

Since the measurement of absolute electron conductivity or mobility tends to vary between laboratories and other experimental conditions, it is generally more reliable to compare the electron mobility of two materials measured in the same experimental setup, i.e., a new material may be tested against a common reference material such as Bphen whose mobility values have been published. The relative measurements can be carried out according to methods reported in the literature, such as: Yasuda, T. et al., *Jpn. J. Appl. Phys.*, Vol 41(9):5626-5629 (2002), Kulkarni, A. et al., *Chem. Mater.*, 16:4556-4573 (2004), Naka, S., *Applied Physics Letters*, 76(2):197-199 (2000), and Strohriegl, P., et al., *Adv. Mater.*, 14(20):1439-1452 (2002). The charge carrier mobility of a material may be estimated by application of a suitable experimental technique, such as time-of-flight (TOF), space charge limited current (SCLC) measurement, or field-effect (FE) methods, according to standard techniques.

One of skill in the art would recognize other combinations of materials that would achieve the electron conductivity contrast and thus be useful for the present invention. As demonstrated by the exemplary combinations, the electron impeding layer can be the same material as the emissive layer host.

To sum, an electron impeding layer is a layer between the emissive layer and the cathode that exhibits one or more of the following properties:

a) When used in an OLED in combination with a potentially emissive electron transporting layer such as $Alq_3$, emission is produced in the electron transporting layer when sufficiently high voltages are provided for much thicker IMP layers. The electron transporting layer may not be a material that typically emits when holes are forced into the electron transporting layer. Accordingly, in one embodiment, the device includes an organic layer consisting essentially of a material such that when said material is used in a similar device wherein the first organic layer is $Alq_3$, increasing the thickness of the second organic layer will cause emission from the first organic layer.

b) The electron impeding material can have a relative electron mobility and/or electron conductivity less than, or substantially less than, typical and specified hole blocking materials, such as Bphen, $BAlq_2$, HPT, or BAlq. Preferably, the IMP layer has a relative electron conductivity that is not more than 0.001 of the electron mobility of Bphen, preferably not more than 0.0005 of the electron mobility of Bphen, and more preferably not more than 0.0001 of the electron mobility of Bphen.

c) The electron impeding material can be a hole transporting material, i.e., a material having a hole mobility greater than its electron mobility. Thus, in one embodiment, the device includes an organic layer consisting essentially of a material having a hole mobility greater than its electron mobility, such as TCTA, Irppz, NPD, TPD, mCP, and derivatives thereof.

d) The electron impeding material can be an ambipolar material. Thus, in one embodiment, the device includes an organic layer consisting essentially of an ambipolar material, such as mCBP.

In a preferred embodiment, the emissive dopant has a HOMO that is about −5 eV or higher. In another preferred embodiment, the HOMO of the electron impeding layer material is at least about 0.5 lower than the HOMO of the emissive dopant. See FIG. 62. In yet another preferred embodiment, the band gap of the electron impeding layer material is larger than the band gap of the emissive dopant. FIGS. 63a and 63b depict an energy level diagram for a device having an exemplary electron impeding layer.

In a preferred embodiment, the electron impeding layer is a neat layer.

Preferably, the electron impeding layer has a thickness of about 20 Å to about 75 Å, preferably about 50 Å. If the electron impeding layer is too thin, the layer may not provide a continuous impediment to the electron flow. If the electron impeding layer is too thick, the extra thickness may provide too great an impediment to the electron flow and lead to exciton formation in the first organic layer.

In one embodiment, the present invention provides a device that emits blue light. In a preferred embodiment, the emissive dopant has a peak in the emission spectra that is less than about 500 nm, preferably less than 450 nm. The light emitted preferably has CIE coordinates of ($X \le 0.2$, $Y \le 0.3$). In a specific preferred embodiment, the emissive dopant is tris N-2,6 dimethylphenyl-2-phenylimidazole, referred to herein as compound 1.

In a preferred embodiment, the device exhibits increased efficiency relative to an otherwise equivalent device without the means for accumulating electrons, e.g., an otherwise equivalent device except that the electron impeding layer is replaced with an electron transport layer. A device of the present invention preferably has an unmodified external quantum efficiency is greater than about 5%. In preferred embodiments, the device exhibits increased efficiency, increased voltage, and a lifetime that is the same or better relative to an otherwise equivalent device without the means for accumulating electrons, e.g., without the electron impeding layer.

In another embodiment, the OLED comprises an anode; a cathode; an organic emissive layer disposed between the anode and the cathode, the organic emissive layer comprising an emissive layer host and an emissive dopant, wherein the HOMO of the emissive layer host is at least about 0.5 eV lower, preferably about 0.5 eV to about 0.8 eV lower, than the HOMO of the emissive dopant; a first organic layer disposed between the organic emissive layer and the cathode; a second organic layer disposed between, and in direct contact with, the organic emissive layer and the first organic layer; wherein the second organic layer consists essentially of a hole transporting material or an ambipolar material.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting.

Material Definitions

As used herein, abbreviations refer to materials as follows:

| | |
|---|---|
| CBP: | 4,4'-N,N-dicarbazole-biphenyl |
| m-MTDATA | 4,4',4''-tris(3-methylphenylphenylamino)triphenylamine |
| $Alq_3$: | 8-tris-hydroxyquinoline aluminum |
| Bphen: | 4,7-diphenyl-1,10-phenanthroline |
| n-BPhen: | n-doped BPhen (doped with lithium) |
| $F_4$-TCNQ: | tetrafluoro-tetracyano-quinodimethane |
| p-MTDATA: | p-doped m-MTDATA (doped with $F_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | N,N'-diphenyl-N-N'-di(1-naphthyl)-benzidine |
| TPD: | N,N'-diphenyl-N-N'-di(3-tolyl)-benzidine |
| HPT: | 2,3,6,7,10,11-hexaphenyltriphenylene |
| BAlq: | aluminum(III)bis(2-methyl-8-hydroxyquinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT:PSS: | an aqueous dispersion of poly(3,4-ethylenedioxythiophene) with polystyrenesulfonate (PSS) |

EXAMPLES

Specific representative embodiments of the invention will now be described, including how such embodiments may be made. It is understood that the specific methods, materials, conditions, process parameters, apparatus and the like do not necessarily limit the scope of the invention.

Example 1

Synthesis of fac-mc3

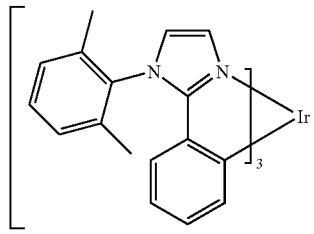

mc3

A 50 mL Schlenk tube flask was charged with N-(2,6-dimethyl phenyl)-2-phenylimidazole (5.30 g, 21 mmol) and tris(acetylacetonate)iridium(III) (1.96 g, 4.0 mmol). The reaction mixture was stirred under a nitrogen atmosphere and heated at 240° C. for 48 hours. After cooling, the solidified mixture was washed first with absolute ethanol followed by hexane. The residue was further purified by a silica gel column to give fac-mc3 (3.10 g). The product was further purified by vacuum sublimation. $^1$H and MS results confirmed the desired compound. $\lambda_{max}$ of emission=476, 504 nm ($CH_2Cl_2$ solution at room temperature), CIE=(0.21, 0.43), Eox=0.05 V, irreversible reduction at Epc=−2.85 V (vs. Fc$^+$/Fc, in 0.10M $^n$Bu$_4$NPF$_6$ solution (DMF) with Pt working and auxiliary electrodes and a non-aqueous Ag/Ag$^+$ reference electrode, and scan rates of 100 mVs$^{-1}$).

Example 2

Synthesis of fac-mc25

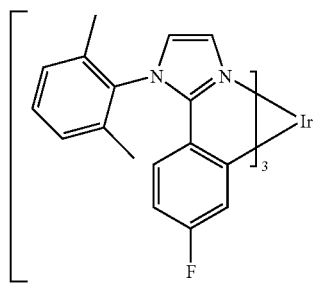

mc25

A 50 mL Schlenk tube flask was charged with N-(2,6-dimethyl phenyl)-2-(4-fluoro phenyl)imidazole (8.50 g, 32 mmol) and tris(acetylacetonate)iridium(III) (3.14 g, 6.4 mmol). The reaction mixture was stirred under a nitrogen atmosphere and heated at 240° C. for 48 hours. After cooling, the solidified mixture was washed first with absolute ethanol followed by hexane. The residue was further purified by a silica gel column to give fac-mc25 (1.60 g). The product was further purified by vacuum sublimation. $^1$H and MS results confirmed the desired compound. $\lambda_{max}$ of emission=456, 486 nm ($CH_2Cl_2$ solution at room temperature), CIE=(0.20, 0.32).

Example 3

Synthesis of fac-mc6

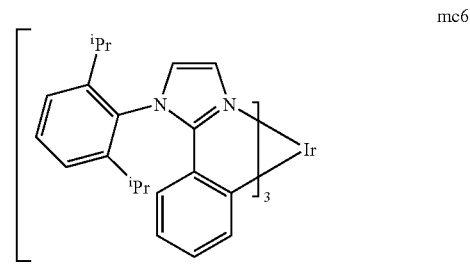

mc6

A 50 mL Schlenk tube flask was charged with N-(2,6-diisopropyl phenyl)-2-phenylimidazole (7.60 g, 25 mmol), tris(acetylacetonate)iridium(III) (2.45 g, 5.0 mmol) and tridecane (1 mL). The reaction mixture was stirred under a nitrogen atmosphere and heated at 240° C. for 48 hours. After cooling, the solidified mixture was washed first with absolute ethanol followed by hexane. The residue was further purified by a silica gel column to give fac-mc6 (1.5 g). The product was further purified by vacuum sublimation. $^1$H and MS results confirmed the desired compound. $\lambda_{max}$ of emission=476, 504 nm ($CH_2Cl_2$ solution at room temperature), CIE=(0.22, 0.43).

Example 4

Synthesis of fac-mc4

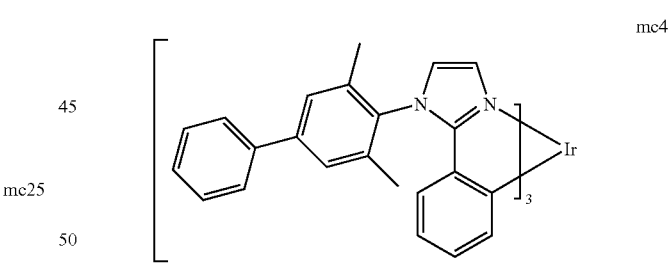

mc4

A 2-neck 50 mL round bottom flask was charged with N-(2,6-dimethyl-4-phenylbenzene)-2-phenylimidazole (4.95 g, 15.3 mmol) and tris(acetylacetonate)iridium(III) (1.25 g, 2.54 mmol). The reaction mixture was stirred under a light nitrogen purge and heated at 230° C. for 20 hours. After cooling, the solidified mixture was dissolved with methylene chloride, transferred to a 100 mL flask, and evaporated without exposure to light. The residue was further purified by silica gel (treated with triethylamine) chromatography using 20% EtOAc/Hexanes as eluent to give fac-mc4 (~1.0 g). This product was then recrystallized from diethyl ether. Attempts at sublimation of the dopant were unsuccessful due to the thermal properties of the compound. $^1$H and MS results confirmed the structure of the compound. $\lambda_{max}$ of emission=475, 505 nm (methylene chloride solution at room temperature), CIE=

(0.20, 0.41), Eox=0.05 V, quasi-reversible reduction at Epc=−2.9 V (vs. Fc+/Fc, in 0.1 OM Bu″$_4$NPF$_6$ solution (DMF) with Pt working and auxiliary electrodes and a non-aqueous Ag/Ag+ reference electrode, and scan rates of 100 mVs$^{-1}$).

Example 5

Synthesis of mc3-Cl

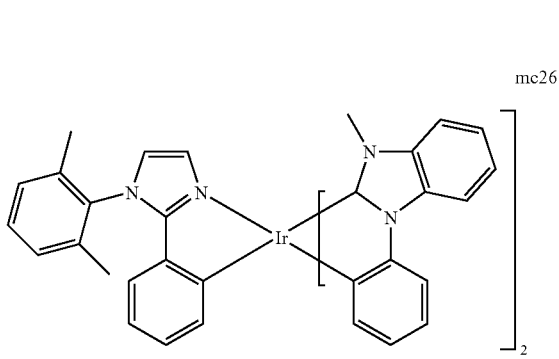

A 50 ml rounded flask was charged with 1.26 g of 2-phenyl-3-(2,6-dimethylphenyl)-imidazoline, 938 mg of IrCl$_3$, and a mixture of 2-ethoxyethanol (24 mL) and water (6 mL). The reaction mixture was heated at 100° C. for 24 hrs. The reaction mixture was cooled to ambient temperature and the desired product was isolated by filtration.

Example 6

Synthesis of mc26

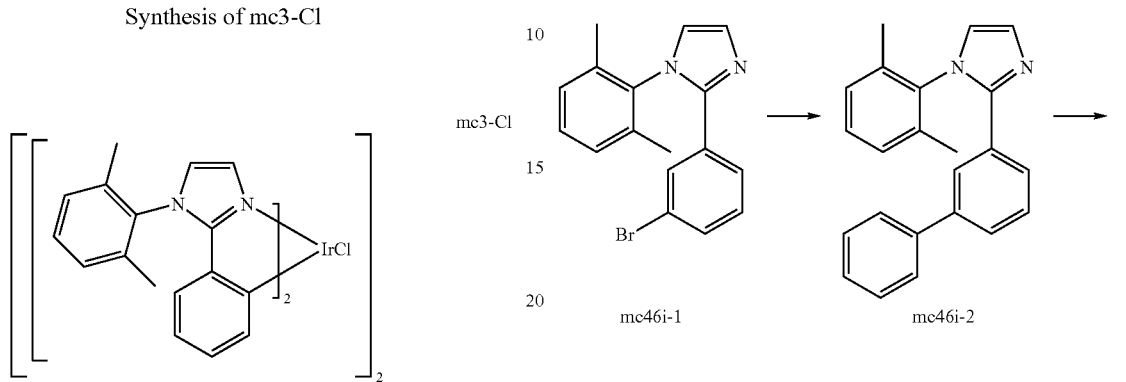

A 25 ml rounded flask was charged with 57 mg of silver (I) oxide, 82 mg of 1-(3,4-dimethylphenyl)-3-methyl-benzimidazolate iodide, 118 mg of hi1 and 10 ml of dichloroethane. The reaction was stirred and heated with a heating mantle at 75° C. for 6 hours in the dark under nitrogen while protected from light with aluminum foil. The reaction mixture was cooled to ambient temperature and concentrated under reduced pressure. Filtration through Celite using dichloromethane as the eluent was performed to remove the silver(I) salts. A yellow solution was obtained and further purified by flash column chromatography on silica gel using dichloromethane as the eluent; the desired product was isolated.

Example 7

Synthesis of fac-mc46

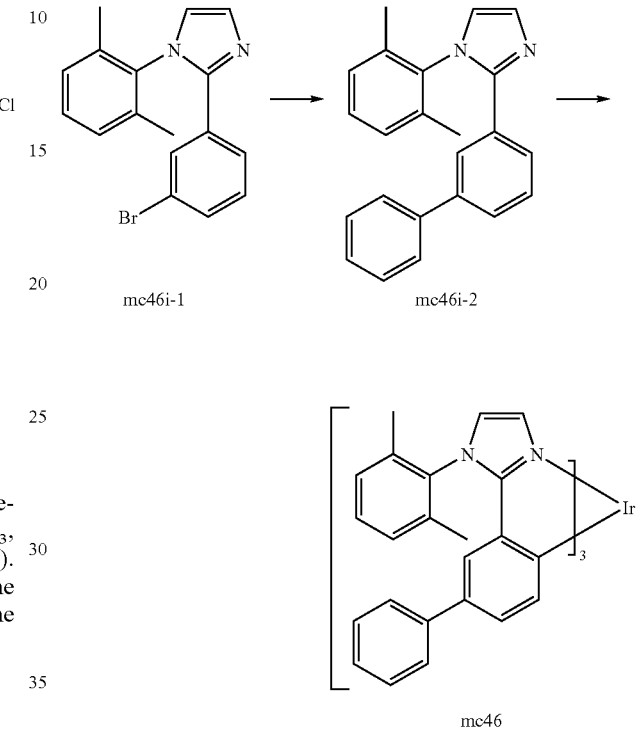

Step 1

A round bottom flask was charged with a solution of Pd(OAc)$_2$ (134 mg, 0.6 mmole), mc46i-1 (7.86 g, 24 mmole), phenylboronic acid (3.7 g, 28.8 mmole), 2 M solution of K$_2$CO$_3$ (32.4 ml), triphenylphosphine (630 mg, 2.4 mmole) and 50 ml of dimethoxyethane. The reaction mixture was heated to reflux for 17 hrs. Then the mixture was diluted with water and the aqueous layer was extracted with EtOAc. The organic layers were washed with brine and dried (MgSO$_4$). After removal of the solvent, the residue was purified by column chromatography on silca gel (10% EtOAc in hexanes) to give mc46i-2 (7 g, 90%).

Step 2

A 2-neck 50 mL round bottom flask was charged mc46i-2 (1 g, 3 mmol) and tris(acetylacetonate)iridium(III) (377 mg, 0.77 mmol). The reaction mixture was stirred under a light nitrogen purge and heated at 200° C. for 20 hours. After cooling, the solidified mixture was dissolved with methylene chloride, transferred to a 100 mL flask, and evaporated without exposure to light. The residue was further purified by silica gel (treated with triethylamine) chromatography using 20% EtOAc/Hexanes as eluent to give fac-mc46 (338 mg). $^1$H and MS results confirmed the structure of the compound. $\lambda_{max}$ of emission=481 nm, 511 nm (methylene chloride solution at room temperature), CIE=(0.21, 0.46), Eox=0.09 V, irreversible reduction at Epc=−3.1 V (vs. Fc+/Fc, in 0.10 M Bu″$_4$NPF$_6$ solution (DMF) with Pt working and auxiliary electrodes and a non-aqueous Ag/Ag+ reference electrode, and scan rates of 100 mVs$^{-1}$).

Example 8

Synthesis of mc47

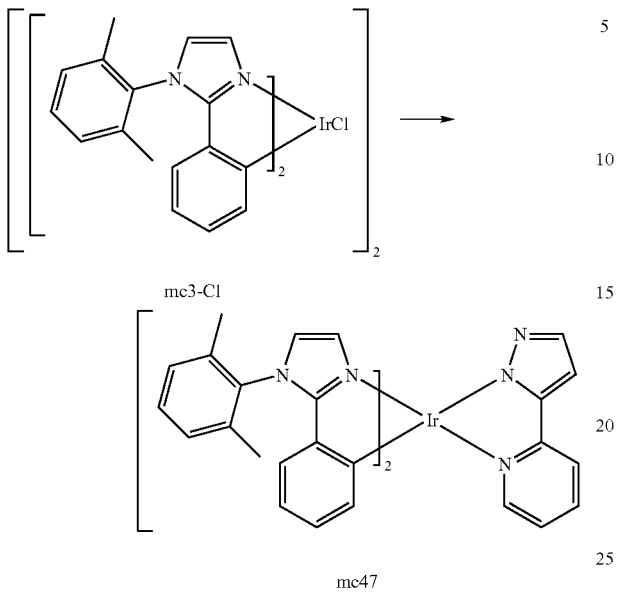

A 50 mL round bottom flask was charged mc3-CI (162 mg, 1.12 mmol), silver trifluoromethansulfonate (576 mg, 2.24 mmol), 10 ml of methanol and 10 ml of dichloromethane. The reaction mixture was stirred at room temperature for 2 hours. The reaction mixture was filtered and the filtrate was concentrated to dryness. The residue was transfer to a 50 mL round bottom flask which was charged with 2-pyrazopyridine (325 mg, 2.24 mmole), Sodium hydride (94.2 mg for 60% in mineral oil, 2.35 mmole) and 20 ml of anhydrous acetontrile. The reaction mixture was stirred under a light nitrogen purge and heated at 81° C. for 20 hours. After cooling, the reaction mixture was concentrated to dryness. The residue was further purified by silica gel (treated with triethylamine) chromatography using 40% EtOAc/methylene chloride as eluent to give mc47 (700 mg). $^1$H and MS results confirmed the structure of the compound. $\lambda_{max}$ of emission=467, 494 nm (methylene chloride solution at room temperature), CIE=(0.20, 0.40), Eox=0.38 V(i), irreversible reduction at Epc=−3.06 V (vs. Fc$^+$/Fc, in 0.10M Bu$^n_4$NPF$_6$ solution (DMF) with Pt working and auxiliary electrodes and a non-aqueous Ag/Ag$^+$ reference electrode, and scan rates of 100 mVs$^{-1}$).

Example 9

Synthesis of mc54

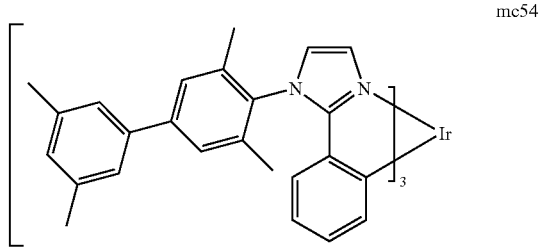

A 1-neck 50 mL round bottom flask was charged with N-(2,6-dimethyl-4-(3,5-dimethylphenyl)benzene)-2-phenylimidazole (4.5 g, 12.8 mmol) and tris(acetylacetonate)iridium(III) (1.57 g, 3.2 mmol). The reaction mixture was stirred under a nitrogen atmosphere and heated at 200° C. for 60 hours. After cooling, the solidified mixture was dissolved with methylene chloride and purified by silica gel (treated with triethylamine) chromatography using 20% dichloromethane/hexanes as eluent. The solvent was removed and the product was then recrystallized from dichloromethane/methanol and filtered yielding 1.4 grams. The material was slurried in hot ethyl acetate and filtered to yield 1.2 grams of bright yellow solid. The material was further purified by sublimation. $^1$H and MS results confirmed the structure of the compound. $\lambda_{max}$ of emission=476 nm (methylene chloride solution at room temperature), CIE=(0.2.3, 0.43).

Example 10

Synthesis of mc48

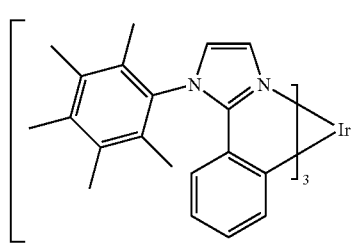

Step 1

A one neck 3000 ml round bottom flask was charged with pentamethylbenzene (61.2 g, 0.414 mol) and 1 L of dichloromethane. The mixture was cooled in an ice bath and nitronium tetrafluoroborate (50 g, 0.376 mol) was added in portions. The mixture was allowed to warm to room temp and stirred for 16 hours. The reaction was cooled in an ice bath and quenched with 1 liter of water. The layers are allowed to separate and the organic layer was dried with magnesium sulfate and filtered. The solvent was removed by rotary evaporation and the product was purified by distillation.

Step 2

A one neck 2000 ml round bottom flask was charged with 50 grams of 1-nitro-2,3,4,5,6-pentamethylbenzene and 1000 ml methanol. A solution of 50 g of ammonium chloride and 200 ml of water was then added. Zinc dust (50 g) was then added in portions. The mixture was allowed to stir for 20 hours. The solids were filtered and the solvent was removed from the mother liquor. The product was purified by silica gel column with dichlormethane as the eluent. The good fractions are combined to yield pentamethylaniline as a white solid.

Step 3

A one neck 1000 ml round bottom flask wsa charged pentamethylaniline (36 g, 0.221 mol), 40% aqueous glyoxal (40 g, 0.221, mol), and 300 ml methanol. The mixture was stirred at room temperature for 20 hours and then benzaldehyde (47 g, 0.442 mol) and ammonium chloride (23.6 g, 0.442 mmol) were added. The mixture was heated to reflux for 1 hour and then 30 ml of phosphoric acid was added. The reaction was heated at reflux for 24 hours and then allowed to cool to room temperature. The methanol was removed by rotary evaporation. Ethyl acetate (500 ml) was added and the mixture is made basic with sodium hydroxide and water. The layers were separated and the organic layer was washed with brine, dried with magnesium sulfate, and the solvent removed. The mixture was purified by silica gel column with an 80% hexane/ethyl acetate to 50% hexane/ethyl acetate gradient as the eluent. The good fractions were combined and the solvent removed by rotary evaporation. The solid was further purified by vacuum distillation to yield N-(2,3,4,5,6-pentamethyl-benzene)-2-phenylimidazole.

Step 4

A 1-neck 50 mL round bottom flask was charged with N-(2,3,4,5,6-pentamethyl-benzene)-2-phenylimidazole (5.5 g, 18.9 mmol) and tris(acetylacetonate)iridium(III) (2.3 g, 4.7 mmol). The reaction mixture was stirred under a light nitrogen purge and heated at 200° C. for 60 hours. After cooling, the solidified mixture was dissolved with dichloromethane and purified by silica gel (treated with triethylamine) chromatography using dichloromethane as eluent. The good fractions were combined and evaporated. The material was dissolved in dichloromethane and isolated by silica gel column chromatography (treated with triethylamine) using 50% dichloromethane/hexanes as the eluent. The product was crystallized from chlorobenzene and hexane to yield 0.85 grams of mc48 as a bright yellow solid. The material was further purified by sublimation. $^1$H and MS results confirmed the structure of the compound. $\lambda_{max}$ of emission=476 nm (dichloromethane solution at room temperature), CIE=(0.23, 0.43).

Example 11

Synthesis of mc49i-1

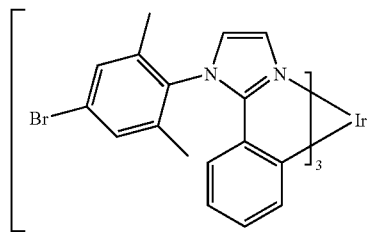

mc49i-1

A 1-neck 50 mL round bottom flask was charged with N-(2,6-dimethyl-4-bromobenzene)-2-phenylimidazole (3.0 g, 9.2 mmol) and tris(acetylacetonate)iridium(III) (1.12 g, 2.3 mmol). The reaction mixture was stirred under a light nitrogen purge and heated at 200° C. for 48 hours. After cooling, the solidified mixture was dissolved with methylene chloride and purified by silica gel (treated with triethylamine) chromatography using 20% dichloromethane/hexanes as eluent. The good fractions were combined and the solvent removed by rotary evaporation. The product was then recrystallized from dichloromethane/methanol and filtered yielding 0.17 grams of fac mc49i-1.

Example 12

Synthesis of mc49

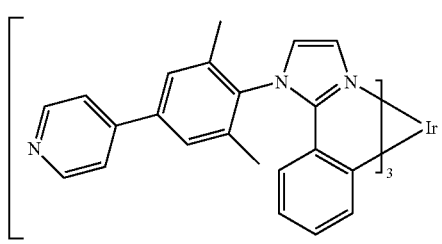

mc49

A 1-neck 100 ml round bottom flask was charged with mc49i-1 (0.15 g, 0.13 mmol), 4-pyridineboronic acid, (0.06 g, 0.0.39 mmol), palladium acetate (2 mg, 9×10$^{-6}$ mol), triphenylphosphine (10 mg, 4×10$^{-5}$ mmol), potassium carbonate (0.14 g, 1 mmol), 20 ml 1,2-dimethoxyethane, and 10 ml water. The mixture was heated to reflux for 6 hours and then allowed to cool to room temperature. The mixture was extracted with dichloromethane and water. The organic layer was dried with magnesium sulfate and filtered. The solvent was removed and the product was purified by silica gel column (treated with triethylamine) using 95% ethyl acetate/methanol as the eluent. The product was crystallized from dichloromethane/hexanes.

Example 13

Synthesis of mc50

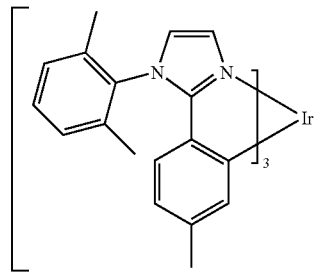

mc50

A 50 mL round bottom flask was charged with N-(2,6-dimethylphenyl)-2-(p-tolylimidazole (4.50 g, 19 mmol) and tris(acetylacetonate)iridium(III) (1.87 g, 3.81 mmol). The reaction mixture was stirred under a light nitrogen purge and heated in a sand bath at 200° C. for 96 hours. After cooling, the solidified mixture was dissolved with methylene chloride, transferred to a 100 mL flask, and evaporated without exposure to light. The residue was further purified by silica gel (treated with triethylamine) chromatography using 10% methyelene chloride/hexanes as eluent to give fac-tris[N-(2, 6-dimethyl phenyl)-2-p-tolylimidazole]iridium(III) (1.2 g). This product was then recrystallized from methylene chloride/hexanes to give 0.80 g as yellow crystals. Sublimation of the product yielded 0.42 g as yellow crystals. NMR and MS results confirmed the structure of the compound. $\lambda_{max}$ of emission=472, 502 nm (methylene chloride solution at room temperature), CIE=(0.21, 0.40), Tg=363.8° C. Eox=0.04 V, Ered=Not Detected (vs. Fc$^+$/Fc, in 0.10M Bu″$_4$NPF$_6$ solution (DMF) with Pt working and auxiliary electrodes and a non-aqueous Ag/Ag$^+$ reference electrode, and scan rates of 100 mVs$^{-1}$).

Example 14

Synthesis of mc51

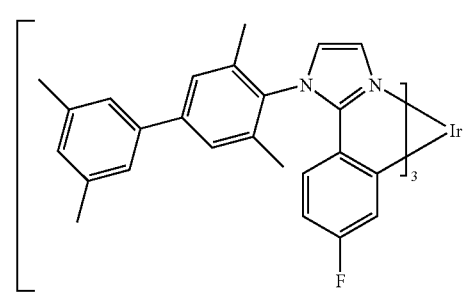

mc51

Step 1

55.0 g (275 mmol) 4-bromo-2,6-dimethylaniline and 39.0 g glyoxal (40% solution, 275 mmol) were stirred in 500 mL methanol in a 1 L round bottom flask for 16 hours. 68.3 g 4-fluorobenzaldehyde (550 mmol) and 29.4 g (550 mmol) ammonium chloride were then added and the mixture was allowed to achieve reflux for 2 hours. 38.5 mL phosphoric acid (85%) was added dropwise over 10 minutes and the mixture continued at reflux for 18 hours. The mixture was then evaporated of methanol and the residue poured into 700 mL water. 50% NaOH was added until the pH=9 and the mixture then extracted three times with ethyl acetate in a separatory funnel. The combined organic layers were dried over anhydrous $MgSO_4$, filtered and evaporated of solvent to give a dark residue. The ligand was purified on a large column of silica using a gradient of 20% ethyl acetate/hexanes-30% ethyl acetate/hexanes. The product fractions were evaporated of solvent and the residue distilled via kugelrohr distillation. The resultant product was recrystallized from hexanes to give 12.5 g N-(4-bromo-2,6-dimethylphenyl)-2-(4-fluorophenyl) imidazole as a clean white solid. MS confirmed.

Step 2

8.5 g (24.6 mmol) N-(4-bromo-2,6-dimethylphenyl)-2-(4-fluorophenyl)imidazole, 4.43 g (29.5 mmol) 3,5-dimethylphenylboronic acid, 0.17 g (0.74 mmol) palladium (II) acetate, 9.17 g (66.5 mmol) potassium carbonate and 0.65 g (2.46 mmol) triphenylphosphine were refluxed in 350 mL 1,2-dimethoxyethane and 130 mL water for 18 hours under $N_2$ atmosphere. The cooled mixture was then transferred to a separatory funnel whereupon the water was removed. The organic material was then enriched with ethyl acetate and extracted from water. The organic layer was dried over anhydrous $MgSO_4$, filtered and evaporated of solvent to give a light residue. The residue was then purified on a silica gel column using 50% ethyl acetate/hexanes as eluent. The pure fractions were evaporated of solvent the solids collected on a funnel with hexanes to give 8.34 g N-(2,6-dimethyl-4-{3,5-dimethylphenyl}phenyl)-2-(4-fluoro phenyl)imidazole as a bright white solid. MS confirmed.

Step 3

A 50 mL round bottom flask was charged with N-(2,6-dimethyl-4-{3,5-dimethylphenyl}phenyl)-2-(4-fluorophenyl)imidazole (6.30 g, 17 mmol) and tris(acetylacetonate) iridium(III) (1.67 g, 3.48 mmol). The reaction mixture was stirred under a light nitrogen purge and heated in a sand bath at 180° C. for 48 hours. After cooling, the solidified mixture was dissolved with methylene chloride, transferred to a 100 mL flask, and evaporated without exposure to light. The residue was further purified by silica gel (treated with triethylamine) chromatography using 20% Methyelene Chloride/Hexanes as eluent to give fac-tris[N-(2,6-dimethyl-4-{2,5-dimethylphenyl}phenyl)-2-(4-fluorophenyl)imidazole] iridium(III) as 1.7 g. A repeat of the chromatography gave 1.13 g product. The product was then recrystallized three times from methylene chloride/hexanes, methylene chloride/methanol and finally methylene chloride/hexanes to give 0.75 g mc51 as a yellow solid. Sublimation of the product yielded a negligible amount of purified material as the solids went into a melt and decomposed during the process. NMR and MS results confirmed the structure of the compound. $\lambda_{max}$ of emission=454, 786 nm (methylene chloride solution at room temperature), CIE=(0.19, 0.33).

Example 15

Synthesis of mc52

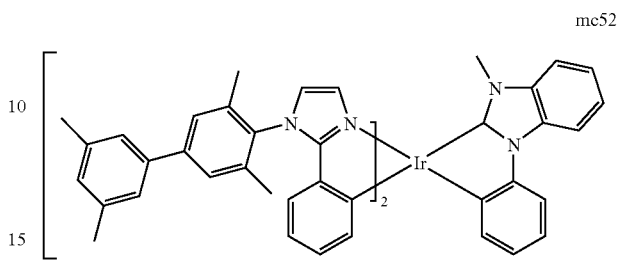

Step 1

To a 100 mL round bottom flask was added 5.0 g (14.2 mmol) N-(2,6-dimethyl-4-(3,5-dimethylphenyl)benzene)-2-phenylimidazole and 2.55 g (7.1 mmol) iridium chloride hexahydrate in 50 mL 2-methoxyethanol and 10 mL water. The mixture was refluxed under $N_2$ atmosphere for 17 hours. The mixture was then cooled and the solids collected on a filter and rinsed with methanol and hexanes. The amount of chloro-bridged dimer achieved was 6.32 g and was used in the next step without further purification.

Step 2

In a 100 mL round bottom flask was dissolved 3.0 g (1.62 mmol) chloro-bridged dimer in 60 mL 1,2-dichloroethane. 1.12 g (4.83 mmol) silver oxide was then added and the mixture was allowed to reflux for 10 minutes under $N_2$ atmosphere. 1.08 g (3.22 mmol) 1-phenyl-3-methyl-benzimidazolate iodide was added to the mixture and the mixture was heated for 1 minute at reflux followed by cooling. The mixture was then filtered and the solids rinsed with methylene chloride. The filtrate was then evaporated down and the residue purified on a silica gel column (treated with triethylamine) using 40% methylene chloride/hexanes. The pure fractions were evaporated of solvent and the solids recrystallized from methylene chloride/hexanes to give ~1.8 g er-bis [N-(2,6-dimethyl-4-{2,5-dimethylphenyl}phenyl)-2-phenylimidazole]-N-phenyl-3-methylbenzimidazole iridium (III). The solids were then stirred in 1.5 L acetonitrile in a quartz chamber and photoisomerized with 254 nm UV light in a rayonet under $N_2$ atmosphere. After 72 hours, photoisomerization to the fac isomer was complete to afford mc52.

Example 16

Synthesis of mc37

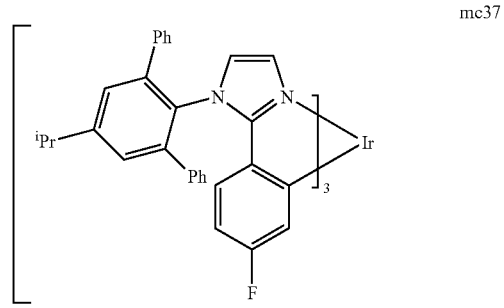

Step 1

2,6-dibromo-4-isopropyl aniline (87.9 g, 0.3 mol) in EtOH (400 mL) was treated with 40% aq glyoxal (43.5 g, 0.3 mol) for overnight at r.t. A dark brown mixture was formed. NH$_4$Cl (32.1 g, 0.6 mol) in 200 mL H$_2$O was added followed by 4-fluorobenzaldehyde (63.6 g, 0.6 mol). The resulting mixture was refluxed for 2 h. H$_3$PO$_4$ (42 mL, 85%) was added over a period of 10 min. The mixture was then stirred at reflux for 4 days. After removal of most of the EtOH, the dark residue was poured onto ice (300 g) and neutralized with aq 50% KOH solution until the pH 9 (about 90 mL). The resulting mixture was extracted with EtOAc. The organic phases were combined and washed with NaHCO$_3$ solution once and dried (Na$_2$SO$_4$). The solvent was removed and the residue was distilled on Aldrich Kugelrohr, first at 135° C. to remove any low boiling point impurities, then to collect fraction at 210° C. The resulting crude product can be further purified by silica gel column with EtOAc/Hexanes (1:4) as eluent. Yield is 8.0 g. The ligand was confirmed by GC-MS.

Step 2

To a 500 mL round flask was added above phenyl imidazole (8.0 g, 18 mmol), phenylboronic acid (5.4 g, 44 mmol), palladium(II) acetate (0.25 g, 1.1 mmol), triphenylphosphine (1.2 g, 4.4 mmol), sodium carbonate (12.6 g, 119 mmol), and 200 mL of DME and 100 mL of water. The reaction was heated to reflux and stirred under a nitrogen atmosphere for 12 hours. The mixture was extracted with ethyl acetate and further purified by a silica gel column. Yield is 5.2 g. The ligand was confirmed by GC-MS.

Step 3

N-(2,6-diphenyl-4-isopropyl phenyl)-2-(4-fluro phenyl) imidazole (0.43 g, 1.0 mmol) and tris(acetylacetonate)iridium(III) (0.12 g, 0.25 mmol) were added to a flask containing 5 mL of ethyleneglycol. The reaction mixture was heated to reflux and stirred under a nitrogen atmosphere for 24 hours. After cooling, the precipitate formed was filtered and washed with ethanol. The residue was extracted with CH$_2$Cl$_2$ and further purified by a silica gel column to give fac-tris[N-(2,6-diphenyl-4-isopropyl phenyl)-2-(4-fluorophenyl)imidazole]iridium(III) (0.15 g). $^1$H NMR result confirmed the desired compound. $\lambda_{max}$ of emission=460, 490 nm, CIE=(0.20, 0.34), Eox=0.18 V (r), Ered=-3.00 V (q) (vs. Fc$^+$/Fc).

Example 17

Synthesis of oa9

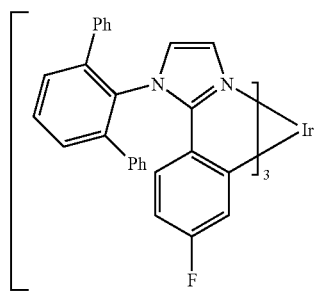

oa9

Step 1

2,6-dibromoaniline (87.9 g, 0.3 mol) in EtOH (400 mL) was treated with 40% aq glyoxal (43.5 g, 0.3 mol) for overnight at r.t. A dark brown mixture was formed. NH$_4$Cl (32.1 g, 0.6 mol) in 200 mL H$_2$O was added followed by 4-fluroben-zadehyde (63.6 g, 0.6 mol). The resulting mixture was refluxed for 2 h. H$_3$PO$_4$ (42 mL, 85%) was added over a period of 10 min. The mixture was then stirred at reflux for 4 days. After removal of most of the EtOH, the dark residue was poured onto ice (300 g) and neutralized with aq 50% KOH solution until the pH 9 (about 90 mL). The resulting mixture was extracted with EtOAc. The organic phases were combined and washed with NaHCO$_3$ solution once and dried (Na$_2$SO$_4$). The solvent was removed and the residue was distilled on an Aldrich Kugelrohr, first at 135° C. to remove any low boiling point impurities, then to collect fraction at 220° C. The resulting crude product can be further purified by silica gel column with EtOAc/Hexanes (1:4) as eluent. Yield was 7.5 g. The ligand was confirmed by GC-MS.

Step 2

To a 500 mL round flask was added above phenyl imidazole (7.5 g, 19 mmol), phenylboronic acid (6.1 g, 50 mmol), palladium(II) acetate (0.28 g, 1.25 mmol), triphenylphosphine (1.3 g, 5.0 mmol), sodium carbonate (14.3 g, 135 mmol), and 200 mL of DME and 100 mL of water. The reaction was heated to reflux and stirred under a nitrogen atmosphere for 12 hours. The mixture was extracted with ethyl acetate and further purified by a silica gel column to yield 5.0 g of the desired ligand, the structure of which was confirmed by GC-MS.

Step 3

N-(2,6-diphenylphenyl)-2-(4-fluorophenyl)imidazole (3.9 g, 10 mmol) and tris(acetylacetonate)iridium(III) (1.2 g, 2.5 mmol) were added to a flask containing 40 mL of ethylene glycol. The reaction mixture was heated to reflux and stirred under a nitrogen atmosphere for 24 hours. After cooling, the precipitate formed was filtered and washed with ethanol. The residue was extracted with CH$_2$Cl$_2$ and further purified by a silica gel column to give oa9 (2.3 g). $^1$H NMR confirmed the structure. $\lambda_{max}$ emission=462, 492 nm, CIE=(0.21, 0.36).

Example 18

Synthesis of oa8

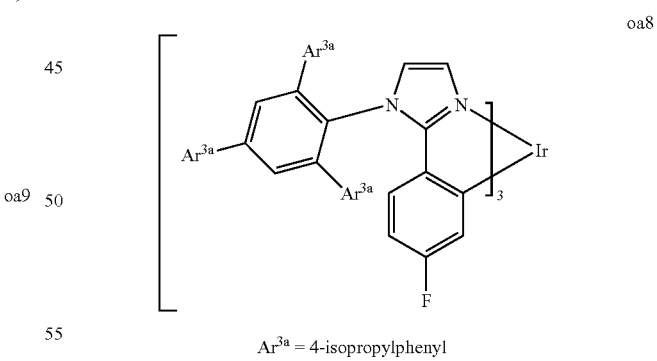

oa8

Ar$^{3a}$ = 4-isopropylphenyl

Step 1

2,4,6-tribromoaniline (98.9 g, 0.3 mol) in EtOH (500 mL) was treated with 40% aq glyoxal (43.5 g, 0.3 mol) for overnight at r.t. A dark brown mixture was formed. Solid NH$_4$Cl (32.1 g, 0.6 mol) was added followed by 4-flurobenzadehyde (63.6 g, 0.6 mol). The resulting mixture was refluxed for 2 h. H$_3$PO$_4$ (42 mL, 85%) was added over a period of 10 min. The mixture was then stirred at reflux for 4 days. After removal of most of the EtOH, the dark residue was poured onto ice (300 g) and neutralized with aq 50% KOH solution until the pH 9

(about 90 mL). The resulting mixture was extracted with EtOAc. The organic phases were combined and washed with NaHCO$_3$ solution once and dried (Na$_2$SO$_4$). The solvent was removed and the residue was distilled on an Aldrich Kugelrohr, first at 135° C. to remove any low boiling point impurities, then to collect a fraction at 240° C. The resulting crude product can be further purified by silica gel column with EtOAc/Hexanes (1:4) as eluent. Yield was 3.0 g. The ligand was confirmed by GC-MS.

Step 2

To a 500 mL round flask was added above phenyl imidazole (4.0 g, 8.5 mmol), 4-isopropylphenylboronic acid (5.0 g, 30.5 mmol), palladium(II) acetate (0.17 g, 0.76 mmol), triphenylphosphine (0.79 g, 0.30 mmol), sodium carbonate (8.73 g, 82 mmol), and 200 mL of DME and 100 mL of water. The reaction was heated to reflux and stirred under a nitrogen atmosphere for 12 hours. The mixture was extracted with ethyl acetate and further purified by a silica gel column. Yield was 4.0 g. The ligand was confirmed by GC-MS.

Step 3

N-(2,4,6-tri(4-isopropylphenyl)phenyl)-2-(4-fluorophenyl)imidazole (3.3 g, 5.6 mmol) and tris(acetylacetonate)iridium(III) (0.68 g, 1.4 mmol) were added to a flask containing 40 mL of ethylene glycol. The reaction mixture was heated to reflux and stirred under a nitrogen atmosphere for 24 hours. After cooling, the precipitate formed was filtered and washed with ethanol. The residue was extracted with CH$_2$Cl$_2$ and further purified by a silica gel column to give oa8 (1.0 g). $^1$H NMR result confirmed the desired compound. $\lambda_{max}$ emission=460, 490 nm, CIE=(0.20, 0.35). Eox=0.24 V, Ered=−2.80 V (q) (vs. Fc$^+$/Fc, in 0.10M Bu$^n_4$NPF$_6$ solution (DMF) with Pt working and auxiliary electrodes and a non-aqueous Ag/Ag$^+$ reference electrode, and scan rates of 100 mVs$^{-1}$).

Example 19

Synthesis of ii1

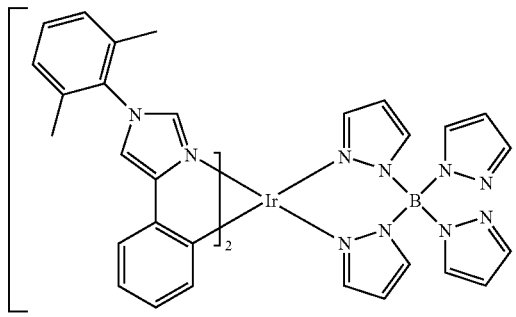

Step 1

One 250 ml flask was charged with 4-phenyl imidazole (7.08 g, 49.12 mmole), 2-iodo-m-xylene (9.5 g, 40.93 mmole), copper (5.721 g, 90.046 mmole); 18-crown-6 (1.081 g, 4.09 mmole), K$_2$CO$_3$ (21.49 g, 155.53 mmole) and tetrahydronaphthalene (90 ml). Reaction was heated to 180 C for 68 hrs. Reaction mixture was then filtered through Celite and the filtrate was concentrated to dryness. The residue was subjected to kugelrohr distillation and 4 g of ligand was obtained. (39%).

Step 2

One 25 ml of flask was charged with ligand (0.82 g, 3.339 mmole), IrCl$_3$ (0.61 g, 1.67 mmole), water (2 ml) and 2-ethoxyethanol (8 ml). Reaction mixture was heated to 100 C for 20 h. Reaction was then filtered and the precipitation was collected to the chloro-bridge dimer (0.78 g, 65%).

Step 3

A 50 mL round bottom flask was charged with dimer (400 mg, 0.277 mmol), Silver trifluoromethansulfonate (142 mg, 0.55 mmol), 10 ml of methanol and 10 ml of dichloromethane. The reaction mixture was stirred at room temperature for 2 hours. The reaction mixture was filtered and the filtrate was concentrated to dryness. The residue was transfer to a 50 mL round bottom flask which was charged with potassium tetrapyrazoborate (176 mg, 0.554 mmole) and 20 ml of anhydrous acetontrile. The reaction mixture was stirred under a light nitrogen purge and heated at 81° C. for 20 hours. After cooling, the reaction mixture was concentrated to dryness. The residue was further purified by chromatography (Al$_2$O$_3$, basic) using 40% heptane/methylene chloride as eluent to give target compound (200 mg, 37%) $^1$H and MS results confirmed the structure of the compound. $\lambda_{max}$ of emission=427, 457, 483 nm (methylene chloride solution at room temperature).

Example 20

Synthesis of mc46a

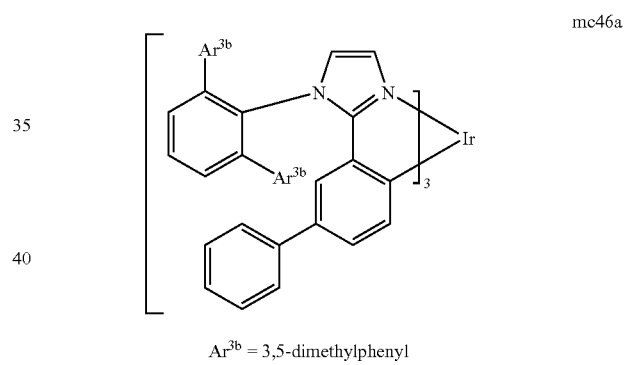

Ar$^{3b}$ = 3,5-dimethylphenyl

Step 1

As per general procedure to prepare N-2,6-dibromophenyl-2-phenylimidazoles.

Step 2

A round bottom flask was charged with a solution of Pd(OAc)$_2$ (188 mg, 0.84 mmole), dibromo compound (5.12 g, 12.9 mmole), 3,5-dimethylphenylboronic acid (5.1 g, 34 mmole), 2 M solution of K$_2$CO$_3$ (45.9 ml), triphenylphosphine (881 mg, 3.36 mmole) and 90 ml of dimethoxyethane. The reaction mixture was heated to reflux for 17 hrs. Then the mixture was diluted with water and the aqueous layer was extracted with EtOAc. The organic layers were washed with brine and dried (MgSO$_4$). After removal of the solvent, the residue was purified by column chromatography on silca gel (10% EtOAc in hexanes) to give ligand (4 g, 70%).

Step 3

A 2-neck 50 mL round bottom flask was charged with ligand (4 g, 9.15 mmol) and tris(acetylacetonate)iridium(III) (1.12 g, 2.28 mmol). The reaction mixture was stirred under a light nitrogen purge and heated at 200° C. for 20 hours. After cooling, the solidified mixture was dissolved with methylene chloride, transferred to a 100 mL flask, and evaporated without exposure to light. The residue was further purified by silica gel (treated with triethylamine) chromatography using 20% EtOAc/Hexanes as eluent to give fac-tris complex (1 g). ¹H and MS results confirmed the structure of the compound. $\lambda_{max}$ of emission=466, 492 nm (methylene chloride solution at room temperature), CIE=(0.21, 0.38), Eox=0.17 V (vs. Fc⁺/Fc, in 0.10M Bu"₄NPF₆ solution (DMF) with Pt working and auxiliary electrodes and a non-aqueous Ag/Ag⁺ reference electrode, and scan rates of 100 mVs⁻¹).

Example 21

Synthesis of mc48f

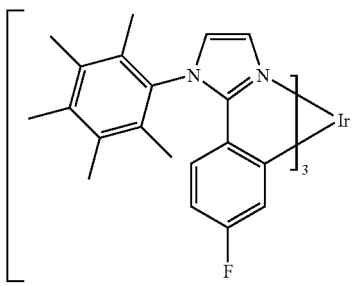

mc48f

Step 1
A one neck 1000 ml round bottom flask was charged with 200 ml of xylenes and N-(2-chlororethyl)-4-flourobenzamide (18.5 g, 92 mmol). Phosphorous pentachloride (28.7 g, 138 mmol) was added slowly and the mixture was then heated to reflux for 1 hour. Pentamethyl aniline (15 g, 92 mmol) was then added and the mixture was allowed to heat at reflux for 18 hours. After cooling, the solids that were formed were collected by vacuum filtration. The solids were dissolved in a mixture or dichloromethane, water, and ammonium hydroxide. The dichloromethane layer was separated, washed with water, and dried over magnesium sulfate. The mixture was filtered, the solvent removed, and the N-(2,3,4,5,6-pentamethyl-benzene)-2-(4-flurophenyl)imidazolidine purified by vacuum distillation.

Step 2
N-(2,3,4,5,6-pentamethyl-benzene)-2-(4-flurophenyl) imidazolidine (10 grams, 34 mmol) was dissolved in 200 ml acetonitrile. A finely ground mixture of 33% potassium permagenate on montmorillonite K10 (24 grams, 34 mmol of KMnO₄) was added portion wise. The mixture was stirred at room temperature for 4 hours and then quenched with ethanol. After stirring for 30 minutes the mixture was filtered through celite and the solvent was then removed from the filtrate by rotary evaporation. The product was purified by dissolving in ethyl acetate and washing with a dilute acetic acid solution. After phase separation, the ethyl acetate layer was washed with water and then dried over magnesium sulfate. The mixture was filtered and the solvent removed. The N-(2,3,4,5,6-pentamethyl-benzene)-2-(4-flurophenyl)imidazole was further purified by column chromatography using 70% hexane/ethyl acetate as the eluent. The good fractions were combined and the solvent removed.

Step 3
N-(2,3,4,5,6-pentamethyl-benzene)-2-(4-flurophenyl)imidazole (5 g, 16.2 mmol) and tris(acetylacetonate)iridium (III) (1.6 g, 3.2 mmol) were added to a 50 ml round bottom flask and heated to 200° C. for 48 hours under a nitrogen atmosphere. After cooling, the solidified mixture was dissolved with dichloromethane and purified by silica gel (treated with triethylamine) chromatography using 30% dichloromethane/hexane as eluent. The good fractions were combined and evaporated. The product was crystallized from ethyl acetate.

Example 22

Synthesis of oa8c

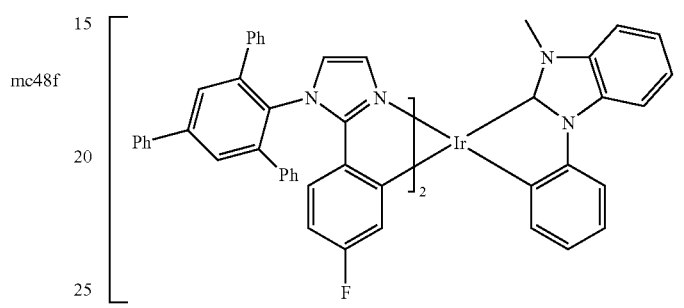

oa8c

Step 1
N-(2,4,6-triphenyl-benzene)-2-(4-flurophenyl)imidazole (2.5 g, 5.4 mmol) and iridium (III) trichloride (0.97 g, 2.7 mmol) were heated to reflux in 25 ml 2-methoxyethanol and 10 ml water for 24 hours. After cooling the solids were filtered and washed with ethanol.

Step 2
The chloro bridged dimer (2.0 g, 0.86 mmol) was dissolved in 100 ml 1,2-dichloroethane and heated to reflux. Silver oxide (0.8 g, 3.4 mmol) was added followed by 1-phenyl-3-methyl-imidazolium iodide (0.50 g, 1.7 mmol). The mixture was heated at reflux for about 20 minutes. The filtrate was then evaporated down and the residue purified on a silica gel column (treated with triethylamine) using dichloromethane as the eluent. The pure fractions were evaporated of solvent and the solids recrystallized from methylene chloride/hexanes.

Example 23

Synthesis of oa8c

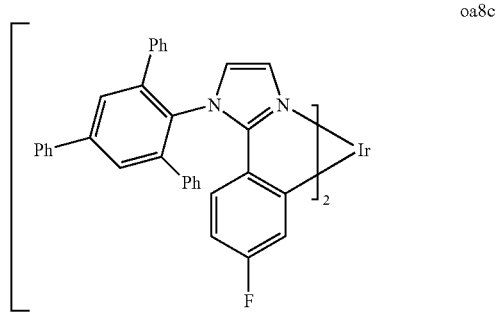

oa8c

Step 1: Synthesis of N-(2-chloroethyl)-4-fluorobenzamide
In a 1 L round bottom flask, 50.4 g sodium hydroxide (1.26 mol) was dissolved in 500 mL water (~10% solution). 66.6 g (0.574 mol) 2-chloroethylamine hydrochloride was then added and the solution stirred in an ice bath at 0° C. until the salt was completely dissolved. 100 g (0.631 mol) 4-fluorobenzoyl chloride was then added dropwise via an addition funnel into the vigorously stirred solution. After addition, the solution stirred at 0° C. for 1 hour followed by stirring at room temperature for 1 hour. The cloudy mixture was then filtered to remove the water and the solids washed with ether and then filtered to give ~118 g crude (slightly wet) benzamide (Alternatively, the solids could be dissolved in methylene chloride, dried with magnesium sulfate, filtered and evaporated to completely remove water from the solids). These solids were recrystallized from 120 ml EtOAc/200 mL hexanes to give 88.2 g crystalline N-(2-chloroethyl)-4-fluorobenzamide after hexanes wash and drying (an additional 6.22 g benzamide recrystallized from the original water mother liquor). NMR confirmed the structure of this compound (81.4% total yield).
Step 2: Synthesis of N-(2,4,6-tribromophenyl)-2-(4-fluorophenyl)imidazoline To a dried 3 L round bottom flask equipped with stirbar was added 55.6 g (0.276 mol) N-(2-chloroethyl)-4-fluorobenzamide. This solid was then dissolved in 600 mL anhydrous m-xylene under $N_2$ atmosphere and light heat. 86.1 g (0.413 mol) phosphorus pentachloride was then added and the mixture was allowed to reflux under $N_2$ for 2 hours (completely dissolving the $PCl_5$). The solution was then cooled whereupon 100 g (0.303 mol) tribromoaniline was added (Additionally, a base trap was attached to the condenser to neutralize generating HCl gas). This mixture was allowed to reflux for 20 hours. The solution was then allowed to cool and the imidazoline collected on a filter and washed with toluene followed by hexanes. The solids were then dissolved in methylene chloride and extracted with diluted $NH_4OH$ twice. The organic layer was dried over $MgSO_4$, filtered and evaporated of solvent to give ~65 g imidazoline. Recrystallization was achieved from methylene chloride/hexanes. NMR confirmed the structure of this compound.
Step 3: Aromatization of N-(2,4,6-tribromophenyl)-2-(4-fluorophenyl)imidazoline 59.2 g (0.124 mol) N-(2,4,6-tribromophenyl)-2-(4-fluorophenyl)imidazoline was added to a 2 L flask equipped with stirbar. ~1 L MeCN was added and the mixture stirred at room temperature until the solids were dissolved. 33% $KMnO_4$/Montmorillonite was added in portions (0.248 mol) to the stirred mixture over a period of a few hours. After stirring overnight, the mixture was quenched with 200 mL EtOH and then poured over a celite mat to remove the oxidant. The filtrate was evaporated of solvent and the residue purified on a silica gel column using 20% EtOAc/MeCl$_2$ as eluent. The product fractions were evaporated of solvent to give 18.8 g crude imidazole recrystallized from MeCl$_2$/Hexanes (17.4 g, 29.4% yield). The product was confirmed by NMR.
Step 4: Synthesis of N-(2,4,6-triphenylphenyl)-2-(4-fluorophenyl)imidazole 13.36 g (28.1 mmol) N-(2,4,6-tribromophenyl)-2-(4-fluorophenyl)imidazole, 14.1 g (104 mmoL) phenylboronic acid, 2.21 g (8.40 mmol) triphenylphosphine, 0.63 g (2.81 mmol) Pd(II) acetate, and 31.4 g (228 mmol) potassium carbonate were added to a 2 L round bottom flask equipped with stir bar and refluxed in 800 mL DME/400 mL water overnight under $N_2$ atmosphere. The mixture was then cooled, added to a separatory funnel and the water removed. The organic mixture was then enriched with 800 mL EtOAc and extracted with 2×400 mL portions of water. The organic layer was then dried over $MgSO_4$, filtered and evaporated of solvent. Next, the residue was solubilized with 200 mL MeCl$_2$ and dried on silica. This silica was then layered on top of a silica gel column that was eluted with a gradient of 30% EtOAc/hexanes-50% EtOAc/hexanes. The pure fractions, after evaporation of solvent, gave 9.3 g N-(2,4,6-triphenylphenyl)-2-(4-fluorophenyl)imidazole upon recrystallization from CH$_2$Cl$_2$/hexanes (71.0% yield). The product was confirmed by NMR.
Step 5: Ligation to form oa8c The ligand from the preceding step was used to prepare oa8c following the procedure of Example 20.

Device Fabrication Examples

OLED devices were prepared with compounds listed in FIG. 3 using the following general procedures.

The starting substrates were glass substrates coated with indium tin oxide (ITO) of 80 nm thickness and sheet resistance <25 ohms/square, purchased from Colorado Concept Coatings LLC. All subsequent thin films were deposited by thermal evaporation at a pressure of <10e-6 Torr. The cathode consisted of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

Prior to device fabrication, the substrates were cleaned by sonication in soap solution, rinsed with deionized water, and boiled in isopropanol. After the cleaning procedure, the substrates were dried under an $N_2$ flow followed by O$_2$ plasma and UV ozone treatments.

Organic layers of the OLEDs were sequentially deposited by thermal evaporation from resistively heated alumina crucibles onto the substrates, at room temperature, at a base pressure of <10e-6 Torr. The rate of a single-component layer was controlled with one Inficon thickness monitor located close to the substrate. The specific rates for each material are given in Table 1 below. For the two-component emissive layer the rate of the dopant was controlled with an additional crystal monitor located close to the dopant evaporation source. The additional monitor was not exposed to the major flow of the host.

TABLE 1

| Material | Deposition Rate (Å) |
|---|---|
| CuPc | 0.3 |
| NPD | 1.5 |
| CBP | 3.0 |
| mCBP | 3.0 |
| Mcp | 3.0 |
| HPT | 1.0 |
| BAlq2 | 2.0 |
| Alq3 | 2.5 |
| LiF | 0.5 |
| Al | 2.0 |

FIGS. 4, 5, 24, 33, 43, and 45 list the configurations of the devices that were prepared. The configurations are reported in the following format, exemplified for Device B.

Device B: CuPc(100)/NPD(300)/CBP:cmpd A(6%,300)/HPT(100)/BAlq2(300)

The definitions for materials CuPc, NPD, CBP, HPT, and BAlq2 have been given above; the structure of Compound A (abbreviated as "cmpd A") is given in FIG. 3. The numbers in parentheses refer to the thickness of the layer in Angstroms, and the percentage after cmpd A refers to the weight percent of compound A in that layer.

Current-voltage measurements were made with a Keithley source meter (model 2400). Spectra and light intensity were measured using a PhotoResearch 705 Model Spectrophotometer and calibrated photodiode. FIGS. 6-23, 25-32, 34-42, 44, and 46-48 depict the performance of the devices.

Figure 52:
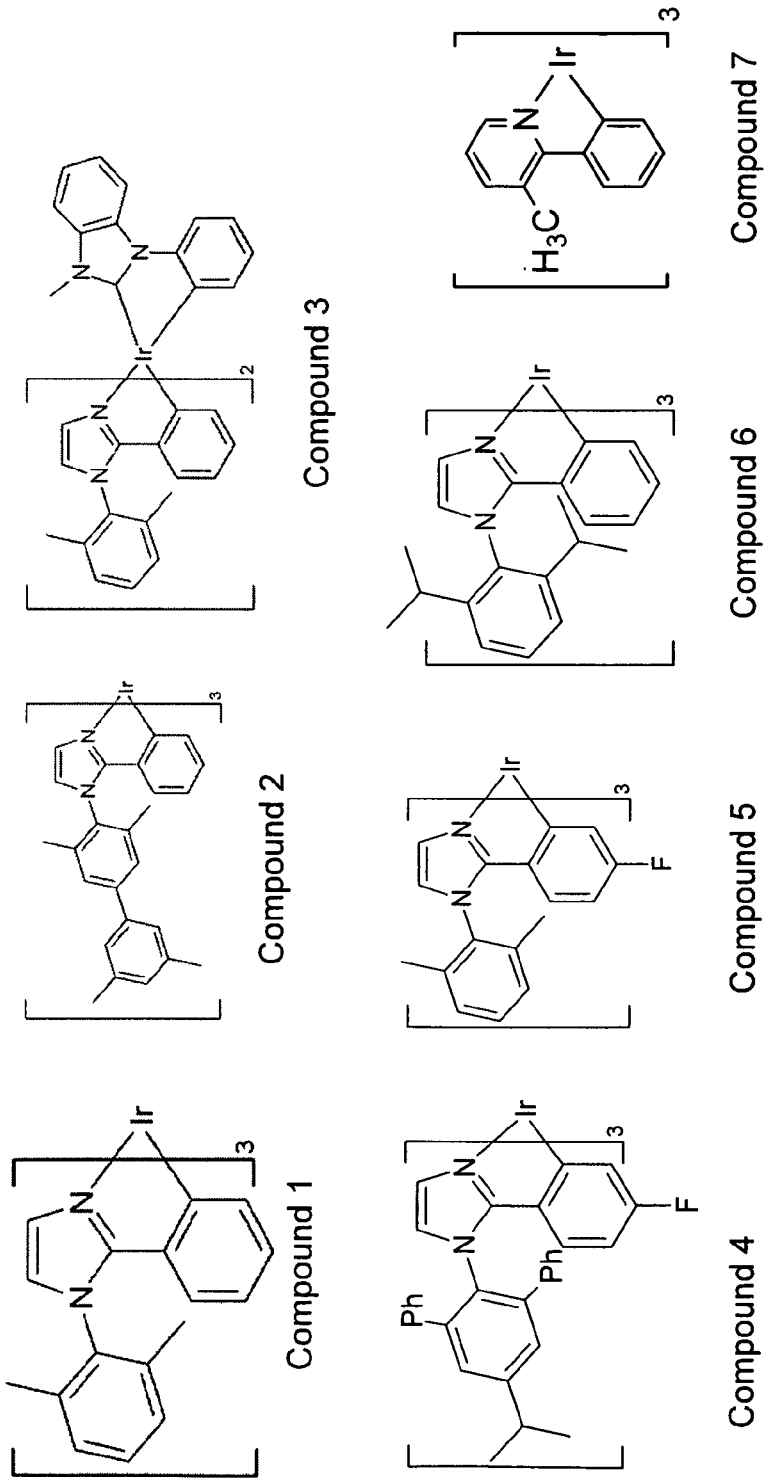
FIG. 52 shows the structures of compounds 1-5.

The devices in Examples 24 and 25 are fabricated in high vacuum (<$10^{-7}$ Torr) by thermal evaporation. The anode electrode is about 800 Å of indium tin oxide (ITO). Organic layers were deposited at rates between 0.3 to 3.0 Å/s. The cathode consists of 10 Å of LiF, deposited at 0.1 Å/s, followed by 1,000 Å of Al, deposited at 2 Å/s. All devices are encapsulated with a glass lid sealed with an epoxy resin in a nitrogen glove box (<1 ppm of $H_2O$ and $O_2$) immediately after fabrication, and a moisture getter was incorporated inside the package. The exemplary emissive dopants are shown in FIG. 52.

Example 24

Specific exemplary devices of the invention (numbered in bold) as well as comparative devices are listed in Table 3. It is understood that the specific methods, materials, conditions, process parameters, apparatus and the like do not necessarily limit the scope of the invention.

TABLE 3

Exemplary Devices and Comparative Devices

| Ex. | Structure (All thicknesses are in angstroms, and doping concentration are wt %.) |
|---|---|
| 1 | CuPc (100)/NPD (300)/mCBP: compound 1 (9%, 300)/mCP (50)/Balq (400)/LiF/Al |
| 2 | CuPc (100)/NPD (300)/mCBP: compound 1 (9%, 300)/Balq (400)/LiF/Al |
| 3 | CuPc (100)/NPD (300)/mCBP: compound 1 (18%, 300)/mCP (50)/Balq (400)/LiF/Al |
| 4 | CuPc (100)/NPD (300)/mCBP: compound 1 (18%, 300)/Balq (400)/LiF/Al |
| 5 | CuPc (100)/NPD (300)/mCBP: compound 1 (9%, 300)/mCBP (50)/Balq (400)/LiF/Al |
| 6 | CuPc (100)/NPD (300)/mCP: compound 1 (9%, 300)/mCP (50)/Balq (400)/LiF/Al |
| 7 | CuPc (100)/NPD (300)/mCP: compound 1 (9%, 300)/Balq (400)/LiF/Al |
| 8 | CuPc (100)/NPD (300)/mCP: compound 1 (9%, 300)/mCBP (50)/Balq (400)/LiF/Al |
| 9 | CuPc (100)/NPD (300)/mCBP: compound 2 (9%, 300)/mCP (50)/Balq (400)/LiF/Al |
| 10 | CuPc (100)/NPD (300)/mCBP: compound 2 (9%, 300)/Balq (400)/LiF/Al |
| 11 | CuPc (100)/NPD (300)/mCP: compound 3 (9%, 300)/mCP (50)/Balq (400)/LiF/Al |
| 12 | CuPc (100)/NPD (300)/mCP: compound 3 (9%, 300)/mCBP (50)/Balq (400)/LiF/Al |
| 13 | CuPc (100)/NPD (300)/mCP: compound 3 (9%, 300)/Balq (400)/LiF/Al |
| 14 | CuPc (100)/NPD (300)/mCBP: compound 4 (9%, 300)/mCBP (50)/Balq (400)/LiF/Al |
| 15 | CuPc (100)/NPD (300)/mCBP: compound 4 (9%, 300)/Balq (400)/LiF/Al |
| 16 | CuPc (100)/NPD (300)/mCBP: compound 4 (9%, 300)/mCP (50)/Balq (400)/LiF/Al |
| 17 | CuPc (100)/NPD (300)/mCP: compound 5 (9%, 300)/mCP (50)/Balq (100)/Alq (400)/LiF/Al |
| 18 | CuPc (100)/NPD (300)/mCP: compound 5 (9%, 300)/Balq (100)/Alq (400)/LiF/Al |

Figure 53:
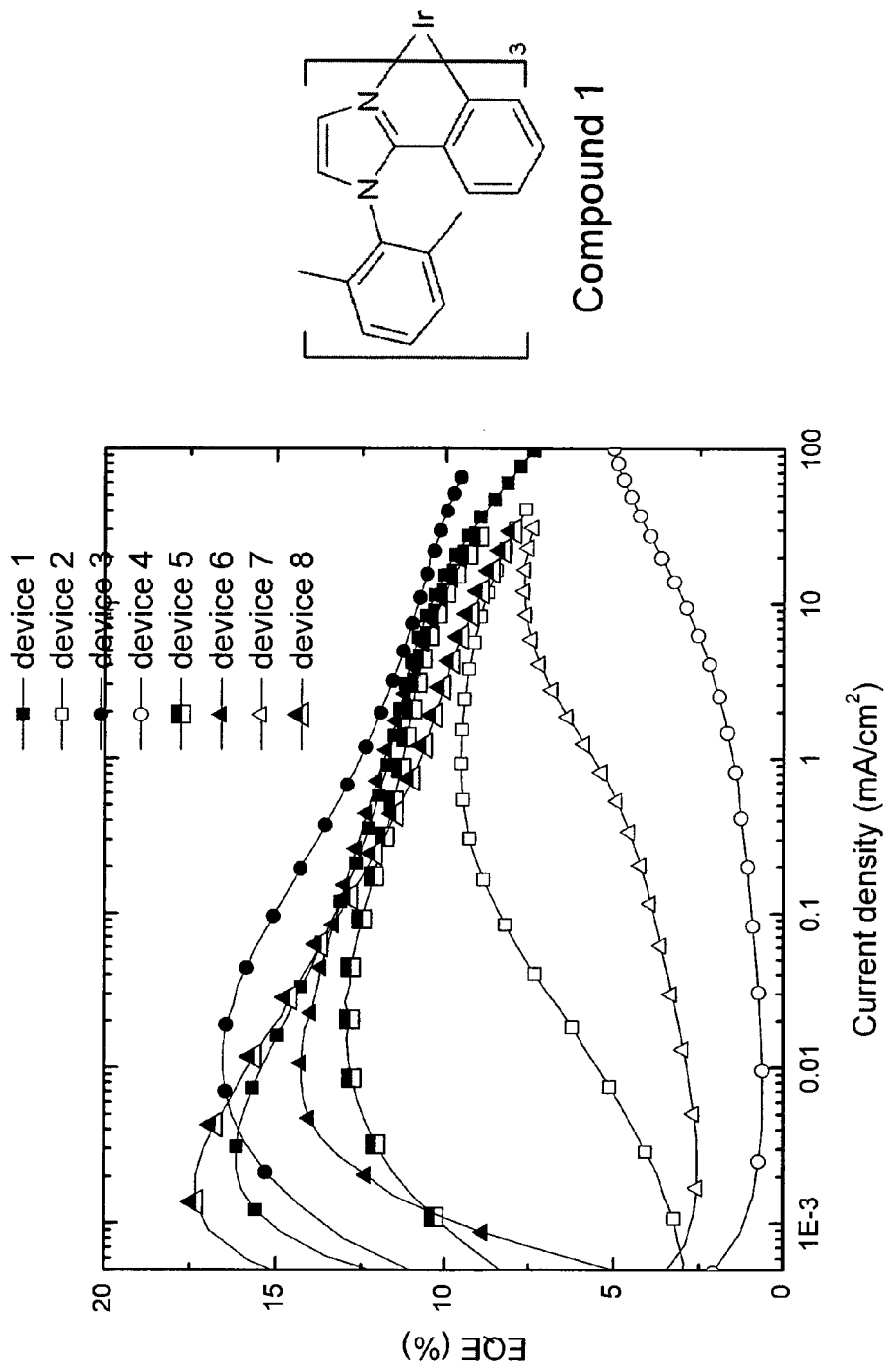
FIG. 53 shows the external quantum efficiency versus current density for compound 1 devices.
Figure 54:
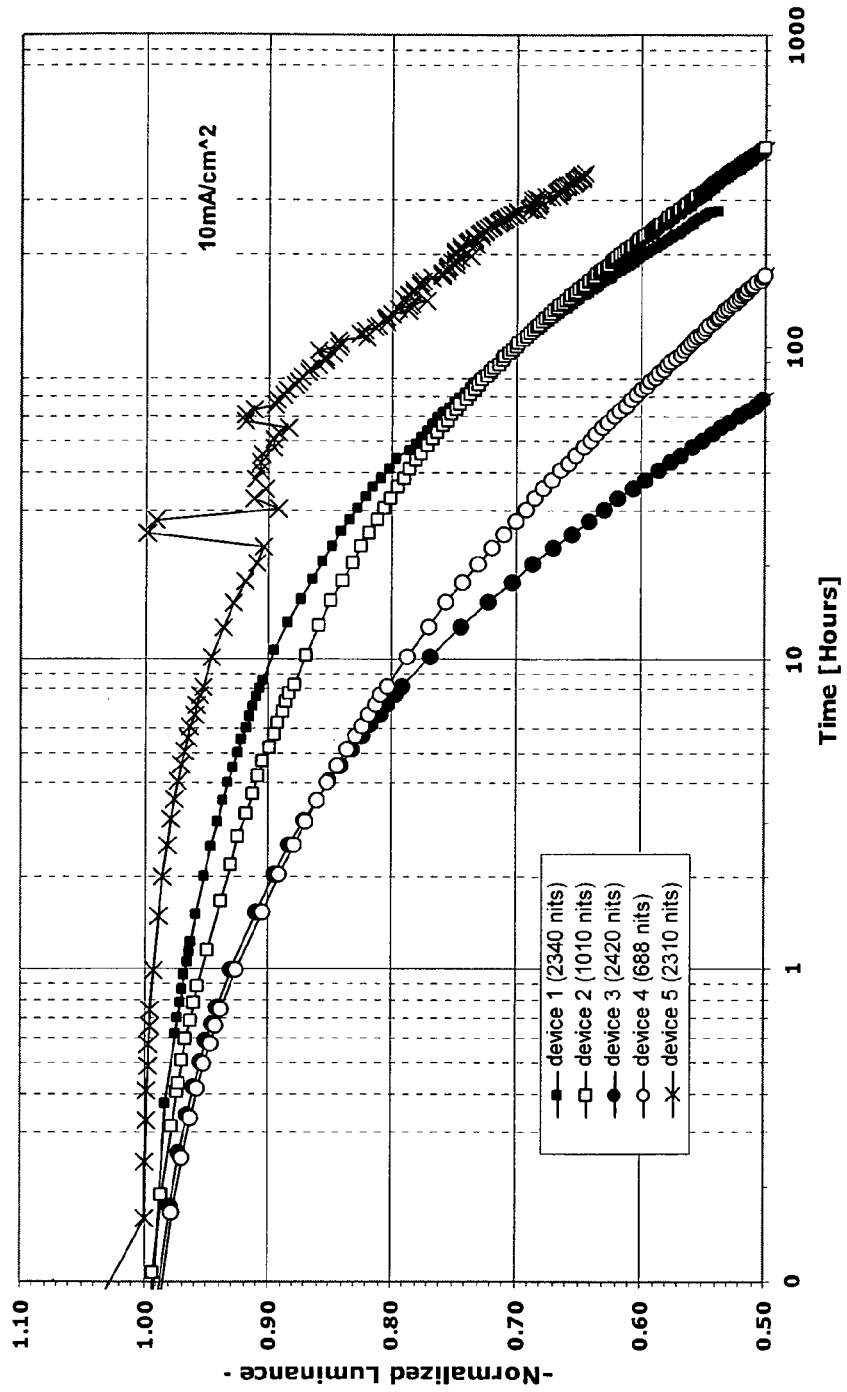
FIG. 54 shows the lifetime at room temperature with 10 mA/cm² for compound 1 devices.

FIG. 53 shows that among the devices utilizing dopant compound 1, the external quantum efficiency is higher for the exemplary devices including an electron impeding layer (devices 1, 3, 5, 6, and 8) relative to comparative devices without such a layer (devices 2, 4, and 7, shown by fully open symbols). FIG. 54 shows that exemplary devices 1, 3, and 5 have the same or better lifetime relative to comparative devices 2 and 4.

Figure 55:
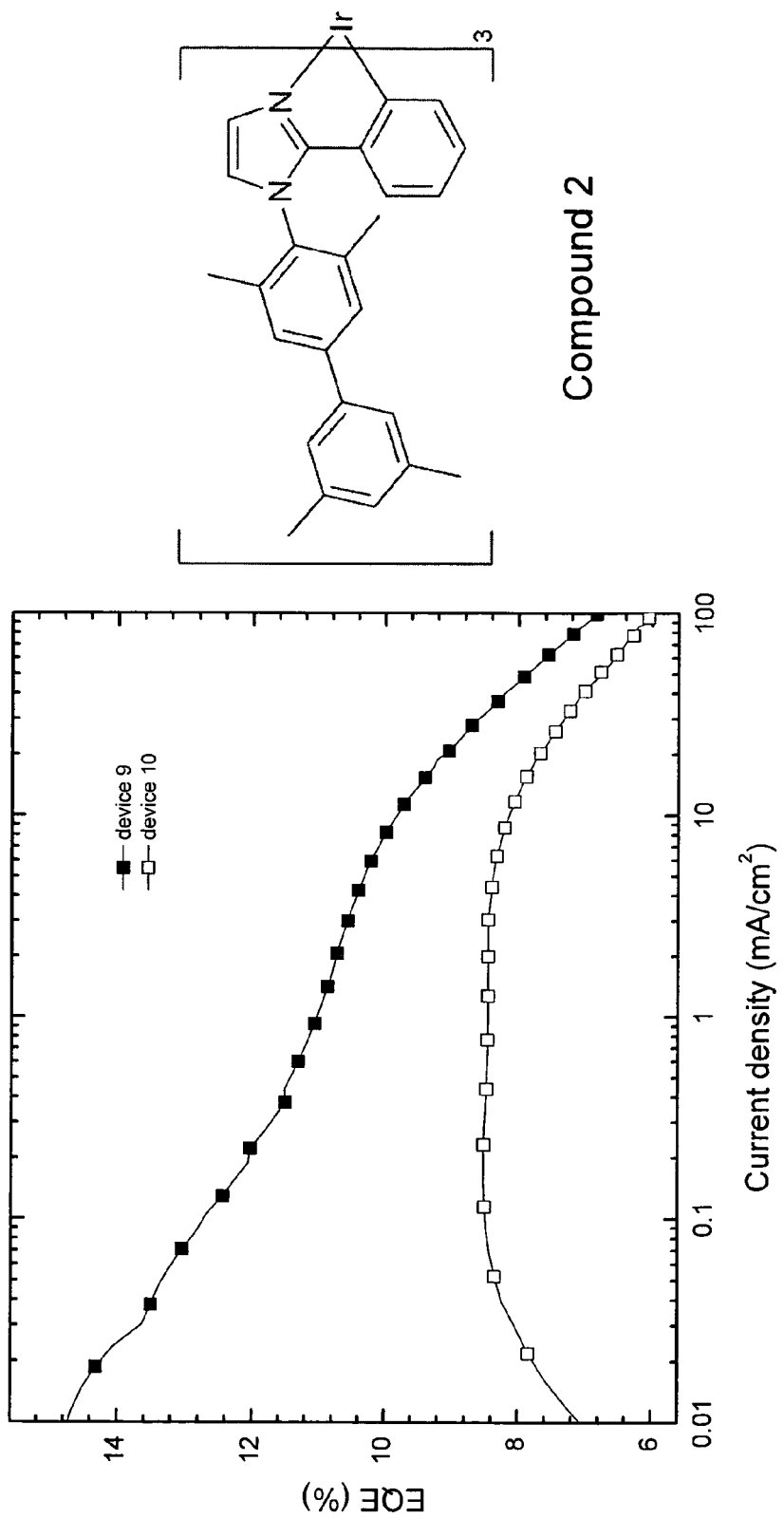
FIG. 55 shows the external quantum efficiency versus current density for compound 2 devices.

FIG. 55 shows that for the devices utilizing dopant compound 2, the external quantum efficiency is higher for the exemplary device 9 including an electron impeding layer relative to comparative device 10 without such a layer.

Figure 56:
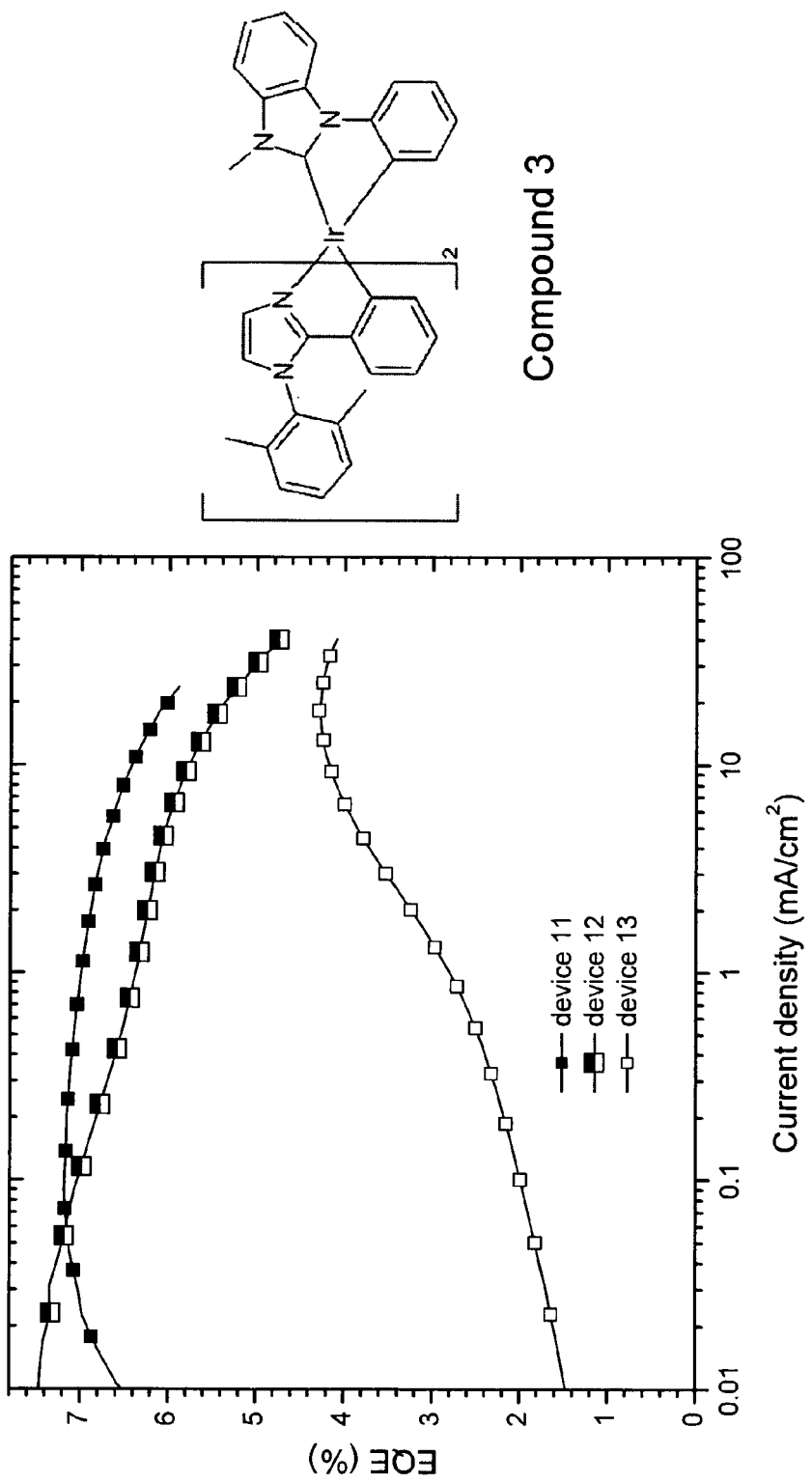
FIG. 56 shows the external quantum efficiency versus current density for compound 3 devices.

FIG. 56 shows that among the devices utilizing dopant compound 3, the external quantum efficiency is higher for the exemplary devices including an electron impeding layer (devices 11 and 12) relative to comparative device 13 without such a layer.

Figure 58:
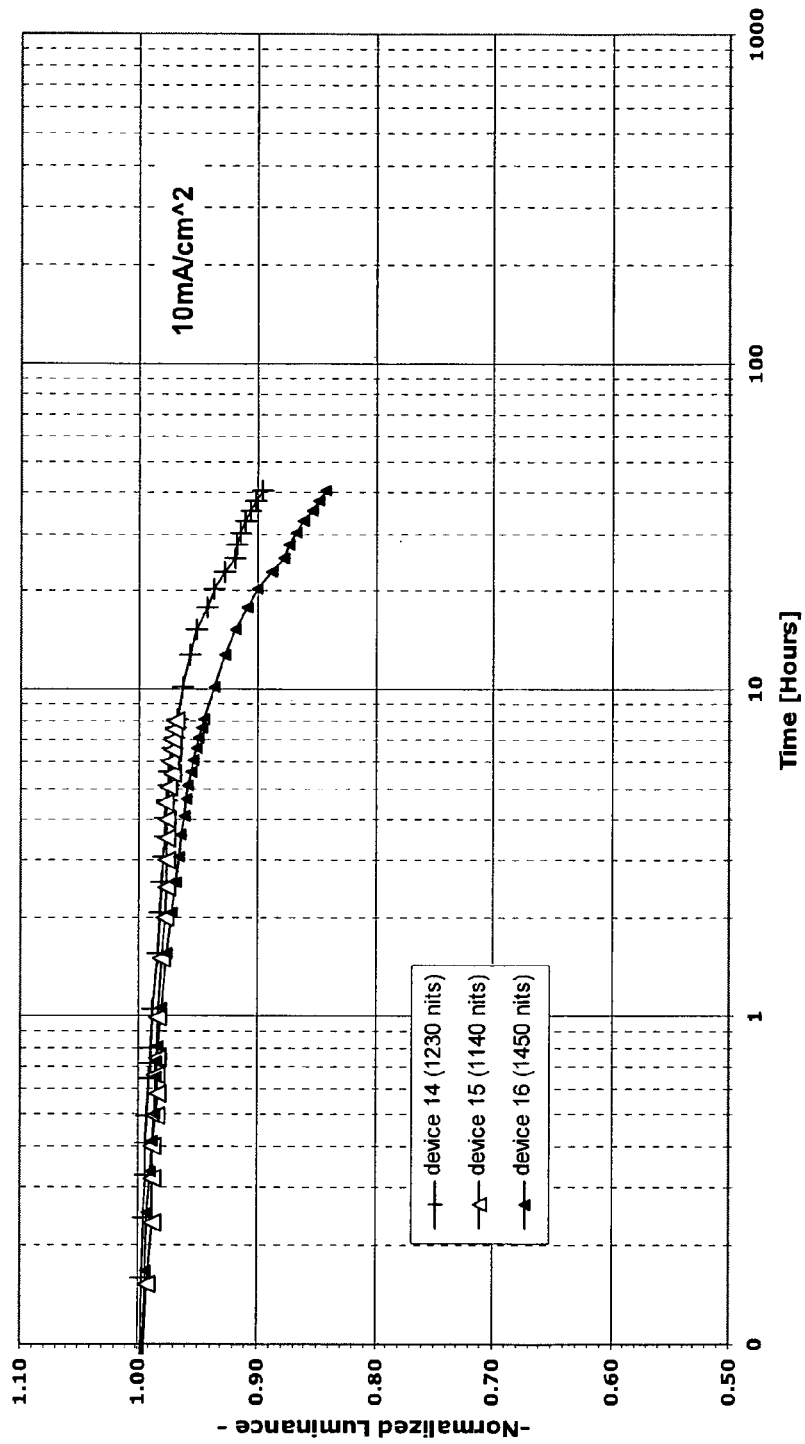
FIG. 58 shows the lifetime at room temperature with 10 mA/cm² for compound 4 devices.

FIG. 57 shows that among the devices utilizing dopant compound 4, the external quantum efficiency is higher for the exemplary devices including an electron impeding layer (devices 14 and 16) relative to comparative device 15 without such a layer. FIG. 58 shows that the exemplary devices have the same or better lifetime relative to the comparative device.

Figure 59:
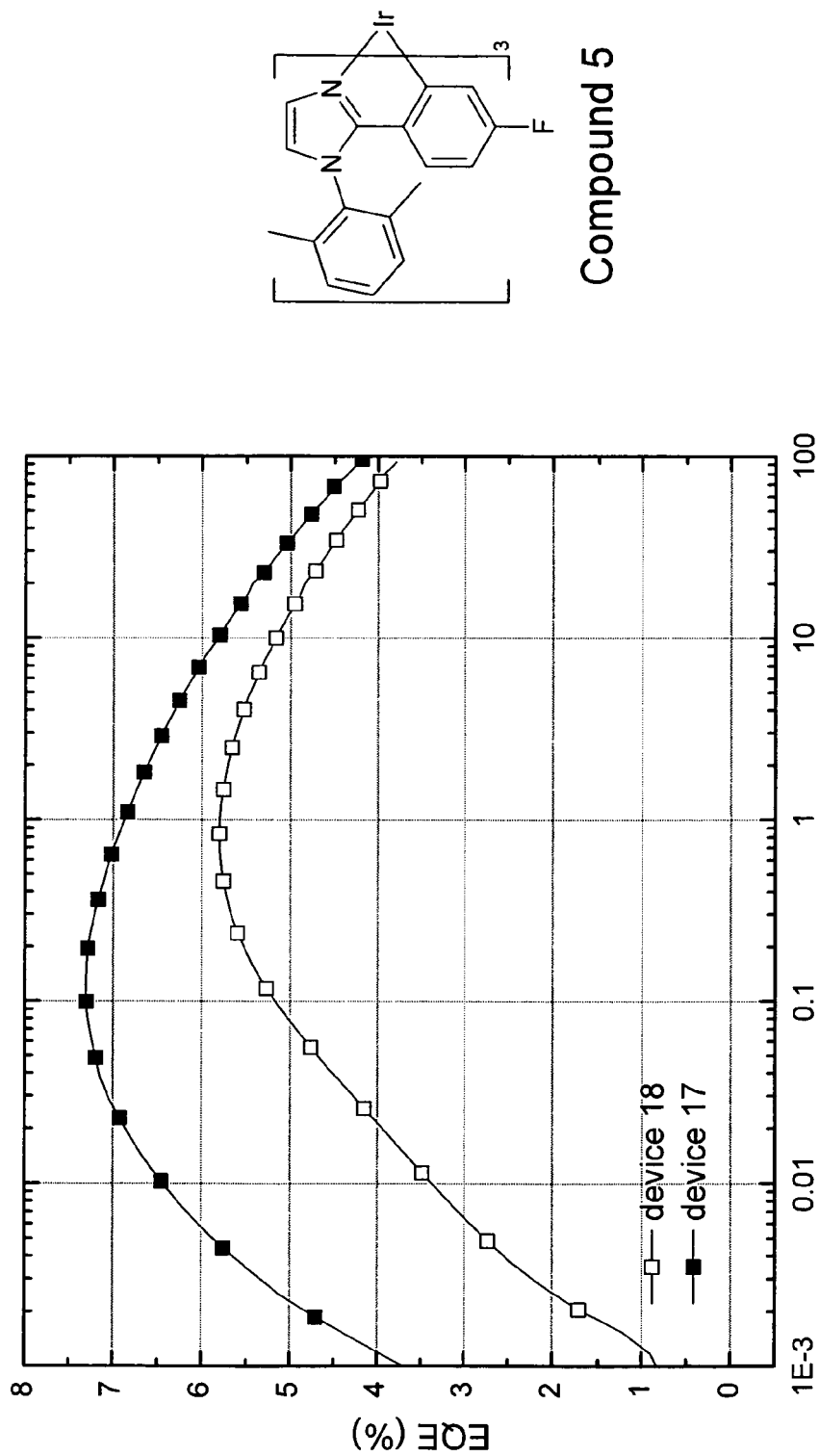
FIG. 59 shows the external quantum efficiency versus current density for compound 5 devices.

FIG. 59 shows that for the devices utilizing dopant compound 5, the external quantum efficiency is higher for the exemplary device 17 including an electron impeding layer relative to comparative device 18 without such a layer.

Example 25

Exemplary devices A-D include an electron impeding layer of variable thickness. Comparative devices E and F include a hole blocking layer of variable thickness.

TABLE 4

Exemplary Devices and Comparative Devices

| Ex. | Structure (All thicknesses are in angstroms, and doping concentration are wt %.) |
|---|---|
| A | CuPc (100)/NPD (300)/mCBP: compound 6 (9%, 300)/Alq$_3$ (400)/LiF/Al |
| B | CuPc (100)/NPD (300)/mCBP: compound 6 (9%, 300)/mCBP (20)/Alq$_3$ (400)/LiF/Al |
| C | CuPc (100)/NPD (300)/mCBP: compound 6 (9%, 300)/mCBP (50)/Alq$_3$ (400)/LiF/Al |
| D | CuPc (100)/NPD (300)/mCBP: compound 6 (9%, 300)/mCBP (100)/Alq$_3$ (400)/LiF/Al |
| E | Ir(ppy)$_3$ (100)/NPD (300)/CBP: compound 7 (8%, 300)/HPT (50)/Alq$_3$ (450)/LiF/Al |
| F | Ir(ppy)$_3$ (100)/NPD (300)/CBP: compound 7 (8%, 300)/HPT (150)/Alq$_3$ (350)/LiF/Al |

Figure 60:
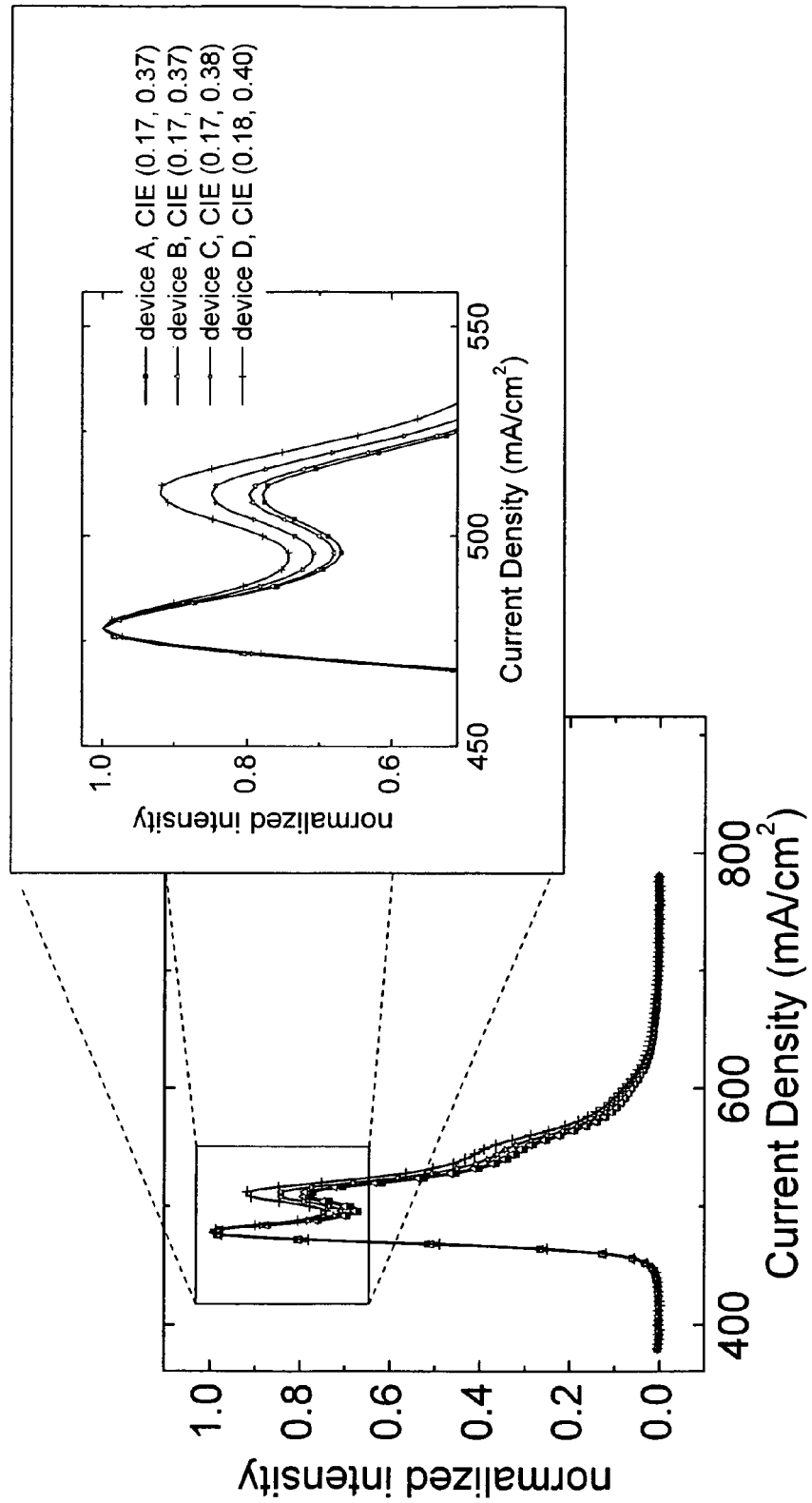
FIG. 60 shows the emission of devices as the thickness of an electron impeding layers is increased.

FIG. 60 shows that as the thickness of the electron impeding layer increases, the amount of emission in the electron transport layer increases.

Figure 61:
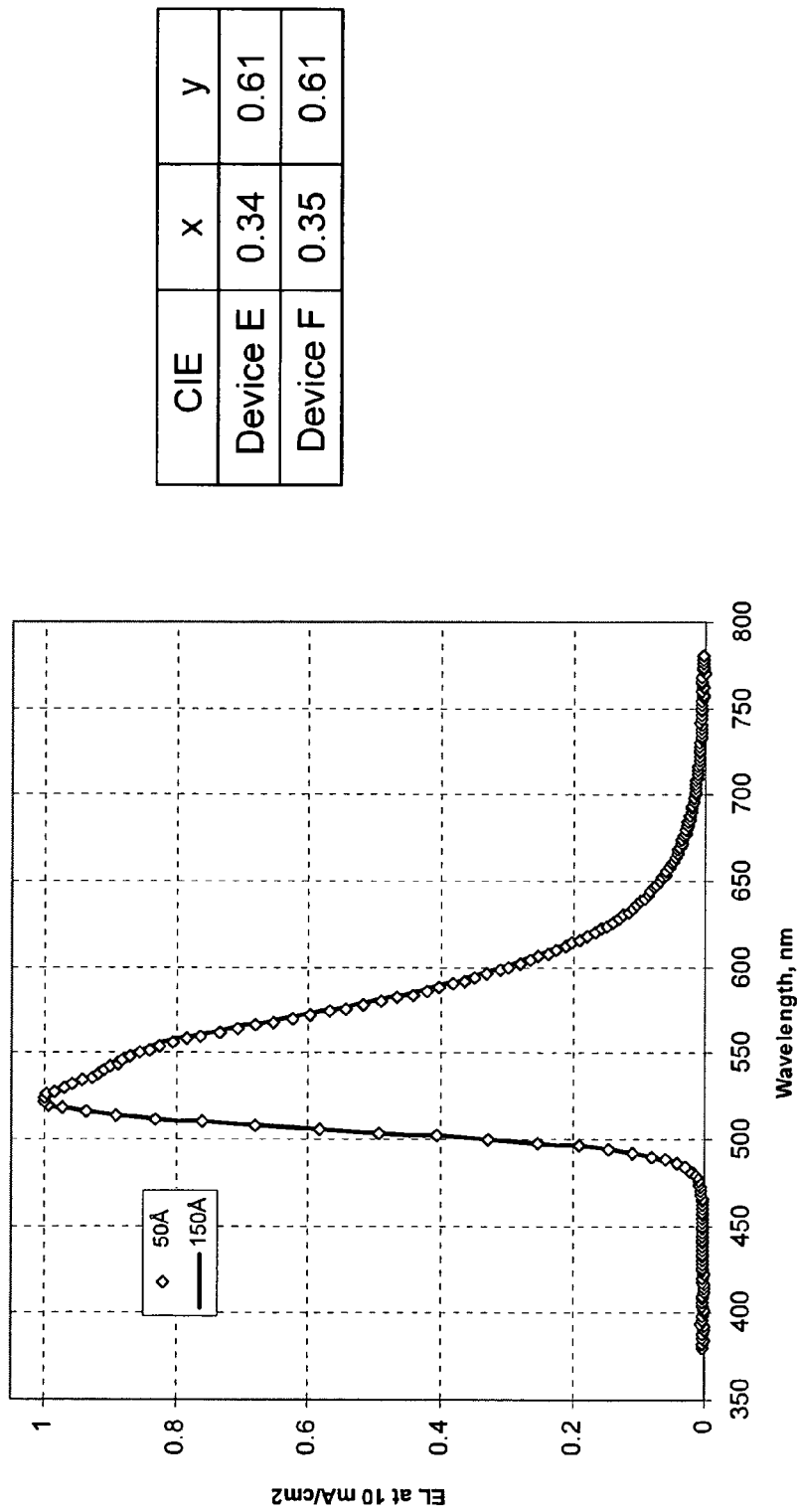
FIG. 61 shows the emission of devices as the thickness of a hole blocking layer is increased.

FIG. 61 shows that as the thickness of the hole blocking layer increases, there is no shift in emission.

All of the above publications, patents and patent applications are herein incorporated by reference in their entirety to the same extent as if each individual publication, patent or patent application was specifically and individually indicated to be incorporated by reference in its entirety.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. A phosphorescent compound, wherein the phosphorescent compound is a neutral metal complex of a bidentate, tridentate, tetradentate, pentadentate, or hexadentate ligand; wherein the ligand comprises:
   a first ring directly bonded to the metal, the first ring being an imidazole;
   a second ring as a substitution on the first ring and not directly bonded to the metal, the second ring being an aryl or heteroaryl ring substituted at both ortho positions by groups other than H or halide, wherein the ortho position substitutions do not form a fused ring with the second ring;
   a third ring as a substitution on the first ring, the third ring being an aryl or heteroaryl ring directly bonded to the metal;
   wherein the metal complex is an organometallic complex;
   wherein the metal is selected from the group consisting of the non-radioactive metals with atomic numbers greater than 40; and
   wherein the photoluminescent emission spectrum of the phosphorescent compound is blue-shifted compared to a comparative compound of identical structure except without the ortho position substitutions on the second ring.

2. The phosphorescent compound of claim 1, wherein both the ortho position substitutions on the second ring are aryl or heteroaryl groups.

3. The compound according to claim 2, wherein the metal is selected from the group consisting of Re, Ru, Os, Rh, Ir, Pd, Pt, and Au.

4. The compound according to claim 3, wherein the metal is selected from the group consisting of Os, Ir, and Pt.

5. The compound according to claim 4, wherein the metal is Ir.

6. The compound according to claim 2, wherein the second ring is further substituted by one or more aryl, heteroaryl, or electron withdrawing groups.

7. The compound according to claim 6, wherein the second ring is further substituted by a triphenylene group.

8. The compound according to claim 6, wherein the second ring is further substituted by a group that comprises a carbazole.

9. The compound according to claim 2, wherein the substituents at the ortho positions of the second ring are diarylaminoaryl groups.

10. The compound according to claim 2, which has a highest energy peak in a phosphorescence emission spectrum at a wavelength less than about 480 nm.

11. The compound according to claim 2, which is a homoleptic compound.

12. The compound according to claim 2, which is a heteroleptic compound.

13. The compound according to claim 2, which is a sublimable compound.

14. The compound according to claim 2, wherein the second ring is attached to a nitrogen atom of the first ring.

15. The compound according to claim 2, wherein the first and third rings collectively comprise a monoanionic bidentate ligand.

16. The compound according to claim 2, wherein the third ring is selected from the group consisting of phenyl, pyridyl, thiophenyl, furanyl, pyrrolyl, triazolyl, and pyrimidyl.

17. The compound according to claim 2, wherein the third ring is a phenyl ring substituted by one or two fluorine groups.

18. The compound according to claim 2, wherein the first and third rings are comprised within a monoanionic tridentate ligand.

19. The compound according to claim 2, wherein the first and third rings collectively comprise a neutral bidentate ligand.

20. The compound according to claim 2, wherein the metal complex comprises a bidentate, monoanionic, N,N-donor ligand.

21. The compound according to claim 2, wherein the metal complex comprises a carbene donor.

22. The compound according to claim 21, wherein the carbene donor is part of a bidentate, monoanionic ligand.

23. The compound according to claim 2, wherein the triplet energy of the arene or heteroarene corresponding to the second ring is greater than about 2.5 eV.

24. The compound according to claim 2, wherein the molecular weight of the arene or heteroarene corresponding to the second ring is greater than about 230 g/mol.

25. The compound according to claim 2, wherein the molecular weight of the arene or heteroarene corresponding to the second ring is greater than about 430 g/mol.

26. The compound according to claim 2, wherein the molecular weight of the arene or heteroarene corresponding to the second ring is greater than about 530 g/mol.

27. The compound according to claim 2, wherein the molecular weight of the arene or heteroarene corresponding to the second ring is greater than about 750 g/mol.

28. The compound according to claim 2, wherein the calculated singlet-triplet gap of the compound is less than about 0.4 eV.

29. The compound according to claim 2, wherein the calculated singlet-triplet gap of the compound is less than about 0.3 eV.

30. The compound according to claim 2, wherein the calculated singlet-triplet gap of the compound is less than about 0.2 eV.

31. The compound according to claim 2, wherein the calculated singlet-triplet gap of the compound is less than about 0.1 eV.

32. The compound according to claim 2, wherein the reduction potential of the ligand is less negative than that of the corresponding ligand with a methyl group in place of the second ring by at least about 0.1 V.

33. The compound according to claim 2, wherein the reduction potential of the ligand is less negative than that of the corresponding ligand with a methyl group in place of the second ring by at least about 0.2 V.

34. The compound according to claim 2, wherein the reduction potential of the ligand is less negative than that of the corresponding ligand with a methyl group in place of the second ring by at least about 0.3 V.

35. The compound according to claim 2, wherein the reduction potential of the ligand is less negative than that of the corresponding ligand with a methyl group in place of the second ring by at least about 0.4 V.

36. The compound according to claim 2, wherein the reduction potential of the ligand is less negative than that of the corresponding ligand with a methyl group in place of the second ring by at least about 0.5 V.

37. The compound according to claim 2, wherein delta E is less than about 0.6 eV;
wherein:

delta $E$=(triplet energy)–(modified electrochemical gap);

the triplet energy is the energy of the highest energy peak in the phosphorescence emission spectrum of said metal complex, in eV; and the modified electrochemical gap is the difference between the oxidation potential of the metal complex and the reduction potential of the neutral compound corresponding to the ligand.

38. The compound according to claim 37, wherein delta E is less than about 0.5 eV.

39. The compound according to claim 37, wherein delta E is less than about 0.4 eV.

40. The compound according to claim 37, wherein delta E is less than about 0.3 eV.

41. The compound according to claim 37, wherein delta E is less than about 0.2 eV.

42. An organic light emitting device comprising an anode, a cathode, and an emissive layer, wherein the emissive layer is located between the anode and the cathode, and the emissive layer comprises a phosphorescent compound according to claim 2, and optionally a host.

43. The compound according to claim 1, wherein the first ring is coordinated via a first nitrogen to the metal.

44. The compound according to claim 43, wherein the second ring is attached to a second nitrogen of the first ring.

45. The compound according to claim 1, wherein the metal is selected from the group consisting of Re, Ru, Os, Rh, Ir, Pd, Pt, and Au.

46. The compound according to claim 45, wherein the metal is selected from the group consisting of Os, Ir, and Pt.

47. The compound according to claim 46, wherein the metal is Ir.

48. The compound according to claim 1, wherein the second ring is further substituted by one or more aryl, heteroaryl, or electron withdrawing groups.

49. The compound according to claim 1, wherein the second ring is further substituted by a triphenylene group.

50. The compound according to claim 1, wherein the second ring is further substituted by a group that comprises a carbazole.

51. The compound according to claim 1, wherein the groups other than H or halide are alkyl groups.

52. The compound according to claim 51, wherein the groups other than H or halide are alkyl groups comprising two or more carbons.

53. The compound according to claim 1, wherein the groups other than H or halide are aryl groups.

54. The compound according to claim 1, wherein the groups other than H or halide are heteroaryl groups.

55. The compound according to claim 1, which has a highest energy peak in a phosphorescence emission spectrum at a wavelength less than about 480 nm.

56. The compound according to claim 1, which is a homoleptic compound.

57. The compound according to claim 1, which is a heteroleptic compound.

58. The compound according to claim 1, which is a sublimable compound.

59. The compound according to claim 1, wherein the first and third rings collectively comprise a monoanionic bidentate ligand.

60. The compound according to claim 59, wherein the third ring is a benzene, naphthalene, quinoline, isoquinoline, pyridine, pyrimidine, pyridazine, pyrrole, oxazole, thiazole, oxadiazole, thiadiazole, furan, or thiophene ring.

61. The compound according to claim 59, wherein the third ring is selected from the group consisting of phenyl, pyridyl, thiophenyl, furanyl, pyrrolyl, triazolyl, and pyrimidyl.

62. The compound according to claim 1, wherein the first and third rings collectively comprise a monoanionic tridentate ligand.

63. The compound according to claim 1, wherein the first and third rings collectively comprise a neutral bidentate ligand.

64. The compound according to claim 1, wherein the groups other than H or halide are selected from either (i) the group consisting of methyl, ethyl, n-propyl, isopropyl, and tert-butyl, or (ii) the following groups:

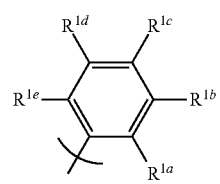

d1

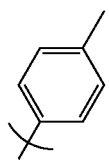

d2

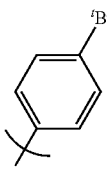

d3

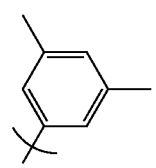

d4

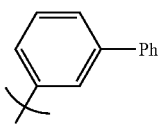

d5

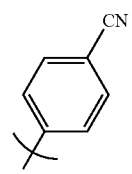

d6

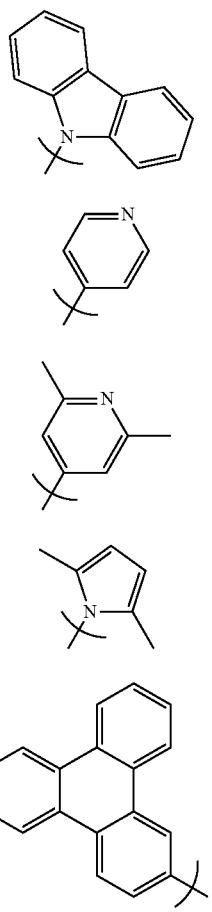
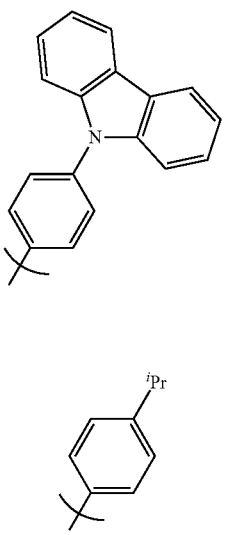
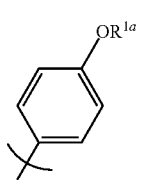
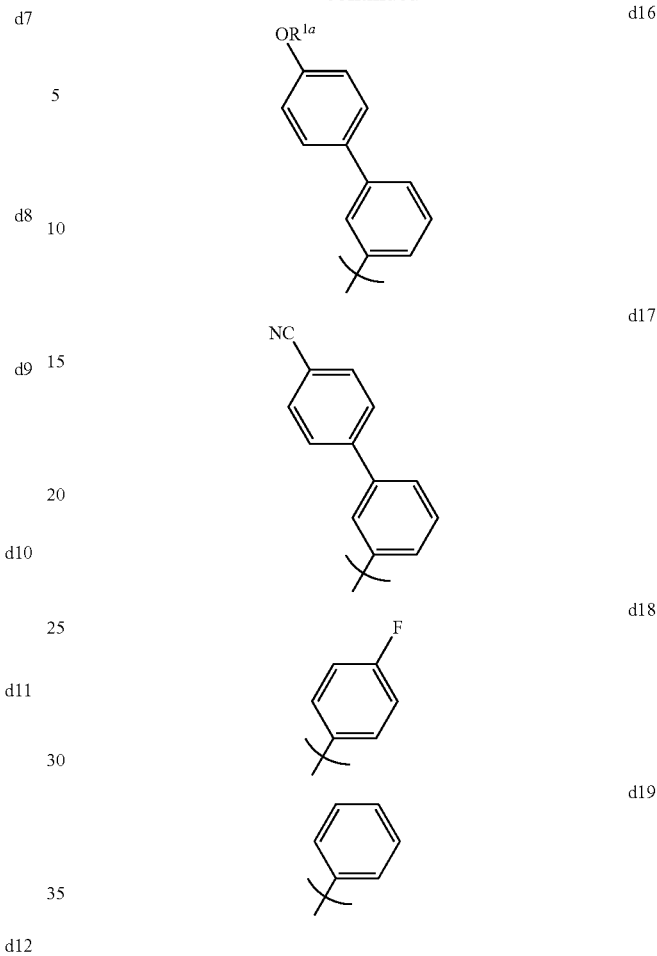

wherein:
R$^{1a-e}$ are each independently selected from the group consisting of hydrogen, hydrocarbyl, heteroatom substituted hydrocarbyl, cyano, and F;
in addition, any two of R$^{1a-e}$ may be linked to form a ring.

65. The compound according to claim 1, wherein the second ring is selected from 2,6-dimethylphenyl; 2,4,6-trimethylphenyl; 2,3,4,5,6-pentamethylphenyl; 2,6-dimethyl-4-phenylphenyl; 2,6-dimethyl-4-(3,5-dimethylphenyl)phenyl; 2,6-dimethyl-4-(2,6-dimethylphenyl)phenyl; 2,6-dimethyl-4-(4-pyridyl)phenyl; 2,6-dimethyl-4-(2,6-dimethyl-4-pyridyl)phenyl; 2,4-dimethyl-3-naphthyl; 2,6-dimethyl-4-cyanophenyl; 2,6-dimethyl-4-(9-carbazolyl)phenyl; 2,6-dimethyl-4-(9-phenyl-3-carbazolyl)phenyl; 2,6-dimethyl-4-(2,6-dimethyl-4-cyanophenyl)phenyl; 2,6-di-isopropylphenyl; 2,4,6-tri-isopropylphenyl; 2,6-di-isopropyl-4-phenylphenyl; 2,6-di-isopropyl-4-(3,5-dimethylphenyl)phenyl; 2,6-di-isopropyl-4-(2,6-dimethylphenyl)phenyl; 2,6-di-isopropyl-4-(4-pyridyl)phenyl; 2,6-di-isopropyl-4-(2,6-dimethyl-4-pyridyl)phenyl; 2,4-di-isopropyl-3-naphthyl; 2,6-di-isopropyl-4-cyanophenyl; 2,6-di-isopropyl-4-(9-carbazolyl)phenyl; 2,6-di-isopropyl-4-(9-phenyl-3-carbazolyl)phenyl; 2,6-di-isopropyl-4-(2,6-dimethyl-4-cyanophenyl)phenyl; 2,6-di-tert-butylphenyl; 2,6-di-tert-butyl-4-(3,5-dimethylphenyl)phenyl; 2,6-bis(trimethylsilyl)phenyl; 2,6-bis(dimethylphenylsilyl)phenyl; and 2,6-bis(trimethylsilyl)-4-(3,5-dimethylphenyl)-phenyl; 2,6-di-phenylphenyl; 2,6-di(4-isopropylphenyl)-4-isopropylphenyl; 2,6-di(4-isopropylphenyl)-4-methylphenyl; 2,6-di(4-isopropylphenyl)-4-tert-butylphenyl; 2,4,6-triphenylphenyl;

2,6-di-(4-isopropylphenyl)phenyl; 2,6-di-(3,5-dimethylphenyl)phenyl; 2,4,6-tri(4-isopropylphenyl)phenyl; 2,6-di-(4-tert-butylphenyl)phenyl; 2;6-di-(4-fluorophenyl)phenyl; 2,6-di-(9-carbazolyl)-4-isopropylphenyl; 2,6-di-(9-phenyl-3-carbazolyl)-4-isopropylphenyl; 2,6-di-(4-methoxyphenyl) phenyl; 2,6-diphenyl-4-fluorophenyl; 2,6-di-(2-triphenylenyl)phenyl; 2,6-di-(2-triphenylenyl)-4-isopropylphenyl; 2,6-di-(2,6-dimethyl-4-pyridyl)phenyl; 2,6-di-(4-cyanophenyl)-4-isopropylphenyl; 2,6-di-2-naphthylphenyl; 2,6-di-(4-phenylphenyl)-4-isopropylphenyl; 2,6-di-(3-phenylphenyl)-4-isopropylphenyl; 2,6-di-(4-diphenylaminophenyl)phenyl; 2,6-di-(4-dimethylaminophenyl)phenyl; 2,6-di-(4-trimethylsilylphenyl)phenyl; 2,6-di-(4-triphenylsilylphenyl)phenyl; 2,6-di-(4-diphenylmethylsilylphenyl)phenyl; and c1-c7 and c9 as follows:

wherein:

$R^{1a-e}$ are each independently selected from the group consisting of hydrocarbyl comprising two or more carbons, heteroatom substituted hydrocarbyl, aryl, and heteroaryl;

$R^{b-d}$ are each independently selected from the group consisting of H, F, cyano, alkoxy, aryloxy, hydrocarbyl, heteroatom substituted hydrocarbyl, aryl, and heteroaryl; in addition, any two of $R^{1b-d}$ may be linked to form a ring; and $Ar^{1,2,3}$ are each independently aryl or heteroaryl.

66. The compound according to claim 1, wherein the first ring is selected from f1-f4 as follows:

-continued

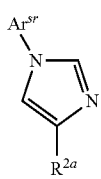
f4 wherein:
Ar$^{sr}$ is the second ring;
R$^{1a,b}$ are each independently selected from the group consisting of hydrogen, hydrocarbyl, and heteroatom substituted hydrocarbyl, cyano, and F; in addition, R$^{1a,b}$ may be linked to form a ring; and
for rings f2, f3, and f4: R$^{2a}$ is the third ring;
for ring f1: R$^{2b}$ is the third ring and R$^{2a}$ is selected from the group consisting of hydrogen, hydrocarbyl, heteroatom substituted hydrocarbyl, cyano, and F.

67. The compound according to claim 1, wherein the third ring is selected from t1-t10 as follows:

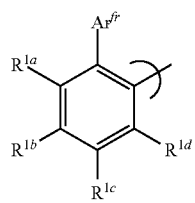
t1

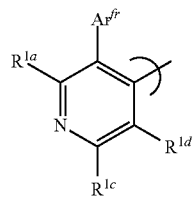
t2

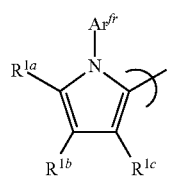
t3

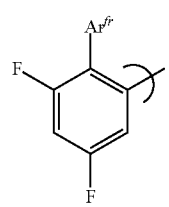
t4

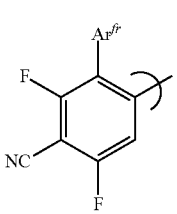
t5

-continued

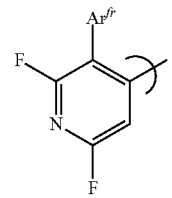
t6

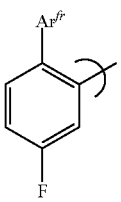
t7

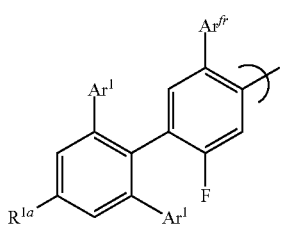
t8

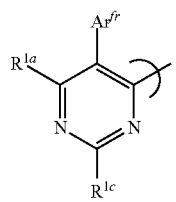
t9

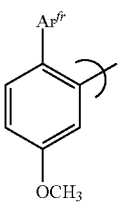
t10 wherein:
Ar$^{fr}$ is the first ring;
Ar$^{1}$ is aryl or heteroaryl; and
R$^{1a-d}$ are each independently selected from the group consisting of hydrogen, hydrocarbyl, heteroatom substituted hydrocarbyl, cyano, and F; in addition, any two of R$^{1a-d}$ may be linked to form a ring.

68. The compound according to claim 1, wherein the ligand is selected from I1-I7, I20-I22, I41-I46 as follows:

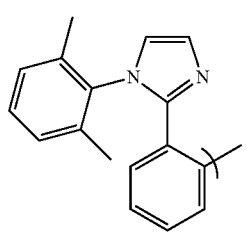
I1

-continued

I2
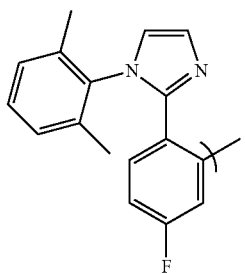

I3
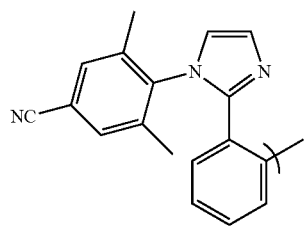

I4
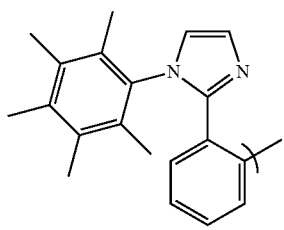

I5
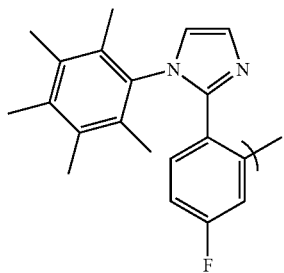

I6
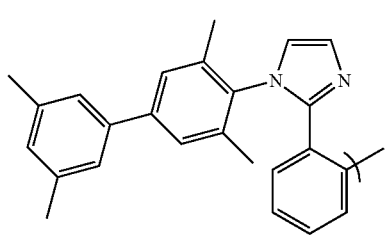

I7
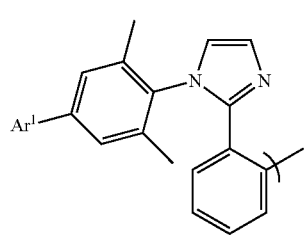

wherein:
Ar¹ is aryl or heteroaryl;

I20
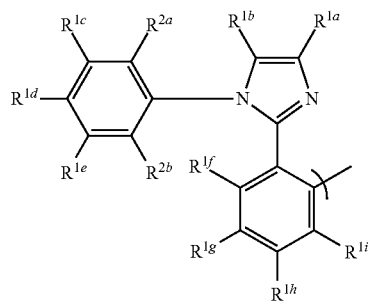

I21
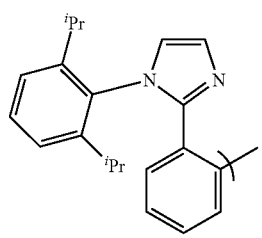

I22
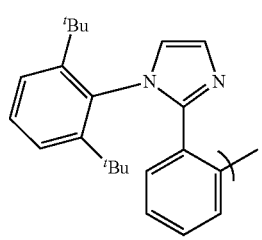

wherein:
R$^{1a\text{-}i}$ are each independently selected from the group consisting of hydrogen, hydrocarbyl, heteroatom substituted hydrocarbyl, cyano, and F;
R$^{2a,b}$ are each independently selected from the group consisting of hydrocarbyl comprising two or more carbons, heteroatom substituted hydrocarbyl, aryl, and heteroaryl;

I41
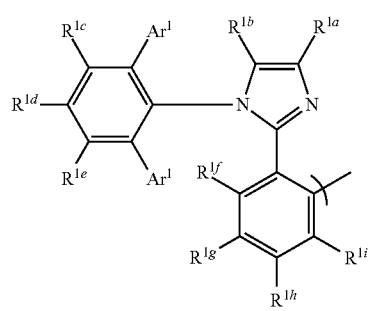

I42
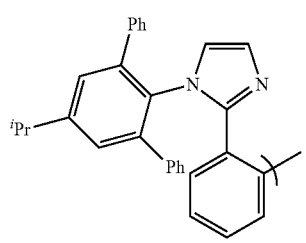

-continued
I43
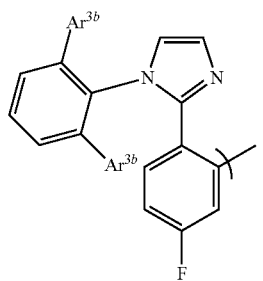
I44
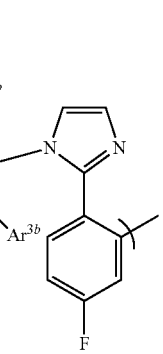
I45
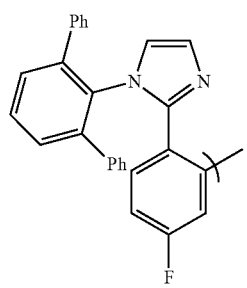
I46
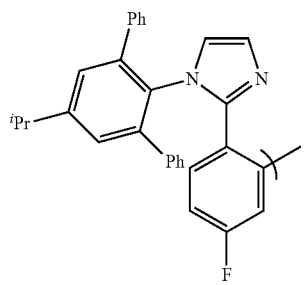
wherein:
R$^{1a-i}$ are each independently selected from the group consisting of hydrogen, hydrocarbyl, heteroatom substituted hydrocarbyl, cyano, and F;
Ar$^1$ is aryl or heteroaryl;
Ar$^{3a}$ is 4-isopropylphenyl; and
Ar$^{3b}$ is 3,5-dimethylphenyl.
69. The compound according to claim 1, wherein the metal complex is selected from the following:
mc3
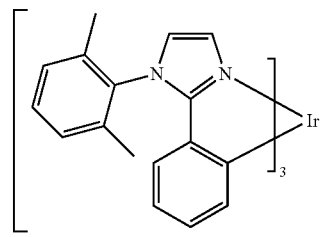
mc50
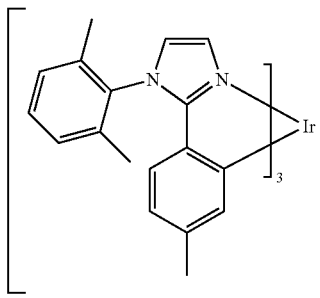
mc48
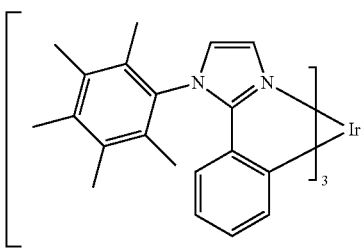
mc25
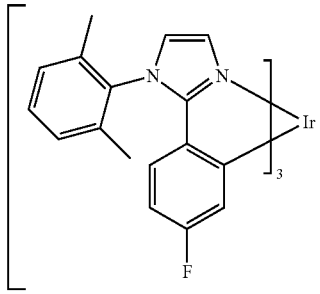
mc46
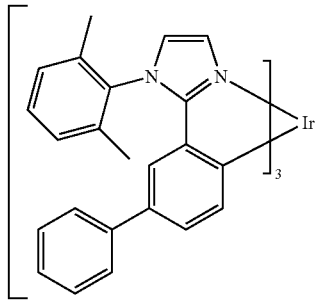

mc5
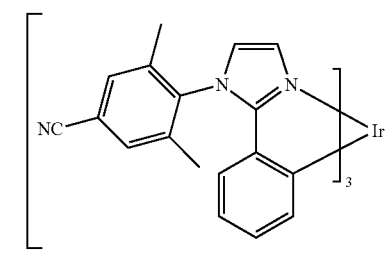
mc4
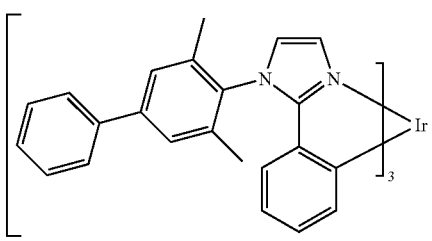
mc54
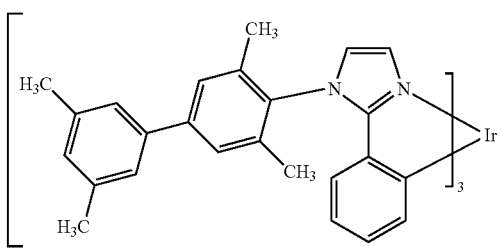
mc51
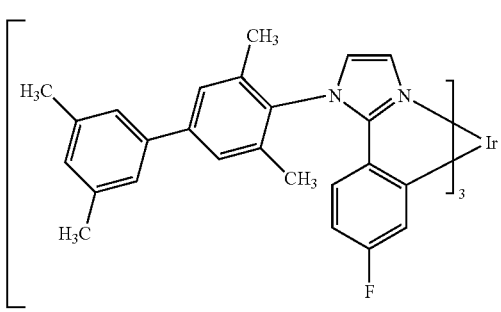
mc26a
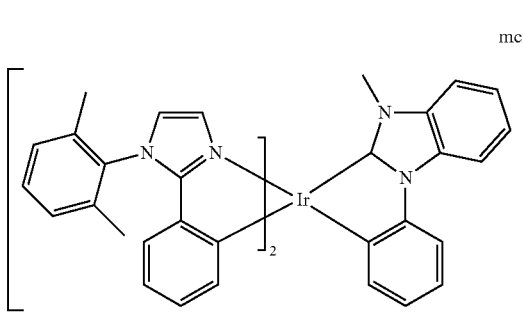
mc26
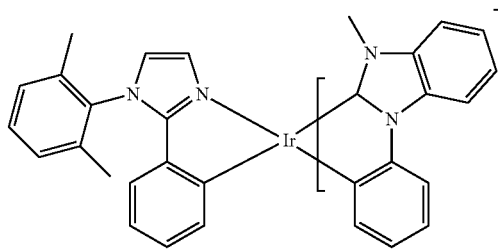
mc39
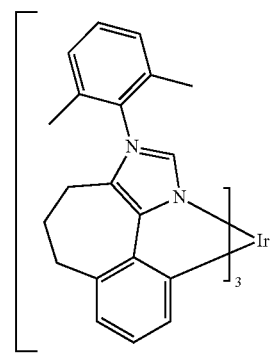
mc49
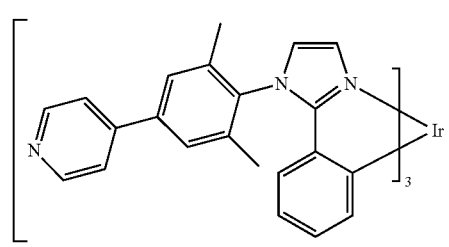
mc6
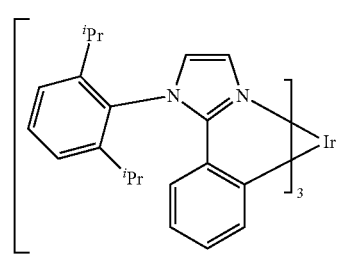
mc9
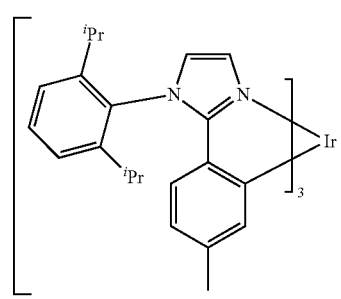

mc8 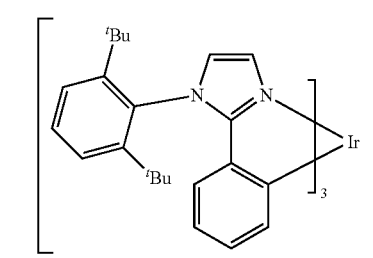
mc4b 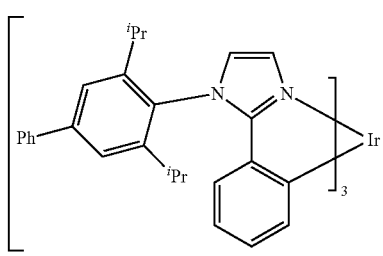
mc38b 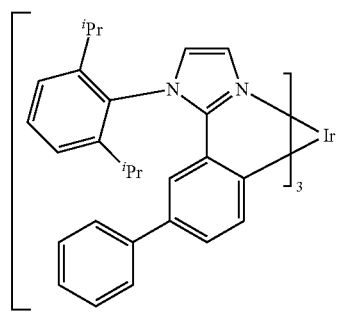
mc15 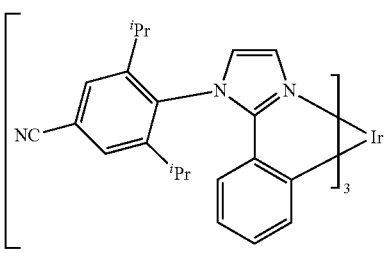
mc26b 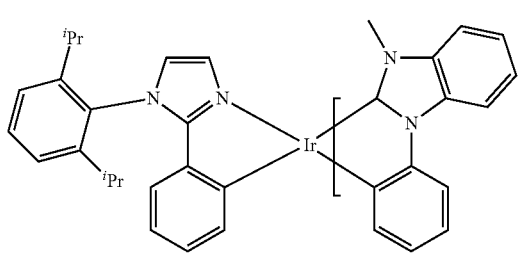
mc28b 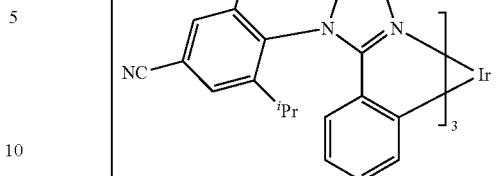
mc32b 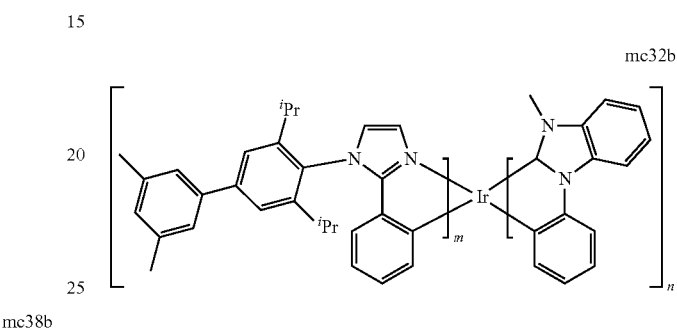
mc34b 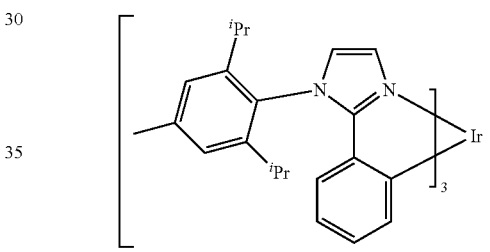
mc35b 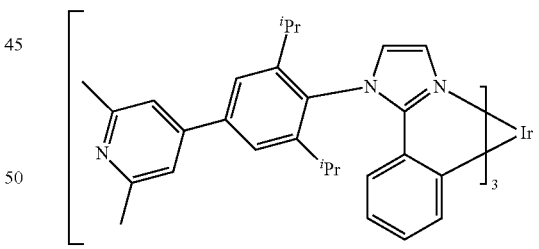
mc29b 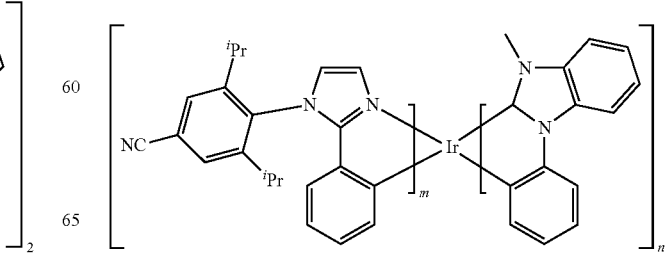

-continued
mc30b
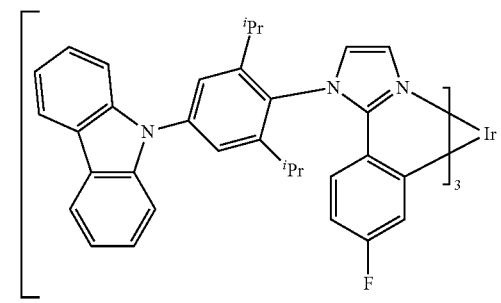
mc31b
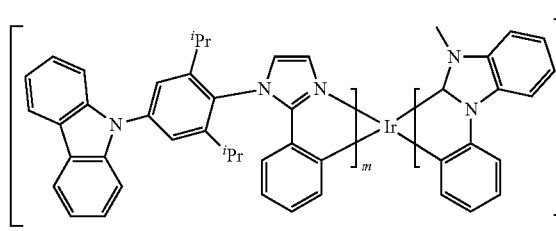
mc42b
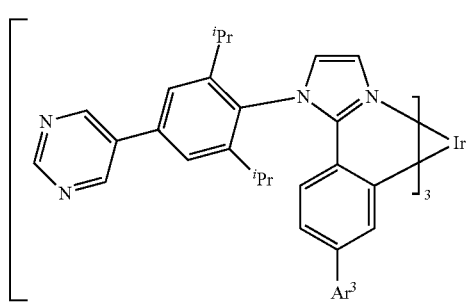
mc43b
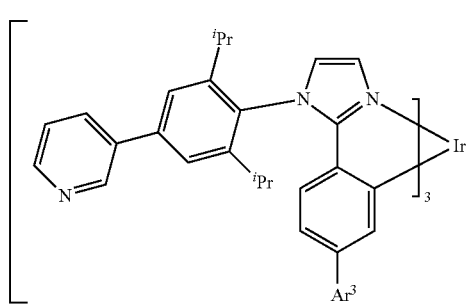
mc44b
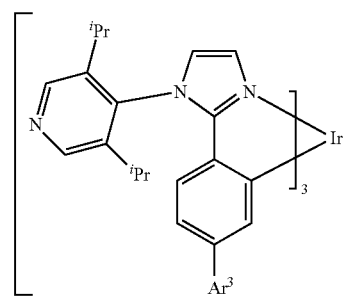
wherein:
Ar³ is aryl or heteroaryl;
m is 1, 2 or 3; and
n is an integer selected to satisfy the valency of the metal;
mc37
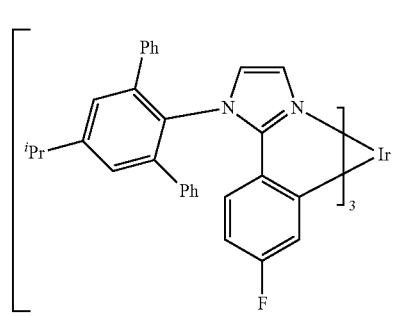
oa9
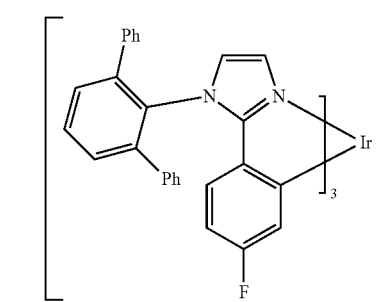
oa4
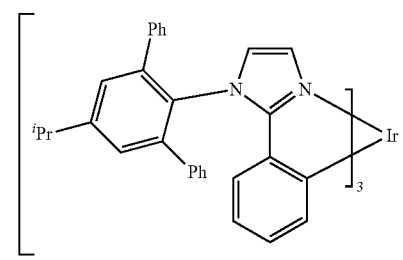
oa6
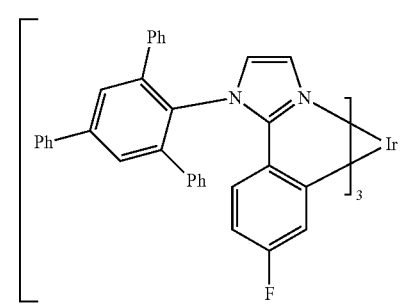
oa8
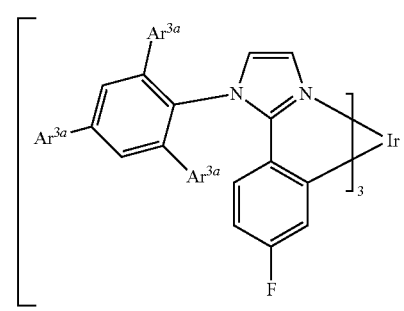

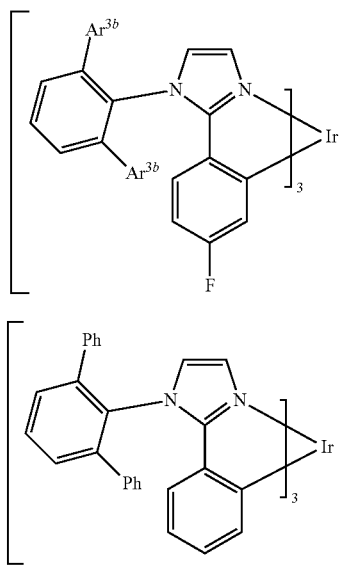
wherein:
Ar$^{3a}$ is 4-isopropylphenyl; and
Ar$^{3b}$ is 3,5-dimethylphenyl;
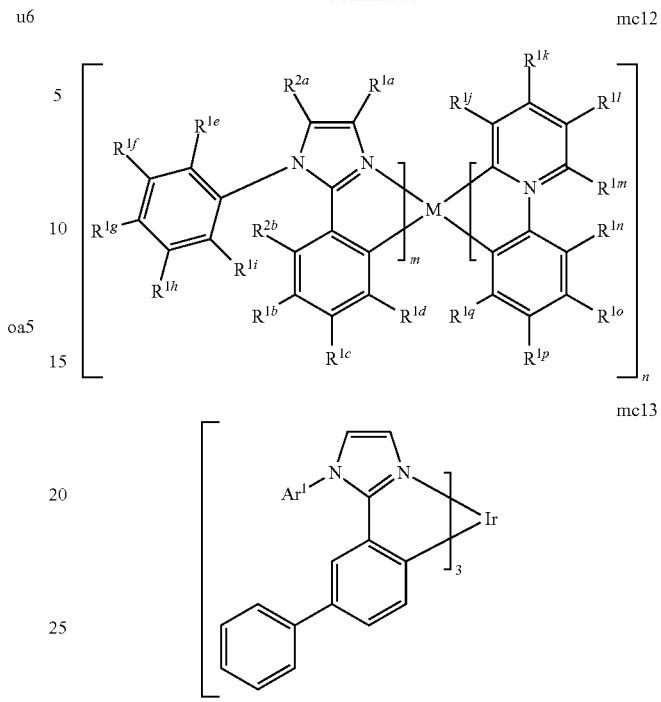
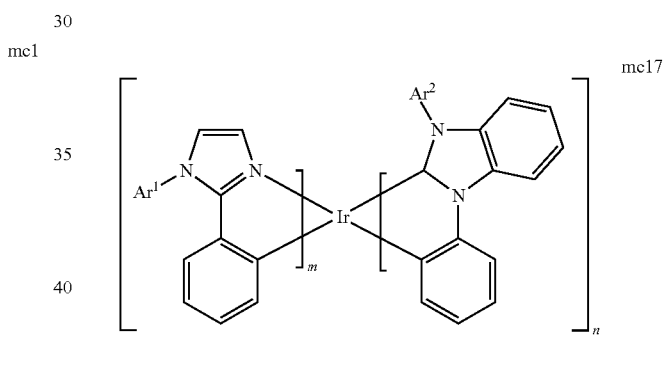
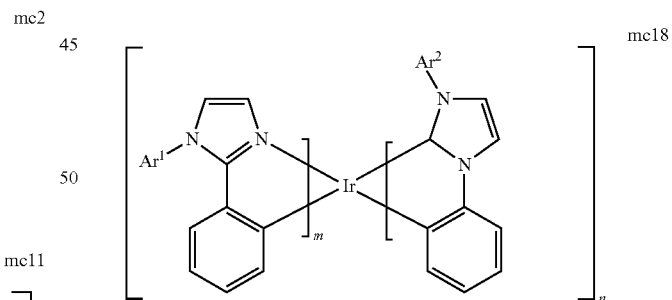
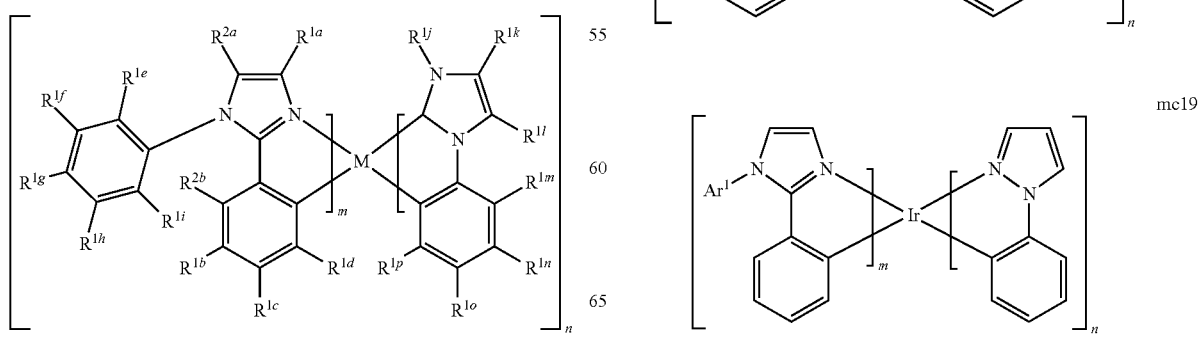

-continued
mc20
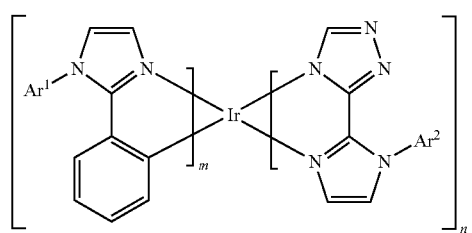
mc21
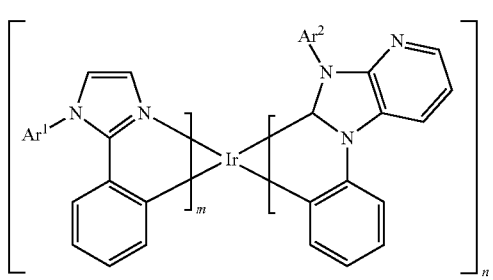
mc22
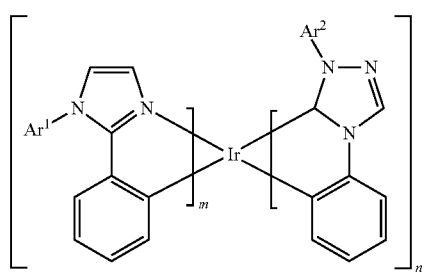
mc23
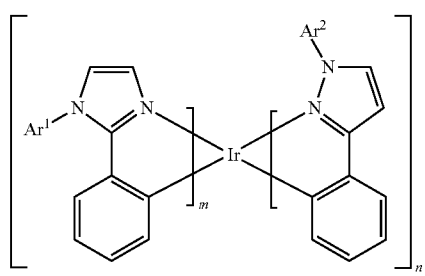
mc24
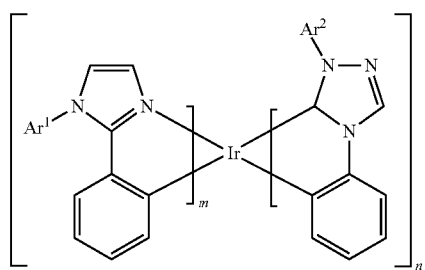
-continued
mc27
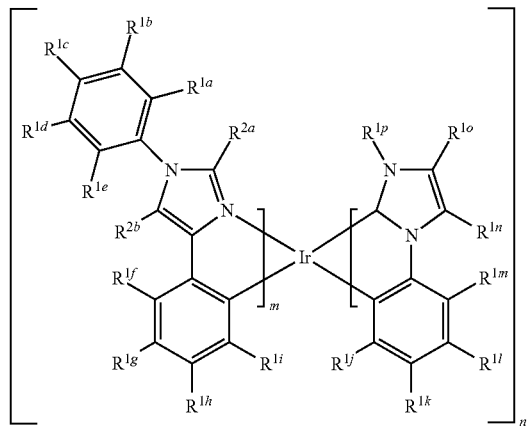
mc36
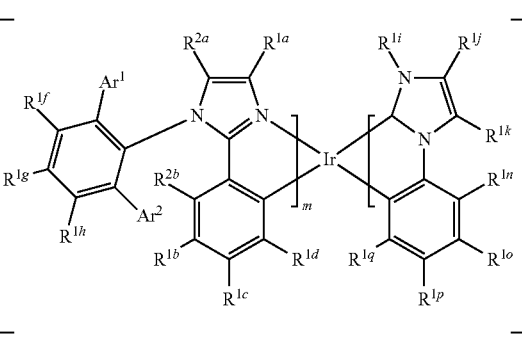
oa11
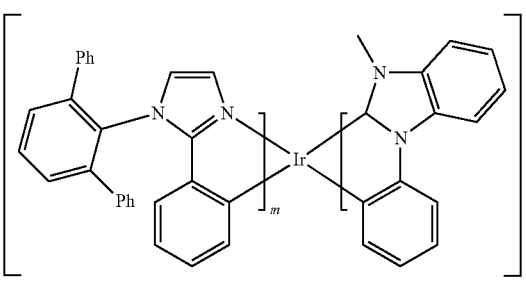
mc51b
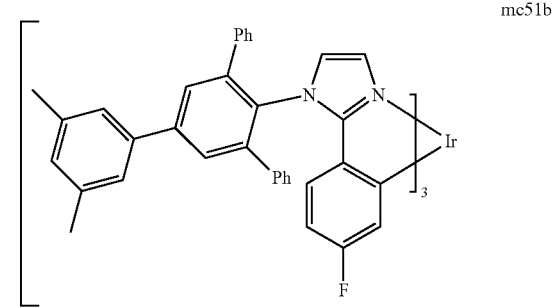

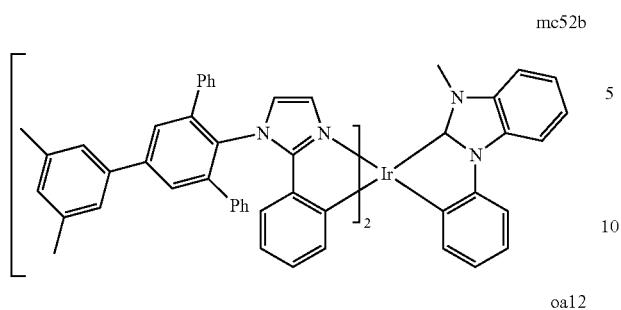
mc52b
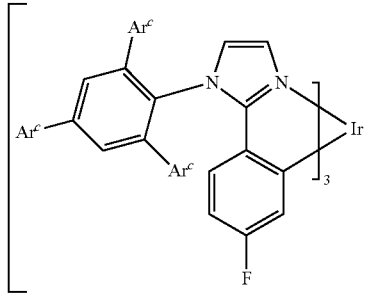
oa12
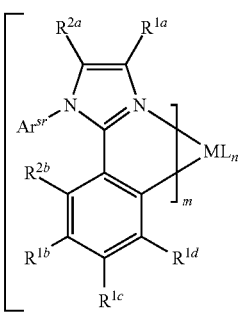
oa1
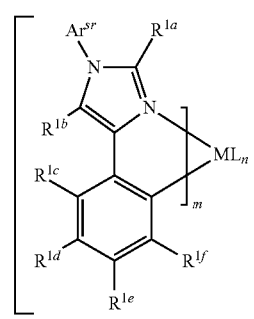
oa2
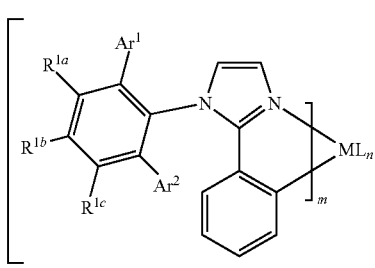
oa3
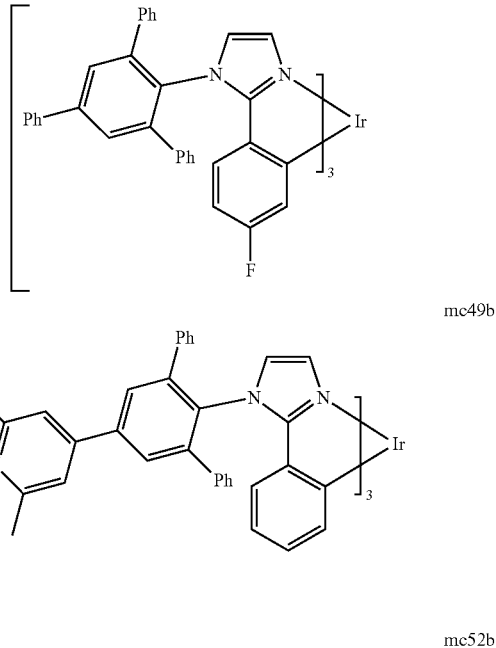
oa8b
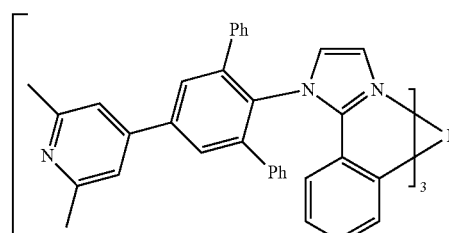
mc49b
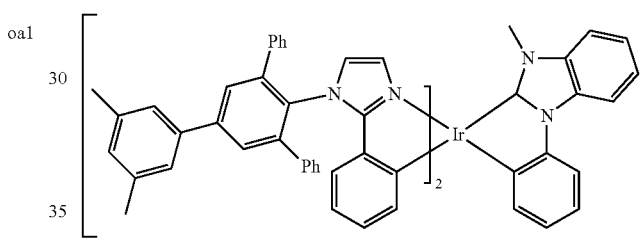
mc52b
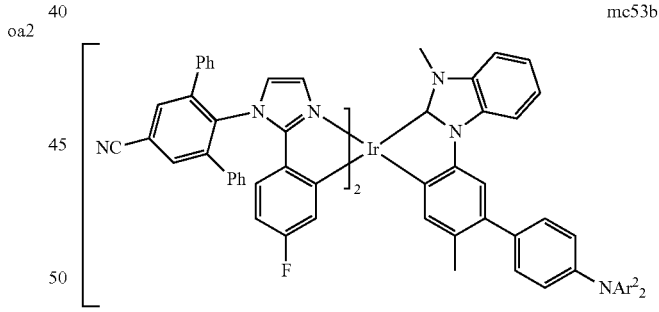
mc53b
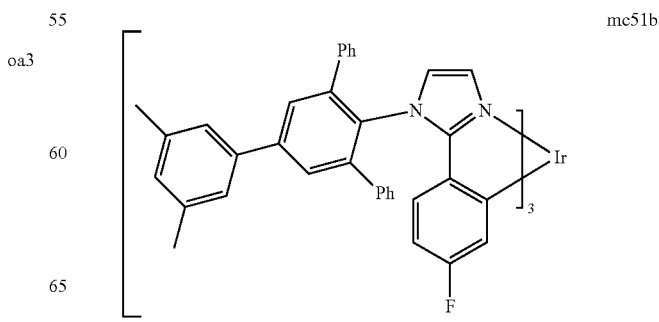
mc51b -continued

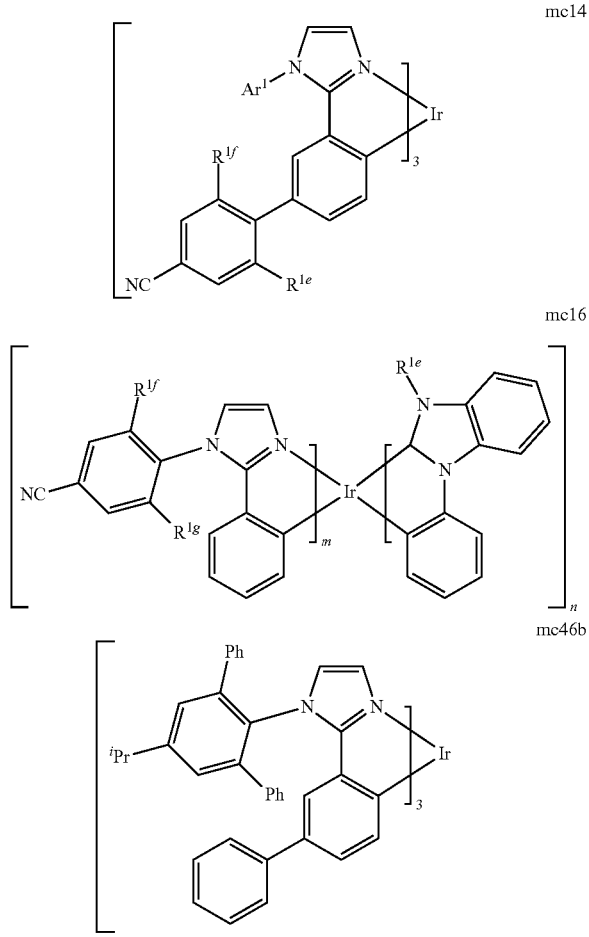

wherein:
$R^{2a-c}$, $R^{1a-d}$, $R^{1f-h}$, and $R^{1j-q}$ are each independently selected from the group consisting of hydrogen, hydrocarbyl, heteroatom substituted hydrocarbyl, cyano, and F; and wherein $R^{1e}$ and $R^{1i}$ are each independently aryl, heteroaryl, or alkyl; with the proviso that, for any of the preceding variables that represent an ortho position substitution on the second ring, the variable represents a group that is not H or a halide;
$Ar^{1-3}$ are aryl or heteroaryl, with the proviso that for any $Ar^1$ that is a substitution on the first ring, $Ar^1$ is the second ring;
$Ar^{sr}$ is the second ring;
$Ar^c$ is 9-carbazolyl or substituted 9-carbazolyl;
$L_n$ are ancillary ligands, which may be the same or different;
m is 1, 2 or 3;
n is an integer selected to satisfy the valency of M; and
M is a metal selected from the group consisting of Re, Ru, Os, Rh, Ir, Pd, Pt, and Au; and compounds m1-m72 as follows:

| Specific Structure | General Structure | $R^{1a}$ | $R^{1b}$ | $R^{1c}$ | $R^{1d}$ | $R^{1e}$ | $R^{1f}$ |
|---|---|---|---|---|---|---|---|
| m1 | gs1 | CH$_3$ | H | CH$_3$ | H | H | H |
| m2 | gs1 | CH$_3$ | H | CH$_3$ | H | H | F |
| m3 | gs1 | CH$_3$ | H | CH$_3$ | F | H | F |
| m4 | gs1 | CH$_3$ | H | CH$_3$ | F | Ph | F |
| m5 | gs1 | $^i$Pr | H | $^i$Pr | H | H | H |
| m6 | gs1 | $^i$Pr | H | $^i$Pr | H | H | F |
| m7 | gs1 | $^i$Pr | H | $^i$Pr | F | H | F |
| m8 | gs1 | $^i$Pr | H | $^i$Pr | F | Ph | F |
| m9 | gs1 | Ph | $^i$Pr | Ph | H | H | H |
| m10 | gs1 | Ph | $^i$Pr | Ph | H | H | F |
| m11 | gs1 | Ph | $^i$Pr | Ph | F | H | F |
| m12 | gs1 | Ph | $^i$Pr | Ph | F | Ph | F |
| m13 | gs1 | Ph | $^i$Pr | Ph | H | H | H |
| m14 | gs1 | Ph | $^i$Pr | Ph | H | H | F |
| m15 | gs1 | Ph | $^i$Pr | Ph | F | H | F |
| m16 | gs1 | Ph | $^i$Pr | Ph | F | Ph | F |
| m17 | gs1 | 3,5-Me$_2$Ph | H | 3,5-Me$_2$Ph | H | H | H |
| m18 | gs1 | 3,5-Me$_2$Ph | H | 3,5-Me$_2$Ph | H | H | F |
| m19 | gs1 | 3,5-Me$_2$Ph | H | 3,5-Me$_2$Ph | F | H | F |
| m20 | gs1 | 3,5-Me$_2$Ph | H | 3,5-Me$_2$Ph | F | Ph | F |
| m21 | gs1 | 3,5-Me$_2$Ph | H | 3,5-Me$_2$Ph | H | H | H |
| m22 | gs1 | 3,5-Me$_2$Ph | H | 3,5-Me$_2$Ph | H | H | F |
| m23 | gs1 | 3,5-Me$_2$Ph | H | 3,5-Me$_2$Ph | F | H | F |
| m24 | gs1 | 3,5-Me$_2$Ph | H | 3,5-Me$_2$Ph | F | Ph | F |
| m25 | gs2 | CH$_3$ | H | CH$_3$ | H | H | H |
| m26 | gs2 | CH$_3$ | H | CH$_3$ | H | H | F |
| m27 | gs2 | CH$_3$ | H | CH$_3$ | F | H | F |
| m28 | gs2 | CH$_3$ | H | CH$_3$ | F | Ph | F |
| m29 | gs2 | $^i$Pr | H | $^i$Pr | H | H | H |
| m30 | gs2 | $^i$Pr | H | $^i$Pr | H | H | F |
| m31 | gs2 | $^i$Pr | H | $^i$Pr | F | H | F |
| m32 | gs2 | $^i$Pr | H | $^i$Pr | F | Ph | F |
| m33 | gs2 | Ph | $^i$Pr | Ph | H | H | H |
| m34 | gs2 | Ph | $^i$Pr | Ph | H | H | F |
| m35 | gs2 | Ph | $^i$Pr | Ph | F | H | F |
| m36 | gs2 | Ph | $^i$Pr | Ph | F | Ph | F |
| m37 | gs2 | Ph | $^i$Pr | Ph | H | H | H |
| m38 | gs2 | Ph | $^i$Pr | Ph | H | H | F |
| m39 | gs2 | Ph | $^i$Pr | Ph | F | H | F |
| m40 | gs2 | Ph | $^i$Pr | Ph | F | Ph | F |
| m41 | gs2 | 3,5-Me$_2$Ph | H | 3,5-Me$_2$Ph | H | H | H |
| m42 | gs2 | 3,5-Me$_2$Ph | H | 3,5-Me$_2$Ph | H | H | F |
| m43 | gs2 | 3,5-Me$_2$Ph | H | 3,5-Me$_2$Ph | F | H | F |
| m44 | gs2 | 3,5-Me$_2$Ph | H | 3,5-Me$_2$Ph | F | Ph | F |
| m45 | gs2 | 3,5-Me$_2$Ph | H | 3,5-Me$_2$Ph | H | H | H |
| m46 | gs2 | 3,5-Me$_2$Ph | H | 3,5-Me$_2$Ph | H | H | F |
| m47 | gs2 | 3,5-Me$_2$Ph | H | 3,5-Me$_2$Ph | F | H | F |
| m48 | gs2 | 3,5-Me$_2$Ph | H | 3,5-Me$_2$Ph | F | Ph | F |
| m49 | gs3 | CH$_3$ | H | CH$_3$ | H | H | H |
| m50 | gs3 | CH$_3$ | H | CH$_3$ | H | H | F |
| m51 | gs3 | CH$_3$ | H | CH$_3$ | F | H | F |
| m52 | gs3 | CH$_3$ | H | CH$_3$ | F | Ph | F |
| m53 | gs3 | $^i$Pr | H | $^i$Pr | H | H | H |
| m54 | gs3 | $^i$Pr | H | $^i$Pr | H | H | F |
| m55 | gs3 | $^i$Pr | H | $^i$Pr | F | H | F |
| m56 | gs3 | $^i$Pr | H | $^i$Pr | F | Ph | F |
| m57 | gs3 | Ph | $^i$Pr | Ph | H | H | H |
| m58 | gs3 | Ph | $^i$Pr | Ph | H | H | F |
| m59 | gs3 | Ph | $^i$Pr | Ph | F | H | F |
| m60 | gs3 | Ph | $^i$Pr | Ph | F | Ph | F |
| m61 | gs3 | Ph | $^i$Pr | Ph | H | H | H |
| m62 | gs3 | Ph | $^i$Pr | Ph | H | H | F |
| m63 | gs3 | Ph | $^i$Pr | Ph | F | H | F |
| m64 | gs3 | Ph | $^i$Pr | Ph | F | Ph | F |
| m65 | gs3 | 3,5-Me$_2$Ph | H | 3,5-Me$_2$Ph | H | H | H |
| m66 | gs3 | 3,5-Me$_2$Ph | H | 3,5-Me$_2$Ph | H | H | F |
| m67 | gs3 | 3,5-Me$_2$Ph | H | 3,5-Me$_2$Ph | F | H | F |
| m68 | gs3 | 3,5-Me$_2$Ph | H | 3,5-Me$_2$Ph | F | Ph | F |
| m69 | gs3 | 3,5-Me$_2$Ph | H | 3,5-Me$_2$Ph | H | H | H |

-continued

| Specific Structure | General Structure | $R^{1a}$ | $R^{1b}$ | $R^{1c}$ | $R^{1d}$ | $R^{1e}$ | $R^{1f}$ |
|---|---|---|---|---|---|---|---|
| m70 | gs3 | 3,5-Me$_2$Ph | H | 3,5-Me$_2$Ph | H | H | F |
| m71 | gs3 | 3,5-Me$_2$Ph | H | 3,5-Me$_2$Ph | F | H | F |
| m72 | gs3 | 3,5-Me$_2$Ph | H | 3,5-Me$_2$Ph | F | Ph | F | wherein gs1, gs2, and gs3 are:

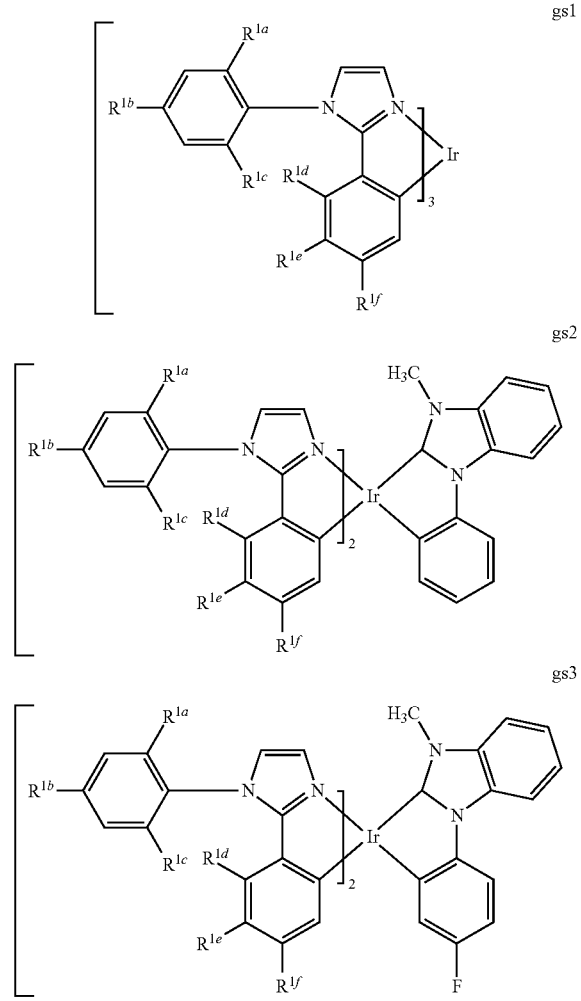

70. The compound according to claim 1, wherein the metal complex comprises a bidentate, monoanionic, N,N-donor ligand.

71. The compound according to claim 1, wherein the metal complex comprises a carbene donor.

72. The compound according to claim 71, wherein the carbene donor is part of a bidentate, monoanionic ligand.

73. The compound according to claim 1, wherein the triplet energy of the arene or heteroarene corresponding to the second ring is greater than about 2.5 eV.

74. The compound according to claim 1, wherein the molecular weight of the arene or heteroarene corresponding to the second ring is greater than about 230 g/mol.

75. The compound according to claim 74, wherein the molecular weight of the arene or heteroarene corresponding to the second ring is greater than about 430 g/mol.

76. The compound according to claim 74, wherein the molecular weight of the arene or heteroarene corresponding to the second ring is greater than about 530 g/mol.

77. The compound according to claim 74, wherein the molecular weight of the arene or heteroarene corresponding to the second ring is greater than about 750 g/mol.

78. The compound according to claim 1, wherein the calculated singlet-triplet gap of the compound is less than about 0.4 eV.

79. The compound according to claim 78, wherein the calculated singlet-triplet gap of the compound is less than about 0.3 eV.

80. The compound according to claim 78, wherein the calculated singlet-triplet gap of the compound is less than about 0.2 eV.

81. The compound according to claim 78, wherein the calculated singlet-triplet gap of the compound is less than about 0.1 eV.

82. The compound according to claim 1, wherein the reduction potential of the ligand is less negative than that of the corresponding ligand with a methyl group in place of the second ring by at least about 0.1 V.

83. The compound according to claim 82, wherein the reduction potential of the ligand is less negative than that of the corresponding ligand with a methyl group in place of the second ring by at least about 0.2 V.

84. The compound according to claim 82, wherein the reduction potential of the ligand is less negative than that of the corresponding ligand with a methyl group in place of the second ring by at least about 0.3 V.

85. The compound according to claim 82, wherein the reduction potential of the ligand is less negative than that of the corresponding ligand with a methyl group in place of the second ring by at least about 0.4 V.

86. The compound according to claim 82, wherein the reduction potential of the ligand is less negative than that of the corresponding ligand with a methyl group in place of the second ring by at least about 0.5 V.

87. The compound according to claim 1, wherein delta E is less than about 0.6 eV; wherein:

delta $E$=(triplet energy)−(modified electrochemical gap);

the triplet energy is the energy of the highest energy peak in the phosphorescence emission spectrum of said metal complex, in eV; and the modified electrochemical gap is the difference between the oxidation potential of the metal complex and the reduction potential of the neutral compound corresponding to the ligand.

88. The compound according to claim 87, wherein delta E is less than about 0.5 eV.

89. The compound according to claim 87, wherein delta E is less than about 0.4 eV.

90. The compound according to claim 87, wherein delta E is less than about 0.3 eV.

91. The compound according to claim 87, wherein delta E is less than about 0.2 eV.

92. An organic light emitting device comprising an anode, a cathode, and an emissive layer, wherein the emissive layer is located between the anode and the cathode, and the emissive layer comprises a phosphorescent compound according to claim 1, and optionally a host.

93. The compound of claim 1, wherein the emission spectrum of the compound has a peak wavelength at less than 500 nm.

* * * * *

UNITED STATES PATENT AND TRADEMARK OFFICE
CERTIFICATE OF CORRECTION

PATENT NO. : 9,051,344 B2  
APPLICATION NO. : 11/241981  
DATED : June 9, 2015  
INVENTOR(S) : Chun Lin et al.

Page 1 of 5

It is certified that error appears in the above-identified patent and that said Letters Patent is hereby corrected as shown below:

In the Specification:
Column 22, Lines 18-25 - delete

" 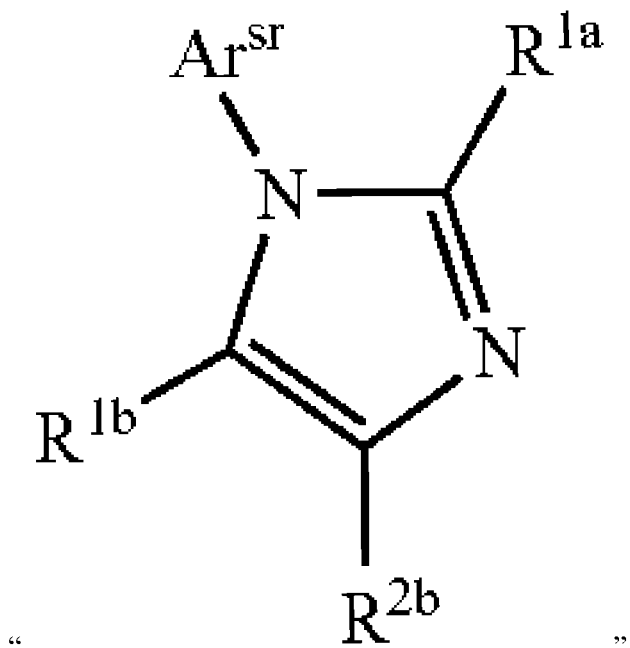 "

Signed and Sealed this
First Day of December, 2015

Michelle K. Lee
*Director of the United States Patent and Trademark Office*

CERTIFICATE OF CORRECTION (continued)
U.S. Pat. No. 9,051,344 B2

Column 22, Lines 18-25 Cont'd

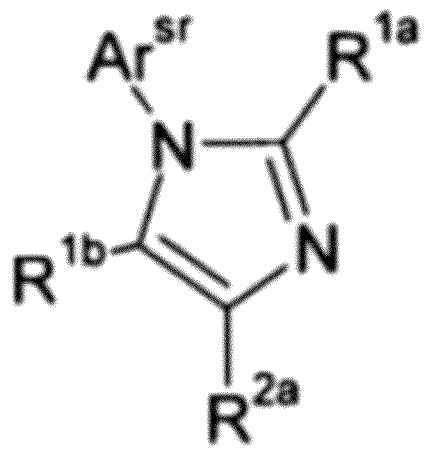

and insert -- --

In the Claims:
Claim 65, Column 81, Lines 35-42 - delete

"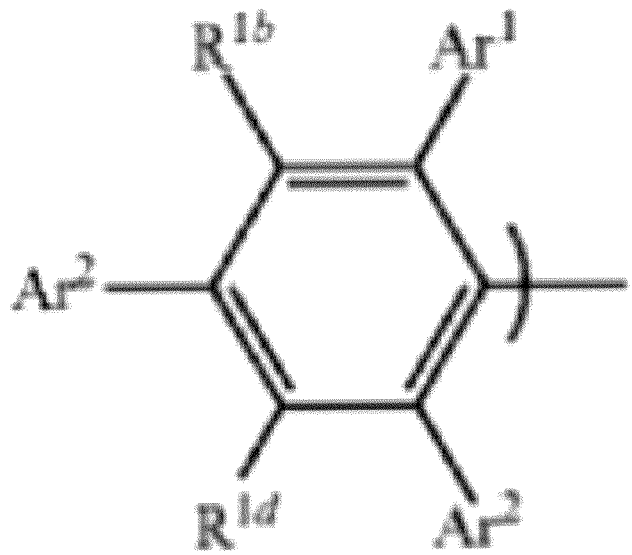"

and insert --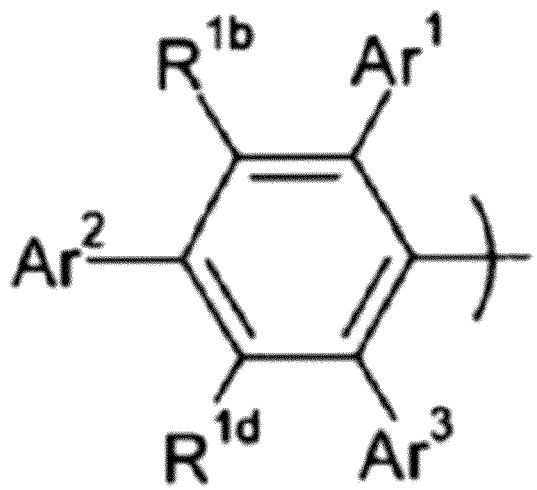--

Claim 66, Column 82, Lines 54-59 - delete

CERTIFICATE OF CORRECTION (continued)
U.S. Pat. No. 9,051,344 B2

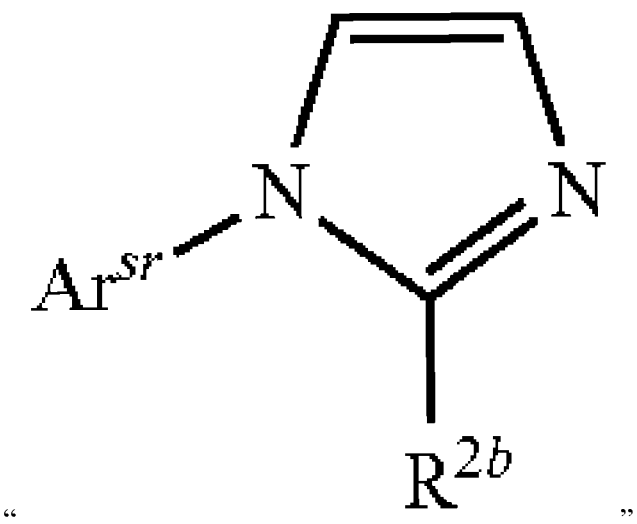

"                                                "

and insert -- 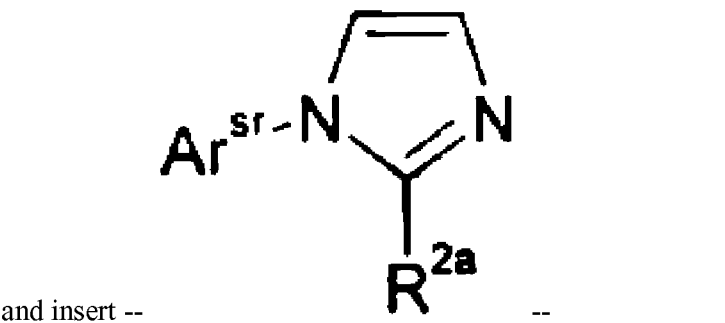 --

Claim 68, Column 87, Lines 17-28 - delete

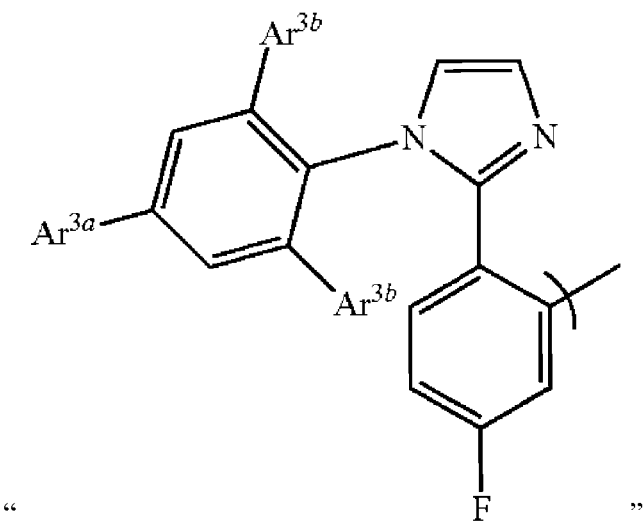

"                                                "

Claim 68, Column 87, Lines 17-28 Cont'd

CERTIFICATE OF CORRECTION (continued)
U.S. Pat. No. 9,051,344 B2

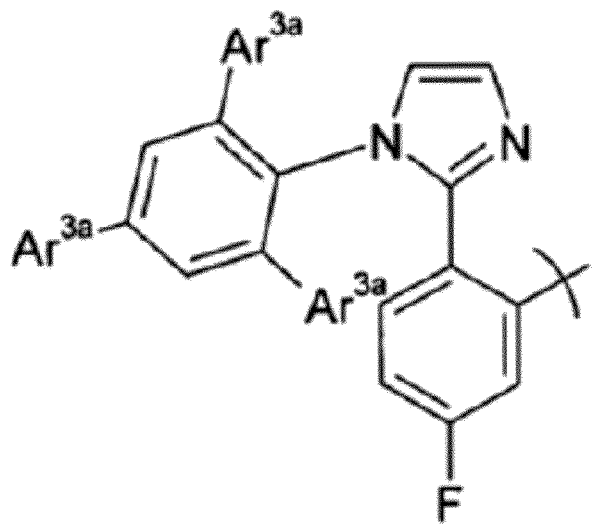

and insert --                                                                 --

Claim 69, Column 96, Lines 3-17 - delete

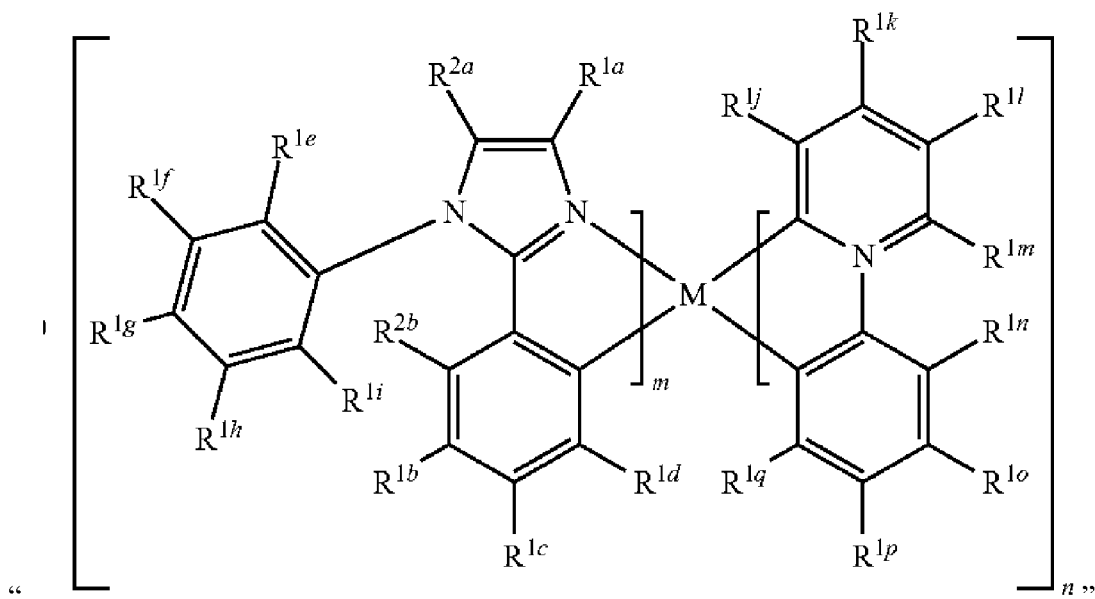

"                                                                                                                     "

Claim 69, Column 96, Lines 3-17 Cont'd

CERTIFICATE OF CORRECTION (continued)
U.S. Pat. No. 9,051,344 B2 and insert -- 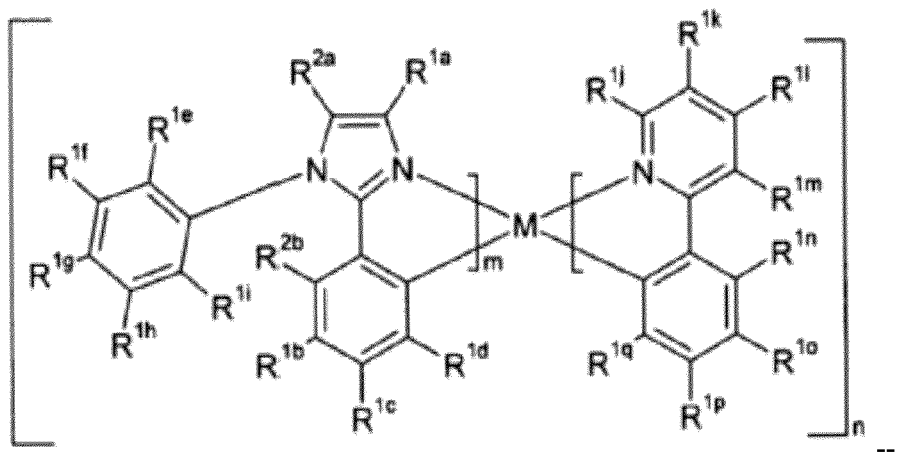 --

Claim 69, Column 102, Lines 11-12 - delete

"m1 0 m1 1"

and insert

-- m10 m11 --